(12) United States Patent
Gray et al.

(10) Patent No.: US 11,134,896 B2
(45) Date of Patent: Oct. 5, 2021

(54) TRANSCUTANEOUS ANALYTE SENSORS, APPLICATORS THEREFOR, AND ASSOCIATED METHODS

(71) Applicant: DexCom, Inc., San Diego, CA (US)

(72) Inventors: John Michael Gray, San Diego, CA (US); Jennifer Blackwell, San Diego, CA (US); Paul V. Neale, San Diego, CA (US); Justen Deering England, San Francisco, CA (US); Andrew Joncich, Madison, WI (US); Cameron Brock, San Francisco, CA (US); Peter C. Simpson, Cardiff, CA (US); Thomas Metzmaker, San Diego, CA (US); Neel Narayan Shah, Carlsbad, CA (US); Mark Douglas Kempkey, Vista, CA (US); Patrick John Castagna, San Diego, CA (US); Warren Terry, Poway, CA (US); Jason Halac, San Diego, CA (US); Christian Michael Andre George, San Diego, CA (US); Daniel E. Apacible, Chula Vista, CA (US); John Charles Barry, San Diego, CA (US); Maria Noel Brown Wells, Vista, CA (US); Kenneth Pirondini, San Diego, CA (US); Andrew Michael Reinhardt, Santee, CA (US); Jason C. Wong, San Diego, CA (US); Remy E. Gagnon, San Diego, CA (US); David DeRenzy, San Diego, CA (US); Randall Scott Koplin, San Diego, CA (US); Alan Baldwin, San Jose, CA (US); Young Woo Lee, San Diego, CA (US); David A. Keller, Encinitas, CA (US); Louise Emma van den Heuvel, Somerville, MA (US); Carol Wood Sutherland, Somerville, MA (US)

(73) Assignee: DexCom, Inc., San Diego, CA (US)

(*) Notice: Subject to any disclaimer, the term of this patent is extended or adjusted under 35 U.S.C. 154(b) by 0 days.

(21) Appl. No.: 17/200,671

(22) Filed: Mar. 12, 2021

(65) Prior Publication Data

US 2021/0219919 A1    Jul. 22, 2021

Related U.S. Application Data

(63) Continuation of application No. 16/016,493, filed on Jun. 22, 2018, which is a continuation of application
(Continued)

(51) Int. Cl.
*A61B 5/145* (2006.01)
*A61B 5/00* (2006.01)
*A61B 5/1473* (2006.01)

(52) U.S. Cl.
CPC .......... *A61B 5/6849* (2013.01); *A61B 5/0004* (2013.01); *A61B 5/14503* (2013.01);
(Continued)

(58) Field of Classification Search
CPC ............ A61B 5/14532; A61B 5/68335; A61B 5/0002; A61B 5/0004; A61B 5/05;
(Continued)

(56) References Cited

U.S. PATENT DOCUMENTS

| 4,367,967 A | 1/1983 | Albert, Jr. |
| 4,672,734 A | 6/1987 | Kawada et al. |

(Continued)

FOREIGN PATENT DOCUMENTS

| EP | 0729366 B1 | 7/2002 |
| EP | 1 475 113 A1 | 11/2004 |

(Continued)

OTHER PUBLICATIONS

Communication pursuant to Rules 70(2) and 70a(2) EPC for European Application No. 18825284.5, dated Mar. 4, 2021, 1 page.
(Continued)

*Primary Examiner* — Navin Natnithithadha
(74) *Attorney, Agent, or Firm* — Knobbe Martens Olson & Bear LLP

(57) ABSTRACT

The present embodiments relate generally to applicators of on-skin sensor assemblies for measuring an analyte in a host, as well as their method of use and manufacture. In some aspects, an applicator for applying an on-skin sensor assembly to a skin of a host is provided. The applicator includes an applicator housing, a needle carrier assembly comprising an insertion element configured to insert a sensor of the on-skin sensor assembly into the skin of the host, a holder releasably coupled to the needle carrier assembly and configured to guide the on-skin sensor assembly while coupled to the needle carrier assembly, and a drive assembly configured to drive the insertion element from a proximal starting position to a distal insertion position, and from the distal insertion position to a proximal retraction position.

30 Claims, 85 Drawing Sheets

Related U.S. Application Data

No. 16/016,354, filed on Jun. 22, 2018, now Pat. No. 10,863,944.

(60) Provisional application No. 62/524,247, filed on Jun. 23, 2017, provisional application No. 62/658,486, filed on Apr. 16, 2018.

(52) U.S. Cl.
CPC ...... *A61B 5/14532* (2013.01); *A61B 5/14546* (2013.01); *A61B 5/6833* (2013.01); *A61B 5/6848* (2013.01); *A61B 5/1473* (2013.01); *A61B 2560/063* (2013.01)

(58) Field of Classification Search
CPC .............. A61B 5/1411; A61B 5/14503; A61B 5/14507; A61B 5/14514; A61B 5/14546; A61B 5/1473; A61B 5/14735; A61B 5/1486; A61B 5/14865; A61B 5/1495; A61B 5/6801; A61B 5/6833; A61B 5/6848; A61B 5/6849; A61B 5/72; A61B 17/3468; A61B 5/14; A61B 5/145; A61B 5/1468; A61B 5/150022; A61B 2017/3492; A61B 2560/0223; A61B 2560/045; A61B 2562/18; Y02A 90/26; A61M 5/14244; A61M 5/1723; A61M 2005/1585
USPC .......................................... 600/309, 345–366
See application file for complete search history.

(56) References Cited

U.S. PATENT DOCUMENTS

| | | | |
|---|---|---|---|
| 5,196,025 A | 3/1993 | Ranalletta et al. | |
| 5,314,441 A | 5/1994 | Cusack et al. | |
| 5,318,583 A | 6/1994 | Rabenau et al. | |
| 5,360,405 A | 11/1994 | Yoon | |
| 5,527,334 A | 6/1996 | Kanner et al. | |
| 5,586,553 A | 12/1996 | Halili et al. | |
| 5,807,375 A | 9/1998 | Gross et al. | |
| 5,984,940 A | 11/1999 | Davis et al. | |
| 6,102,896 A | 8/2000 | Roser | |
| 6,175,752 B1 | 1/2001 | Say et al. | |
| 6,186,982 B1 | 2/2001 | Gross et al. | |
| 6,248,067 B1* | 6/2001 | Causey, III | A61B 5/0002 128/903 |
| 6,368,141 B1 | 4/2002 | VanAntwerp et al. | |
| 6,560,471 B1 | 5/2003 | Heller et al. | |
| 6,607,509 B2 | 8/2003 | Bobroff et al. | |
| 6,607,543 B2 | 8/2003 | Purcell et al. | |
| 6,695,860 B1 | 2/2004 | Ward et al. | |
| 6,809,653 B1 | 10/2004 | Mann et al. | |
| 6,960,192 B1 | 11/2005 | Flaherty et al. | |
| 7,003,341 B2 | 2/2006 | Say et al. | |
| 7,097,637 B2 | 8/2006 | Triplett et al. | |
| 7,120,483 B2 | 10/2006 | Russell et al. | |
| 7,144,404 B2 | 12/2006 | Whitson et al. | |
| 7,150,755 B2 | 12/2006 | Levaughn et al. | |
| 7,207,974 B2 | 4/2007 | Safabash et al. | |
| 7,223,276 B2 | 5/2007 | List et al. | |
| 7,297,136 B2 | 11/2007 | Wyrick | |
| 7,303,549 B2 | 12/2007 | Flaherty et al. | |
| 7,407,493 B2 | 8/2008 | Cane' | |
| 7,455,663 B2 | 11/2008 | Bikovsky | |
| 7,481,819 B2 | 1/2009 | Koeppel et al. | |
| 7,530,964 B2 | 5/2009 | Lavi et al. | |
| 7,572,237 B2 | 8/2009 | Saikley et al. | |
| 7,582,059 B2 | 9/2009 | Funderburk et al. | |
| 7,682,338 B2 | 3/2010 | Griffin | |
| 7,697,967 B2 | 4/2010 | Stafford | |
| 7,699,807 B2 | 4/2010 | Faust et al. | |
| 7,731,691 B2 | 6/2010 | Cote et al. | |
| 7,736,338 B2 | 6/2010 | Kavazov et al. | |
| 7,789,857 B2 | 9/2010 | Moberg et al. | |
| 7,846,132 B2 | 12/2010 | Gravesen et al. | |
| 7,850,652 B2 | 12/2010 | Liniger et al. | |
| 7,896,844 B2 | 3/2011 | Thalmann et al. | |
| 7,955,297 B2 | 6/2011 | Radmer et al. | |
| 7,985,203 B2 | 7/2011 | Haueter et al. | |
| 8,025,658 B2 | 9/2011 | Chong et al. | |
| 8,079,961 B2 | 12/2011 | Saikley et al. | |
| 8,128,597 B2 | 3/2012 | Cross et al. | |
| 8,172,804 B2 | 5/2012 | Bikovsky | |
| 8,172,805 B2 | 5/2012 | Mogensen et al. | |
| 8,226,615 B2 | 7/2012 | Bikovsky | |
| 8,262,618 B2 | 9/2012 | Scheurer | |
| 8,298,172 B2 | 10/2012 | Nielsen et al. | |
| 8,366,682 B2 | 2/2013 | Wyrick | |
| 8,366,729 B2 | 2/2013 | Levaughn et al. | |
| 8,409,140 B2 | 4/2013 | Ejlersen et al. | |
| 8,409,145 B2 | 4/2013 | Raymond et al. | |
| 8,439,838 B2 | 5/2013 | Mogensen et al. | |
| 8,475,432 B2 | 7/2013 | Moberg et al. | |
| 8,483,792 B2 | 7/2013 | Slomski et al. | |
| 8,500,654 B2 | 8/2013 | Goldenberg | |
| 8,512,245 B2 | 8/2013 | Markle et al. | |
| 8,562,567 B2 | 10/2013 | Gundberg | |
| 8,615,281 B2 | 12/2013 | Yodfat et al. | |
| 8,672,962 B2 | 3/2014 | Brenneman | |
| 8,747,363 B2 | 6/2014 | Nielsen et al. | |
| 8,764,657 B2 | 7/2014 | Curry et al. | |
| 8,870,822 B2 | 10/2014 | Thalmann et al. | |
| 8,880,138 B2 | 11/2014 | Cho | |
| D719,267 S | 12/2014 | Vaccarella | |
| 8,932,256 B2 | 1/2015 | Chong et al. | |
| 9,060,727 B2 | 6/2015 | Saikley et al. | |
| 9,186,098 B2 | 11/2015 | Lee et al. | |
| 9,192,717 B2 | 11/2015 | Cote et al. | |
| 9,215,992 B2 | 12/2015 | Donnay et al. | |
| D746,994 S | 1/2016 | Lewis, Jr. et al. | |
| 9,265,453 B2 | 2/2016 | Curry et al. | |
| 9,295,786 B2 | 3/2016 | Gottlieb et al. | |
| 9,380,975 B2 | 7/2016 | Karbowniczek et al. | |
| 9,399,094 B2 | 7/2016 | Krag et al. | |
| 9,402,544 B2 | 8/2016 | Yee et al. | |
| 9,533,092 B2 | 1/2017 | Gyrn | |
| 9,615,779 B2 | 4/2017 | Pryor et al. | |
| 9,675,285 B2 | 6/2017 | Christian | |
| 9,687,183 B2 | 6/2017 | Donnay et al. | |
| D794,801 S | 8/2017 | Newhouse et al. | |
| 9,724,032 B2 | 8/2017 | Brenneman | |
| 9,788,771 B2 | 10/2017 | Stafford | |

(56) References Cited

U.S. PATENT DOCUMENTS

| | | |
|---|---|---|
| 9,808,574 B2 | 11/2017 | Yodfat et al. |
| D815,289 S | 4/2018 | Evers et al. |
| D816,229 S | 4/2018 | Frick et al. |
| 9,931,065 B2 | 4/2018 | Pryor et al. |
| 10,010,280 B2 | 7/2018 | Donnay et al. |
| 10,076,606 B2 | 9/2018 | Ambruzs et al. |
| D829,889 S | 10/2018 | Hwang et al. |
| D831,831 S | 10/2018 | Newhouse et al. |
| 10,194,842 B2 | 2/2019 | Peterson et al. |
| 10,194,843 B2 | 2/2019 | Peterson et al. |
| D842,996 S | 3/2019 | Frick et al. |
| 10,292,632 B2 | 5/2019 | Lee et al. |
| 10,327,679 B2 | 6/2019 | Peterson et al. |
| 10,335,066 B2 | 7/2019 | Peterson et al. |
| 10,376,187 B2 | 8/2019 | Peterson et al. |
| 10,376,637 B2 | 8/2019 | Gyrn et al. |
| 10,456,064 B2 | 10/2019 | Peterson et al. |
| D870,291 S | 12/2019 | Barry et al. |
| D904,629 S | 12/2020 | Debock et al. |
| 10,863,944 B2 * | 12/2020 | Gray .................. A61B 5/6849 |
| 10,881,340 B2 | 1/2021 | Curry et al. |
| 10,881,341 B1 | 1/2021 | Curry et al. |
| 10,905,377 B2 * | 2/2021 | Gray .................. A61B 5/14503 |
| 10,952,657 B2 | 3/2021 | Curry et al. |
| 10,959,654 B2 | 3/2021 | Curry et al. |
| 11,000,216 B2 | 5/2021 | Curry et al. |
| 11,051,725 B2 | 7/2021 | Pace et al. |
| 2002/0029058 A1 | 3/2002 | Levaughn et al. |
| 2003/0028126 A1 | 2/2003 | List |
| 2003/0187470 A1 | 10/2003 | Chelak et al. |
| 2004/0133164 A1 | 7/2004 | Funderburk et al. |
| 2004/0138588 A1 | 7/2004 | Saikley et al. |
| 2005/0049553 A1 | 3/2005 | Triplett et al. |
| 2005/0090850 A1 | 4/2005 | Thoes et al. |
| 2005/0149089 A1 | 7/2005 | Trissel et al. |
| 2005/0283114 A1 | 12/2005 | Bresina et al. |
| 2006/0007017 A1 | 1/2006 | Mann et al. |
| 2006/0229512 A1 | 10/2006 | Petisce et al. |
| 2006/0235285 A1 | 10/2006 | Brister et al. |
| 2006/0241517 A1 | 10/2006 | Fowler et al. |
| 2006/0241669 A1 | 10/2006 | Stout et al. |
| 2006/0247671 A1 | 11/2006 | LeVaughn |
| 2006/0258939 A1 | 11/2006 | Pesach et al. |
| 2006/0258990 A1 | 11/2006 | Weber |
| 2006/0287630 A1 | 12/2006 | Hommann |
| 2007/0027381 A1 | 2/2007 | Stafford |
| 2007/0060814 A1 | 3/2007 | Stafford |
| 2007/0073129 A1 | 3/2007 | Shah et al. |
| 2007/0078322 A1 | 4/2007 | Stafford |
| 2007/0156094 A1 | 7/2007 | Safabash et al. |
| 2007/0167907 A1 | 7/2007 | Deslierres et al. |
| 2007/0173706 A1 | 7/2007 | Neinast et al. |
| 2007/0191702 A1 | 8/2007 | Yodfat et al. |
| 2007/0233167 A1 | 10/2007 | Weiss et al. |
| 2007/0249922 A1 | 10/2007 | Peyser et al. |
| 2007/0255302 A1 | 11/2007 | Koeppel et al. |
| 2007/0293747 A1 | 12/2007 | Douglas et al. |
| 2008/0007141 A1 | 1/2008 | Deck |
| 2008/0009805 A1 | 1/2008 | Ethelfeld |
| 2008/0027474 A1 | 1/2008 | Curry et al. |
| 2008/0031941 A1 | 2/2008 | Pettersson |
| 2008/0051714 A1 | 2/2008 | Moberg et al. |
| 2008/0051718 A1 | 2/2008 | Kavazov et al. |
| 2008/0051730 A1 | 2/2008 | Bikovsky |
| 2008/0051738 A1 | 2/2008 | Griffin |
| 2008/0097246 A1 | 4/2008 | Stafford |
| 2008/0114227 A1 | 5/2008 | Haar et al. |
| 2008/0139903 A1 | 6/2008 | Bruce et al. |
| 2008/0161656 A1 | 7/2008 | Bruce et al. |
| 2008/0167641 A1 | 7/2008 | Hansen et al. |
| 2008/0188798 A1 | 8/2008 | Weber |
| 2008/0249383 A1 | 10/2008 | Sass et al. |
| 2008/0249473 A1 | 10/2008 | Rutti et al. |
| 2008/0269683 A1 | 10/2008 | Bikovsky |
| 2008/0281270 A1 | 11/2008 | Cross et al. |
| 2009/0012472 A1 | 1/2009 | Ahm et al. |
| 2009/0054812 A1 | 2/2009 | Mace |
| 2009/0082728 A1 | 3/2009 | Bikovsky |
| 2009/0088689 A1 | 4/2009 | Carter |
| 2009/0124979 A1 | 5/2009 | Raymond et al. |
| 2009/0221893 A1 | 9/2009 | Herndon |
| 2009/0259147 A1 | 10/2009 | Saikley et al. |
| 2009/0264719 A1 | 10/2009 | Markle et al. |
| 2009/0264825 A1 | 10/2009 | Cote et al. |
| 2009/0306695 A1 | 12/2009 | Brenneman |
| 2010/0010529 A1 | 1/2010 | Shi |
| 2010/0025174 A1 | 2/2010 | Dayton |
| 2010/0145377 A1 | 6/2010 | Lai et al. |
| 2010/0185178 A1 | 7/2010 | Sharp et al. |
| 2010/0228226 A1 | 9/2010 | Nielsen |
| 2010/0317935 A1 | 12/2010 | Roe et al. |
| 2010/0324392 A1 | 12/2010 | Yee et al. |
| 2010/0331642 A1 | 12/2010 | Bruce et al. |
| 2010/0331824 A1 | 12/2010 | Moberg et al. |
| 2011/0060287 A1 | 3/2011 | Ambruzs et al. |
| 2011/0082484 A1 | 4/2011 | Saravia et al. |
| 2011/0098656 A1 | 4/2011 | Burnell et al. |
| 2011/0106126 A1 | 5/2011 | Love et al. |
| 2011/0144463 A1 | 6/2011 | Pesach et al. |
| 2011/0144683 A1 | 6/2011 | Butz |
| 2011/0178461 A1 | 7/2011 | Chong et al. |
| 2011/0230735 A1 | 9/2011 | Wolfe et al. |
| 2011/0288574 A1 | 11/2011 | Curry et al. |
| 2011/0319729 A1 | 12/2011 | Donnay et al. |
| 2012/0010642 A1 | 1/2012 | Lee et al. |
| 2012/0083679 A1 | 4/2012 | Saikley et al. |
| 2012/0150123 A1 | 6/2012 | Lawrence et al. |
| 2012/0179106 A1 | 7/2012 | Cote et al. |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0190951 A1 | 7/2012 | Curry et al. |
| 2012/0197098 A1 | 8/2012 | Donnay et al. |
| 2012/0197222 A1 | 8/2012 | Donnay et al. |
| 2012/0265042 A1 | 10/2012 | Neinast et al. |
| 2012/0303043 A1 | 11/2012 | Donnay |
| 2013/0150691 A1 | 6/2013 | Pace et al. |
| 2013/0172695 A1 | 7/2013 | Nielsen et al. |
| 2013/0267811 A1 | 10/2013 | Pryor et al. |
| 2013/0267812 A1 | 10/2013 | Pryor et al. |
| 2013/0267813 A1 | 10/2013 | Pryor et al. |
| 2014/0058223 A1 | 2/2014 | Markle et al. |
| 2014/0142604 A1 | 5/2014 | Brenneman |
| 2014/0187876 A1 | 7/2014 | Ohkoshi |
| 2014/0276586 A1 | 9/2014 | Swaney et al. |
| 2015/0025338 A1 | 1/2015 | Lee et al. |
| 2016/0058344 A1 | 3/2016 | Peterson et al. |
| 2016/0058470 A1 | 3/2016 | Peterson et al. |
| 2016/0058471 A1 | 3/2016 | Peterson et al. |
| 2016/0058472 A1 | 3/2016 | Peterson et al. |
| 2016/0058473 A1 | 3/2016 | Peterson et al. |
| 2016/0058474 A1 | 3/2016 | Peterson et al. |
| 2016/0106349 A1 | 4/2016 | Pryor et al. |
| 2016/0128615 A1 | 5/2016 | Curry et al. |
| 2016/0287150 A1 | 10/2016 | Yu |
| 2017/0042457 A1 | 2/2017 | Pace et al. |
| 2017/0055851 A1 | 3/2017 | Al-Ali |
| 2017/0112534 A1 | 4/2017 | Schoonmaker et al. |
| 2017/0127985 A1 | 5/2017 | Thompson et al. |
| 2017/0188910 A1 | 7/2017 | Halac et al. |
| 2017/0188911 A1 | 7/2017 | Halac et al. |
| 2018/0064376 A1 | 3/2018 | Stafford |
| 2018/0368771 A1 | 12/2018 | Gray et al. |
| 2018/0368772 A1 | 12/2018 | Gray et al. |
| 2018/0368773 A1 | 12/2018 | Gray et al. |
| 2018/0368774 A1 | 12/2018 | Gray et al. |
| 2019/0076073 A1 | 3/2019 | Donnay et al. |
| 2019/0120785 A1 | 4/2019 | Halac et al. |
| 2019/0336055 A1 | 11/2019 | Shah et al. |
| 2019/0357818 A1 * | 11/2019 | Pryor .................. A61B 5/0004 |
| 2020/0178899 A1 | 6/2020 | Chae et al. |
| 2020/0196919 A1 | 6/2020 | Rao et al. |
| 2020/0289748 A1 | 9/2020 | Lanigan et al. |
| 2020/0352480 A1 | 11/2020 | Lucisano et al. |

(56) References Cited

U.S. PATENT DOCUMENTS

| | | |
|---|---|---|
| 2021/0000399 A1 | 1/2021 | Curry et al. |
| 2021/0000400 A1 | 1/2021 | Curry et al. |
| 2021/0007651 A1 | 1/2021 | Donnay et al. |
| 2021/0022654 A1 | 1/2021 | Curry et al. |
| 2021/0038137 A1 | 2/2021 | Curry et al. |
| 2021/0052224 A1 | 2/2021 | Gray et al. |
| 2021/0113126 A1 | 4/2021 | Donnay et al. |

FOREIGN PATENT DOCUMENTS

| | | |
|---|---|---|
| JP | 2006-346160 A | 12/2006 |
| WO | WO 2005/046780 A1 | 5/2005 |
| WO | WO 2006/038044 A2 | 4/2006 |
| WO | WO 2006/067217 A2 | 6/2006 |
| WO | WO 2006/075016 A1 | 7/2006 |
| WO | WO 2006/077262 A1 | 7/2006 |
| WO | WO 2007/031125 A1 | 3/2007 |
| WO | WO 2008/065646 A1 | 6/2008 |
| WO | WO 2008/078319 A1 | 7/2008 |
| WO | WO 2008/083379 A1 | 7/2008 |
| WO | WO 2008/115409 A1 | 9/2008 |
| WO | WO 2008/124597 A1 | 10/2008 |
| WO | WO-2009010396 A1 | 1/2009 |
| WO | WO-2010091005 A1 | 8/2010 |
| WO | WO-2012103429 A2 | 8/2012 |
| WO | WO-2016120920 A1 | 8/2016 |
| WO | WO-2017098277 A1 | 6/2017 |

OTHER PUBLICATIONS

Co-pending U.S. Appl. No. 29/717,217, inventors BARRY; John Charles et al., filed Dec. 16, 2019, 15 pages.

Extended European Search Report for Application No. 18825284.5 dated Feb. 15, 2021, 6 pages.

International Preliminary Report on Patentability for Application No. PCT/US2018/039122 dated Jan. 2, 2020, 99 pages.

International Search Report and Written opinion for Application No. PCT/US2018/039122 dated Dec. 7, 2018, 106 pages.

Office Action from Australian Patent Application No. 2018295116, dated Jul. 8, 2020, 5 pages.

Office Action from Canadian Patent Application No. 3,064,094, dated May 12, 2021, 4 pages.

Office Action from Australian Patent Application No. 2018295116, dated Jul. 5, 2021, 3 pages.

* cited by examiner

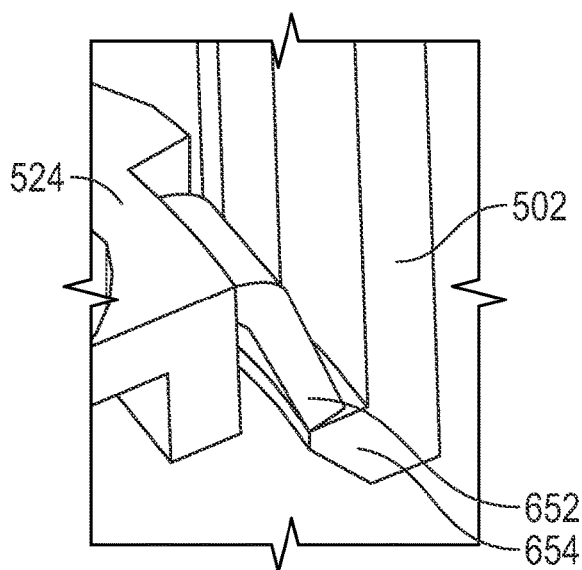
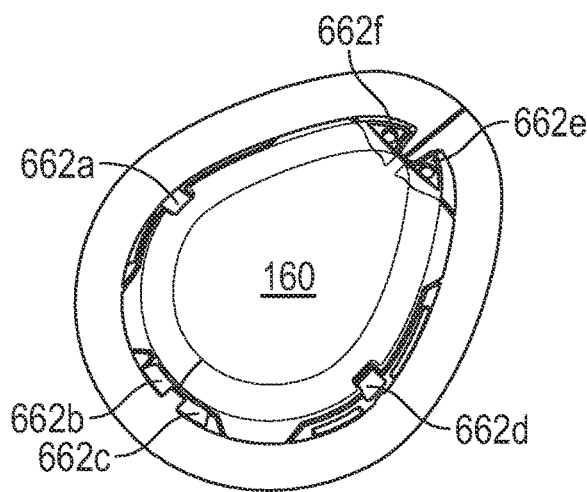
FIG. 6F          FIG. 6G
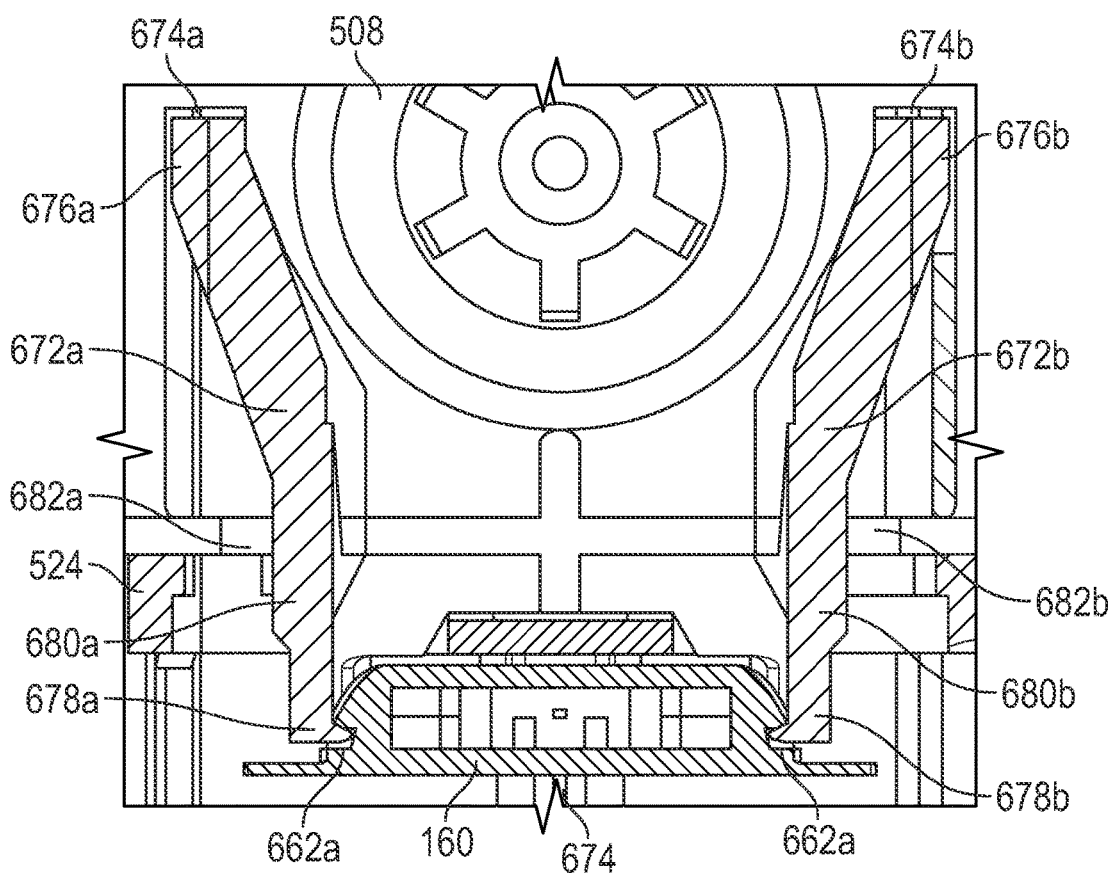
FIG. 6H

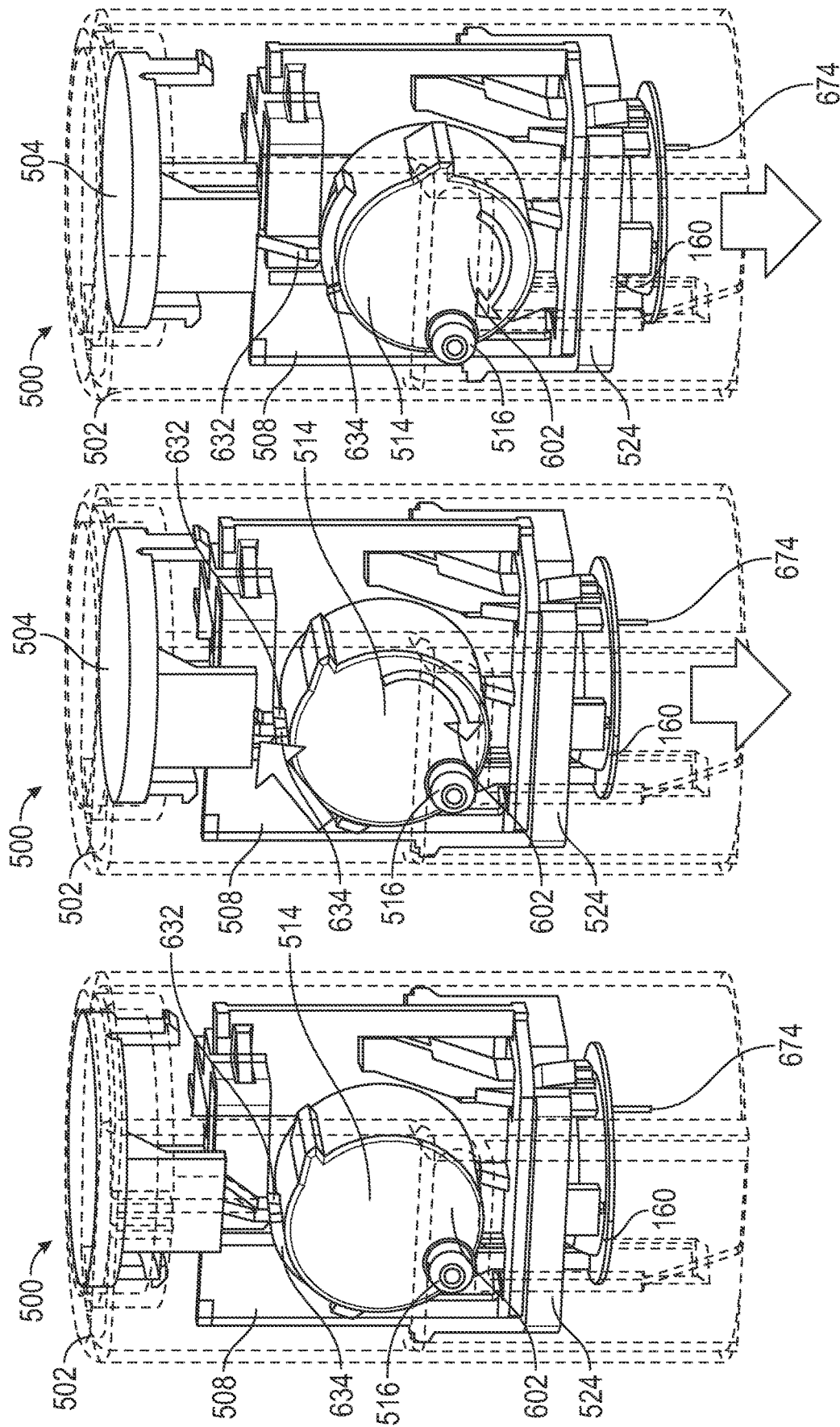

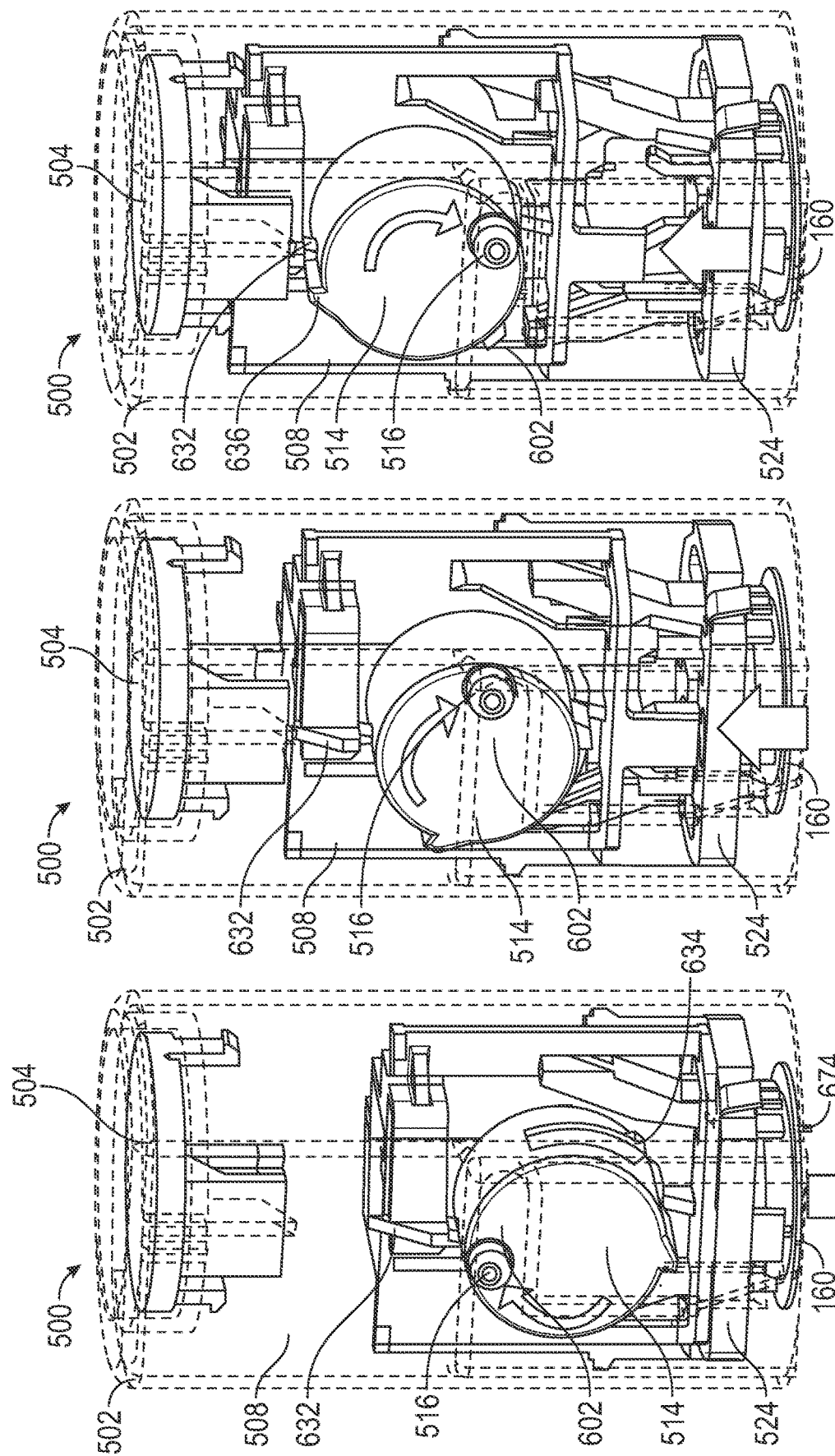

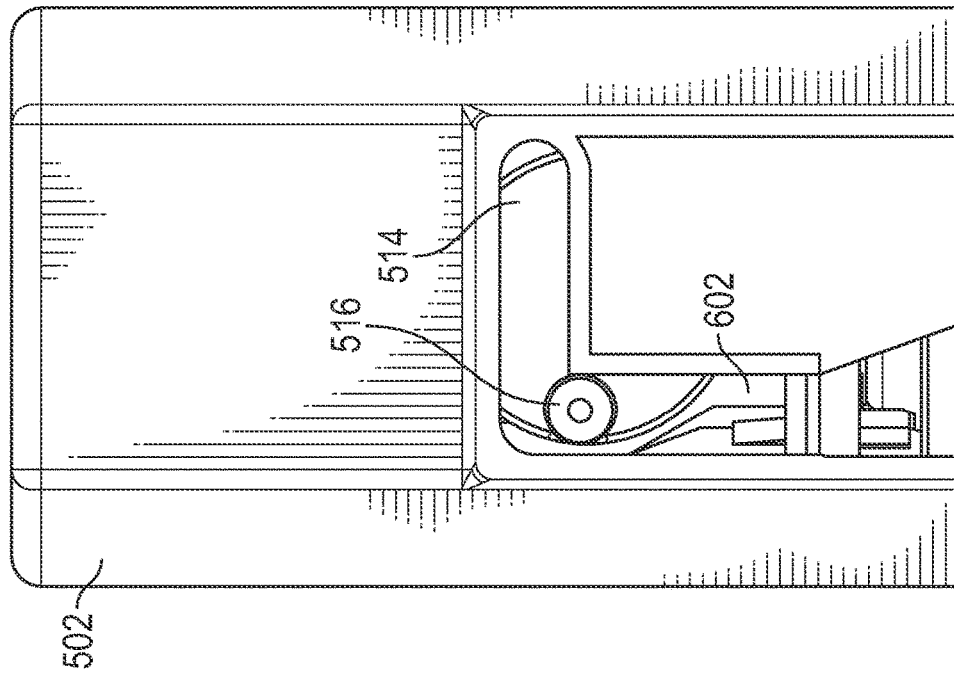
FIG. 11F
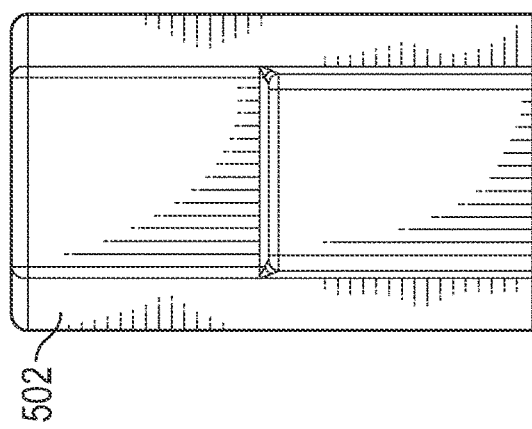
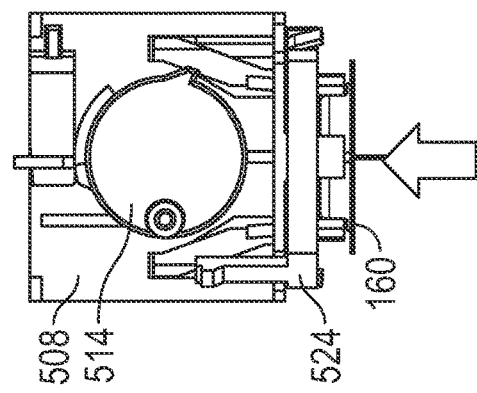
FIG. 11E

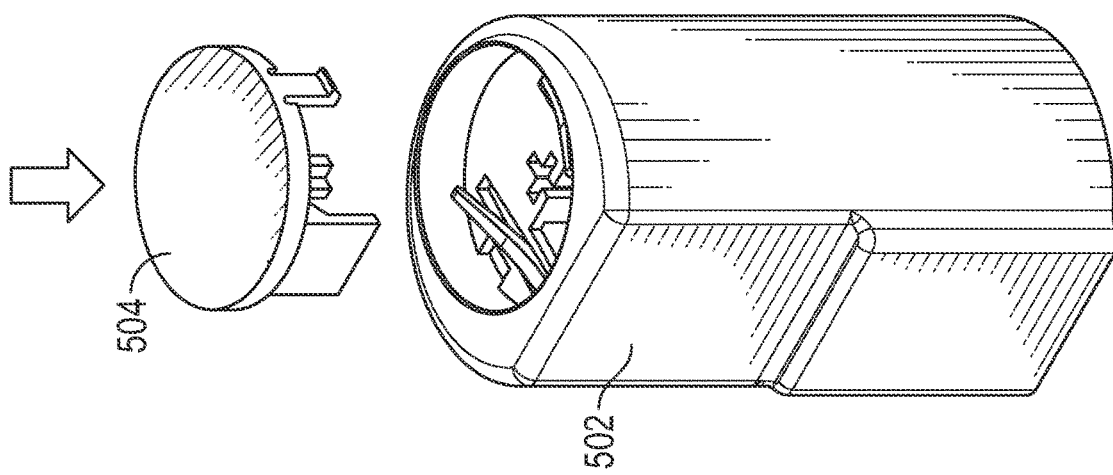
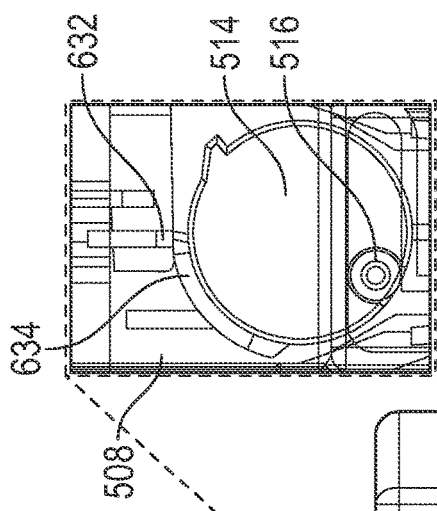
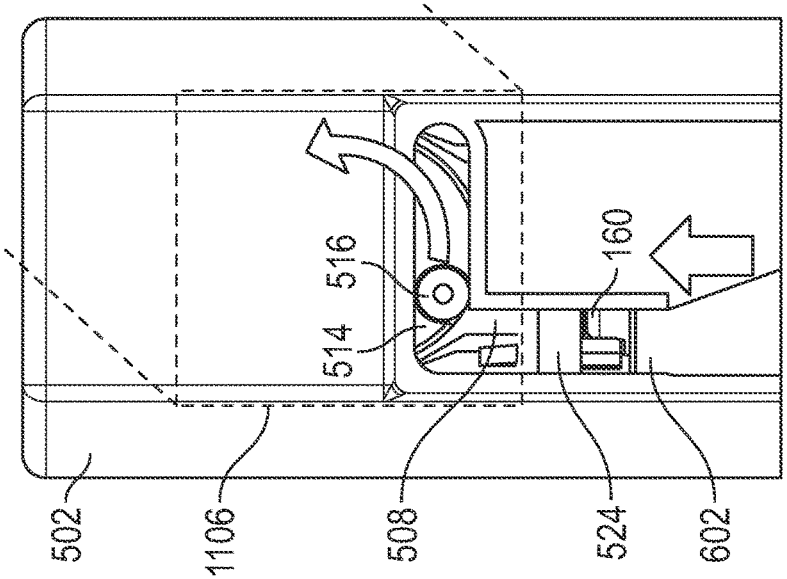
FIG. 11J
FIG. 11H
FIG. 11G

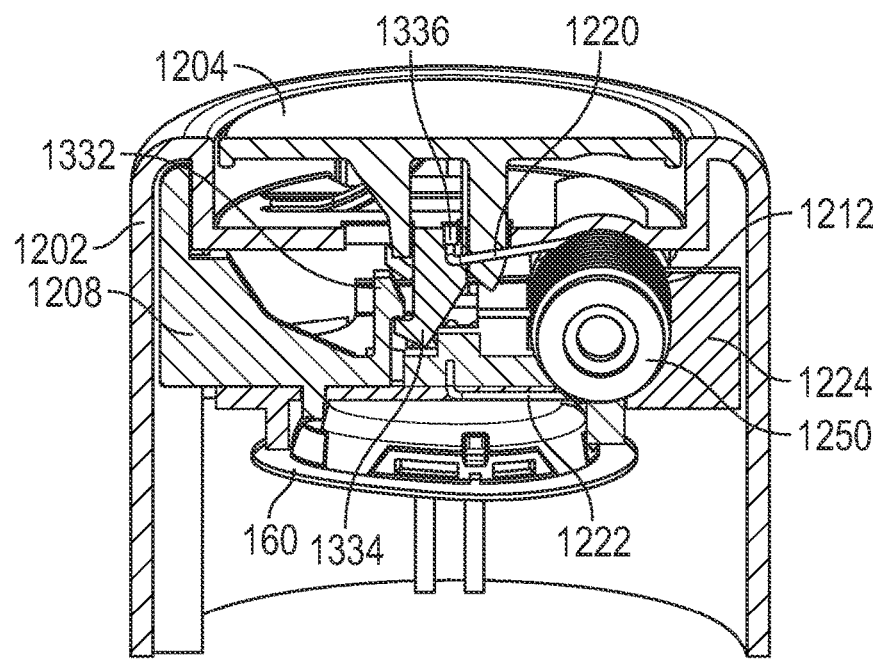
FIG. 13A
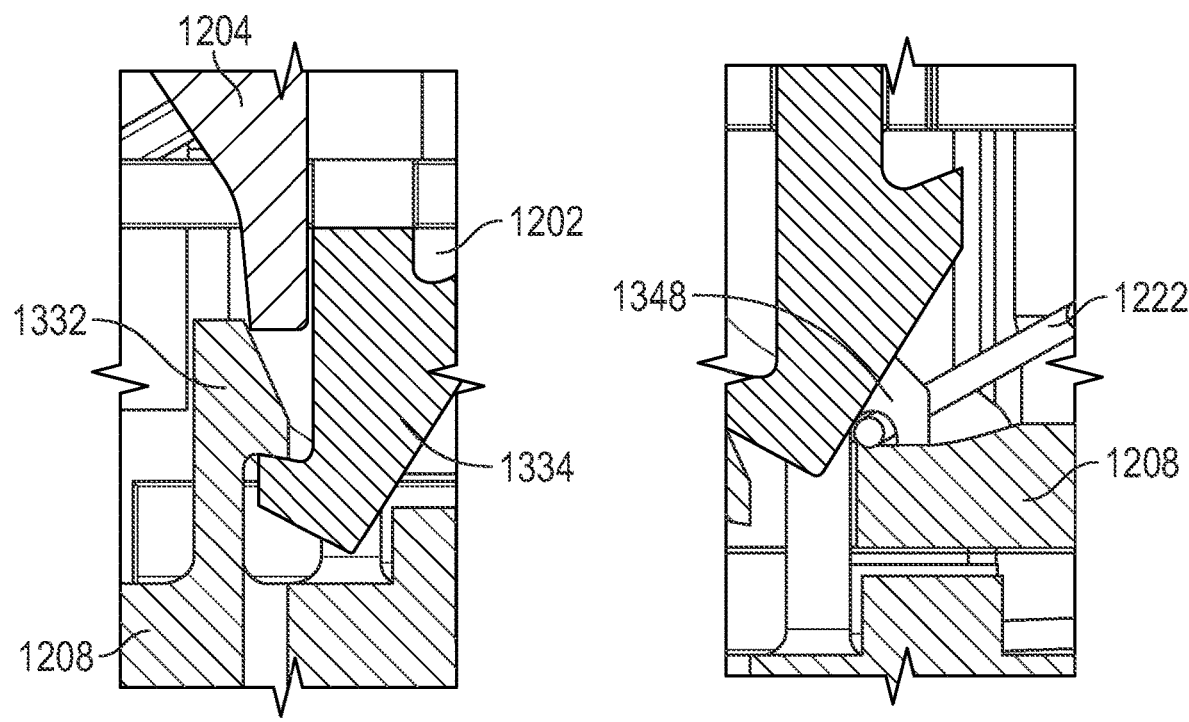
FIG. 13B
FIG. 13C

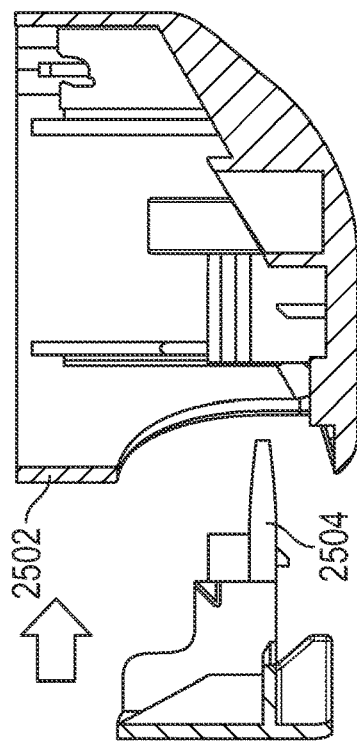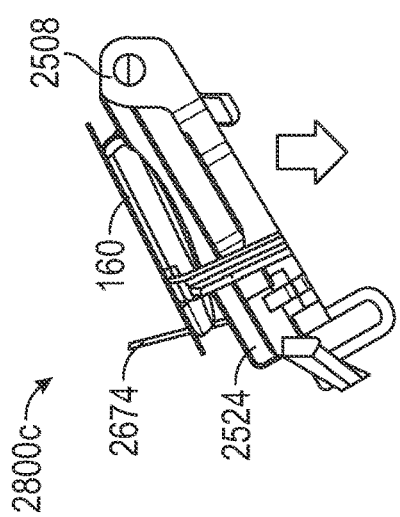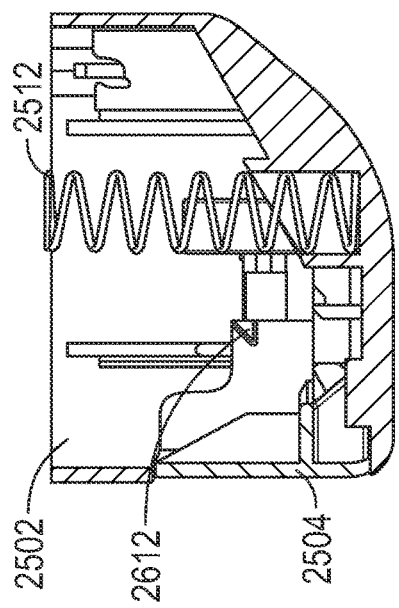
FIG. 28D
FIG. 28E
FIG. 28F

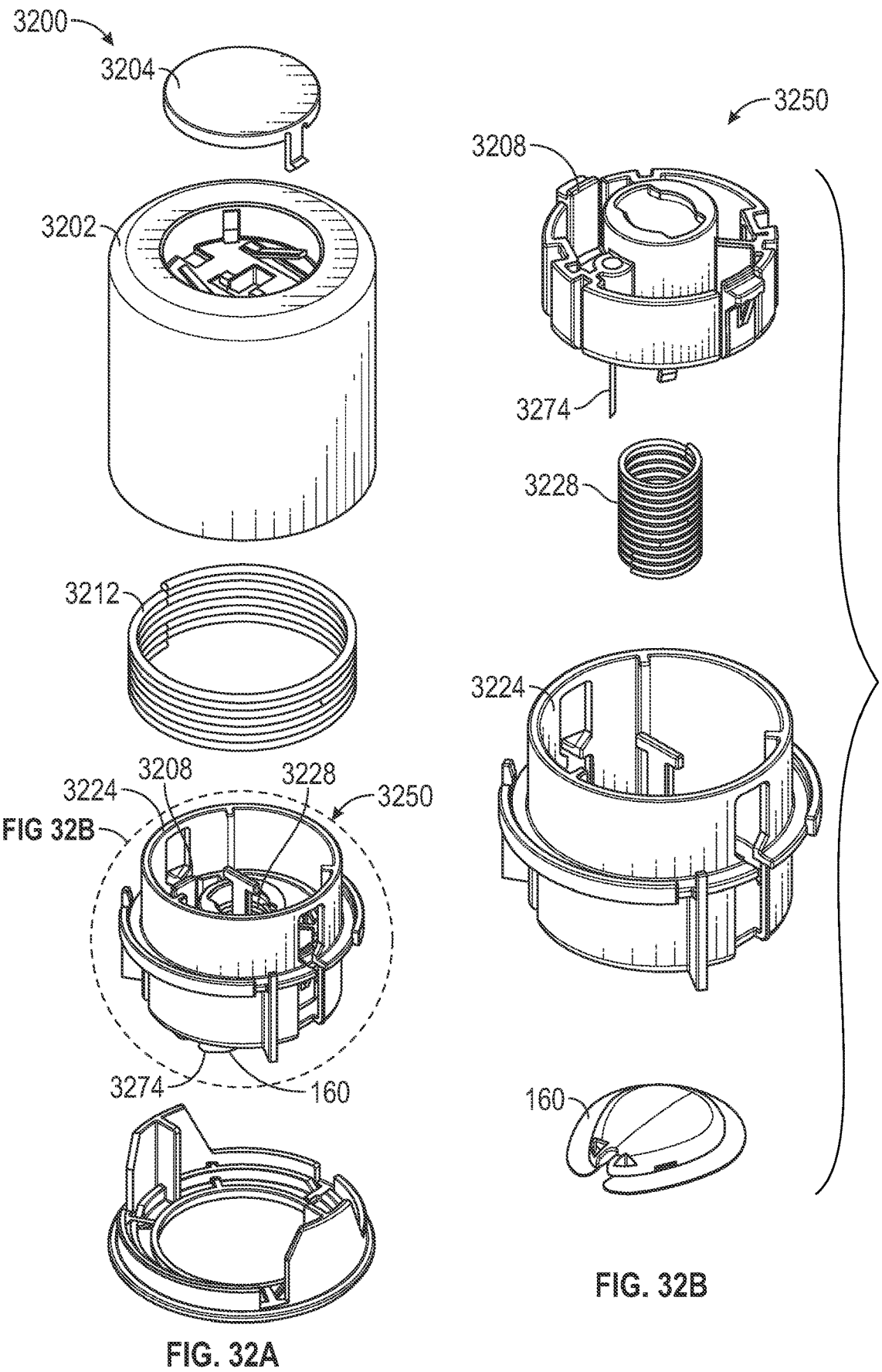

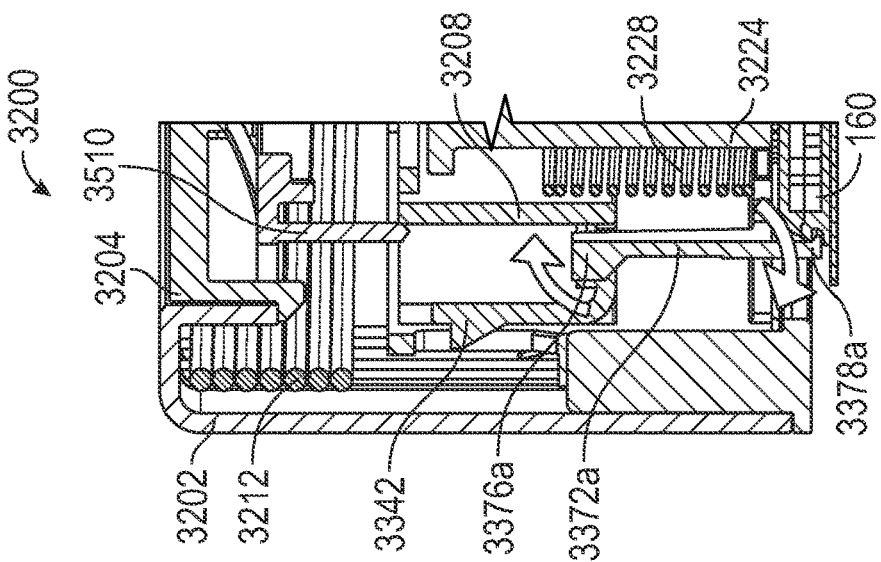
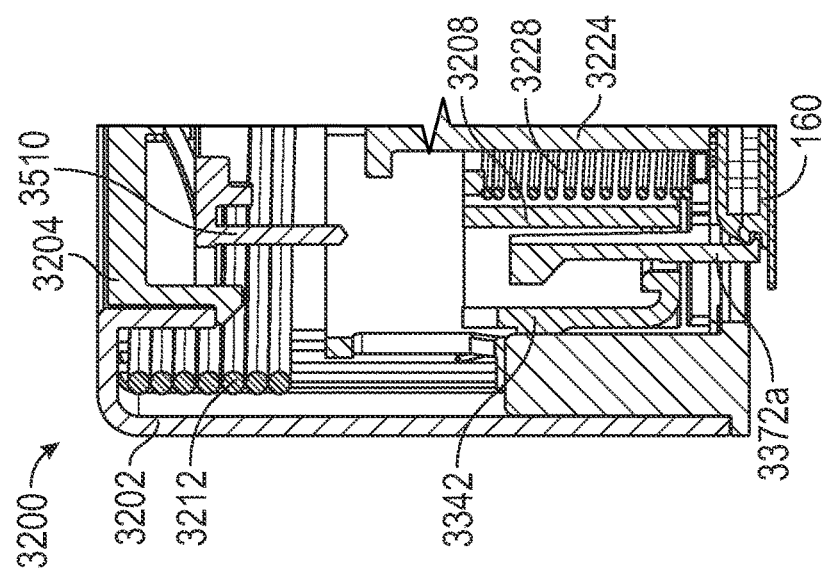
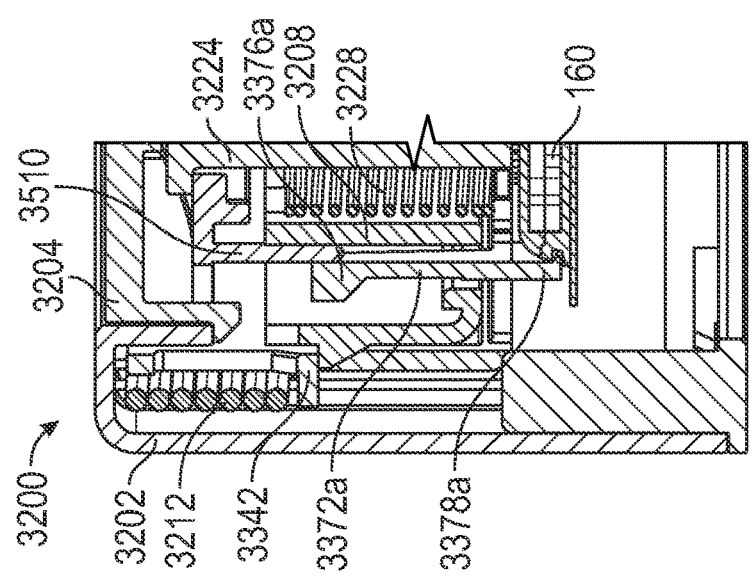

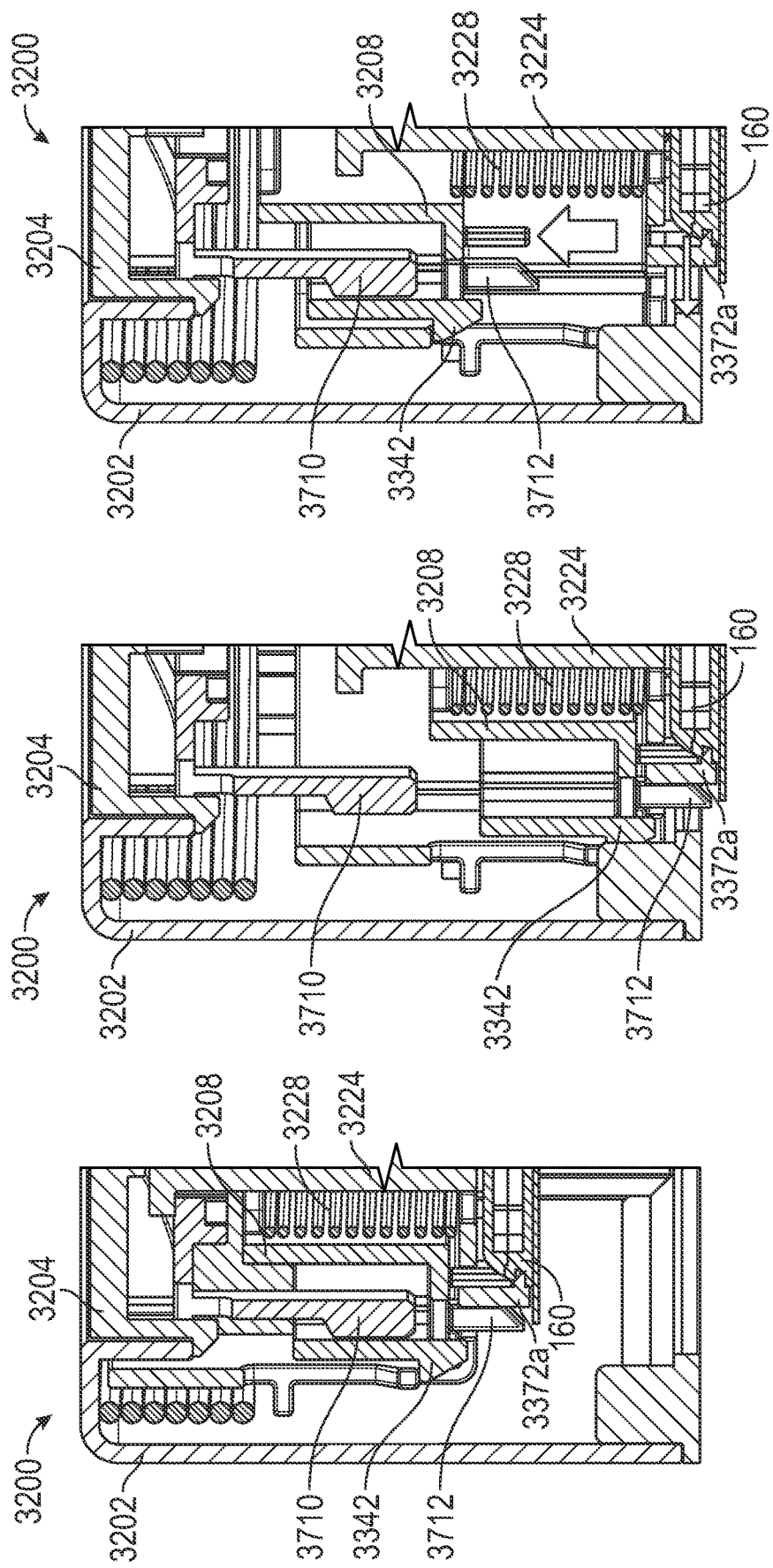

6500

6502
Provide an applicator comprising an applicator housing, a needle carrier assembly comprising an insertion element configured to insert a sensor of the on-skin assembly into the skin of the host, a holder releasably coupled to the needle carrier assembly and configured to hold the on-skin assembly while coupled to the needle carrier assembly, a drive assembly, and an activation element 6504
Activate the activation element, wherein activating the activation element causes the drive assembly to drive the insertion element in a distal direction to a distal insertion position and in a proximal direction from the distal insertion position to a proximal retraction position, thereby inserting the sensor of the on-skin sensor assembly into the skin of the host

FIG. 65

| Activation Element 6610 | | | Energy Source 6650 | | |
|---|---|---|---|---|---|
| Push or Pull | Switch or Toggle | Slide | Compression Spring | Extension Spring | Single or Double Torsion Spring |
| Deflect | Rotate | Deform/Flex | Clock Spring | Power Spring | Leaf Spring |

| Insertion Element 6620 | | | Insertion/Retraction Mechanism 6660 | | |
|---|---|---|---|---|---|
| Open-sided Needle | Deflected-tip Needle | Curved or Bent Needle | Scotch Yoke | Barrel Cam | Opposing Springs Mechanism |
| Sensor tip | Circumferential Needle | | Reverse Toggling Mechanism | Flexible Linkage | Spring Linkage |

| On-Skin Sensor Assembly Retention 6630 | | | Sensor Retention 6670 | | |
|---|---|---|---|---|---|
| Undercut/Snap Feature | Press Fit | Deformable / Elastomeric Element | User Removable | Mechanism-Removable | Ex-Vivo Support Feature |
| Frangible Element | Adhesive | | | In-Vivo Support Feature | |

| Energy Storage 6640 | |
|---|---|
| Pre-Loaded | Mechanism Loaded | User Loaded |

FIG. 66

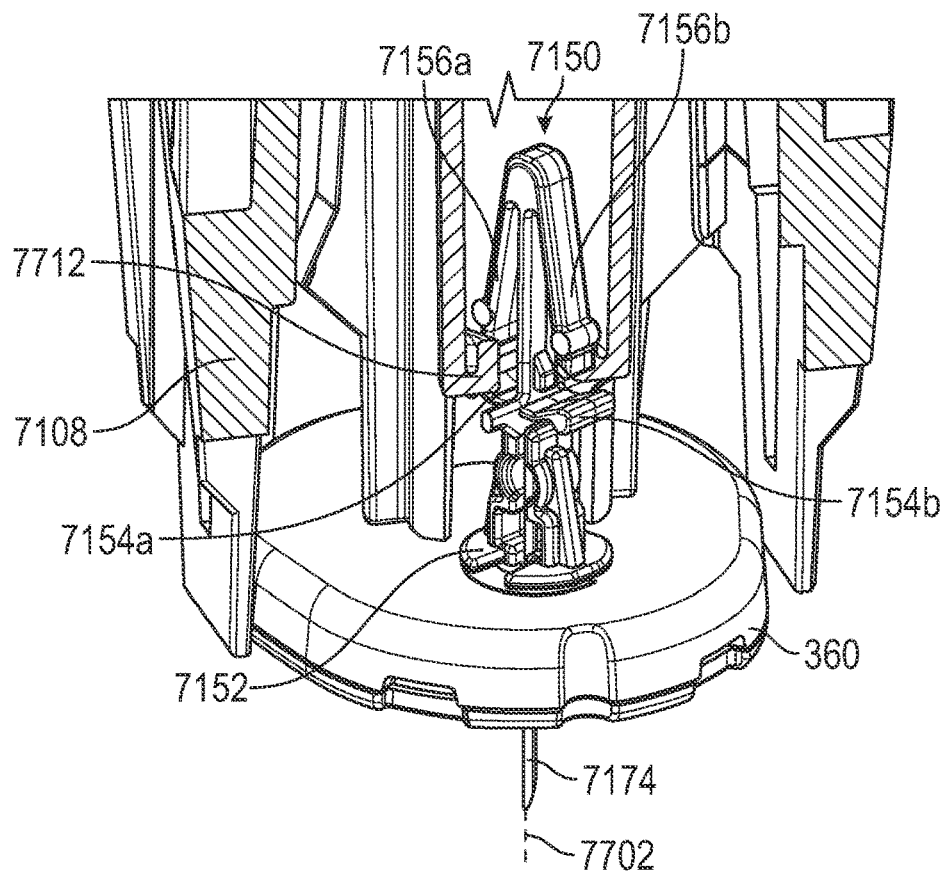
FIG. 77
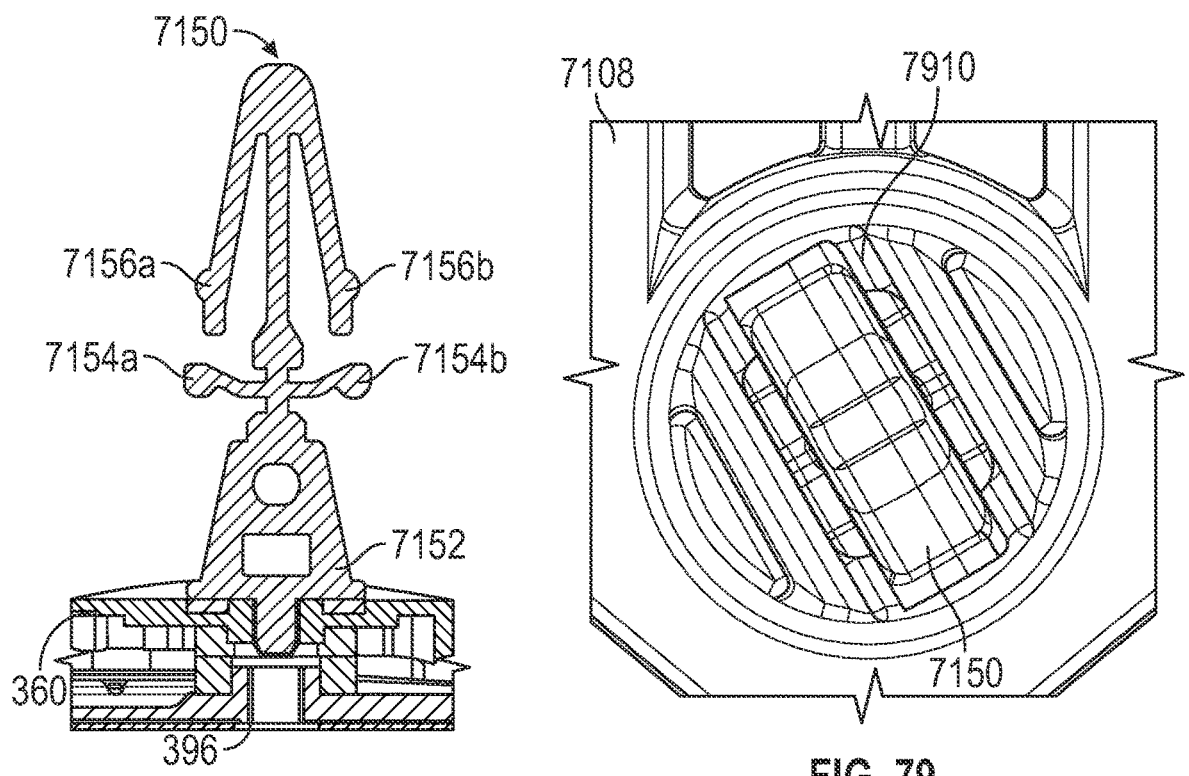
FIG. 78
FIG. 79

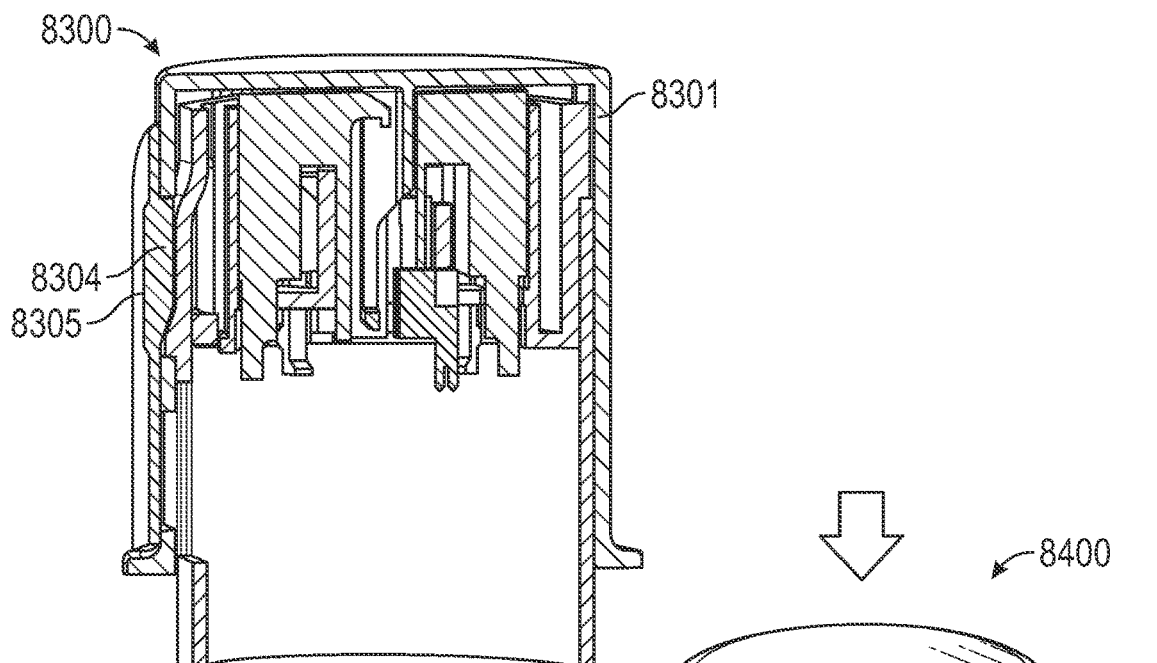
FIG. 83
FIG. 84
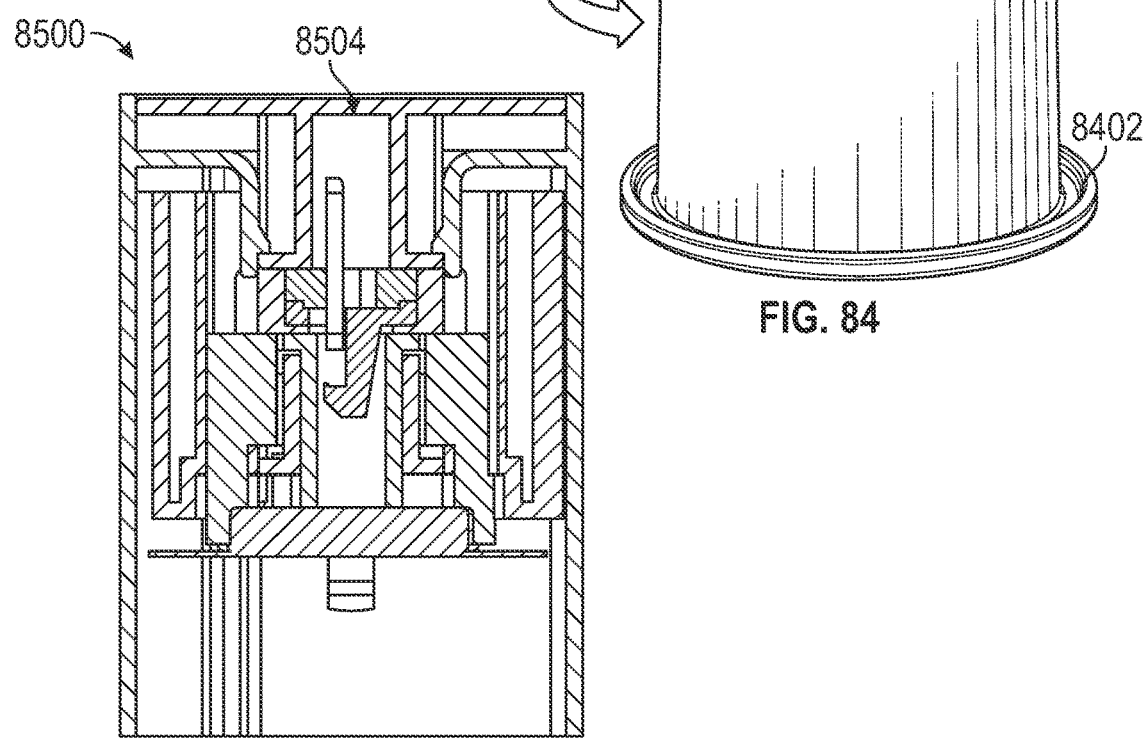
FIG. 85

8900

8902
Provide an applicator comprising a housing having an activation element, an insertion assembly, and a retraction assembly 8904
Activate the activation element, wherein activating the activation element causes the insertion assembly to translate a needle carrier assembly and the on-skin sensor assembly in a distal direction from a proximal position to a distal insertion position, thereby inserting a sensor of the on-skin sensor assembly at least partially into the skin of the host, and the retraction assembly to translate the needle carrier assembly in a proximal direction from the distal insertion position to a proximal retracted position, the retraction assembly configured to activate in response to on-skin sensor assembly contacting the skin of the host

FIG. 89

TRANSCUTANEOUS ANALYTE SENSORS, APPLICATORS THEREFOR, AND ASSOCIATED METHODS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/016,493, filed Jun. 22, 2018, which is a continuation of U.S. application Ser. No. 16/016,354, filed Jun. 22, 2018, which claims the benefit of U.S. Provisional Application No. 62/524,247, filed Jun. 23, 2017 and U.S. Provisional Application No. 62/658,486, filed Apr. 16, 2018. Each of the aforementioned applications is incorporated by reference herein in its entirety, and each is hereby expressly made a part of this specification.

FIELD

Systems and methods for measuring an analyte in a host are provided. More particularly, systems and methods are provided for applying a transcutaneous analyte measurement system to a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

The process of applying the sensor to the person is important for such a system to be effective and user friendly. The application process should result in the sensor assembly being attached to the person in a state where it is capable of sensing glucose level information, communicating the sensed data to the transmitter, and transmitting the glucose level information to the receiver.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The present systems and methods relate to systems and methods for measuring an analyte in a host, and for applying a transcutaneous analyte measurement system to a host. The various embodiments of the present systems and methods for applying the analyte measurement system have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

An applicator for applying an on-skin sensor assembly to a skin of a host is provided. The applicator includes an applicator housing, a needle carrier assembly, which includes an insertion element configured to insert a sensor of the on-skin sensor assembly into the skin of the host, a holder releasably coupled to the needle carrier assembly and configured to guide the on-skin sensor assembly while coupled to the needle carrier assembly, and a drive assembly configured to drive the insertion element from a proximal starting position to a distal insertion position, and from the distal insertion position to a proximal retraction position.

In some embodiments, the on-skin sensor assembly includes an electronics unit. In some embodiments, the sensor is connected to the electronics unit in the applicator housing. In some embodiments, the holder is configured to release the on-skin sensor assembly after the sensor is inserted at least partially into the skin of the host. In some embodiments, the applicator further includes an activation element configured to activate the drive assembly. In some embodiments, the activation element includes a deflectable feature. In some embodiments, the deflectable feature is configured to provide resistance to activation. In some embodiments, the deflectable feature is configured to return the activation element to a starting position. In some embodiments, the activation element includes one of a button, a switch, a toggle, a slide, a trigger, and a knob. In some embodiments, the applicator further includes a safety element configured to prevent operation of the activation element. In some embodiments, the safety element includes a tab coupled to the activation element by at least one frangible member. In some embodiments, the distal direction and the proximal direction extend along an insertion axis of the insertion element. In some embodiments, the holder includes an elastomer.

In a first aspect, the applicator housing includes a guide. The drive assembly includes a rotating drive element coupled to the needle carrier assembly and includes a pin configured to travel in the guide during rotation of the rotating drive element, and a spring configured to, upon activation of the drive assembly, rotate the rotating drive element in a single rotational direction thereby driving the insertion element from the proximal starting position to the distal insertion position, and from the distal insertion position to the proximal retraction position. In some embodiments, the rotating drive element is configured to convert rotational motion into linear motion. In some embodiments, the rotating drive element includes a wheel cam. In some embodiments, the pin is radially offset from an axis of rotation of the rotating drive element. In some embodiments, the pin is positioned approximately 30 degrees from a bottom center orientation relative to the axis of rotation of the rotating drive element when the insertion element is in the proximal starting position. In some embodiments, the pin is positioned approximately 180 degrees from a bottom center orientation relative to the axis of rotation of the rotating drive element when the insertion element is in the distal insertion position. In some embodiments, the pin is positioned approximately 330 degrees from a bottom center orientation relative to the axis of rotation of the rotating drive element when the needle carrier assembly is in the proximal retracted position. In some embodiments, the pin travels in the guide in a direction perpendicular to a direction of extension of the insertion element. In some embodiments, the guide includes a slot. In some embodiments, the slot is stationary during sensor insertion. In some embodiments, the slot includes a horizontal slot. In some embodiments, the slot includes a vertical slot configured to receive at least the pin of the rotating drive element when loaded through a bottom of the applicator housing. In some embodiments, the applicator housing is stationary. In some embodiments, the rotating drive element further includes a protrusion in contact with a retention element configured to prevent the rotating drive element from rotating. In some embodiments, the applicator further includes an activation element configured to deflect the retention element, thereby allowing the rotating drive element to rotate. In some embodiments, the rotating drive element further includes a protrusion configured to decouple the on-skin sensor assembly from the needle carrier assembly. In some embodiments, the protrusion is configured to apply a force to the on-skin sensor assembly during rotation of the rotating drive element. In some embodiments, the protrusion of the rotating drive element is configured to pass through a slot in the needle carrier assembly as the rotating drive element rotates.

In a second aspect, the drive assembly includes a torsion spring. The torsion spring includes a first end coupled to the applicator housing, and a second end coupled to the needle carrier assembly. Upon activation of the drive assembly, the first end and the second end unwind in opposite directions, thereby driving the insertion element from the proximal starting position to the distal insertion position, and from the distal insertion position to the proximal retraction position. In some embodiments, the first end and the second end unwinding in opposite directions drives the torsion spring in an arc. In some embodiments, the arc extends in a direction perpendicular to the distal direction and the proximal direction. In some embodiments, a spool coupled to the torsion spring. In some embodiments, the torsion spring is wrapped around the spool. In some embodiments, the second end of the torsion spring is configured to drive the insertion element. In some embodiments, the torsion spring is a double torsion spring. In some embodiments, the first end of the torsion spring is coupled to a protrusion of the applicator housing. In some embodiments, the second end of the torsion spring is coupled to a protrusion of the needle carrier assembly.

In a third aspect, the drive assembly further includes a linkage element, which includes a first end coupled to the first end of the torsion spring, a second end coupled to the second end of the torsion spring, and a hinge substantially aligned with a winding axis of the torsion spring. In some embodiments, the linkage element includes a flexible linkage.

In a fourth aspect, the drive assembly includes a linkage element, which includes a first end coupled to the applicator housing, a second end coupled to the needle carrier assembly, and a hinge disposed between the first end and the second end. The drive assembly further includes a torsion spring, which includes a first end coupled to the needle carrier assembly, and a second end coupled to the linkage element between the second end and the hinge. Upon activation of the drive assembly, the second end is configured to drive the linkage element such that the insertion element is driven from the proximal starting position to the distal insertion position, and from the distal insertion position to the proximal retracted position.

In a fifth aspect, the drive assembly includes a linkage element, which includes a first end coupled to the applicator housing, a second end coupled to the needle carrier assembly, and a hinge disposed between the first end and the second end. The drive assembly further includes a torsion spring, which includes a first end coupled to the applicator housing, and a second end coupled to the linkage element between the first end and the hinge. Upon activation of the drive assembly, the second end is configured to drive the linkage element such that the insertion element is driven the proximal starting position to the distal insertion position, and from the distal insertion position to the proximal retracted position.

In a sixth aspect, the drive assembly includes a linkage element, which includes a first end coupled to the applicator housing, a second end coupled to the needle carrier assembly, and a hinge disposed between the first end and the second end. The drive assembly further includes an extension spring coupled to the linkage element. Upon activation of the drive assembly, the extension spring is configured to drive the linkage element such that the insertion element is driven in the distal direction to the distal insertion position and in the proximal direction from the distal insertion position.

In a seventh aspect, the drive assembly includes a leaf spring, which includes a first end coupled to the applicator housing, and a second end coupled to the needle carrier assembly. Upon activation of the drive assembly, the leaf spring is configured to decompress, thereby driving the insertion element at least in the distal direction to the distal insertion position.

In an eighth aspect, the drive assembly includes a linkage element, which includes a first end coupled to the applicator housing, a second end coupled to the needle carrier assembly, and a hinge disposed between the first end and the second end. The drive assembly further includes a leaf spring, which includes a first end coupled to the needle carrier assembly, and a second end coupled to the linkage element between the second end and the hinge. Upon activation of the drive assembly, the leaf spring is configured to decompress, thereby driving the insertion element in the distal direction to the distal insertion position and in the proximal direction from the distal insertion position.

In a ninth aspect, the drive assembly includes a leaf spring, which includes a first end coupled to the applicator housing, and a second end coupled to the needle carrier assembly. Upon activation of the drive assembly, the leaf spring is configured to decompress, thereby driving the insertion element at least in the distal direction to the distal insertion position.

In a tenth aspect, the drive assembly includes a linkage element, which includes a first end coupled to the applicator housing, a second end coupled to the needle carrier assembly; and a hinge disposed between the first end and the second end. The drive assembly further includes a leaf spring, which includes a first end coupled to the needle carrier assembly, and a second end coupled to the linkage element between the second end and the hinge. Upon activation of the drive assembly, the leaf spring is configured to decompress, thereby driving the insertion element in the distal direction to the distal insertion position and in the proximal direction from the distal insertion position.

In an eleventh aspect, the drive assembly includes an insertion spring configured to, upon activation of the drive assembly, drive the insertion element in the distal direction to the distal insertion position, and a retraction spring in contact with the needle carrier assembly and configured to drive the insertion element from the distal insertion position to the proximal retracted position. In some embodiments, the insertion spring includes a compression spring. In some embodiments, the retraction spring includes a leaf spring. In some embodiments, the retraction spring is configured retract the insertion element from the skin of the host. In some embodiments, upon activation of the drive assembly, a portion of energy stored in the insertion spring is transferred to the retraction spring as the insertion spring drives the insertion element in the distal direction. In some embodiments, the insertion spring includes a first end coupled to the applicator housing and a second end coupled to the holder, and the holder is coupled to the needle carrier assembly while the insertion spring drives the insertion element in the distal direction to the distal insertion position and decoupled from the needle carrier assembly when the retraction spring drives the insertion element in the proximal direction from the distal insertion position. In some embodiments, the insertion element is configured to travel in an arc when driven in the distal direction and in the proximal direction.

In a twelfth aspect, the drive assembly includes a rotating drive element, which includes a ridge configured to slide along a channel in the needle carrier assembly, the ridge defining a variable cam path around at least a portion of a circumference of the rotating drive element, and a torsion spring configured to, upon activation of the drive assembly, rotate the rotating drive element thereby driving the insertion element in a distal direction to a distal insertion position and in a proximal direction from the distal insertion position based on the variable cam path. In some embodiments, the torsion spring is configured to, upon activation of the drive assembly, rotate the rotating drive element in a single direction through an angle of greater than zero degrees and less than 360 degrees. In some embodiments, the rotating drive element includes a barrel cam. In some embodiments, the rotating drive element is configured to rotate in a plane substantially perpendicular to the proximal direction and the distal direction.

In a thirteenth aspect, the drive assembly includes a guide member coupled to the applicator housing, a hub configured to slide along the guide member, the hub in contact with a reverse toggling element through a first portion of travel along the guide member and in contact with the needle carrier assembly through a second portion of travel along the guide member. The reverse toggling element includes a fulcrum, a first end in contact with the hub through the first portion of travel along the guide member, and a second end coupled with the needle carrier assembly. The drive assembly further includes a spring configured to, upon activation of the drive assembly drive the hub in a proximal direction through the first portion of travel along the guide member, thereby driving the insertion element in the distal direction to the distal insertion position, and drive the hub in the proximal direction through the second portion of travel along the guide member, thereby driving the insertion element in the proximal direction from the distal insertion position.

In a fourteenth aspect, the drive assembly includes a first spring configured to, upon activation of the drive assembly, drive the needle carrier assembly in the distal direction to a distal insertion position, and a second spring configured to drive the needle carrier assembly in the proximal direction from the distal insertion position. In some embodiments, the first spring and the second spring are precompressed before activation of the drive assembly. In some embodiments, at least a portion of energy stored in the first spring is transferred to the second spring as the needle carrier assembly is driven in the distal direction to the distal insertion position.

In some embodiments, the holder includes at least one retention element configured to immobilize the holder to the applicator housing upon the needle carrier assembly reaching the distal insertion position. In some embodiments, the holder further includes a retention element configured to releasably couple the on-skin sensor assembly to the holder as the needle carrier assembly travels in the distal direction to the distal insertion position, and decouple the on-skin sensor assembly from the holder as the needle carrier assembly travels in the proximal direction from the distal insertion position.

In some embodiments, the holder includes a retention element, which includes a first end and a second end. The first end is immobilized in a guide of the needle carrier assembly thereby releasably coupling the second end to the on-skin sensor assembly as the needle carrier assembly travels in the distal direction to the distal insertion position, and the first end is unseated from the guide of the needle carrier assembly thereby decoupling the second end from the on-skin sensor assembly as the needle carrier assembly travels in the proximal direction from the distal insertion position and separates from the holder.

In some embodiments, the needle carrier assembly includes a retention element releasably coupling the on-skin sensor assembly to the holder as the needle carrier assembly travels in the distal direction to the distal insertion position, and the retention element is configured to deform sufficiently to decouple from the on-skin sensor assembly as the needle carrier assembly travels in the proximal direction from the distal insertion position and separates from the holder.

In some embodiments, the holder includes a deformable retention element releasably coupling the on-skin sensor assembly to the holder, the needle carrier assembly in contact with the deformable retention element thereby preventing the deformable retention element from deforming as the needle carrier assembly travels in the distal direction to the distal insertion position. The needle carrier assembly separates from the holder as the needle carrier assembly travels in the proximal direction from the distal insertion position thereby allowing the retention element to deform sufficiently to decouple from the on-skin sensor assembly.

In some embodiments, the needle carrier assembly includes a first retention element configured to releasably couple the holder to the needle carrier assembly, and a second retention element configured to releasably couple the on-skin sensor assembly to one of the holder and the needle carrier assembly.

In some embodiments, the insertion element includes a C-needle having flared edges. In some embodiments, the insertion element includes a deflected-tip needle. In some embodiments, the insertion element includes a needle having a curvilinear profile configured to substantially track a path of insertion of the needle. In some embodiments, the insertion element includes a needle and the needle carrier assembly further includes a needle hub configured as a pass through for the needle during insertion of the sensor and is further configured to enclose a tip of the needle after insertion of the sensor. The insertion element further includes a needle spring configured to drive the needle hub to the tip of the needle after insertion of the sensor.

In some embodiments, the on-skin sensor assembly includes a fill port configured to receive a fluid or gel and a cannula configured to deliver the fluid or gel through the skin of the host.

In some embodiments, the applicator further includes an elastomeric sensor retention element coupled to the applicator housing at a first end and coupled to at least one of the insertion element and the sensor. The elastomeric sensor retention element is configured to retain the sensor within the insertion element prior to activation of the drive assembly. In some embodiments upon activation, the insertion element is configured to progress in the proximal direction such that the elastomeric sensor retention element decouples from the at least one of the insertion element and the sensor.

In some embodiments, the applicator further includes a sensor retention element, which includes a tab configured to retain the sensor within the insertion element prior to activation of the drive assembly.

In some embodiments, the applicator further includes a sensor retention element disposed against at least one of the insertion element and the sensor in a first position and configured to rotate away from the insertion element and the sensor in a second position.

In some embodiments, the applicator further includes a sensor retention sleeve disposed around at least a portion of the insertion element and the sensor. The needle carrier assembly includes a tapered needle hub configured to split the sensor retention sleeve during insertion of the sensor.

In some embodiments, the sensor includes a strain relief feature configured to limit the sensor from bending at a bend radius smaller than a predetermined bend radius. In some embodiments, the strain relief feature includes an elastomeric material.

In some embodiments, the on-skin sensor assembly includes an open cavity configured to receive the sensor and provide an area for the sensor to bend from extending in a substantially horizontal direction to extending in a substantially vertical direction. In some embodiments, the open cavity is configured to guide bodily fluid released from the host as a result of insertion of the sensor at least partially into the skin of the host. In some embodiments, the on-skin sensor assembly includes a wicking material configured to absorb a bodily fluid released from the host as a result of insertion of the sensor at least partially into the skin of the host.

In a fifteenth aspect, a method for applying an on-skin sensor assembly to skin of a host is provided. The method includes providing an applicator, which includes an applicator housing, a needle carrier assembly includes an insertion element configured to insert a sensor of the on-skin sensor assembly into the skin of the host, a holder releasably coupled to the needle carrier assembly and configured to guide the on-skin sensor assembly while coupled to the needle carrier assembly and a drive assembly and an activation element. The method includes activating the activation element, wherein activating the activation element causes the drive assembly to drive the insertion element in a distal direction to a distal insertion position and in a proximal direction from the distal insertion position to a proximal retraction position, thereby inserting the sensor of the on-skin sensor assembly at least partially into the skin of the host. In some embodiments, the distal direction and the proximal direction extend along an insertion axis of the insertion element.

In some embodiments, the applicator housing includes a guide. The drive assembly includes a rotating drive element coupled to the needle carrier assembly and includes a pin configured to travel in the guide during rotation of the rotating drive element, and a spring configured to, upon activation of the drive assembly, rotate the rotating drive element in a single rotational direction thereby driving the insertion element from the proximal starting position to the distal insertion position, and from the distal insertion position to the proximal retraction position. In some embodiments, the rotating drive element is configured to convert rotational motion into linear motion. In some embodiments, the rotating drive element includes a wheel cam. In some embodiments, the pin is radially offset from an axis of rotation of the rotating drive element. In some embodiments, the pin is positioned approximately 30 degrees from a bottom center orientation relative to the axis of rotation of the rotating drive element when the insertion element is in the proximal starting position. In some embodiments, the pin is positioned approximately 180 degrees from a bottom center orientation relative to the axis of rotation of the rotating drive element when the insertion element is in the distal insertion position. In some embodiments, the pin is positioned approximately 330 degrees from a bottom center orientation relative to the axis of rotation of the rotating drive element when the needle carrier assembly is in the proximal retracted position. In some embodiments, the guide includes a slot.

In some embodiments, the drive assembly includes a torsion spring, the torsion spring includes a first end coupled to the applicator housing, and a second end coupled to the needle carrier assembly. Upon activation of the drive assembly, the first end and the second end unwind in opposite directions, thereby driving the insertion element from the proximal starting position to the distal insertion position, and from the distal insertion position to the proximal retraction position. In some embodiments, the first end and the second end unwinding in opposite directions drives the torsion spring in an arc. In some embodiments, the arc extends in a direction perpendicular to the distal direction and the proximal direction.

In some embodiments, the drive assembly includes an insertion spring configured to, upon activation of the drive assembly, drive the insertion element in the distal direction to the distal insertion position, and a retraction spring in contact with the needle carrier assembly and configured to drive the insertion element from the distal insertion position to the proximal retracted position. In some embodiments, the insertion spring includes a compression spring. In some embodiments, the retraction spring includes a leaf spring. In some embodiments, upon activation of the drive assembly, a portion of energy stored in the insertion spring is transferred to the retraction spring as the insertion spring drives the insertion element in the distal direction. In some embodiments, the insertion spring includes a first end coupled to the applicator housing and a second end coupled to the holder. The holder is coupled to the needle carrier assembly while the insertion spring drives the insertion element in the distal direction to the distal insertion position and decoupled from the needle carrier assembly when the retraction spring drives the insertion element in the proximal direction from the distal insertion position. In some embodiments, the insertion element is configured to travel in an arc when driven in the distal direction and in the proximal direction.

In some embodiments, the drive assembly includes a rotating drive element, which includes a ridge configured to slide along a channel in the needle carrier assembly, the ridge defining a variable cam path around at least a portion of a circumference of the rotating drive element, and a torsion spring configured to, upon activation of the drive assembly, rotate the rotating drive element thereby driving the insertion element in a distal direction to a distal insertion position and in a proximal direction from the distal insertion position based on the variable cam path. In some embodiments, the torsion spring is configured to, upon activation of the drive assembly, rotate the rotating drive element in a single direction through an angle of greater than zero degrees and less than 360 degrees. In some embodiments, the rotating drive element includes a barrel cam. In some embodiments, the rotating drive element is configured to rotate in a plane substantially perpendicular to the proximal direction and the distal direction.

In some embodiments, the drive assembly includes a guide member coupled to the applicator housing, a hub configured to slide along the guide member, the hub in contact with a reverse toggling element through a first portion of travel along the guide member and in contact with the needle carrier assembly through a second portion of travel along the guide member. The reverse toggling element includes a fulcrum, a first end in contact with the hub through the first portion of travel along the guide member, and a second end coupled with the needle carrier assembly; The drive assembly further includes a spring configured to, upon activation of the drive assembly, drive the hub in a proximal direction through the first portion of travel along the guide member, thereby driving the insertion element in the distal direction to the distal insertion position, and drive the hub in the proximal direction through the second portion of travel along the guide member, thereby driving the insertion element in the proximal direction from the distal insertion position.

In some embodiments, the drive assembly includes a first spring configured to, upon activation of the drive assembly, drive the needle carrier assembly in the distal direction to a distal insertion position, and a second spring configured to drive the needle carrier assembly in the proximal direction from the distal insertion position. In some embodiments, at least a portion of energy stored in the first spring is transferred to the second spring as the needle carrier assembly is driven in the distal direction to the distal insertion position.

In a sixteenth aspect, an applicator for applying an on-skin sensor assembly to a skin of a host is provided. The applicator includes an insertion assembly configured to translate a needle carrier assembly and the on-skin sensor assembly in a distal direction from an initial proximal position to a distal insertion position. The applicator includes a retraction assembly configured to translate the needle carrier assembly in a proximal direction from the distal inserted position to a proximal retracted position. The retraction assembly is configured to activate in response to the on-skin sensor assembly contacting the skin of the host.

In some embodiments, the insertion assembly includes a first spring. In some embodiments, the retraction assembly includes a second spring. In some embodiments, the insertion assembly further includes a holder configured to guide the needle carrier assembly at least during translation from the initial proximal position to the distal insertion position. In some embodiments, the holder further includes at least one retention element configured to retain the second spring at least during insertion. In some embodiments, the at least one retention element is disposed along an outside of the second coil and configured to contact and retain a coil of the second spring. In some embodiments, the needle carrier assembly further includes at least one backstop feature configured to prevent lateral deflection of the at least one retention element at least during insertion. In some embodiments, the at least one backstop feature is configured not to contact the at least one retention element in the distal insertion position, thereby allowing the second spring to deflect the at least one retention element and activate the retraction assembly. In some embodiments, the second spring is configured to exert a force sufficient to deflect the at least one retention element in the distal insertion position when the on-skin sensor assembly is in contact with the skin of the host. In some embodiments, the applicator further includes an inner housing. In some embodiments, the applicator further includes an outer housing including an activation element configured to activate the insertion assembly. In some embodiments, the activation element is prevented from activating the insertion assembly until the outer housing is translated a predetermined distance in a distal direction with respect to the inner housing. In some embodiments, the inner housing further includes an engagement element and the needle carrier assembly includes a protrusion. The engagement element is configured to engage with the protrusion upon the needle carrier assembly translating in a distal direction beyond a predetermined threshold, thereby preventing the needle carrier assembly from translating in the distal direction beyond the predetermined threshold. In some embodiments, the engagement feature includes a hook. In some embodiments, the needle carrier assembly further includes a hub configured to couple an insertion element to the needle carrier assembly. In some embodiments, the hub is further configured to couple to the on-skin sensor assembly.

In some embodiments, the insertion assembly and the retraction assembly both include the first spring. In some embodiments, the first spring is configured to exert a force between a holder and a deployment sleeve. In some embodiments, the holder includes at least one retention element configured to immobilize the holder to the deployment sleeve. In some embodiments, the applicator further includes a housing and an activation element configured to deflect the at least one retention element, thereby enabling the first spring to translate the holder, the needle carrier assembly and the on-skin sensor assembly from the proximal position to the distal insertion position. In some embodiments, the housing further includes at least one protrusion, and the deployment sleeve includes at least one retention element configured to contact the at least one protrusion of the housing. In some embodiments, the first spring is configured to exert a force sufficient to deflect the at least one retention element of the deployment sleeve when the on-skin sensor assembly is in contact with the skin of the host, thereby freeing the at least one retention element of the deployment sleeve from the at least one protrusion of the housing. In some embodiments, the first spring is further configured to translate the deployment sleeve in the proximal direction. In some embodiments, the needle carrier assembly further includes a protrusion configured to contact the deployment sleeve, thereby causing the needle carrier assembly to translate in the proximal direction.

In a seventeenth embodiment, a needle hub for applying an on-skin sensor assembly to a skin of a host is provided. The needle hub includes at least one upper arm. The needle hub includes a base comprising an anti-rotation feature. The base is configured to be at least partially disposed in an aperture of the on-skin sensor assembly. The needle hub is configured to couple with an insertion element.

In some embodiments, the anti-rotation feature is configured to prevent rotation of the base within the aperture. In some embodiments, the anti-rotation feature includes a key having a shape complementary to at least a portion of the aperture. In some embodiments, the at least one upper arm is configured to be disposed through an aperture in a needle carrier assembly of an applicator. In some embodiments, the at least one upper arm is configured to contact an upper surface of the needle carrier assembly adjacent to the aperture in the needle carrier assembly. In some embodiments, the at least one upper arm is configured to be disposed in a groove in the upper surface of the needle carrier assembly, thereby immobilizing the needle hub with respect to the needle carrier assembly. In some embodiments, the at least one upper arm is flexible. In some embodiments, the at least one upper arm is configured to flex radially inward. In some embodiments, the needle hub further includes at least one lower arm. In some embodiments, the at least one lower arm is configured to contact a lower surface of the needle carrier assembly adjacent to an aperture in the needle carrier assembly. In some embodiments, the insertion element includes a needle. In some embodiments, the needle includes an open side configured to receive a sensor of the on-skin sensor assembly. In some embodiments, the base includes a flat surface configured to mate with a top surface of the on-skin sensor assembly, thereby maintaining the insertion element in a substantially perpendicular orientation to the top surface of the on-skin sensor assembly.

In an eighteenth embodiment, a method for applying an on-skin sensor assembly to skin of a host is provided. The method includes providing an applicator. The applicator includes a housing comprising an activation element. The applicator includes an insertion assembly. The applicator includes a retraction assembly. The method includes activating the activation element. Activating the activation element causes the insertion assembly to translate a needle carrier assembly and the on-skin sensor assembly in a distal direction from a proximal position to a distal insertion position, thereby inserting a sensor of the on-skin sensor assembly at least partially into the skin of the host. Activating the activation element causes the retraction assembly to translate the needle carrier assembly in a proximal direction from the distal inserted position to a proximal retracted position. The retraction assembly is configured to activate in response to on-skin sensor assembly contacting the skin of the host.

In some embodiments, the insertion assembly includes a first spring. In some embodiments, the retraction assembly includes a second spring. In some embodiments, the insertion assembly further includes a holder configured to guide the needle carrier assembly at least during translation from the proximal position to the distal insertion position. In some embodiments, the holder further includes at least one retention element configured to retain the second spring at least during insertion. In some embodiments, the at least one retention element is disposed along an outside of the second coil and configured to contact and retain a coil of the second spring. In some embodiments, the needle carrier assembly further includes at least one backstop feature configured to prevent lateral deflection of the at least one retention element at least during insertion. In some embodiments, the at least one backstop feature is configured not to contact the at least one retention element in the distal insertion position, thereby allowing the second spring to deflect the at least one retention element and activate the retraction assembly. In some embodiments, the second spring is configured to exert a force sufficient to deflect the at least one retention element in the distal insertion position when the on-skin sensor assembly is in contact with the skin of the host. In some embodiments, the second spring includes a tang extending along a diameter of second spring and wherein the at least one retention element is disposed along an inside of the second spring and configured to retain the tang of the second spring. In some embodiments, the housing is an outer housing and the applicator further includes an inner housing. In some embodiments, activating the activation element includes translating the outer housing a predetermined distance in a distal direction with respect to the inner housing. In some embodiments, the inner housing further includes an engagement element and the needle carrier assembly includes a protrusion. The engagement element is configured to engage with the protrusion upon the needle carrier assembly translating in a distal direction beyond a predetermined threshold, thereby preventing the needle carrier assembly from translating in the distal direction beyond the predetermined threshold. In some embodiments, the engagement feature includes a hook. In some embodiments, the needle carrier assembly further includes a needle hub configured to couple the insertion element to the needle carrier assembly.

In some embodiments, the insertion assembly and the retraction assembly both include the first spring. In some embodiments, the first spring is configured to exert a force between a holder and a deployment sleeve. In some embodiments, the holder includes at least one retention element configured to immobilize the holder to the deployment sleeve. In some embodiments, activating the activation element includes deflecting the at least one retention element of the holder, thereby enabling the first spring to translate the holder, the needle carrier assembly and the on-skin sensor assembly from the proximal position to the distal insertion position. In some embodiments, the housing further includes at least one protrusion, and the deployment sleeve includes at least one retention element configured to contact the at least one protrusion of the housing. In some embodiments, the first spring is configured to exert a force sufficient to deflect the at least one retention element of the deployment sleeve when the on-skin sensor assembly is in contact with the skin of the host, thereby freeing the at least one retention element of the deployment sleeve from the at least one protrusion of the housing. In some embodiments, the first spring is further configured to translate the deployment sleeve in the proximal direction. In some embodiments, the needle carrier assembly further includes a protrusion configured to contact the deployment sleeve, thereby causing the needle carrier assembly to translate in the proximal direction.

In a nineteenth aspect, an applicator for applying an on-skin sensor assembly to a skin of a host is provided. The applicator includes a first body releasably coupled to a needle. The applicator further includes a second body releasably coupled to the first body by a frictional engagement. The applicator further includes a spring configured to provide a first force to the first body and second body. The first force can drive the first body and second body in a distal direction. The frictional engagement can be configured to be decoupled by a counter force applied to the on-skin sensor assembly in an opposite direction of the first force.

In some embodiments, the applicator further includes at least one retention element configured to frictionally couple the second body to the first body. In some embodiments, the at least one retention element is formed integral with the second body. In some embodiments, the at least one retention element is frictionally engaged against a wall of the first body. In some embodiments, the counter force decouples the frictional engagement by displacing the at least one retention element from the wall of the first body. In some embodiments, the wall is a backstop. In some embodiments, the wall is configured to prevent the at least one retention element from deflecting.

In some embodiments, the frictional engagement is decoupled by the counter force exceeding a force threshold. In some embodiments, the force threshold is determined by the frictional force between the at least one retention element and the first body. In some embodiments, the threshold is at least 0.5 lbf. In some embodiments, the threshold is at least 1 lbf.

In some embodiments, the first body is configured to retract in a proximal direction upon decoupling of the frictional engagement. In some embodiments, the applicator further includes a second spring. The second spring can be configured to drive the first body in a proximal direction. In some embodiments, the second spring is retained from release by at least one retention element of the second body.

In some embodiments, the decoupling of the frictional engagement is configured to be independent of a distance between the on-skin sensor assembly and a distal end of the applicator. In some embodiments, the first body is configured to retract independent of the distance between the on-skin sensor assembly and the distal end of the applicator. In some embodiments, the counter force applied to the on-skin sensor assembly is provided by the skin of the host opposing the first force. In some embodiments, an interior of the applicator is configured to allow the skin of the host to reside within the interior. In some embodiments, the needle is configured to be inserted into the skin a predetermined depth. In some embodiments, the frictional engagement is configured to decouple at a range of distances between the on-skin sensor assembly and a distal end of the applicator.

This Summary is provided to introduce a selection of concepts further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 6A-6H illustrate cutaway views and perspective views of several features of the applicator of FIG. 5, according to some embodiments.

FIGS. 7A-7F illustrate several cutaway views of the applicator of FIG. 5 during operation, according to some embodiments.

FIGS. 11A-11D and 11J illustrate perspective views while FIGS. 11E-11H illustrate side cutaway views of steps for assembling the applicator of FIG. 5, according to some embodiments.

FIG. 13A-13F illustrate perspective views and cutaway views of several features of the applicator of FIG. 12, according to some embodiments.

FIGS. 24A-24F, 24H, 24J and 24L-24M illustrate cross-sectional views while

FIGS. 28A-28C and 28II illustrate several perspective views while FIGS. 28D-28G illustrate cross-sectional views of assembling the applicator of FIG. 25, according to some embodiments.

FIGS. 32A-34B illustrate exploded perspective views of yet another applicator for an on-skin sensor assembly of an analyte sensor system, according to some embodiments.

FIG. 34A-34D illustrate several cross-sectional views of the applicator of FIG. 32 during operation, according to some embodiments.

FIG. 35A-35C illustrate cross-sectional views of an on-skin sensor assembly retention mechanism of the applicator of FIG. 32, according to some embodiments.

FIG. 37A-37C illustrate cross-sectional views of yet another on-skin sensor assembly retention mechanism of the applicator of FIG. 32, according to some embodiments.

FIG. 65 illustrates a flowchart of a method for applying an on-skin sensor assembly to skin of a host, according to some embodiments.

FIG. 66 illustrates exemplary mechanisms for several features of an applicator configured to apply an on-skin sensor assembly to skin of a host, according to some embodiments.

FIG. 77 illustrates a perspective partial cutaway view of the needle carrier assembly, hub, and on-skin sensor assembly of the applicator of FIGS. 71 and 72, according to some embodiments.

FIG. 78 illustrates a cross-sectional view of the hub and on-skin sensor assembly of the applicator of FIGS. 71 and 72, according to some embodiments.

FIG. 79 illustrates a top view of a portion of the needle carrier assembly and hub of FIGS. 71 and 72, according to some embodiments.

FIG. 83 illustrates a cross-sectional view of an applicator comprising a deformable layer disposed over an activation element, according to some embodiments.

FIG. 84 illustrates a perspective view of an applicator utilizing a twist-to-activate activation mechanism, according to some embodiments.

FIG. 85 illustrates a cross-sectional view of an applicator comprising a top-mounted activation element, according to some embodiments.

FIG. 89 illustrates a flowchart of another method for applying an on-skin sensor assembly to skin of a host, according to some embodiments.

DETAILED DESCRIPTION

The following description and examples illustrate some example embodiments in detail. Those of skill in the art will recognize that there are numerous variations and modifications of this disclosure encompassed by its scope. Accordingly, the description of a certain example embodiment should not be deemed to limit the scope of the present disclosure.

System Introduction

Figure 1:
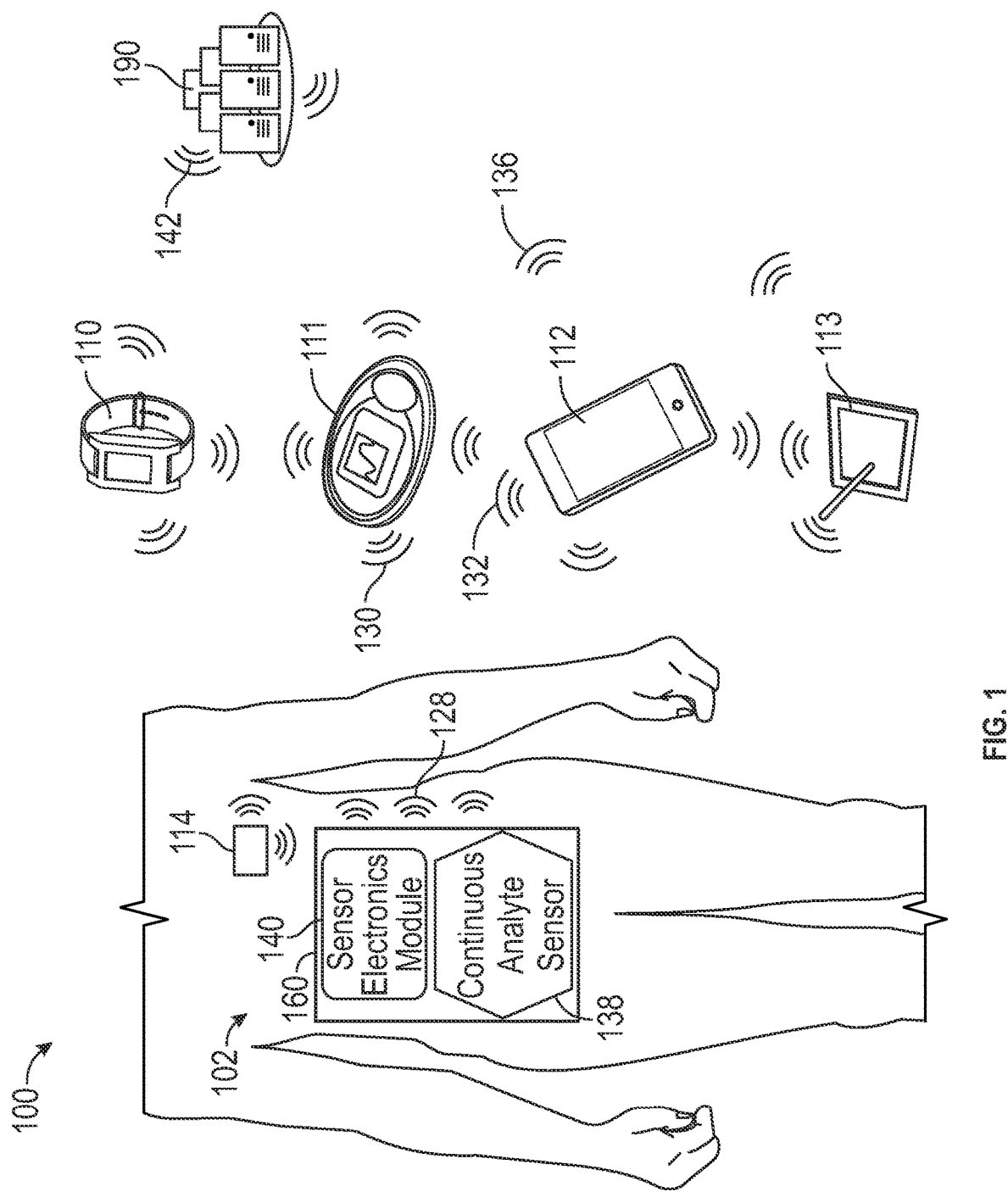
FIG. 1 illustrates a schematic view of a continuous analyte sensor system, according to some embodiments.

FIG. 1 is a diagram depicting an example continuous analyte monitoring system 100 including an analyte sensor system 102 comprising an on-skin sensor assembly 160 configured to be fastened to the skin of a host via a base (not shown). Analyte sensor system 102 is operatively connected to a host and a plurality of display devices 110-114 according to certain aspects of the present disclosure. Example display devices 110-114 may include computers such as smartphones, smartwatches, tablet computers, laptop computers, and desktop computers. In some embodiments, display devices 110-114 may be Apple Watches, iPhones, and iPads made by Apple Inc., or Windows or Google devices. It should be noted that display device 114 alternatively or in addition to being a display device, may be a medicament delivery device that can act cooperatively with analyte sensor system 102 to deliver medicaments to the host. Analyte sensor system 102 may include a sensor electronics module 140 and a continuous analyte sensor 138 associated with sensor electronics module 140. Sensor electronics module 140 may be in direct wireless communication with one or more of the plurality of display devices 110-114 via wireless communications signals. As will be discussed in greater detail below, display devices 110-114 may also communicate amongst each other and/or through each other to analyte sensor system 102. For ease of reference, wireless communications signals from analyte sensor system 102 to display devices 110-114 can be referred to as "uplink" signals 128. Wireless communications signals from, e.g., display devices 110-114 to analyte sensor system 102 can be referred to as "downlink" signals 130. Wireless communication signals between two or more of display devices 110-114 may be referred to as "crosslink" signals 132. Additionally, wireless communication signals can include data transmitted by one or more of display devices 110-113 via "long-range" uplink signals 136 (e.g., cellular signals) to one or more remote servers 190 or network entities, such as cloud-based servers or databases, and receive long-range downlink signals 142 transmitted by remote servers 190.

In embodiments shown by FIG. 1, one of the plurality of display devices may be a custom display device 111 specially designed for displaying certain types of displayable sensor information associated with analyte values received from the sensor electronics module 126 (e.g., a numerical value and an arrow, in some embodiments). In some embodiments, one of the plurality of display devices may be a handheld device 112, such as a mobile phone based on the Android, iOS operating system or other operating system, a palm-top computer and the like, where handheld device 112 may have a relatively larger display and be configured to display a graphical representation of the continuous sensor data (e.g., including current and historic data). Other display devices can include other hand-held devices, such as a tablet 113, a smart watch 110, a medicament delivery device 114, a blood glucose meter, and/or a desktop or laptop computer.

It should be understood that in the case of display device 134e, which may be a medicament delivery device in addition to or instead of a display device, the alerts and/or sensor information provided by continuous analyte sensor 122 vis-à-vis sensor electronics module 126, can be used to initiate and/or regulate the delivery of the medicament to host 120.

During use, a sensing portion of sensor 138 may be disposed under the host's skin and a contact portion of sensor 138 can be electrically connected to electronics unit 140. Electronics unit 140 can be engaged with a housing (e.g., a base) which is attached to an adhesive patch fastened to the skin of the host. In some embodiments, electronics unit 140 is integrally formed with the housing. Furthermore, electronics unit 140 may be disposable and directly coupled to the adhesive patch.

Continuous analyte sensor system 100 can include a sensor configuration that provides an output signal indicative of a concentration of an analyte. The output signal including (e.g., sensor data, such as a raw data stream, filtered data, smoothed data, and/or otherwise transformed sensor data) is sent to the receiver.

In some embodiments, analyte sensor system 100 includes a transcutaneous glucose sensor, such as is described in U.S. Patent Publication No. US-2011-0027127-A1, the entire contents of which are hereby incorporated by reference. In some embodiments, sensor system 100 includes a continuous glucose sensor and comprises a transcutaneous sensor (e.g., as described in U.S. Pat. No. 6,565,509, as described in U.S. Pat. No. 6,579,690, and/or as described in U.S. Pat. No. 6,484,046). The contents of U.S. Pat. Nos. 6,565,509, 6,579,690, and 6,484,046 are hereby incorporated by reference in their entirety.

Various signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entirety. The sensor can extend through a housing, which can maintain sensor 138 on, in or under the skin and/or can provide for electrical connection of sensor 138 to sensor electronics in electronics unit 140.

In some embodiments, description of a base, a housing, a wearable, and/or a transmitter of on-skin sensor assembly 160 may be interchangeable. In other embodiments, a base and a housing of on-skin sensor assembly 160 may be different in the sense that they may be separate components from sensor electronics module 140, e.g., from a transmitter or receiver.

In several embodiments, sensor 138 is in a form of a wire. A distal end of the wire can be formed, e.g., having a conical shape (to facilitate inserting the wire into the tissue of the host). Sensor 138 can include an elongated conductive body, such as an elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than 0.1 inches, less than 0.075 inches, less than 0.05 inches, less than 0.025 inches, less than 0.01 inches, less than 0.004 inches, less than 0.002 inches, less than 0.001 inches, and/or less than 0.0005 inches.

Sensor 138 may have a circular cross section. In some embodiments, the cross section of the elongated conductive body can be ovoid, rectangular, triangular, polyhedral, star-shaped, C-shaped, T-shaped, X-shaped, Y-shaped, irregular, or the like. In some embodiments, a conductive wire electrode is employed as a core. In other embodiments, sensor 138 may be disposed on a substantially planar substrate. To such an electrode, one or two additional conducting layers may be added (e.g., with intervening insulating layers provided for electrical isolation). The conductive layers can be comprised of any suitable material. In certain embodiments, it may be desirable to employ a conductive layer comprising conductive particles (i.e., particles of a conductive material) in a polymer or other binder.

In some embodiments, the materials used to form the elongated conductive body (e.g., stainless steel, titanium, tantalum, platinum, platinum-iridium, iridium, certain polymers, and/or the like) can be strong and hard, and therefore can be resistant to breakage. For example, in several embodiments, the ultimate tensile strength of the elongated conductive body is greater than 80 kPsi and less than 140 kPsi, and/or the Young's modulus of the elongated conductive body is greater than 160 GPa and less than 220 GPa. The yield strength of the elongated conductive body can be greater than 58 kPsi and less than 2200 kPsi.

Electronics unit 140 can be releasably or permanently coupled to sensor 138. Electronics unit 140 can include electronic circuitry associated with measuring and processing the continuous analyte sensor data. Electronics unit 140 can be configured to perform algorithms associated with processing and calibration of the sensor data. For example, electronics unit 140 can provide various aspects of the functionality of a sensor electronics module as described in U.S. Patent Publication No. US-2009-0240120-A1 and U.S. Patent Publication No. US-2012-0078071-A1, the entire contents of which are incorporated by reference herein. Electronics unit 140 may include hardware, firmware, and/or software that enable measurement of levels of the analyte via a glucose sensor, such as sensor 138.

For example, electronics unit 140 can include a potentiostat, a power source for providing power to sensor 138, signal processing components, data storage components, and a communication module (e.g., a telemetry module) for one-way or two-way data communication between electronics unit 140 and one or more receivers, repeaters, and/or display devices, such as devices 110-114. Electronic components can be affixed to a printed circuit board (PCB), or the like, and can take a variety of forms. The electronic components can take the form of an integrated circuit (IC), such as an Application-Specific Integrated Circuit (ASIC), a microcontroller, and/or a processor. The electronics unit 140 may include sensor electronics that are configured to process sensor information, such as storing data, analyzing data streams, calibrating analyte sensor data, estimating analyte values, comparing estimated analyte values with time-corresponding measured analyte values, analyzing a variation of estimated analyte values, and the like. Examples of systems and methods for processing sensor analyte data are described in more detail in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entirety. Electronics unit 140 may communicate with the devices 110-114, and/or any number of additional devices, via any suitable communication protocol. Example communication methods or protocols include radio frequency; Bluetooth; universal serial bus; any of the wireless local area network (WLAN) communication standards, including the IEEE 802.11, 802.15, 802.20, 802.22 and other 802 communication protocols; ZigBee; wireless (e.g., cellular) telecommunication; paging network communication; magnetic induction; satellite data communication; a proprietary communication protocol, open source communication protocol, and/or any suitable wireless communication method.

Additional sensor information is described in U.S. Pat. Nos. 7,497,827 and 8,828,201. The entire contents of U.S. Pat. Nos. 7,497,827 and 8,828,201 are incorporated by reference herein.

Any sensor shown or described herein can be an analyte sensor; a glucose sensor; and/or any other suitable sensor. A sensor described in the context of any embodiment can be any sensor described herein or incorporated by reference. Sensors shown or described herein can be configured to sense, measure, detect, and/or interact with any analyte.

As used herein, the term "analyte" is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products.

In some embodiments, the analyte for measurement by the sensing regions, devices, systems, and methods is glucose. However, other analytes are contemplated as well, including, but not limited to ketone bodies; Acetyl Co A; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; cortisol; testosterone; choline; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular *stomatis* virus, *Wuchereria bancrofti*, yellow fever virus); specific antigens (hepatitis B virus, HIV-1); acetone (e.g., succinylacetone); acetoacetic acid; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and intermediaries in the Citric Acid Cycle.

Many embodiments described herein may use an adhesive to couple a base or housing, a sensor module, a transmitter or electronics unit, and/or a sensor to a host (e.g., to skin of the host). The adhesive can be configured for adhering to skin. The adhesive can include a pad (e.g., that is located between the adhesive and the base). Additional adhesive information, including adhesive pad information, is described in U.S. patent application Ser. No. 14/835,603, which was filed on Aug. 25, 2015. The entire contents of U.S. patent application Ser. No. 14/835,603 are incorporated by reference herein.

As noted above, systems can apply an on-skin sensor assembly to the skin of a host. The on-skin sensor assembly may include a base that comprises an adhesive to couple a glucose sensor to the skin. Other methods are contemplated such as a strap, e.g., a watch band.

Any of the features described in the context of at least FIG. 1 can be applicable to all aspects and embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Throughout this disclosure, reference is made to an on-skin sensor assembly, which may also be described as a wearable. Such on-skin sensor assemblies (see FIGS. 1-4 and 68-70) may be disposable or reusable and may (see FIGS. 68-70) or may not (see FIGS. 2-4) comprise a base or base plate. In some embodiments, on-skin sensor assemblies having a base plate (e.g., FIGS. 68-70) may be reusable, whereas on-skin sensor assemblies without a base plate (e.g., FIGS. 2-4) may be disposable. Although FIG. 1 has already been discussed with respect to on-skin sensor assembly 160, FIGS. 2A-4 and 68-70 describe at least some other embodiments of an on-skin sensor assembly.

Figure 2A:
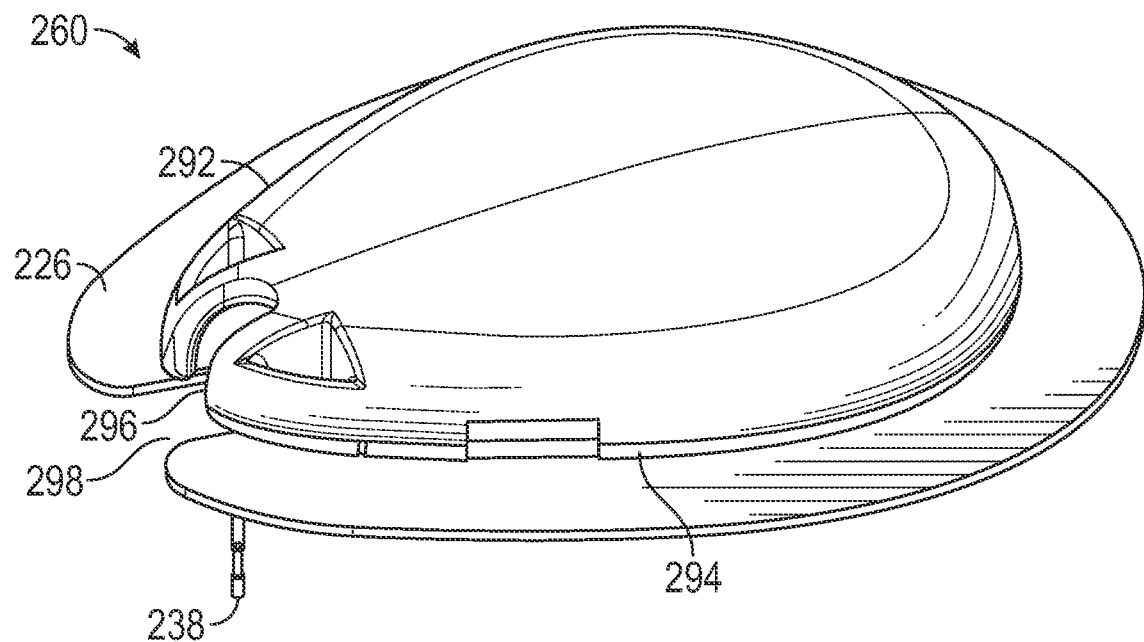
FIGS. 2A-2B illustrate perspective views of an on-skin sensor assembly, according to some embodiments.

FIG. 2A illustrates a perspective view of an on-skin sensor assembly 260, in accordance with some embodiments. On-skin sensor assembly 260 may comprise an outer housing comprising a first, top portion 292 and a second, lower portion 294. In some embodiments, the outer housing may comprise a clamshell design. On-skin sensor assembly 260 may include similar components as electronics unit 140 described above in FIG. 1 (e.g. a potentiostat, a power source for providing power to sensor 138, signal processing components, data storage components, and a communication module (e.g., a telemetry module) for one-way or two-way data communication, a printed circuit board (PCB), an integrated circuit (IC), an Application-Specific Integrated Circuit (ASIC), a microcontroller, and/or a processor). The outer housing may feature a large rounded body having tapered end opposite the large rounded body. The outer housing may further comprise an aperture 296 disposed at the tapered end of the outer housing and adapted for sensor 238 and needle insertion. Aperture 296 may be an opening featuring a U-shaped channel extending through the tapered end of the outer housing. On-skin sensor assembly 260 may further comprise an adhesive patch 226 configured to secure on-skin sensor assembly 260 to skin of the host. As shown, adhesive patch 226 may feature an aperture 298 having a similar shape as aperture 296 and substantially aligned with aperture 296. Sensor 238 may be configured to at least partially extend through apertures 296 and 298. In some embodiments, adhesive patch 226 may comprise an adhesive suitable for skin adhesion, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated.

On-skin sensor assembly 260 may be attached to the host with use of an applicator adapted to provide convenient and secure application. Such an applicator may also be used for inserting sensor 238 through the host's skin, and/or connecting sensor 238 to the electronics unit. Once sensor 238 has been inserted into the skin (and is connected to the electronics unit), the sensor assembly can detach from the applicator.

Figure 2B:
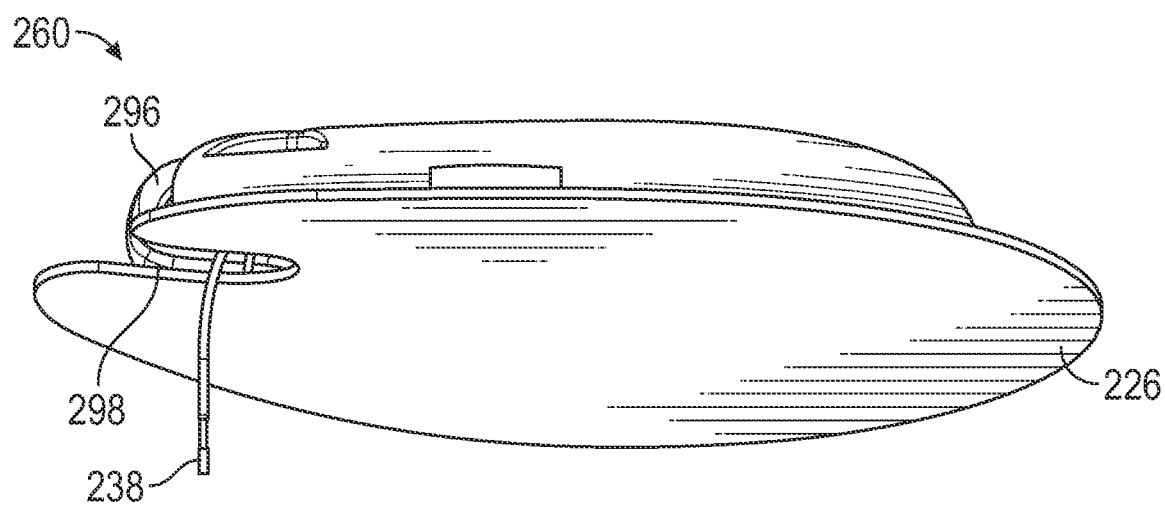

FIG. 2B illustrates a bottom perspective view of on-skin sensor assembly 260 of FIG. 2A. FIG. 2B illustrates aperture 296 disposed to a side of the outer housing, and aperture 298, each adapted for sensor 238 and needle insertion.

Figure 3A:
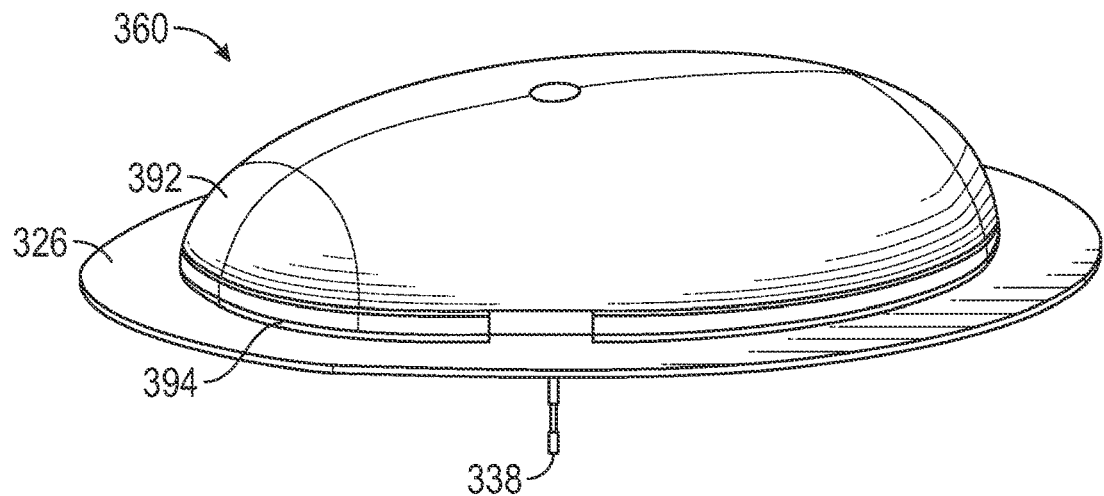
FIGS. 3A-3B illustrate perspective views of another on-skin sensor assembly, according to some embodiments.

FIG. 3A illustrates a perspective view of an on-skin sensor assembly 360, in accordance with some embodiments. On-skin sensor assembly 360 may comprise an outer housing comprising a first, top portion 392 and a second, lower portion 394. In some embodiments, the outer housing may comprise a clamshell design. On-skin sensor assembly 260 may include similar components as electronics unit 140 described above in FIG. 1 (e.g. a potentiostat, a power source for providing power to sensor 138, signal processing components, data storage components, and a communication module (e.g., a telemetry module) for one-way or two-way data communication, a printed circuit board (PCB), an integrated circuit (IC), an Application-Specific Integrated Circuit (ASIC), a microcontroller, and/or a processor). As shown, the outer housing may feature a generally oblong shape. The outer housing may further comprise an sensor assembly aperture 396 disposed substantially through a center portion of outer housing and adapted for sensor 338 and needle insertion through a bottom of on-skin sensor assembly 360. In some embodiments, sensor assembly aperture 396 may be a channel or elongated slot. On-skin sensor assembly 360 may further comprise an adhesive patch 326 configured to secure on-skin sensor assembly 360 to skin of the host. In some embodiments, adhesive patch 326 may comprise an adhesive suitable for skin adhesion on its underside, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated. In some embodiments, adhesive patch 326 may further comprise an adhesive on its topside, e.g., the non-skin contacting side to aid adherence of adhesive patch 326 to a portion of an associated applicator during manufacture and/or to maintain adhesive patch 326 in a substantially flat orientation before deployment to the skin of a host. In some embodiments, the adhesive applied to the topside may be weaker than the adhesive applied to the underside to ensure appropriate transfer of the on-skin sensor assembly to the skin of the host. As shown, adhesive patch 396 may feature an aperture 398 aligned with sensor assembly aperture 396 such that sensor 338 may pass through a bottom of on-skin sensor assembly 360 and through adhesive patch 396.

Figure 3B:
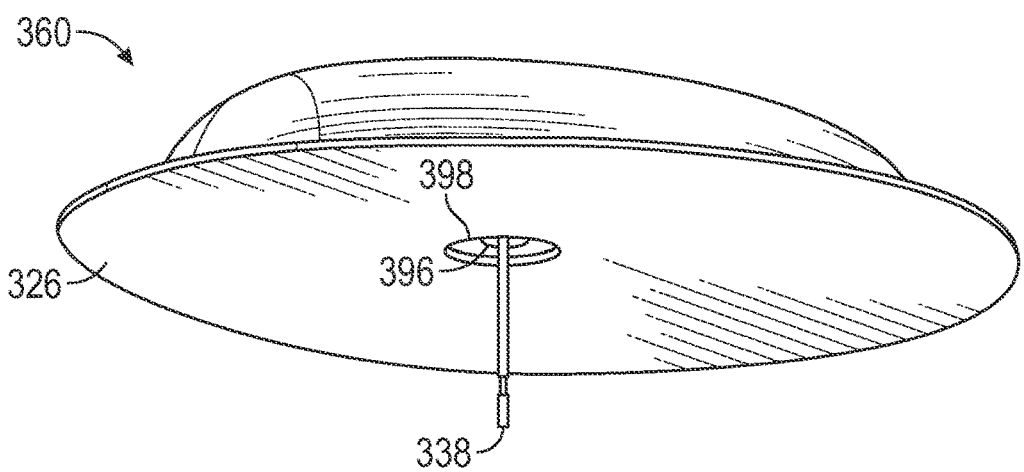

FIG. 3B illustrates a bottom perspective view of on-skin sensor assembly 360 of FIG. 3A. FIG. 3B further illustrates sensor assembly aperture 396 disposed substantially in a center portion of a bottom of on-skin sensor assembly 360, and aperture 398, both adapted for sensor 338 and needle insertion.

Figure 91:
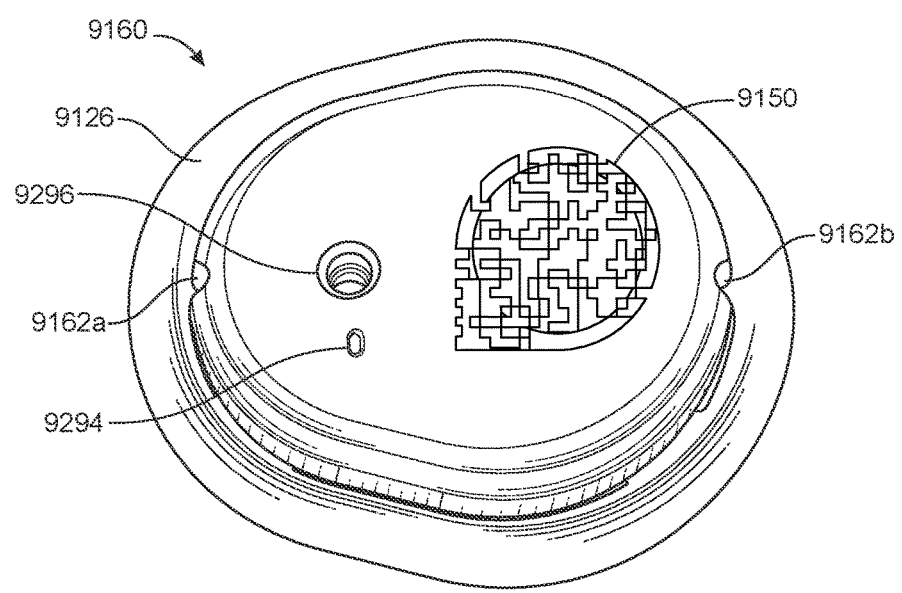
FIG. 91 illustrates a perspective view of an on-skin sensor assembly, according to some embodiments

FIG. 91 illustrates a perspective view of an on-skin sensor assembly 9160, according to some embodiments. On-skin sensor assembly 9160 may be substantially similar to other on-skin sensor assemblies described in this application, such as on-skin sensor assemblies 160, 260, and 360. On-skin sensor assembly 9160 may feature an adhesive patch 9126 and a clamshell design comprising a top shell and a bottom shell, similar to on-skin sensor assembly 360. Further, on-skin sensor assembly 9160 may include a plurality of attachment points 9162a and 9162b, similar to on-skin sensor assembly 160. On-skin sensor assembly 9160 may include an aperture 9296. Aperture 9296 may be a through-hole extending through on-skin sensor assembly 9160. Aperture 9296 may be configured to allow a needle and/or sensor to pass through. In some embodiments, on-skin sensor assembly 9160 may further include an aperture 9294. Aperture 9294 may extend from a top surface of on-skin sensor assembly 9150 a certain depth through on-skin sensor assembly 9160. In some embodiments, aperture 9294 is configured to engage with an anti-rotational feature such as base 7152 of needle hub 7150 described in FIG. 78.

In some embodiments, on-skin sensor assembly 9160 includes an identification tag 9150. Identification tag 9150 may be located on a top surface of on-skin sensor assembly 9150 (as shown), or on a side surface of on-skin sensor assembly. Identification tag 9150 may be an image which resembles a logo or mark identifying the manufacturer of the on-skin sensor assembly. Additionally, identification tag 9150 may be configured to be scanned by a user to pair the on-skin sensor assembly with a device, such as handheld device 112. In some embodiments, identification tag 9150 is a code such as, but not limited to, a QR code, a matrix code, a 2-D barcode, or a 3-D barcode. The code may be imbedded in the image of identification tag 9150.

Figure 4:
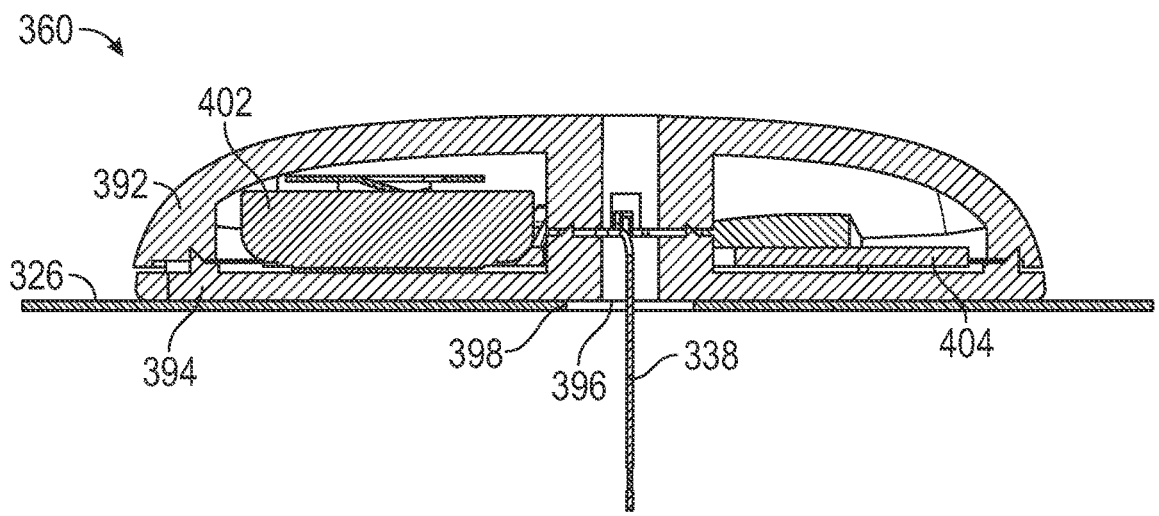
FIG. 4 illustrates a cross-sectional view of the on-skin sensor assembly of FIGS. 3A-3B, according to some embodiments.

FIG. 4 illustrates a cross-sectional view of on-skin sensor assembly 360 of FIGS. 3A and 3B. FIG. 4 illustrates the first, top portion 392 and the second, bottom portion 394 of the outer housing, adhesive patch 326, sensor assembly aperture 396 in the center portion of on-skin sensor assembly 360, aperture 398 in the center portion of adhesive patch 326, and sensor 338 passing through sensor assembly aperture 396. The electronics unit, previously described in connection with FIG. 3A, may further include a circuit board 404 and a battery 402 configured to provide power to at least circuit board 404.

Figure 87:
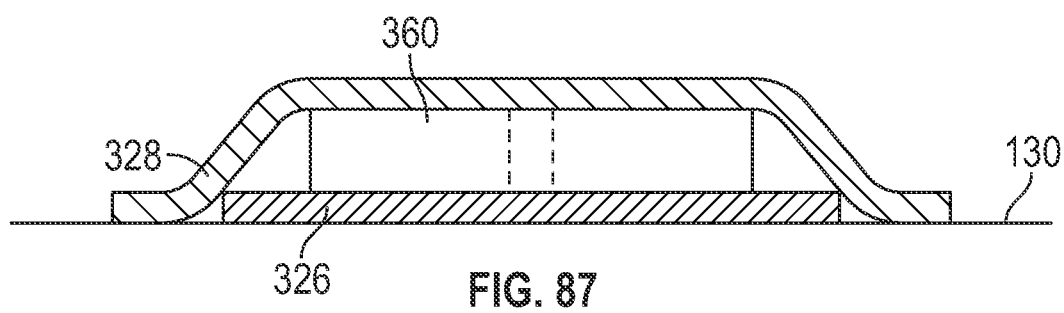
FIG. 87 illustrates a cross-sectional view of on-skin sensor assembly of FIGS. 3A, 3B and 4, further comprising an upper patch 328, according to some embodiments.

FIG. 87 illustrates a cross-sectional view of on-skin sensor assembly 360 of FIGS. 3A, 3B and 4, further comprising an upper patch 328, according to some embodiments. Upper patch 328 may comprise an adhesive suitable for skin adhesion, device adhesion, or a combination thereof, on its underside, for example a pressure sensitive adhesive (e.g., acrylic, rubber-based, or other suitable type) bonded to a carrier substrate (e.g., spun lace polyester, polyurethane film, or other suitable type) for skin and/or device attachment, though any suitable type of adhesive is also contemplated. In some embodiments, such an adhesive may be the same as the adhesive applied to the underside of patch 326. In some other embodiments, the adhesive may be different from the adhesive applied to the underside of patch 326. In some embodiments, upper patch 328 may be shaped as a circle, oval, partial strip, as an X, or as any other shape or form suitable for securing upper patch 328 to lower patch 326 and/or the skin of the host. The upper patch 328 may fully or partially cover on-skin sensor assembly 360. The upper patch 328 may improve adhesion lifespan of on-skin sensor assembly 360 on skin 130 of the host by adding additional adhesive contact area to the surface of the skin 130 and/or providing a single surface covering the wearable that reduces the risk of inadvertent mechanical removal (e.g. catching, snagging, tearing) by reducing catch surfaces/edges on on-skin sensor assembly 360. It is contemplated that reducing surfaces of on-skin sensor assembly 360 that are substantially perpendicular to the body surfaces may improve catch resistance. Such increased wearable lifespan provided by upper patch 328 may be a valuable property, especially as systems move toward and beyond 10-14 day wearable adhesion solutions.

In some embodiments, upper patch 328 may be assembled into any applicator in this description, above on-skin sensor assembly 360, with underside adhesive exposed. Upon deployment of on-skin sensor assembly 360 by the applicator, patch 326 may adhere to skin 130 of the host and upper patch 328 may be adhered over on-skin sensor assembly 360 and onto skin 130 of the host by one or more features of the applicator, for example, a holder and/or needle carrier assembly as described in connection with any figure herein.

Applicator Embodiments

Figure 5:
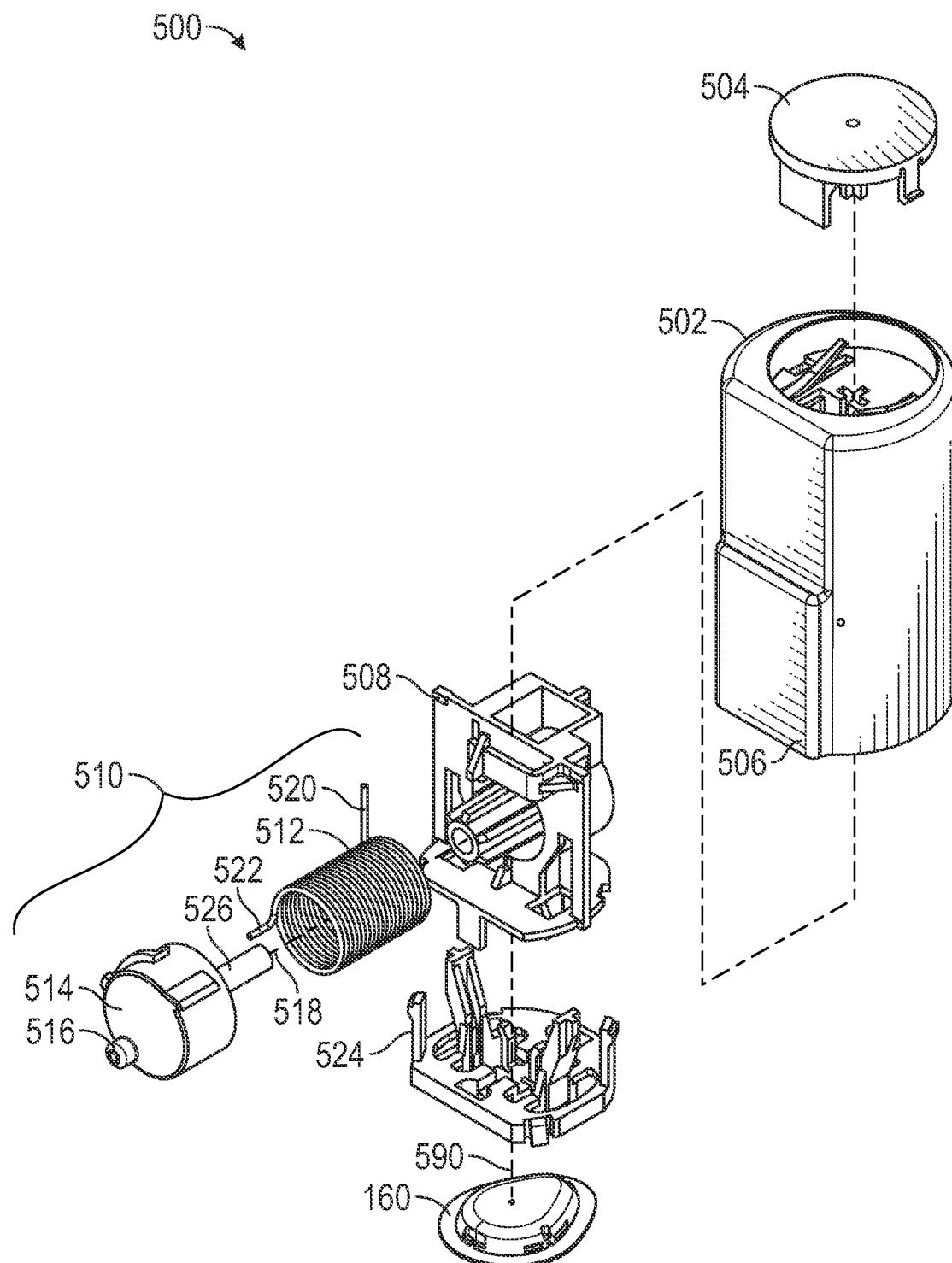
FIG. 5 illustrates an exploded perspective view of the applicator of FIG. 5, according to some embodiments.

FIG. 5 illustrates an exploded perspective view of an applicator 500 for applying on-skin sensor assembly 160 to skin 130 of a host, according to some embodiments. In some embodiments, applicator 500 may include an applicator housing 502 having an opening at its bottom and configured to house at least one or more mechanisms utilized to apply on-skin sensor assembly 160 to skin 130 of a host. Applicator housing 502 may be formed of any suitable material, e.g., a polymer, polycarbonate, ABS, nylon, polyethylene, polypropylene, etc. In some embodiments, applicator housing 502 may be configured to cover at least one feature of applicator housing 502, for example a guide of a reciprocating or back and forth mechanism, e.g., a scotch-yoke mechanism (see FIG. 6B).

Applicator 500 includes an activation element 504 configured to activate a drive assembly of applicator 500. In some embodiments, activation element 504 may be a button, a switch, a toggle, a slide, a trigger, a knob, a rotating member, a component that deforms and/or flexes or any other suitable mechanism for activating a drive assembly of applicator 500.

Applicator 500 may further comprise a needle carrier assembly 508, including an insertion element (not shown in FIG. 5) configured to insert sensor 138 of on-skin sensor assembly 160 (e.g., FIG. 1) at least partially into skin 130 of the host. The insertion element is further illustrated in FIG. 6H as attaching to needle carrier assembly 508 and extending in the distal direction, substantially along an axis of insertion. In some embodiments, needle carrier assembly 508 comprises a needle carrier or shuttle. In some embodiments, the insertion element comprises a needle, for example, an open sided-needle, a deflected-tip needle with a deflected-tip, a curved needle, a polymer-coated needle, a hypodermic needle, or any other suitable type of needle or structure, as will be described in more detail in connection with at least FIGS. 47-50 and 80A-B. In yet other embodiments, insertion element may comprise sensor 138 itself, sufficiently rigid to be inserted partially into skin 130 of the host with minimal or no structural support, such as described in U.S. Pat. No. 9,357,951, which was filed on Sep. 29, 2010, U.S. Patent Publication No. US 2014/0107450, which was filed on Feb. 28, 2013, and U.S. Patent Publication No. US 2015/0289788, which was filed on Apr. 10, 2014. The entire contents of U.S. Pat. No. 9,357,951, U.S. Patent Publication No. 2014/0107450, and U.S. Patent Publication No. 2015/0289788 are incorporated by reference herein.

Applicator 500 may further comprise a drive assembly 510 configured to drive the insertion element of needle carrier assembly 508 in a distal direction to a distal insertion position and in a proximal direction from the distal insertion position to a proximal retraction position. A distal direction may be defined as extending towards an open-ended side of the applicator 500 along a path needle carrier assembly 508 is configured to travel. The distal direction may also be defined as towards the skin of a user. A proximal direction may be defined as a direction extending in a substantially opposite direction from the distal direction. In some embodiments, the distal direction and the proximal direction extend along an insertion axis of the insertion element and of needle carrier assembly 508.

Drive assembly 510 may include a rotating drive element 514 coupled to needle carrier assembly 508 via an axle 526. In some embodiments, rotating drive element 514 comprises a cam feature, e.g., a wheel cam, having a substantially circular or ovoid circumference. Rotating drive element 514 may be configured to rotate with respect to needle carrier assembly 508 about an axis of rotation 518 coincident with a centerline of axle 526. Rotating drive element 514 may further include a pin 516 disposed at a position on a face of rotating drive element 514 displaced radially from axis of rotation 518. Pin 516 is configured to travel in a guide (see FIG. 6B) of applicator housing 502.

Drive assembly 510 may further include a spring 512. Spring 512 may be a torsion spring, a clock spring, a power spring, or any other suitable type of spring. Spring 512 may be formed of any suitable material including but not limited to plastic or metal, e.g., stainless steel. In some embodiments, spring 512 is pre-compressed before activation of the applicator. In some embodiments, spring 512 is configured to be additionally loaded during activation of the applicator. Spring 512 may have a first end 520 coupled to needle carrier assembly 508 and a second end 522 coupled to rotating drive element 514. Spring 512 may be disposed coaxially with axle 526. Spring 512 may be configured to, upon activation of drive assembly 510, rotate rotating drive element 514 in a single direction with respect to needle carrier assembly 508. In some embodiments, spring 512 is configured, upon activation of drive assembly 510, to unwind by rotating greater than zero degrees and less than 360 degrees. In some embodiments, spring 512 is pre-wound between 30 and 1440 degrees.

By virtue of rotating drive element 514 being configured to rotate with respect to needle carrier assembly 508, about axis of rotation 518, and pin 516 being restrained to travel in the guide of applicator housing 502, rotational motion of rotating drive element 514, driven by spring 512, is converted into linear, reciprocating motion of needle carrier assembly 508 along axis 590 and, therefore, of the insertion element (not shown). More specifically, rotation of rotating drive element 514 drives insertion element 508 in the distal direction to the distal insertion position and in the proximal direction from the distal insertion position to the proximal retraction position. Such embodiments may be able to omit handoff mechanisms between aspects of drive assembly 510 that separately drive the needle carrier assembly 508 in the distal and proximate directions by virtue of a single mechanism that converts rotational motion into reciprocating linear motion.

Applicator 500 may further include a holder 524 releasably coupled to needle carrier assembly 508 and configured to guide on-skin sensor assembly 160 while coupled to needle carrier assembly 508. In some embodiments, holder 524 may also be referred to as a carrier or transport member.

Figure 6A:
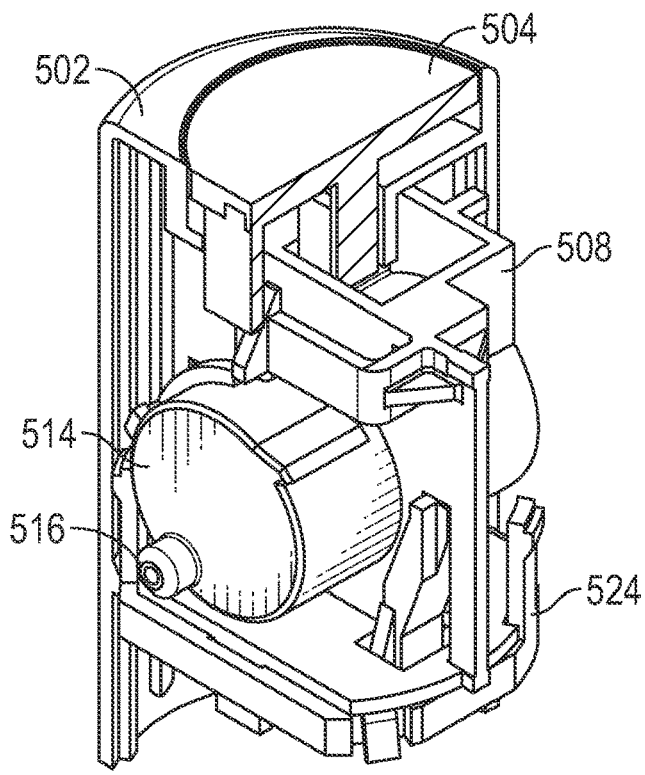

FIG. 6A-6H illustrates cutaway and perspective views of several features of applicator 500 of FIG. 5, according to some embodiments. FIG. 6A illustrates a cutaway view of applicator 500 including applicator housing 502, activation element 504, needle carrier assembly 508, rotating drive element 514, pin 516, and holder 524. Each of these components may have functionality as previously described in connection with at least FIG. 5.

Figure 6B:
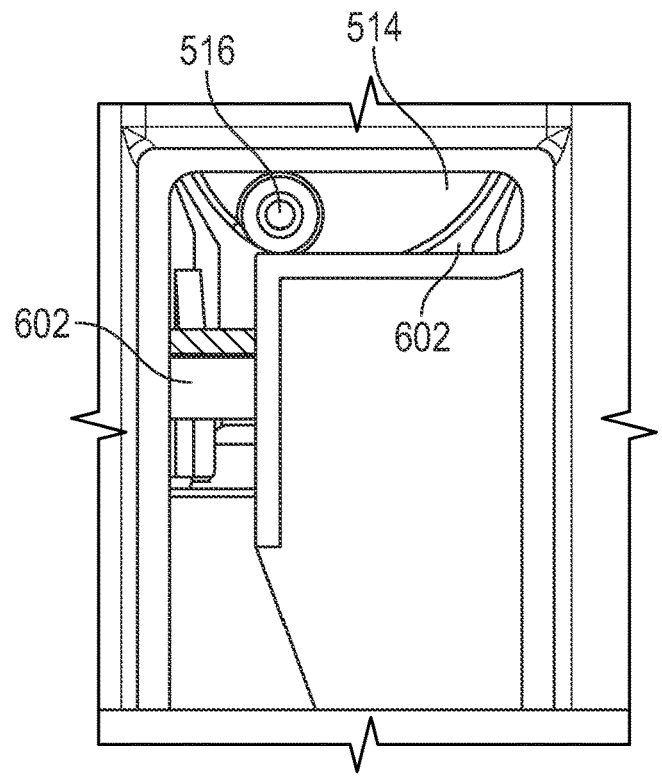

FIG. 6B illustrates guide 582 in applicator housing 502. In some embodiments, guide 582 may comprise a scotch-yoke track in which pin 516 is configured to travel upon activation of drive assembly 510, as rotating drive element 514 rotates.

Figure 6C:
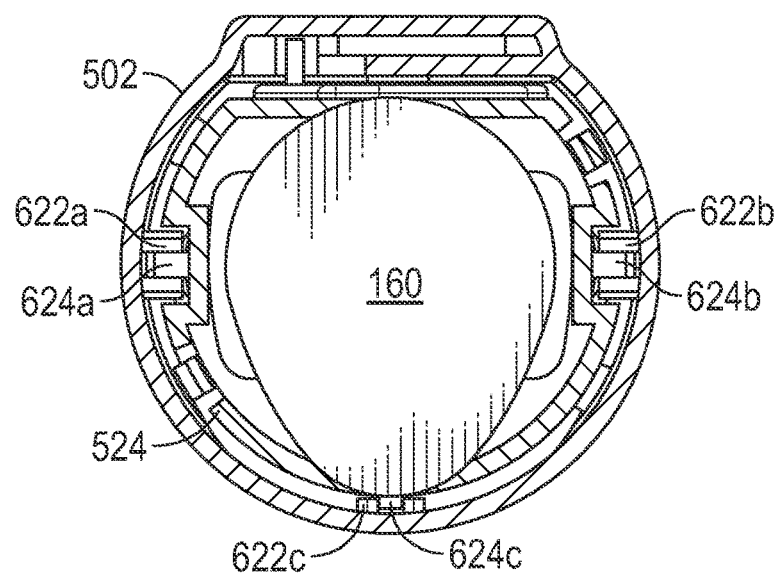

FIG. 6C illustrates a plurality of tracks 622a, 622b, 622c in applicator housing 502 in which a respective one of a plurality of protrusions or ribs 624a, 624b, 624c of needle carrier assembly 508 are configured to slide. Accordingly, tracks 622a-622c in applicator housing 502 define a path of travel for needle carrier assembly 508. In some embodiments, this path of travel is substantially linear and longitudinal. Although three tracks and protrusions are shown in FIG. 6C, any number of tracks and respective protrusions are contemplated. For ease of understanding, FIG. 6C illustrates a partial bottom view of applicator 500, which also shows portions of on-skin sensor assembly 160 and holder 524.

Figure 6D:
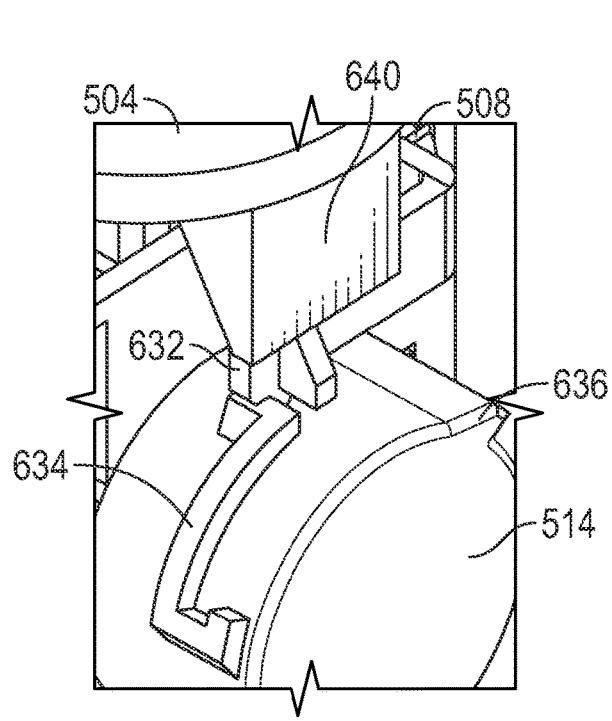

FIG. 6D illustrates an embodiment where needle carrier assembly 508 comprises a locking element 632 configured to prevent rotating drive element 514 from rotating. Specifically, rotating drive element 514 comprises a protrusion 634 in contact with retention element 632, which prevents protrusion 634 from traveling in a path it would otherwise take as spring 512 releases at least a portion of its stored energy in rotating drive element 514. In some embodiments, retention element 632 comprises a deflectable tab formed of a material such as a polymer, polycarbonate, ABS, nylon, polyethylene, polypropylene, or any other suitable material. Activation element 504 comprises a protrusion 640 configured to deflect retention element 632 such that protrusion 634 is no longer held by retention element 632, thereby allowing rotating drive element 514 to rotate and activating drive assembly 510. Rotating drive element 514 further comprises a ridge 636 configured to limit rotation of rotating drive element 514 as rotating drive element 514 rotates and ridge 636 comes in contact with retention element 632.

Figure 6E:
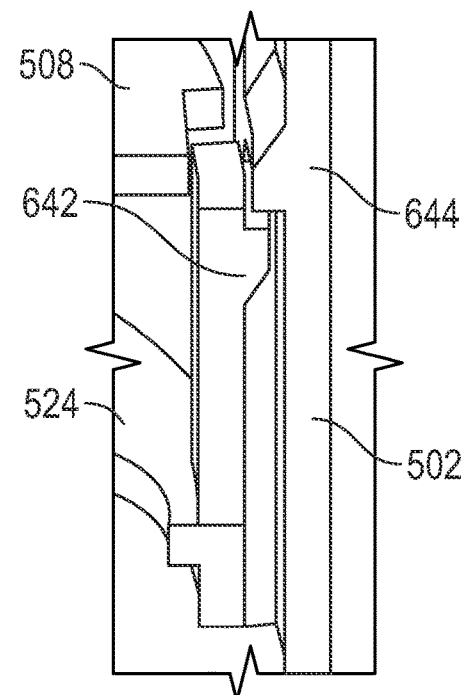

FIG. 6E illustrates a retention element 642 of holder 524 and a stop element 644 of applicator housing 502 configured to immobilize holder 524 to applicator housing 502 upon needle carrier assembly 508 reaching the distal insertion position. In some embodiments, retention element 642 is a deflectable arm, or any other type of protrusion or snap. For example, as needle carrier assembly 508 travels in the distal direction, as a result of spring 512 turning rotating drive element 514, retention element 642 slides along an inside surface of applicator housing 502 until retention element 642 is slightly deflected by stop element 644, then snapping in an outward direction under stop element 644. At this point, needle carrier assembly 508 may be free to progress in the proximal direction as a result of spring 512 further turning rotating drive element 514. Stop element 644 will prevent retention element 642, and so holder 524, from traveling in the proximal direction. In this way, movement of needle carrier assembly 508 in the proximal direction, after reaching the distal insertion position, releases holder 524 from needle carrier assembly 508 and/or on-skin sensor assembly 160.

FIG. 6F illustrates a protrusion 652 of holder 524 and a protrusion 654 of applicator housing 502 configured to prevent holder 524 from travelling beyond the distal insertion position in the distal direction. For example, as holder 524 is driven in the distal direction by needle carrier assembly 508, protrusion 652 travels along an inside surface of the applicator housing 502 until protrusion 652 comes in contact with protrusion 654, at which point holder 524 is prevented from further travel in the distal direction.

FIG. 6G illustrates on-skin sensor assembly 160 including a plurality of attachment points 662a-662f configured to mate with respective retention elements on needle carrier assembly 508 and/or holder 524 while traveling at least partially toward the distal insertion position, in the distal direction, during applicator activation. In some embodiments, attachment points 662a-662f are small grooves or indentations. Although a plurality of attachment points 662a-662f are illustrated, any number of attachment points are contemplated. In some embodiments, the respective retention elements may comprise snap fits, friction fits, interference features, elastomeric grips and/or adhesives configured to couple on-skin sensor assembly 160 with needle carrier assembly 508 and/or holder 524.

Moreover, during pressure fluctuations, such as at high altitude or vacuum during sterilization processes for example, air present within on-skin sensor assembly 160 may exert a deforming force from within the cavity of on-skin sensor assembly 160. Although not shown in FIG. 6G, in some embodiments, on-skin sensor assembly 160 may have at least a portion formed with a reduced thickness or a second material (e.g. an elastomer) and, therefore, reduced strength and rigidity, such that when applicator 500 is exposed to such pressure fluctuations, the portions having the reduced thickness or second material deform in a controlled manner, thereby reducing or eliminating damage that would otherwise occur to on-skin sensor assembly 160 due to undesirable uncontrolled expansion of on-skin sensor assembly 160. The portion formed with reduced thickness or a second material may be selected to direct controlled expansion away from datum and/or retention features securing the on-skin sensor assembly to applicator assembly. Such a feature may be present in any applicator described herein.

FIG. 6H illustrates retention elements 672a, 672b of holder 528 configured to releasably couple on-skin sensor assembly 160 to holder 528 as needle carrier assembly 508 travels in the distal direction to the distal insertion position, and to decouple on-skin sensor assembly 160 from holder 528 as needle carrier assembly 508 travels in the proximal direction from the distal insertion position towards the proximal retraction position. Specifically, retention elements 672a, 672b may each comprise a first end 676a, 676b, a second end 678a, 678b, and a pivot point 680a, 680b. As needle carrier assembly 508 travels in the distal direction to the distal insertion position, first end 676a, 676b of each of retention elements 672a, 672b is immobilized in a respective guide 674a, 674b of needle carrier assembly 508 and each of retention elements 672a, 672b is immobilized against interference points 682a, 682b of needle carrier assembly 508, thereby releasably coupling second ends 678a, 678b to attachment points 662a, 662b of on-skin sensor assembly 160. In some embodiments, guides 674a, 674b comprise a slot or a stop element. Since retention elements 642, 644 and/or protrusions 652, 654 immobilize holder 524 at the distal insertion position (as described in FIG. 6E), as needle carrier assembly 508 travels back in the proximal direction, needle carrier assembly 508 separates from holder 524, thereby separating first ends 676a, 676b of retention elements 672a, 672b from respective slots 674a, 674b, allowing first ends 676a, 676b to deflect inward and second ends 678a, 678b to deflect outward from attachment points 662a, 662b of on-skin sensor assembly 160 as retention elements 672a, 672b rotate about pivot points 680a, 680b. Although two retention elements are illustrated, any number of retention elements are contemplated. Moreover, some alternative mechanisms that may perform such retention and release actions are further described in connection with at least FIGS. 35A-37C below. Any of these alternative mechanisms are contemplated for use with applicator 500.

A brief description of the operation of applicator 500 follows with respect to FIGS. 7A-7F, which illustrate several perspective views of the applicator of FIG. 5 in sequence, during operation, according to some embodiments.

FIG. 7A illustrates a pre-activated state of applicator 500. Applicator housing 502 and slot 582 remain stationary with respect to the skin of the host during activation. Activation element 504 is in a pre-activation position. Insertion assembly 508 is also in a pre-activation position, coupled to holder 524, which is releasably coupled to on-skin sensor assembly 160, as described in connection with at least FIGS. 6A-6H. At least a portion of insertion element 674 of needle carrier assembly 508 is illustrated as protruding, in a distal direction, below on-skin sensor assembly 160. Insertion element 674 may comprises a needle, for example, an open sided-needle, a needle with a deflected-tip, a curved needle, a polymer-coated needle, a hypodermic needle, deflected-tip or any other suitable type of needle or structure, as will be described in more detail in connection with at least FIGS. 47-50 and 80A-B. Insertion element 674 may be configured to guide at least a portion of sensor 138 of on-skin sensor assembly 160. rotating drive element 514 of drive assembly 510 is shown in a pre-activation position, having pin 516 located at a first position within guide 582 of applicator housing 502, and having protrusion 634 in contact with retention element 632. In FIG. 7A, pin 516 is positioned approximately 30 degrees (illustrated as clockwise, though counterclockwise is also contemplated) from a bottom dead center orientation relative to an axis of rotation of rotating drive element 514 that passes through a center of the face on which pin 516 is disposed.

FIG. 7B illustrates a state of applicator 500 at activation. Activation element 504 is illustrated in an activated position, having been pushed longitudinally in the distal direction by a user, for example. In the activated position, activation element 504 deflects retention element 632 such that protrusion 634 of rotating drive element 514 is unimpeded from moving, thus allowing rotating drive element 514 to rotate by the unwinding of spring 512. Since FIG. 7B illustrates applicator 500 just at activation, rotating drive element 514, pin 516, needle carrier assembly 508, insertion element 674, holder 524 and on-skin sensor assembly 160 are still shown in their pre-activation orientations and locations as in FIG. 7A. However, rotating drive element 514 will rotate in the direction of the circular arrow, and needle carrier assembly 508, insertion element 674, holder 524 and on-skin sensor assembly 160 will be driven, by pin 516 under rotating drive element 514 rotation, in the distal direction to the distal insertion position. However, the present disclosure is not so limited, and rotating drive element 514 may be configured to rotate in a direction opposite of the direction of the circular arrow.

FIG. 7C illustrates a state of applicator 500 during activation. Activation element 504 is illustrated in the activated position of FIG. 7B. Rotating drive element 514 is shown as having rotated a portion of a revolution, indicated by the circular arrow, protrusion 634 having advanced beyond retention element 632. Pin 516 is shown as having moved to a second position within guide 582. This second position is shown as being to the left of the first, pre-activation position. Insertion assembly 508, insertion element 674, holder 524 and on-skin sensor assembly 160 are driven in the distal direction toward the distal insertion position when rotating drive element 514 is rotated by a force generated by spring 512.

FIG. 7D illustrates applicator 500 during activation, in the distal insertion position. Activation element 504 is illustrated in the activated position of FIGS. 7B and 7C. Rotating drive element 514 is shown as having rotated clockwise further compared to FIG. 7C, indicated by the circular arrow, protrusion 634 having advanced yet further beyond retention element 632. Pin 516 is shown as having moved to a third position within guide 582, shown as being to the right of the first, pre-activation position and the second, activation position of FIG. 7C. Insertion assembly 508, insertion element 674, holder 524 and on-skin sensor assembly 160 are driven in the distal direction to the distal insertion position as rotating drive element 514 is further rotated by the force generated by spring 512. In this distal insertion position, at least a portion of insertion element 674 as well as at least a portion of sensor 138 of on-skin sensor assembly 160 may be inserted into skin 130 of the host. At this position, retention elements 642, 644 (see FIG. 6) may be engaged and protrusions 652 and 654 (see FIG. 6) may be in contact with one another. In FIG. 7D, pin 516 is positioned approximately 180 degrees (illustrated as clockwise, though counterclockwise is also contemplated) from the bottom dead center orientation relative to the axis of rotation of rotating drive element 514.

FIG. 7E illustrates applicator 500 during activation. Activation element 504 is illustrated in the activated position of FIGS. 7B-7D. Rotating drive element 514 is shown as having rotated further compared to FIG. 7D, indicated by the circular arrow. Pin 516 is shown as having moved to a fourth position within guide 582. This fourth position is shown as being to the right of the first through third positions previously discussed. Insertion assembly 508 and insertion element 674 are now shown as being driven in the proximal direction from the distal insertion position as rotating drive element 514 is further rotated by the force generated by spring 512. Since retention elements 642, 644 (see FIG. 6) are engaged and protrusions 652 and 654 (see FIG. 6) may be in contact with one another, holder 524 and on-skin sensor assembly 160 are shown as separated from needle carrier assembly 508. In the position shown by FIG. 7E, on-skin sensor assembly 160 may also be decoupled from holder 524, as previously described in connection with FIG. 6H.

FIG. 7F illustrates applicator 500 post-activation. Activation element 504 is illustrated in the activated position of FIGS. 7B-7E. Rotating drive element 514 is shown as having rotated further compared to FIG. 7E, indicated by the circular arrow, such that ridge 636 is in contact with retention element 632, thereby restricting further rotation of rotating drive element 514. Pin 516 is shown as having moved to a fifth position within guide 582, which is shown as being to the left of the fourth, right-most position, as pin 516 travels back along guide 582. Insertion assembly 508 and insertion element 674 are shown in the proximal retraction position. Holder 524 and on-skin sensor assembly 160 are shown as separated from needle carrier assembly 508. In the position shown by FIG. 7F, on-skin sensor assembly 160 may also be decoupled from holder 524, as previously described in connection with FIG. 6H. In FIG. 7F, pin 516 is positioned approximately 330 degrees (illustrated as clockwise, though counterclockwise is also contemplated) from the bottom center orientation relative to the axis of rotation of rotating drive element 514.

Figure 8:
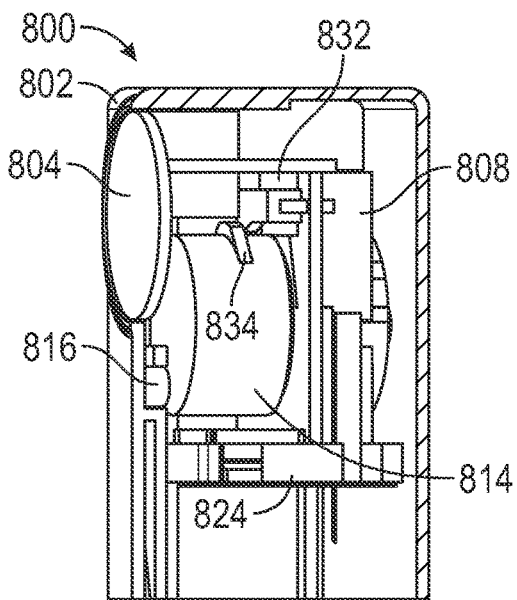
FIG. 8 illustrates a cutaway view of an applicator similar to the applicator of FIG. 5, however, including an activation element on an upper side of an applicator housing, according to some embodiments.
Figure 9:
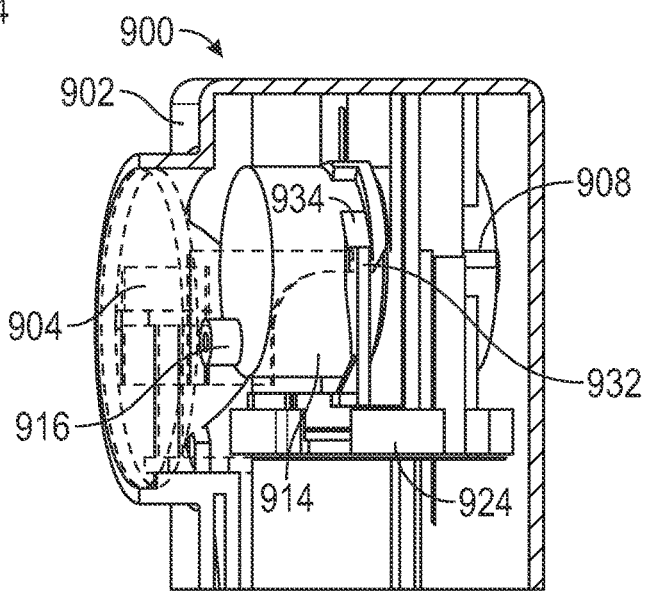
FIG. 9 illustrates a cutaway view of an applicator similar to the applicator of FIG. 5, however, including an activation element on a medial side of an applicator housing, according to some embodiments.
Figure 10:
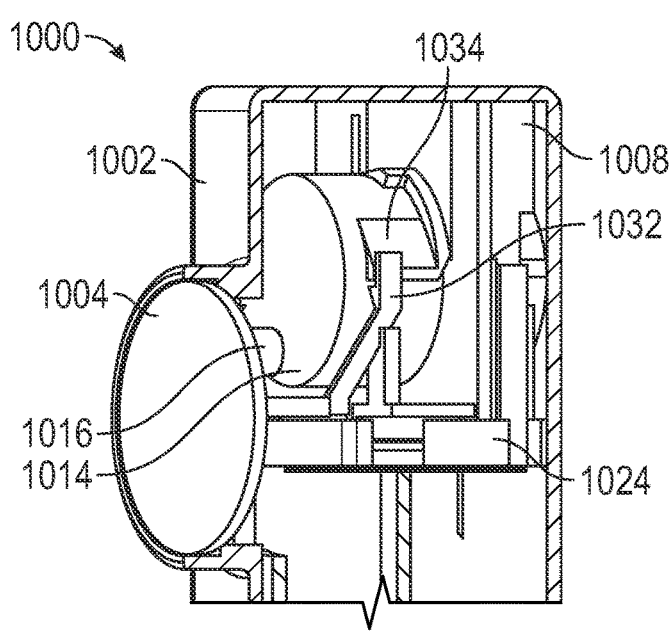
FIG. 10 illustrates a cutaway view of an applicator similar to the applicator of FIG. 5, however, including an activation element on a lower side of an applicator housing, according to some embodiments.

FIGS. 8-10 illustrate cutaway views of applicators 800, 900, 1000 similar to applicator 500 of FIG. 5, however, alternatively having activation elements 804, 904, 1004 disposed on an upper, medial, and lower side of, rather than on a top of, an applicator housing 802, 902, 1002, respectively. Applicators 800, 900, 1000 may comprise substantially all features of applicator 500 and have substantially the same operation. For example, applicator housing 802, 902, 1002, activation element 804, 904, 1004, a needle carrier assembly 808, 908, 1008, a rotating drive element 814, 914, 1014, including a pin 816, 916, 1016 and a protrusion 834, 934, 1034 and a retention element 832, 932, 1032 may correspond substantially to applicator housing 502, activation element 504, needle carrier assembly 508, rotating drive element 514 including pin 516 and protrusion 504, and retention element 502 of applicator 500, respectively.

However, in FIG. 8, activation element 804 is disposed on an upper side, rather than on a top, of applicator housing 802 and may be configured to, upon activation, deflect retention element 832 such that protrusion 834 no longer restrains rotating drive element 814 from rotating under force of a spring (not shown in FIG. 8) similar to spring 512 of applicator 500. In FIG. 9, activation element 904 is disposed on a medial side, rather than on a top, of applicator housing 902 and may be configured to, upon activation, deflect retention element 932 such that protrusion 934 no longer restrains rotating drive element 914 from rotating under force of a spring (not shown in FIG. 9) similar to spring 512 of applicator 500. As shown, due to the medial side location of activation element 904, retention element 932 may be located substantially on a side of rotating drive element 914.

In FIG. 10, activation element 1004 is disposed on a lower side, rather than on a top, of applicator housing 1002 and may be configured to, upon activation, deflect retention element 1032 such that protrusion 1034 no longer restrains rotating drive element 1014 from rotating under force of a spring (not shown in FIG. 10) similar to spring 512 of applicator 500. As shown, due to the lower side location of activation element 1004, retention element 1032 may be located substantially on a side of rotating drive element 1014. 50

An example of steps for assembling an applicator such as applicators 500, 800, 900, 1000 of FIGS. 5 and 8-10 will now be discussed in connection with FIGS. 11A-11I1.

Figure 11A:
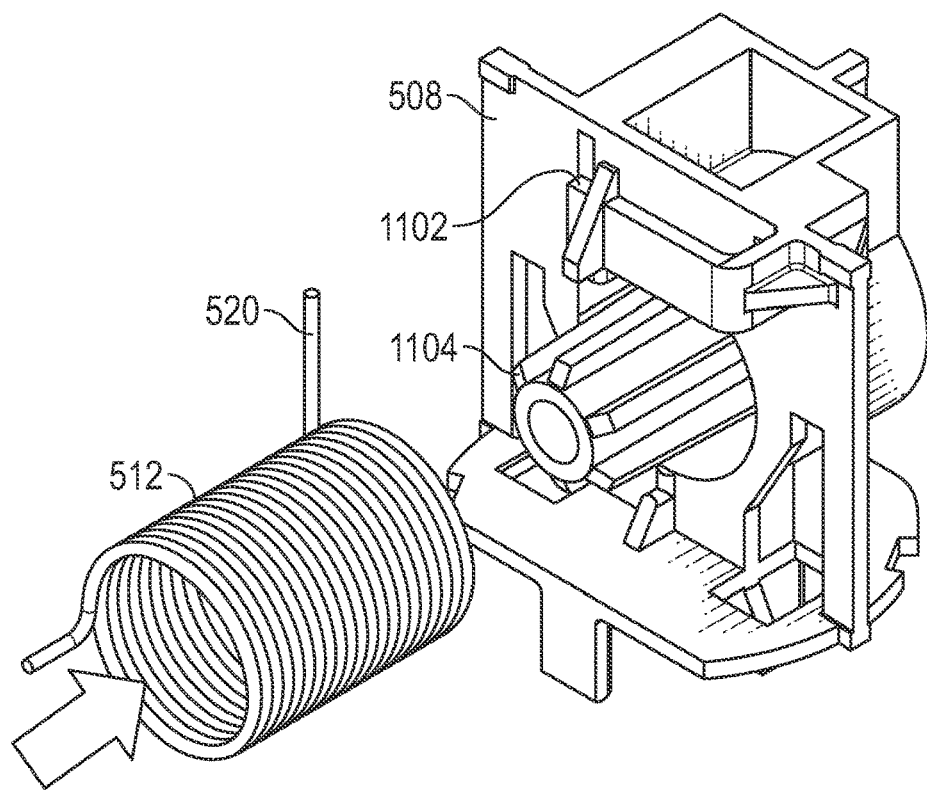

FIG. 11A illustrates coupling first end 520 of spring 512 to needle carrier assembly 508. First end 520 may be coupled to, or disposed against, a protrusion 1102 of needle carrier assembly 508 and spring 512 may be inserted around a hub 1104 of needle carrier assembly 508 such that spring 512 and hub 1104 are disposed coaxially with one another.

Figure 11B:
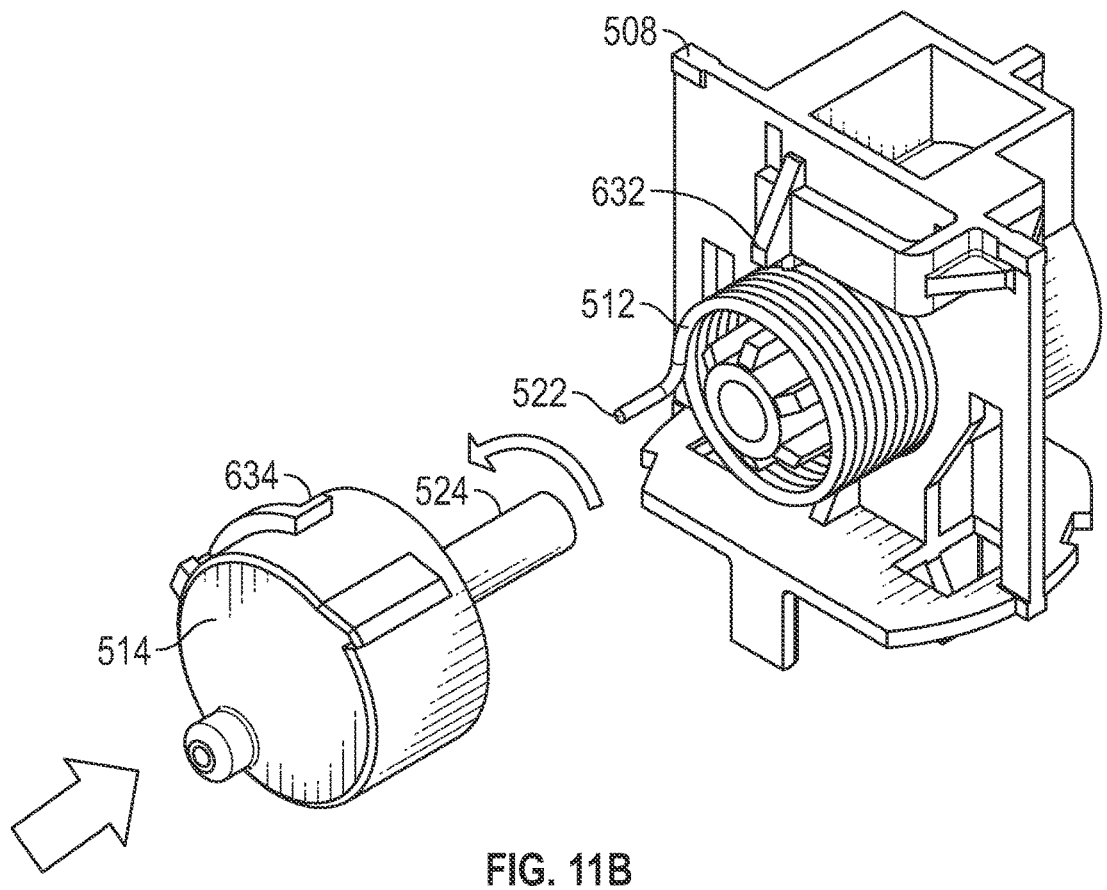

FIG. 11B illustrates coupling second end 522 of spring 512 with rotating drive element 514 and inserting axle 526 into hub 1104 of needle carrier assembly 508 within which axle 526 may rotate. Axle 526, hub 1104, and spring 512 may be disposed coaxially with respect to one another. As shown by the circular arrow, rotating drive element 514 may be rotated about axle 526 in a circular direction opposite of a direction that rotating drive element 514 rotates during activation, thereby pre-storing energy in spring 512. Axle 524 may be fully inserted into the portion of needle carrier assembly 508 such that protrusion 634 is in contact with retention element 632, thereby preventing rotating drive element 514 from rotating until activation. In some embodiments, rotating drive element 514 may be rotated about axle 504 such that spring 512 is only partially wound. In such embodiments, spring 512 may be fully wound at a later stage of assembly. Although FIG. 11B illustrates rotating drive element 514 as having a male-type aspect configured to mate with a female-type aspect of hub 1104, the present disclosure also contemplates rotating drive element 514 as having a female-type aspect configured to mate with a male-type aspect of hub 1104.

Figure 11D:
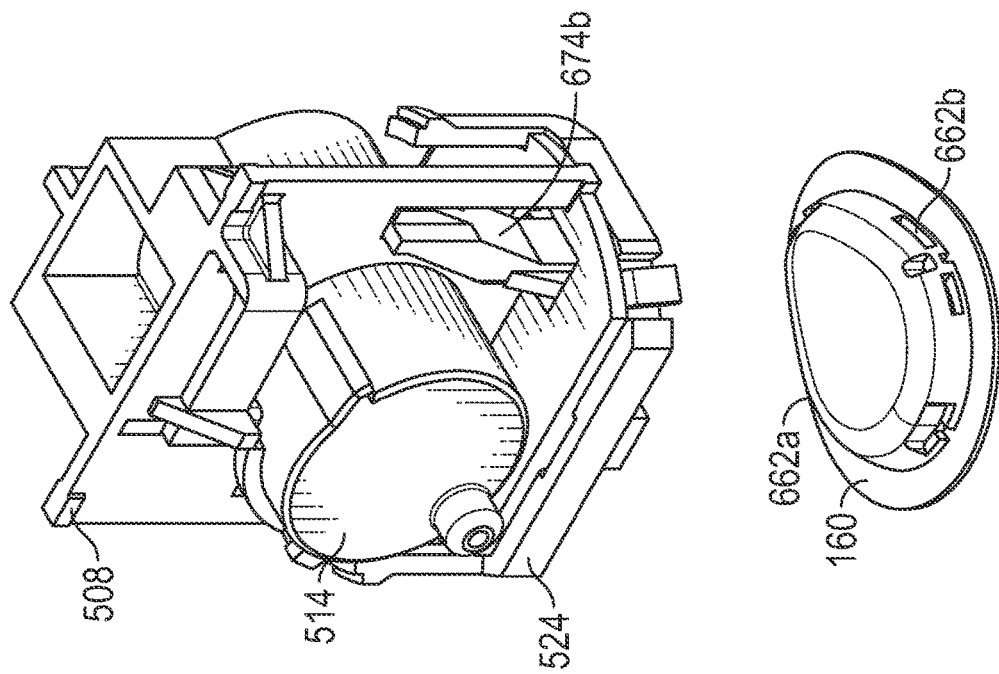
Figure 11C:
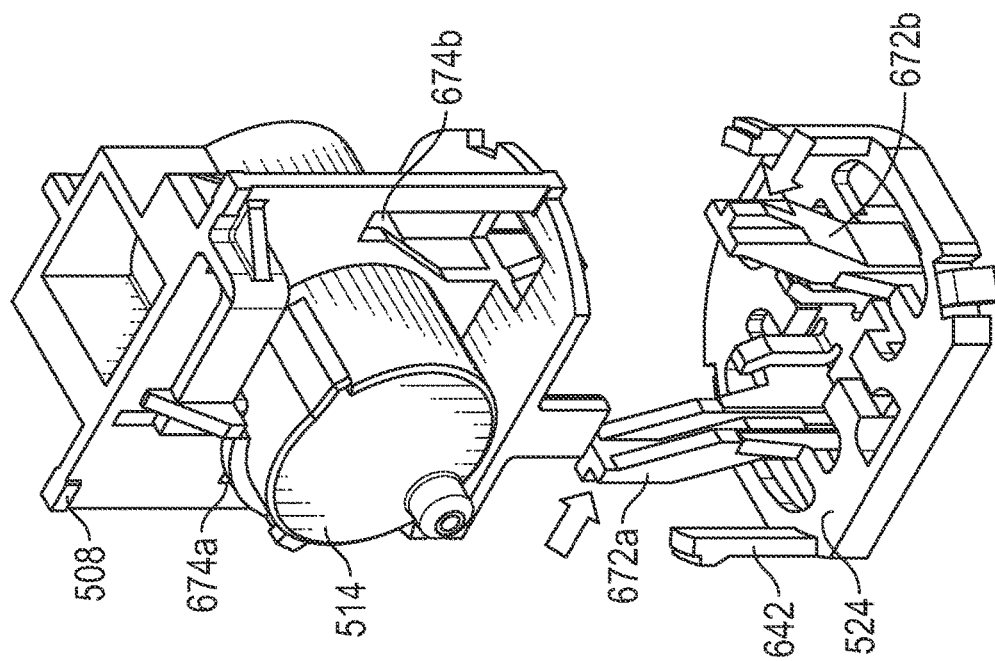

FIG. 11C illustrates pushing retention elements 672a, 672b toward a center of holder 524 and coupling holder 524 to needle carrier assembly 508 by seating first ends 676a, 676b of retention elements 672a, 672b into respective slots 674a, 674b of needle carrier assembly 508.

FIG. 11D illustrates coupling on-skin sensor assembly 160 to holder 524 by snapping second ends 678a, 678b (not shown in FIG. 11D) of retention elements 672a, 672b into attachment points 662a, 662b of on-skin sensor assembly 160. In some embodiments, retention elements 672a, 672b may comprise snap fits, friction fits, interference features, elastomeric grips and/or adhesives.

FIG. 11E illustrates inserting the assembled needle carrier assembly 508, rotating drive element 514, holder 524, and on-skin sensor assembly 160 into applicator housing 502 through the opening in the bottom of applicator housing 502 and through a vertical portion of guide 582 (see FIG. 11F). During such insertion, pin 516 of rotating drive element 514 is inserted along at least the vertical portion of guide 582 in applicator housing 502, as shown in FIG. 11F. Accordingly, spring 512 (not shown in FIGS. 11E, 11F) may not be fully wound at this point, instead being partially wound to the extent that pin 516 of rotating drive element 514 is positioned to be inserted along guide 582 in applicator housing 502.

FIG. 11G illustrates positioning the assembled needle carrier assembly 508, rotating drive element 514, holder 524, and on-skin sensor assembly 160 further in the proximal direction into applicator housing 502 such that pin 516 of rotating drive element 514 follows guide 582 of applicator housing 502, thereby turning rotating drive element 514 fully winding spring 512 (not shown in FIG. 11G) and positioning protrusion 634 in contact with retention element 632 such that the drive assembly, comprising at least rotating drive element 514, having pin 516, and spring 512, are loaded for activation.

FIG. 11H illustrates a magnified cutaway view of area 1106 of FIG. 11G illustrating the relationship between rotating drive element 514, pin 516, guide 582, protrusion 634 and retention element 632.

FIG. 11J illustrates inserting activation element 504 into applicator housing 502.

Figure 12:
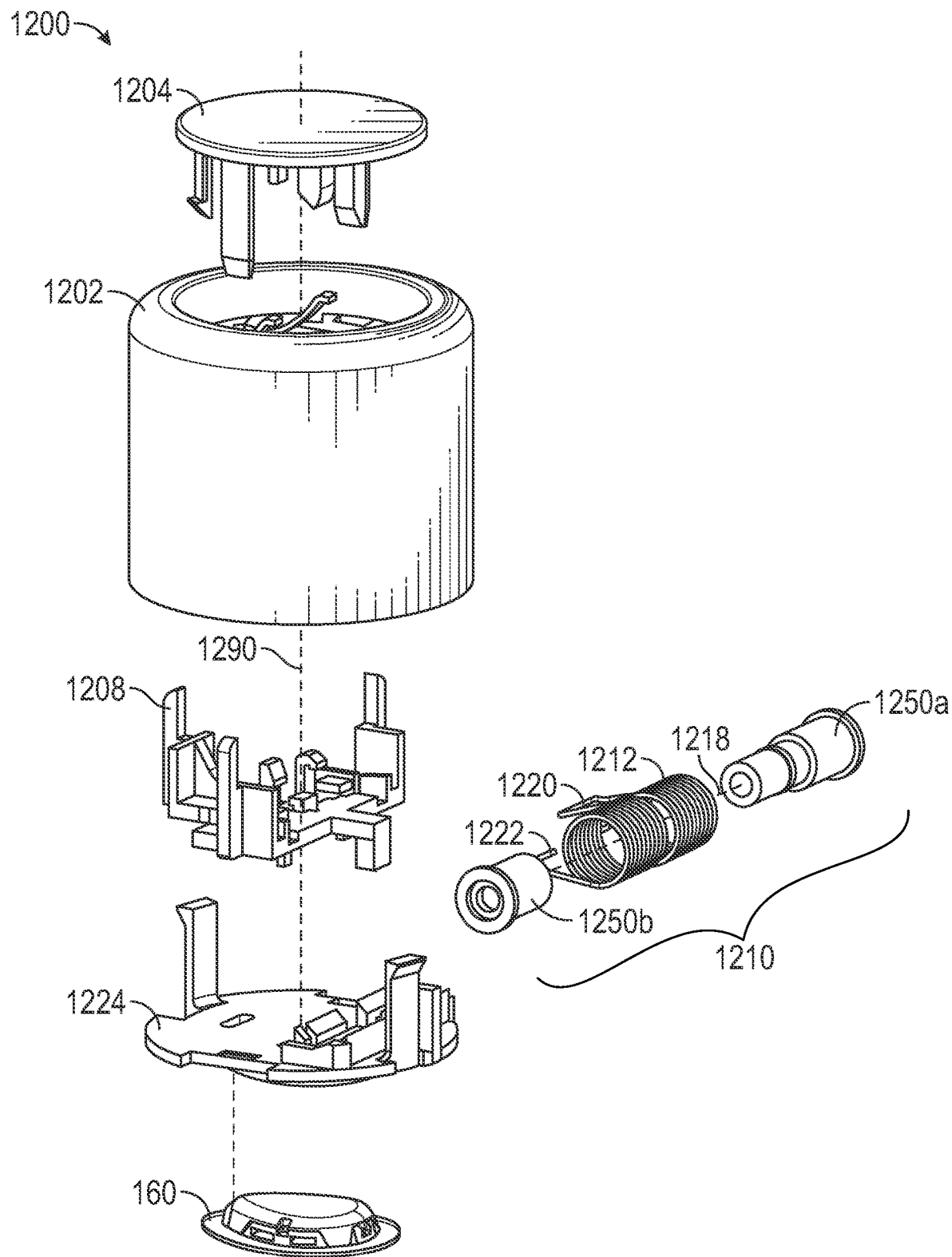
FIG. 12 illustrates an exploded perspective view of another applicator for an on-skin sensor assembly of an analyte sensor system, according to some embodiments.

FIG. 12 illustrates an exploded perspective view of another applicator 1200 for applying an on-skin sensor assembly to a skin of a host, according to some embodiments. Applicator 1200 may include an applicator housing 1202 having an opening in its bottom and configured to house at least one or more mechanisms utilized to apply on-skin sensor assembly 160 to skin 130 (see FIG. 2) of a host.

Applicator 1200 includes an activation element 1204 configured to activate a drive assembly of applicator 1200. In some embodiments, activation element 1204 may be a button, a switch, a toggle, a slide, a trigger, a knob, a rotating member, a component that deforms and/or flexes or any other suitable mechanism for activating a drive assembly of applicator 1200. Applicator 1200 may further comprise a needle carrier assembly 1208, including an insertion element (not shown in FIG. 12) configured to insert sensor 138 of on-skin sensor assembly 160 (e.g., FIG. 1) into skin 130 of the host. In some embodiments, the insertion element comprises a needle, for example a C-needle, as will be described in more detail in connection with at least FIGS. 47-50 and 80A-B.

Applicator 1200 may further comprise a drive assembly 1210 configured to drive the insertion element of needle carrier assembly 1208 in the distal direction to a distal insertion position and in the proximal direction from the distal insertion position to a proximal retraction position. A distal direction may be defined as extending towards an open-ended side of the applicator 1200 along a path needle carrier assembly 1208 is configured to travel. The distal direction may also be defined as towards the skin of a user. A proximal direction may be defined as a direction extending in a substantially opposite direction from the distal direction. In some embodiments, the distal direction and the proximal direction extend along an insertion axis of the insertion element and of needle carrier assembly 1208.

Drive assembly 1210 may include a spring 1212 having a first tang 1220 (e.g., end) and a second tang 1222 (e.g., end). Spring 1212 may be a torsion spring, a double torsion spring, or any other suitable type of spring. Spring 1212 may be supported by a spring spool 1250 comprising a first portion 1250a and an optional second portion 1250b. In some embodiments, spring 1212 is self-supporting and is not supported by a spring spool. First portion 1250a may be configured to couple with second portion 1250b such that spring spool 1250 is disposed coaxially with spring 1212 and provides support for spring 1212 along an axis of rotation 1218 of spring 1212. As will be shown in more detail in connection with FIG. 13, first tang 1220 of spring 1212 may be coupled to applicator housing 1202, e.g., to a hook or protrusion of applicator housing 1202. Second tang 1222 may be coupled to needle carrier assembly 1208, e.g., a hook or protrusion of needle carrier assembly 1208. Upon activation of drive assembly 1210, first tang 1220 and second tang 1222 of spring 1212 unwind in opposite clockwise or counterclockwise directions, thereby driving spring 1212 in an arc and insertion element 1208 in the distal direction to the distal insertion position and in the proximal direction from the distal insertion position. The arc through which drive assembly 1210 travels may extend in a direction approximately perpendicular to the distal direction and the proximal direction, or in an arc defined by the tangs of the spring and the rotation points.

Applicator 1200 may further include a holder 1224 releasably coupled to needle carrier assembly 1208 and configured to guide on-skin sensor assembly 160 while coupled to needle carrier assembly 1208. In some embodiments, holder 1224 may comprise a stripper plate. As will be described in more detail below, on-skin sensor assembly 160 may be stripped from holder 1224 and needle carrier assembly 1208 once on-skin sensor assembly 160 is disposed on skin 130 of the host.

Figure 13D:
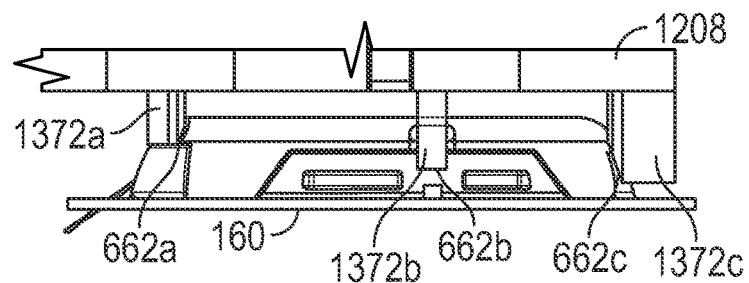

FIG. 13A-13F illustrate perspective and cutaway views of several features of applicator 1200 of FIG. 12, according to some embodiments. FIG. 13A illustrates a cross-sectional view of applicator 1200, including applicator housing 1202 having retention element 1334, activation element 1204, spring spool 1250, spring 1212 having first tang 1220 and second tang 1222, needle carrier assembly 1208 having retention element 1332, holder 1224, and on-skin sensor assembly 160. In some embodiments, retention element 1332 may comprise snap fits, friction fits, interference features, elastomeric grips and/or adhesives configured to couple on-skin sensor assembly 160 with needle carrier assembly 1208 and/or holder 1224. Each of these components may have functionality as previously described in connection with at least FIG. 12. Moreover, first tang 1220 is configured to, upon activation of the drive assembly, rotate about a rotation point 1336. Second tang 1222 is similarly configured.

Figure 13E:
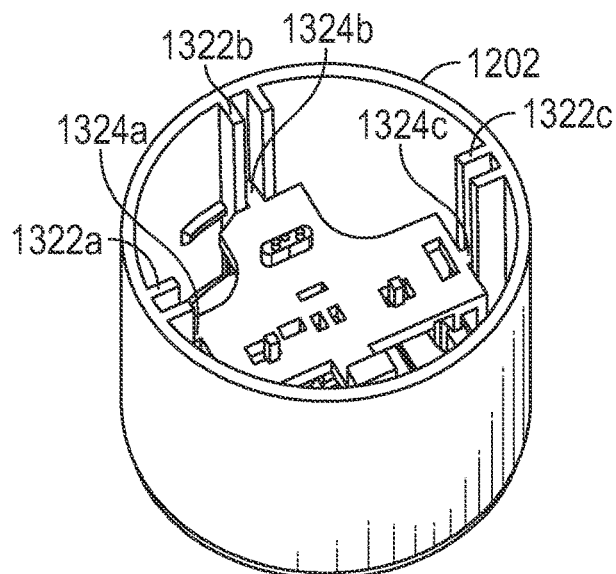
Figure 13F:
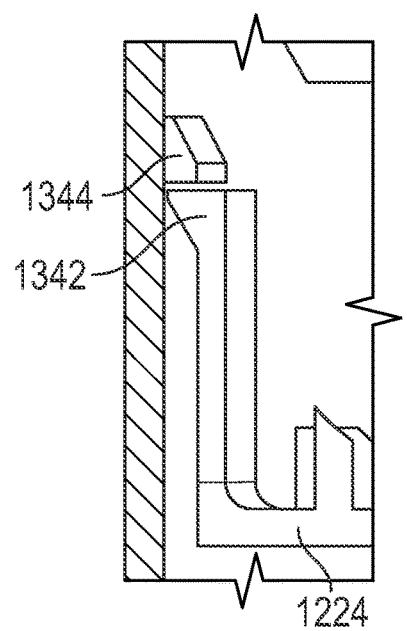

FIG. 13F illustrates a magnified perspective view of a retention element 1342 of holder 1224 and a stop element 1344 of applicator housing 1202 configured to immobilize holder 1228 to applicator housing 1202 upon needle carrier assembly 1208 reaching the distal insertion position. In some embodiments, retention element 1342 is a deflectable arm. For example, as needle carrier assembly 1208 travels in the distal direction, as a result of spring 1212 partially unwinding, retention element 1342 slides along an inside surface of applicator housing 1202 and is deflected by stop element 1344 until retention element 1342 snaps under stop element 1344. In some embodiments, the functionality between retention element 1342 and stop element 1344 may be swapped, e.g., stop element 1344 may be configured to be deflected by and snap over retention element 1342. At this point, though needle carrier assembly 1208 may be free to progress in the proximal direction, as a result of spring 1212 unwinding further, stop element 1344 will prevent retention element 1342, and so holder 1224, from traveling back in the proximal direction. In this way, movement of needle carrier assembly 1208 in the proximal direction after reaching the distal insertion position allows holder 1224 and/or needle carrier assembly 1208 to be released from on-skin sensor assembly 160.

FIG. 13B illustrates a magnified cutaway view of a portion of needle carrier assembly 1208 comprising a retention element 1332 configured to interlock with a retention element 1334 of applicator housing 1202 and prevent needle carrier assembly 1208 from separating from applicator housing 1202 in the loaded, pre-activated position. Activation element 1204 is configured to deflect retention element 1332 such that retention element 1334 no longer holds retention element 1332, thereby allowing spring 1212 to separate needle carrier assembly 1208 from applicator housing 1202 and activating drive assembly 1210.

FIG. 13C illustrates a magnified view of second tang 1222 of a spring coupled to needle carrier assembly 1208, for example, via a hook 1348 configured to immobilize second tang 1222 to needle carrier assembly 1208. The fastening concept described for second tang 1222 in FIG. 13C may also be utilized for first tang 1220.

FIG. 13D illustrates on-skin sensor assembly 160 including a plurality of attachment points 662a-662c configured to mate with respective retention elements 1372a-1372c on needle carrier assembly 1208 and/or holder 1224 while traveling in the distal direction at least partially toward the distal insertion position during applicator activation. In some embodiments, where holder 1224 comprises a stripper plate, holder 1224 may function similarly to a stripper plate in punch and die manufacturing or injection molding processes. Although a plurality of attachment points 662a-662c are illustrated, any number of attachment points are contemplated. In some embodiments, retention elements 1372a-1372c may comprise snap fits, friction fits, interference features, elastomeric grips and/or adhesives.

Retention elements 1372a-1372c of needle carrier assembly 1208 and/or holder 1224 are configured to releasably couple on-skin sensor assembly 160 to holder 1228 as needle carrier assembly 1208 travels in the distal direction to the distal insertion position, and to decouple on-skin sensor assembly 160 from needle carrier assembly 1208 and/or holder 1228 as needle carrier assembly 1208 travels in the proximal direction from the distal insertion position towards the proximal retraction position. Specifically, since retention elements 1342, 1344 immobilize holder 1224 from traveling in the proximal direction at the distal insertion position, as needle carrier assembly 1208 travels back in the proximal direction. This causes needle carrier assembly 1208 to separate from holder 1224 and on-skin sensor assembly 160, thereby decoupling retention elements 1372a-1372c from attachment points 662a-662c of on-skin sensor assembly 160. Although two retention elements are illustrated, any number of retention elements are contemplated. Moreover, alternative mechanisms that may perform such retention and release actions are further described in connection with at least FIGS. 35A-37C below. Any of these alternative mechanisms are contemplated for use with applicator 1200.

FIG. 13E illustrates a perspective view of a plurality of tracks 1322a, 1322b, 1322c in applicator housing 1202 in which a respective plurality of protrusions 1324a, 1324b, 1324c of needle carrier assembly 1208 are configured to slide. Accordingly, tracks 1322a-1322c in applicator housing 1202 define a path of travel for needle carrier assembly 1208. In some embodiments, this path of travel is substantially linear and longitudinal. Although three tracks and protrusions are shown in FIG. 13E, a single track or a plurality of tracks and respective protrusions are contemplated.

A brief description of the operation of applicator 1200 follows with respect to FIGS. 14A-14E, which illustrate several cross-sectional views of the applicator of FIG. 12 during operation, according to some embodiments.

Figure 14A:
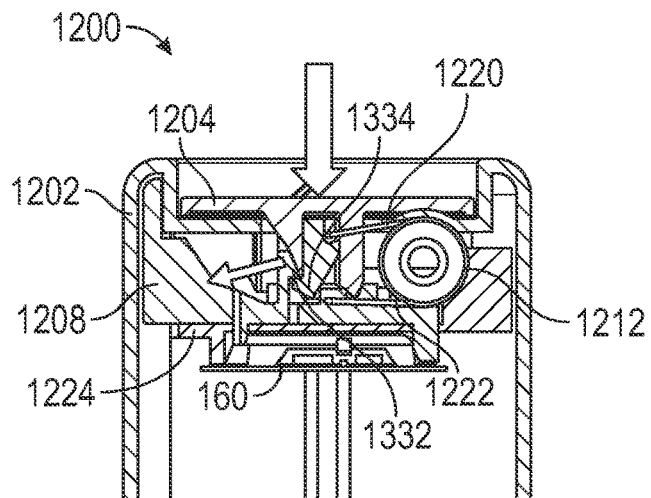
FIGS. 14A-14E illustrate several cross-sectional views of the applicator of FIG. 12 during operation, according to some embodiments.

FIG. 14A illustrates a state of applicator 1200 at activation. Activation element 1204 is illustrated in an activated position, having been pushed longitudinally in the distal direction by a user, for example. In the activated position, activation element 1204 deflects retention element 1332 such that retention element 1334 of applicator housing 1202 does not prevent needle carrier assembly 1208 from moving when spring 1212 unwinds from a pre-wound state. Since FIG. 14A illustrates applicator 1200 just at activation, spring 1212, needle carrier assembly 1208, holder 1224 and on-skin sensor assembly 160 are shown in their pre-activation orientations and locations. However, spring 1212 will unwind partially and needle carrier assembly 1208, holder 1224 and on-skin sensor assembly 160 will be driven, by such unwinding, in the distal direction to the distal insertion position.

Figure 14B:
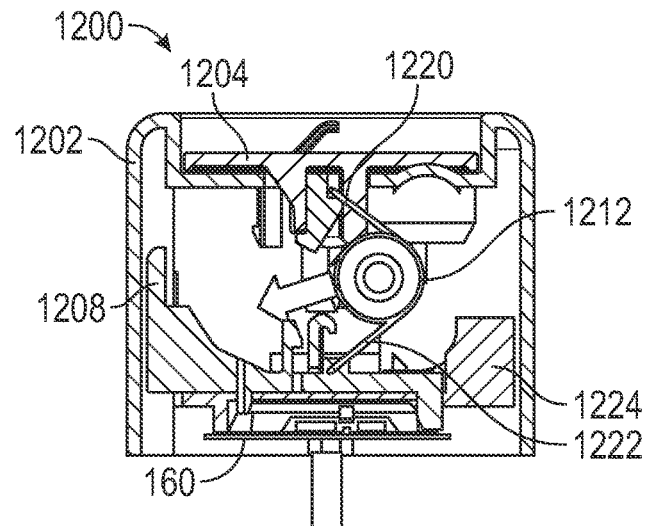

FIG. 14B illustrates a state of applicator 1200 during activation. Activation element 1204 is illustrated in the activated position of FIG. 14A. Spring 1212 has partially unwound such that first tang 1220 unwinds in a first arc-direction and second tang 1222 unwinds in a second arc-direction opposite of the first arc-direction. Spring 1212 travels through an arc-direction approximately perpendicular to the distal direction and the proximal direction, or in an arc defined by the tangs of spring 1212 and their associated rotation points. As a result, needle carrier assembly 1208, insertion element 1374, holder 1224 and on-skin sensor assembly 160 are driven in the distal direction toward the distal insertion position by a force generated by spring 1212.

Figure 14C:
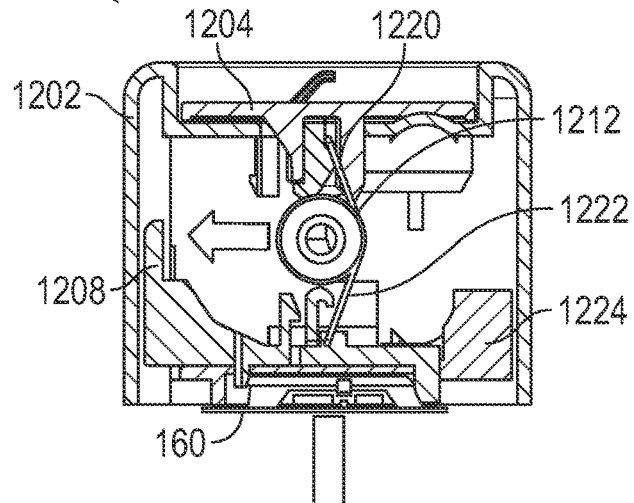

FIG. 14C illustrates applicator 1200 during activation, in a distal insertion position. Activation element 1204 is illustrated in the activated position of FIGS. 14A and 14B. Spring 1212 has unwound further, relative to its position as illustrated in FIGS. 14A and 14B, substantially in the direction of the horizontal arrow. Insertion assembly 1208, holder 1224 and on-skin sensor assembly 160 are driven in the distal direction to the distal insertion position by the force generated by spring 1212. In this distal insertion position, at least a portion of an insertion element coupled to needle carrier assembly 1208 similarly to that shown in FIG. 6 (not shown in FIGS. 14A-14E) as well as at least a portion of sensor 138 of on-skin sensor assembly 160 (e.g., FIG. 1) may be inserted into skin 130 of the host. At this position, although not shown, retention elements 1342, 1344 (see FIG. 13) may be engaged with one another.

Figure 14D:
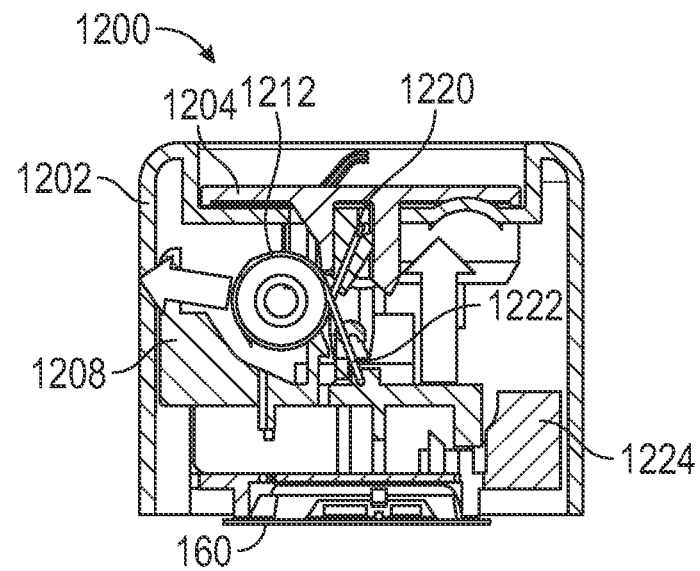

FIG. 14D illustrates applicator 1200 during activation. Activation element 1204 is illustrated in the activated position of FIGS. 14A-14C. Spring 1212 has further unwound and travelled in substantially the same direction as shown by the arrow. Where unwinding of spring 1212 in FIGS. 14A-14C caused movement of the needle carrier assembly 1208 in the distal direction, because spring 1212 is now on an opposite side of the points at which the first tang 1220 and the second tang 1222 are anchored, further unwinding of spring 1212 results in movement of the needle carrier assembly 1208 in the proximal direction toward the proximal retraction position. Since the retention elements (see FIG. 13) are engaged, holder 1224 and on-skin sensor assembly 160 are shown as separated from needle carrier assembly 1208. In the position shown by FIG. 14D, on-skin sensor assembly 160 may also be decoupled from holder 1224, as previously described in connection with call-out 1330 of FIG. 13.

Figure 14E:
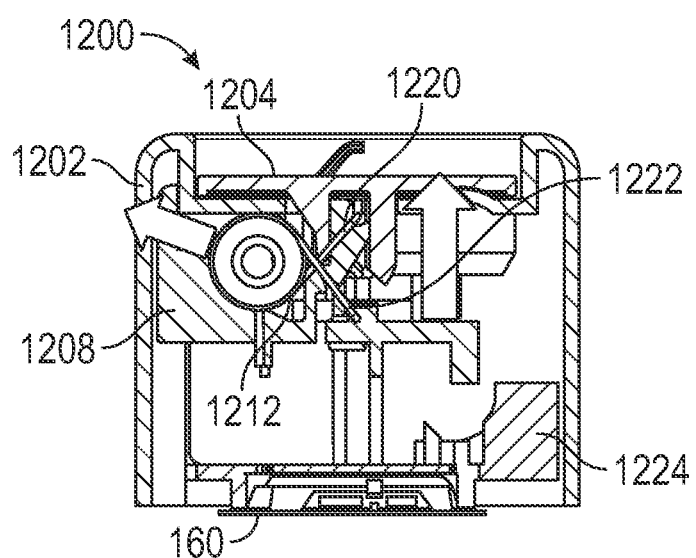

FIG. 14E illustrates applicator 1200 post-activation. Activation element 1204 is illustrated in the activated position of FIGS. 14A-14D. Spring 1212 is illustrated as having unwound further compared to its position as illustrated in FIG. 14D and having travelled substantially in the direction indicated by the arrow. Insertion assembly 1208 has travelled in the proximal direction indicated by the vertical arrow to the proximal retraction position. Holder 1224 and on-skin sensor assembly 160 are shown as separated from needle carrier assembly 1208.

Figure 15:
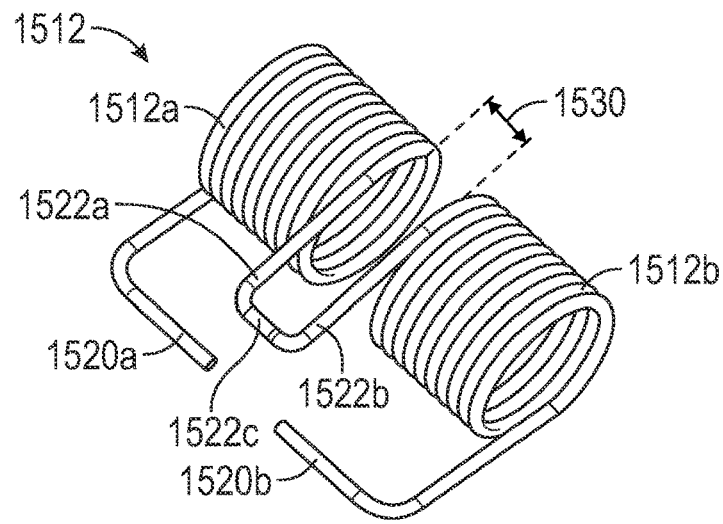
FIG. 15 illustrates a perspective view of an exemplary double torsional spring for use in an applicator for an on-skin sensor assembly of an analyte sensor system, according to some embodiments.
Figure 16:
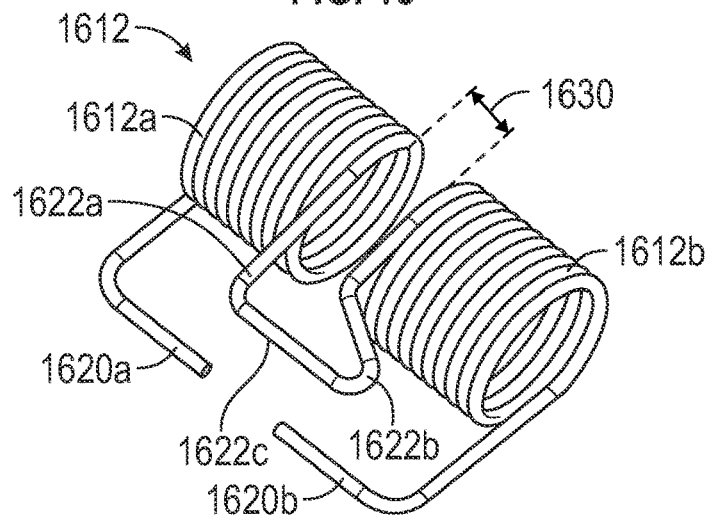
FIG. 16 illustrates a perspective view of another exemplary double torsional spring for use in an applicator for an on-skin sensor assembly of an analyte sensor system, according to some embodiments.
Figure 17:
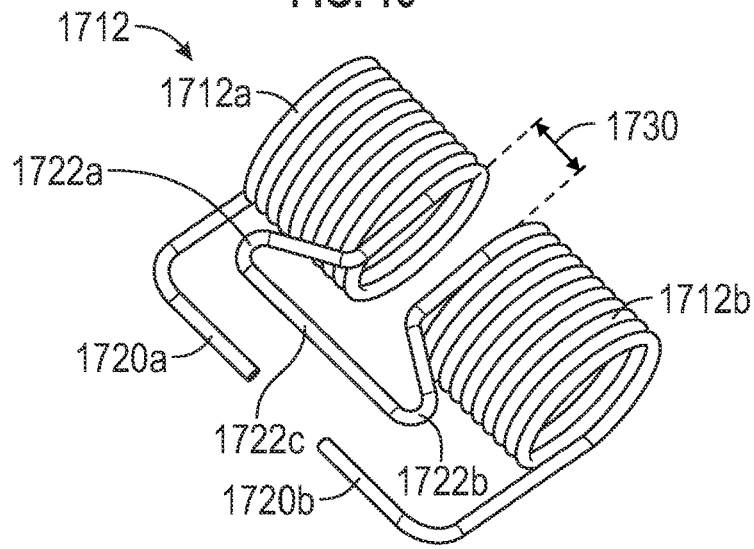
FIG. 17 illustrates a perspective view of yet another exemplary double torsional spring for use in an applicator for an on-skin sensor assembly of an analyte sensor system, according to some embodiments.

FIGS. 15-17 illustrate perspective views of several exemplary double torsional springs that support different configurations of applicator 1200, according to some embodiments. Accordingly, any of the springs described by FIGS. 15-17 may be utilized for spring 1212 previously discussed in connection with FIGS. 12-14E. As shown in FIGS. 15-17, different shaped and/or sized cross-bridges 1522c, 1622c, 1722c of springs 1512, 1612, 1712 may be provided by flaring one or more tangs in a particular direction.

For example, FIGS. 15-17 illustrate double torsional springs 1512, 1612, 1712, each comprising a first winding 1512a, 1612a, 1712a and a second winding 1512b, 1612b, 1712b. Double torsional springs 1512, 1612, 1712 may be formed from a single segment of suitable material, e.g., metal or plastic. First windings 1512a, 1612a, 1712a each comprise a first tang 1520a, 1620a, 1720a and a second tang 1522a, 1622a, 1722a. Second windings 1512b, 1612b, 1712b each comprise a first tang 1520b, 1620b, 1720b and a second tang 1522b, 1622b, 1722b. For each spring 1512, 1612, 1712, second tangs 1522a, 1522b; 1622a, 1622b; 1722a, 1722b may be coupled to one another by a cross-bridge 1522c, 1622c, 1722c. Cross-bridge 1522c of FIG. 15 may have a length substantially equal to a spacing 1530 between first winding 1512a and second winding 1512b defined by the extension of second tangs 1522a, 1522b from first winding 1512a and second winding 1512b, respectively. Cross-bridge 1622c of FIG. 16 may have a length exceeding a spacing 1630 between first winding 1612a and second winding 1612b defined by the extension of second tangs 1622a, 1622b from first winding 1612a and second winding 1612b, respectively, due to second tang 1622b of second winding 1612b being flared toward first tang 1620b of second winding 1612b. Cross-bridge 1722c of FIG. 17 may have a length exceeding a spacing 1730 between first winding 1712a and second winding 1712b defined by the extension of second tangs 1722a, 1722b from first winding 1712a and second winding 1712b, respectively, due to second tang 1722a of first winding 1712a being flared toward first tang 1720a of first winding 1712a and second tang 1722b of second winding 1712b being flared toward first tang 1720b of second winding 1712b to provide the increased length of cross-bridge 1722c compared to either cross-bridge 1522c shown in FIG. 15 or cross-bridge 1622c shown in of FIG. 16.

Figure 18:
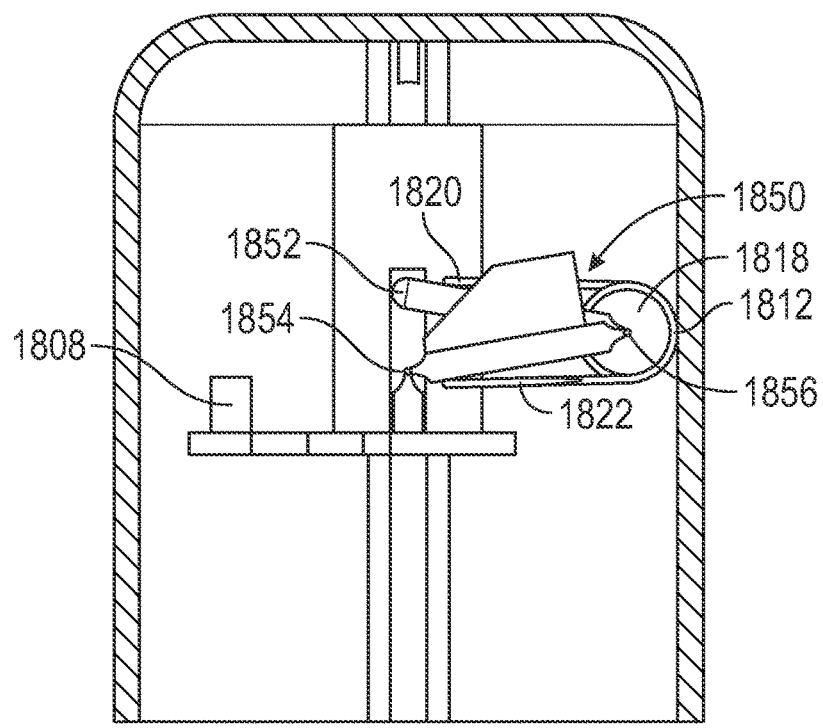
FIG. 18 illustrates a cutaway view of an alternative driving mechanism including a torsional spring and a living hinge for the applicator of FIG. 12, according to some embodiments.

FIGS. 18-23 illustrate alternative drive assemblies for utilization in applicators, such as applicator 1200 of FIG. 12, according to some embodiments. FIG. 18 illustrates a drive assembly comprising a linkage element 1850. In some embodiments, linkage element 1850 may comprise a flex linkage. The flex linkage may contain one or more living hinge(s). In other embodiments, linkage element 1850 may comprise at least two discrete sections configured to pivot about a hinge coupling the at least two discrete sections.

A flex linkage is a type of hinge assembly formed from an extension of a parent material (e.g., polypropylene plastic). The hinge flex linkage is a thin section of the parent material that acts as a bending connection with two larger sections of the parent material. Typically, the larger sections of the parent material as well as the hinge will be made of one continuous piece of the parent material. Since it is relatively thin and typically made from flexible materials, the flex linkage is also able to rotate about one axis by 180 degrees or more—potentially for many thousands or even millions of cycles. Contrary to most hinges, which involve multiple parts assembled in a traditional pivoting mechanism, flex linkages are not a separate entity. They may be described as a purposeful fault line at a predetermined point in the material which is designed such that it does not fail after repeated bending.

Linkage element 1850 has a first end 1852 coupled to an applicator housing 1802, a second end 1854 coupled to a needle carrier assembly 1808, and a hinge 1856 disposed between first end 1852 and second end 1854.

The drive assembly further comprises a spring 1812, which in some embodiments may be a single or double torsion spring. Spring 1812 comprises a first tang 1820 coupled to applicator housing 1802 and/or to linkage element 1850 at first end 1852 or at a position between first end 1852 and hinge 1856. Spring 1812 further comprises a second tang 1822 coupled to needle carrier assembly 1808 and/or to linkage element 1850 at second end 1854 or at a position between second end 1854 and hinge 1856. In some embodiments, hinge 1856 may be aligned with an axis of rotation 1818 of spring 1812 to provide smooth operation as well as to reduce any stresses caused by incompatible movement between linkage element 1850 and spring 1812.

Applicator 1200, utilizing drive assembly 1810, may function substantially as described for applicator 1200 of FIG. 12, however, further including that first end 1852, second end 1854 and hinge 1856 of linkage element 150 move substantially in alignment with first tang 1820, second tang 1822 and axis of rotation 1818 of spring 1812, respectively, during activation.

Figure 19:
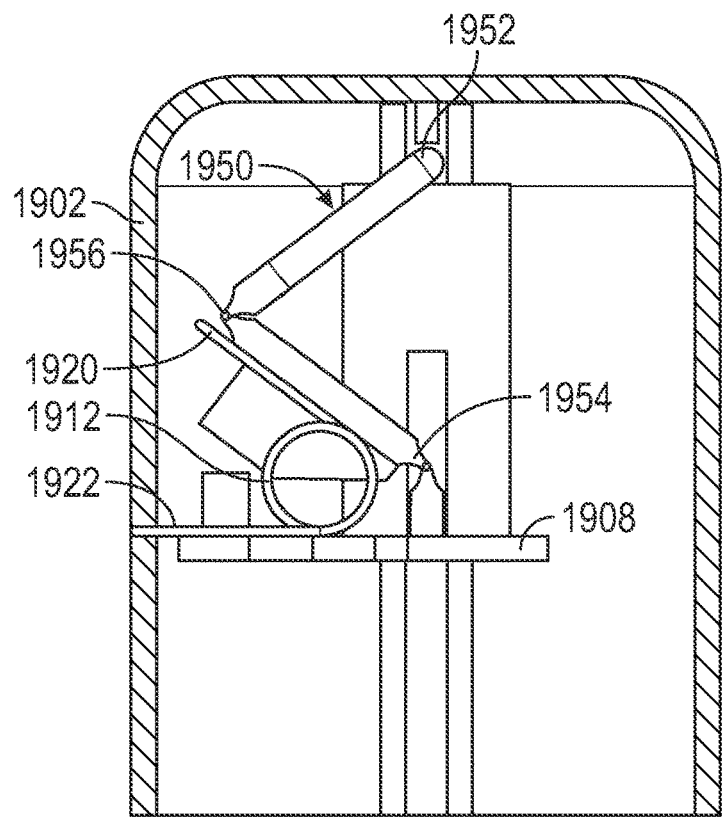
FIG. 19 illustrates a cutaway view of another alternative driving mechanism including a torsional spring and a living hinge for the applicator of FIG. 12, according to some embodiments.

FIG. 19 illustrates another drive assembly comprising a linkage element 1950. Linkage element 1950 has a first end 1952 coupled to an applicator housing 1902, a second end 1954 coupled to a needle carrier assembly 1908, and a hinge 1956 disposed between first end 1952 and second end 1954. The drive assembly further comprises a spring 1912, which in some embodiments may be a single or double torsion spring. Spring 1912 comprises a first tang 1920 coupled to linkage element 1950 between second end 1954 and hinge 1956. Spring 1912 further comprises a second tang 1922 coupled to needle carrier assembly 1908. Upon activation, spring 1912 unwinds and first tang 1952 sweeps an arc while second tang 1954 is held substantially stationary against needle carrier assembly 1908. As first tang 1952 sweeps its arc, first tang 1952 drives linkage element 1950 from the bent position shown, hinge 1956 pivoting, until linkage element 1950 is substantially vertical, and then continuing pivoting until linkage element 1950 is in a substantially mirror orientation from that shown in FIG. 19. This motion drives needle carrier assembly 1908 in the distal direction, reaching the distal insertion position when linkage element 1950 is substantially vertical, and then increasingly in the proximal direction as linkage element 1950 is further driven from the substantially vertical orientation to the substantially mirrored orientation to that shown in FIG. 19.

Figure 20:
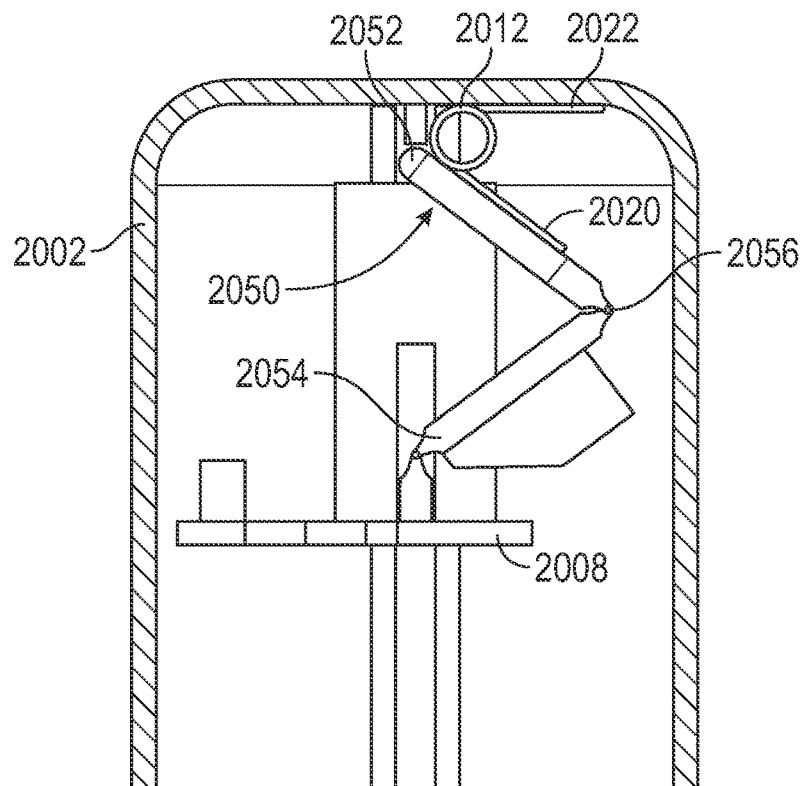
FIG. 20 illustrates a cutaway view of yet another alternative driving mechanism including a torsional spring and a living hinge for the applicator of FIG. 12, according to some embodiments.

FIG. 20 illustrates another drive assembly comprising a linkage element 2050. Linkage element 2050 has a first end 2052 coupled to an applicator housing 2002, a second end 2054 coupled to a needle carrier assembly 2008, and a hinge 2056 disposed between first end 2052 and second end 2054. The drive assembly further comprises a spring 2012, which in some embodiments may be a single or double torsion spring. Spring 2012 comprises a first tang 2020 coupled to linkage element 2050 between first end 2052 and hinge 2056. Spring 2012 further comprises a second tang 2022 coupled to applicator body 2002. Upon activation, spring 2012 unwinds and first tang 2052 sweeps an arc while second tang 2054 is held substantially stationary against applicator body 2002. As first tang 2052 sweeps its arc, first tang 2052 drives linkage element 2050 from the bent position shown, hinge 2056 pivoting, until linkage element 2050 is substantially vertical, and then continuing pivoting until linkage element 2050 is in a substantially mirror orientation from that shown in FIG. 20. This motion drives needle carrier assembly 2008 in the distal direction, reaching the distal insertion position when linkage element 2050 is substantially vertical, and then increasingly in the proximal direction as linkage element 2050 is further driven from the substantially vertical orientation to the substantially mirrored orientation to that shown in FIG. 20.

Figure 21:
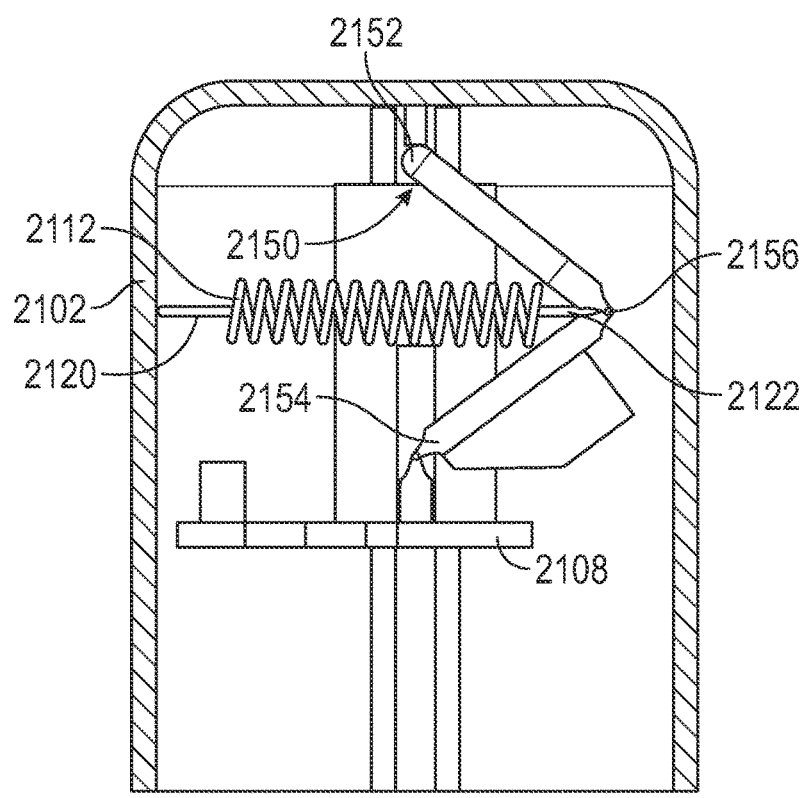
FIG. 21 illustrates a cutaway view of yet another alternative driving mechanism including an extension spring and a living hinge for the applicator of FIG. 12, according to some embodiments.

FIG. 21 illustrates another drive assembly comprising a linkage element 2150. Linkage element 2150 has a first end 2152 coupled to an applicator housing 2102, a second end 2154 coupled to a needle carrier assembly 2108, and a hinge 2156 disposed between first end 2152 and second end 2154. The drive assembly further comprises a spring 2112, which in some embodiments may be an extension spring. A compression spring is also contemplated. However, a compression spring may be coupled between hinge 2156 and the closer side of applicator housing 2102. Spring 2112 comprises a first end 2120 coupled to linkage element 2150 and a second end 2122 coupled to applicator body 2102. In some embodiments, first end 2120 is coupled to linkage element 2150 between first end 2152 and hinge 2156. In other embodiments first end 2120 is coupled to linkage element 2150 at hinge 2156. In yet other embodiments first end 2120 is coupled to linkage element 2150 between hinge 2156 and second end 2154. Upon activation, spring 2112 unwinds through an arc that extends in a direction approximately perpendicular to the distal direction and the proximal direction, or in an arc defined by the tangs of the spring and their respective rotation points, driving linkage element 2150 from the bent position shown, hinge 2156 pivoting, until linkage element 2150 is substantially vertical, and then continuing pivoting until linkage element 2150 is in a substantially mirror orientation from that shown in FIG. 21. This motion drives needle carrier assembly 2108 in the distal direction, reaching the distal insertion position when linkage element 2150 is substantially vertical, and then increasingly in the proximal direction as linkage element 2150 is further driven from the substantially vertical orientation to the substantially mirrored orientation to that shown in FIG. 21.

Figure 22:
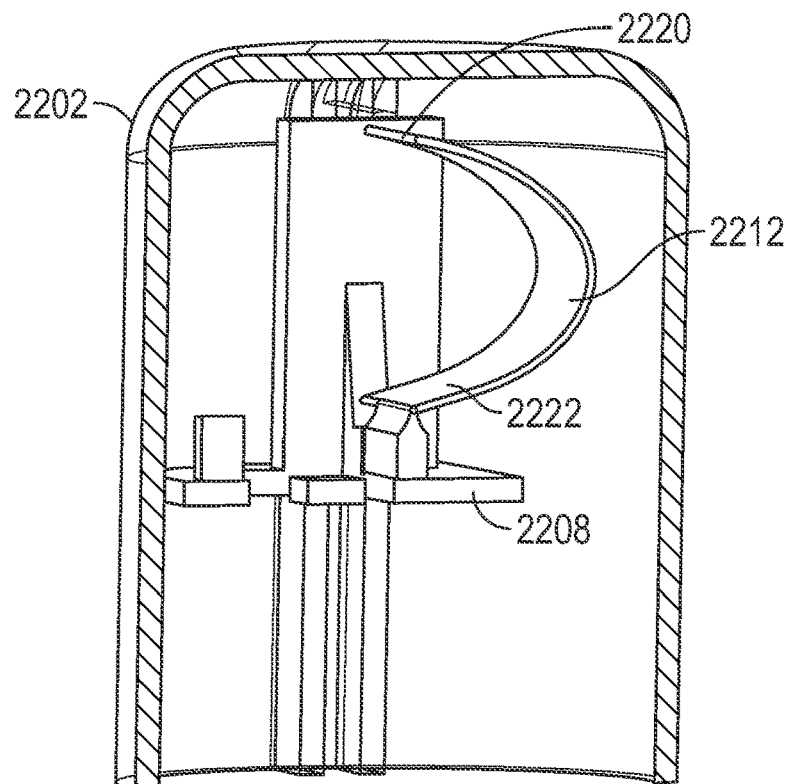
FIG. 22 illustrates a cutaway view of yet another alternative driving mechanism including a leaf spring for the applicator of FIG. 12, according to some embodiments.

FIG. 22 illustrates another drive assembly comprising a leaf spring 2212. Leaf spring 2212 comprises a first end 2220 coupled to an applicator housing 2202 and a second end 2222 coupled to a needle carrier assembly 2208. Upon activation, leaf spring 2212 unloads in a direction substantially parallel to the axis of insertion, driving needle carrier assembly 2208 to the distal insertion position when leaf spring 2212 is unloaded.

Figure 23:
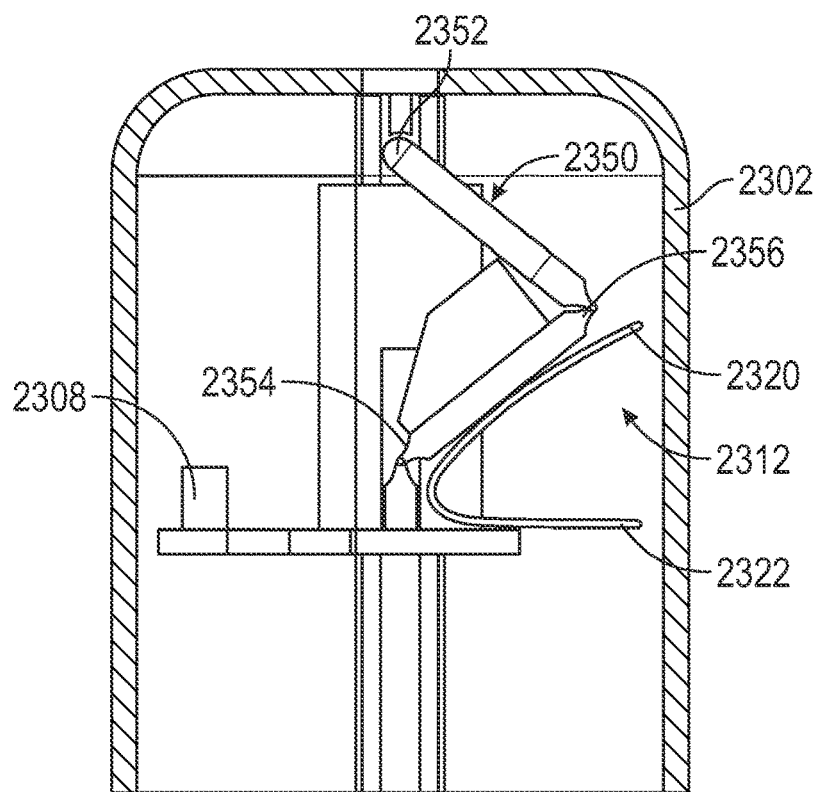
FIG. 23 illustrates a cutaway view of yet another alternative driving mechanism including a leaf spring and a living hinge for the applicator of FIG. 12, according to some embodiments.

FIG. 23 illustrates another drive assembly comprising a linkage element 2350. Drive assembly 2310 is substantially the same as drive assembly 1910 except replacing torsion spring 1912 with leaf spring 2312. Linkage element 2350 has a first end 2352 coupled to an applicator housing 2302, a second end 2354 coupled to a needle carrier assembly 2308, and a hinge 2356 disposed between first end 2352 and second end 2354. The rive assembly further comprises leaf spring 2312 having a first end 2320 coupled to linkage element 2350 between second end 2354 and hinge 2356, and a second end 2322 coupled to needle carrier assembly 2308. Upon activation, spring 2312 unloads and first end 2320 sweeps an arc while second end 2322 is held substantially stationary against needle carrier assembly 2308. As first end 2320 sweeps its arc, first end 2320 drives linkage element 2350 from the bent position shown, hinge 2356 pivoting, until linkage element 2350 is substantially vertical, and then continuing pivoting until linkage element 2350 is in a substantially mirror orientation from that shown in FIG. 23. This motion drives needle carrier assembly 2308 in the distal direction, reaching the distal insertion position when linkage element 2350 is substantially vertical, and then increasingly in the proximal direction as linkage element 2350 is further driven from the substantially vertical orientation to the substantially mirrored orientation to that shown in FIG. 23.

An example of steps for assembling an applicator such as applicator 1200 of FIG. 12 will now be discussed in connection with FIGS. 24A-24M. To the extent any step is compatible, the assembly steps of FIGS. 24A-24M may also apply to any applicator utilizing the drive assemblies described in connection with FIGS. 18-23.

Figure 24A:
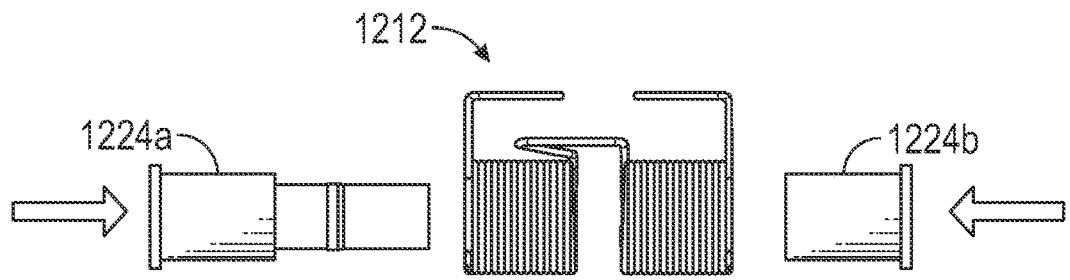
Figure 24B:
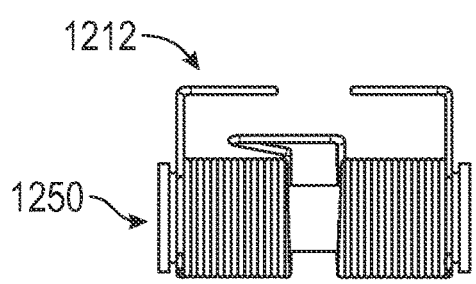
Figure 24C:
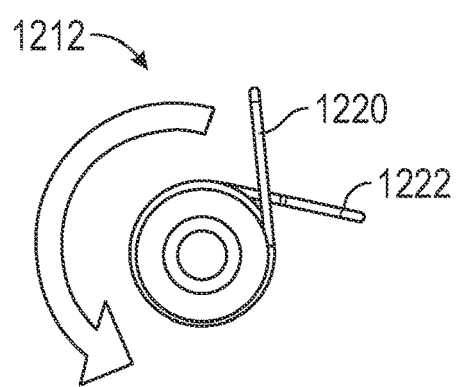
Figure 24D:
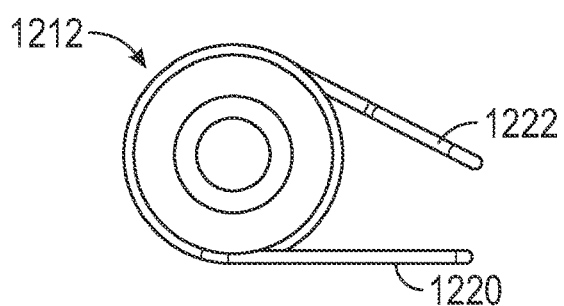

FIG. 24A illustrates coupling first portion 1250a and second portion 1250b of spring spool 1250 together inside the windings of spring 1212. FIG. 24B illustrates the assembled spring spool 1250 and spring 1212. Spring spool 1250 and spring 1212 are disposed coaxially with one another. FIG. 24C illustrates spring 1212 before winding in the direction indicated by the circular arrow, having first tang 1220 and second tang 1222 in the illustrated positions. FIG. 24D illustrates spring 1212 after winding, having first tang 1220 and second tang 1222 in the illustrated positions.

Figure 24E:
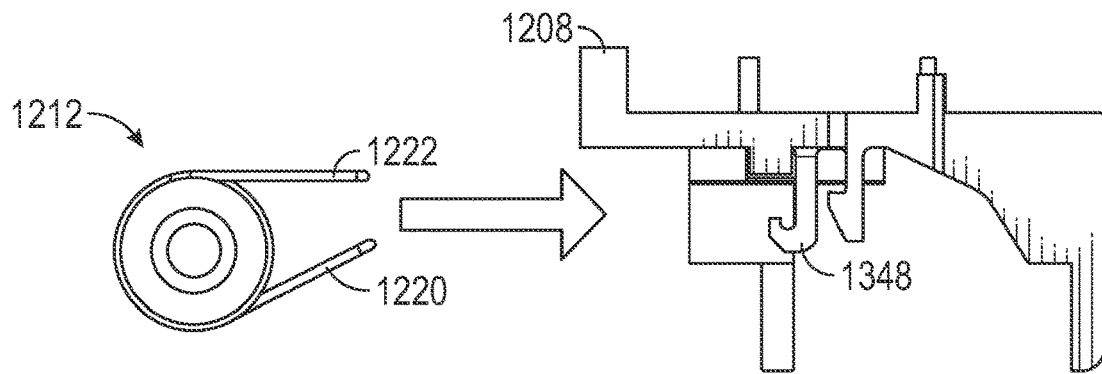
Figure 24F:
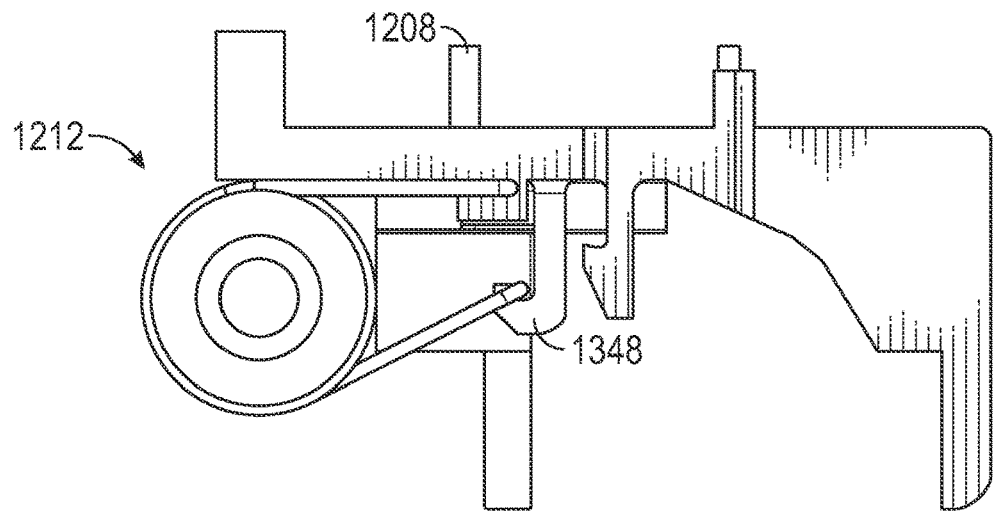
Figure 24G:
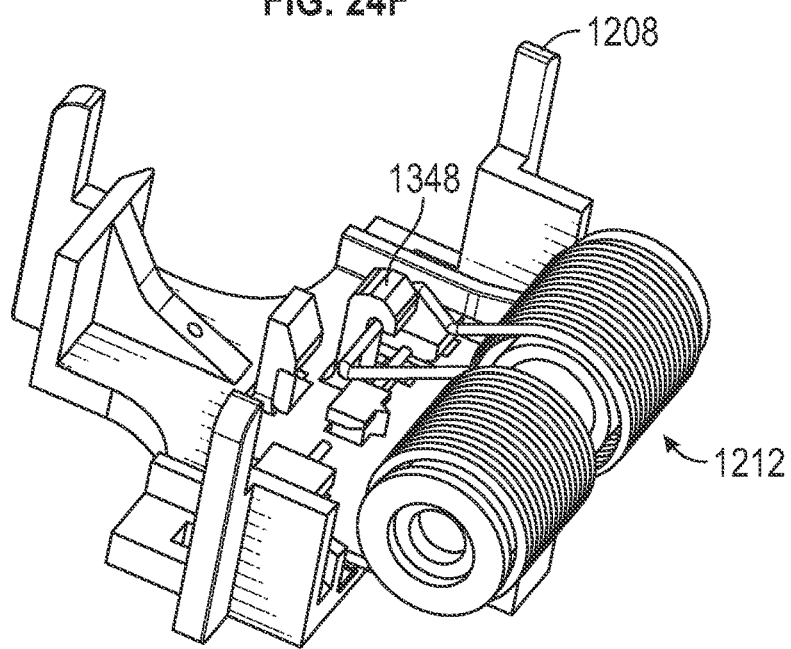
FIGS. 24G and 24K illustrate perspective views of steps for assembling the applicator of FIG. 12, according to some embodiments.

FIG. 24E illustrates coupling wound spring 1212 to needle carrier assembly 1208. In some embodiments, this includes coupling first tang 1220 to a hook 1348 of needle carrier assembly 1208 and coupling second tang 1222 to or disposing second tang 1222 against needle carrier assembly 1208. FIG. 24F illustrates a side view of wound spring 1212 coupled to needle carrier assembly 1208, while FIG. 24G illustrates a perspective view of the arrangement shown in FIG. 24F.

Figure 24H:
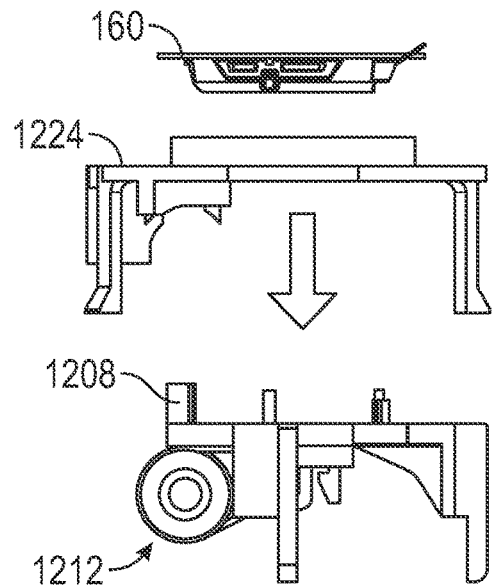
Figure 24J:
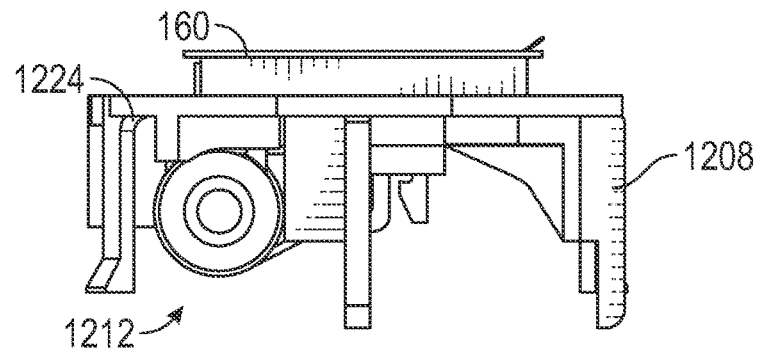
Figure 24K:
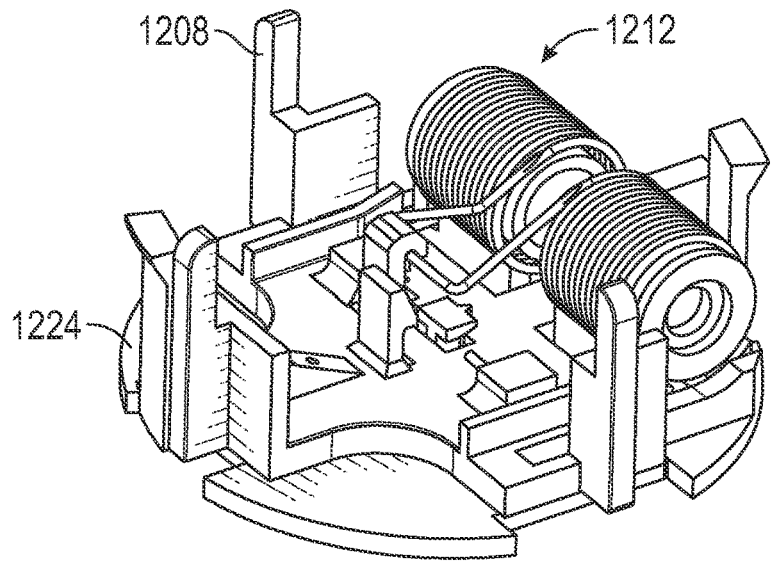

FIG. 24H illustrates coupling holder 1224 to needle carrier assembly 1208 and on-skin sensor assembly 160 to holder 1224. FIG. 24J illustrates a side view of on-skin sensor assembly 160, holder 1224, and needle carrier assembly 1208 assembled, while FIG. 24K illustrates a perspective view of the arrangement shown in FIG. 24J.

Figure 24L:
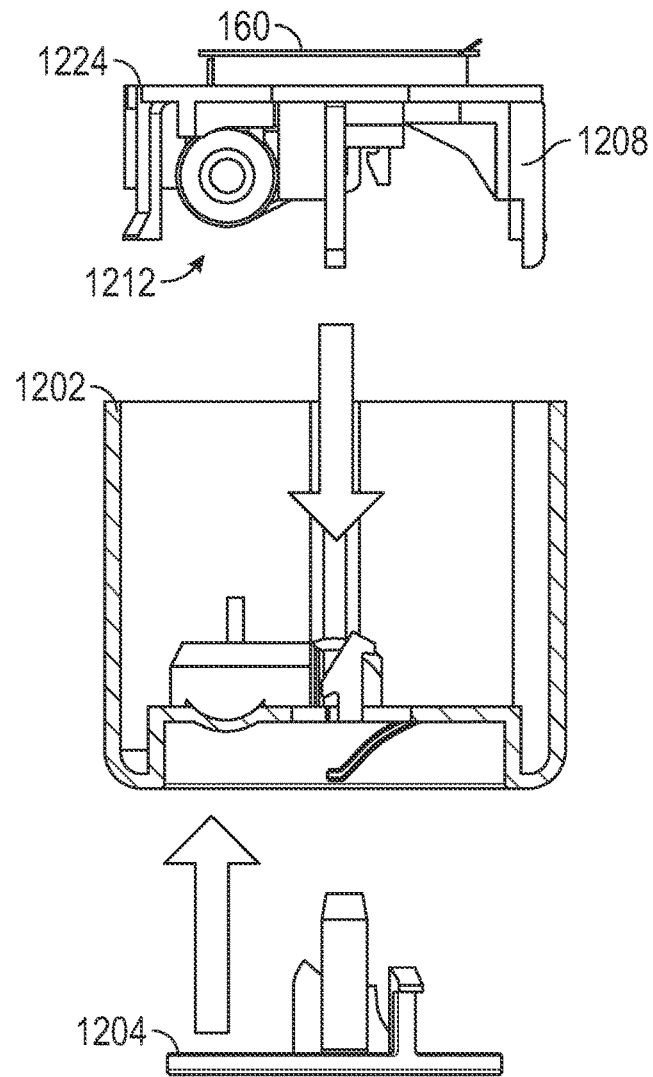
Figure 24M:
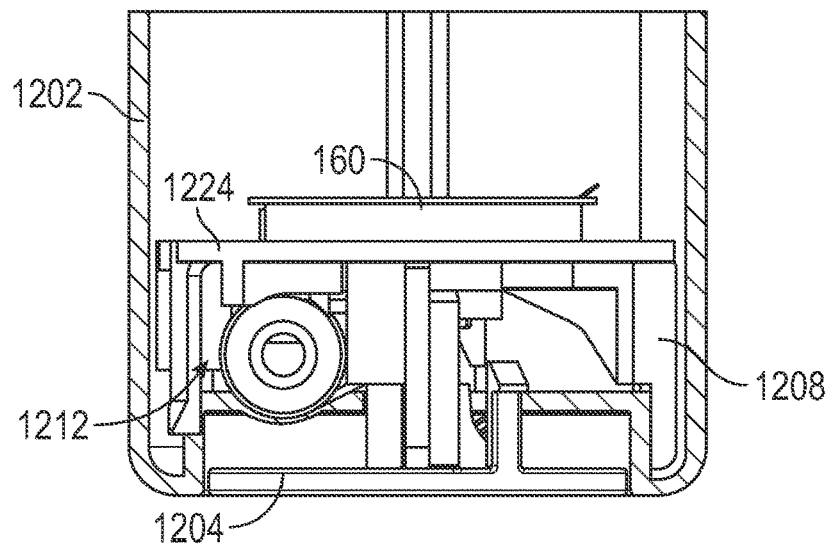

FIG. 24L illustrates assembling the complex including on-skin sensor assembly 160, holder 1224, needle carrier assembly 1208, and spring 1212 into applicator housing 1202 through the opening in the bottom of applicator housing 1202, and insertion of activation element 1204 into applicator housing 1202. FIG. 24M illustrates the result of the assembly shown in FIG. 24L.

Figure 25:
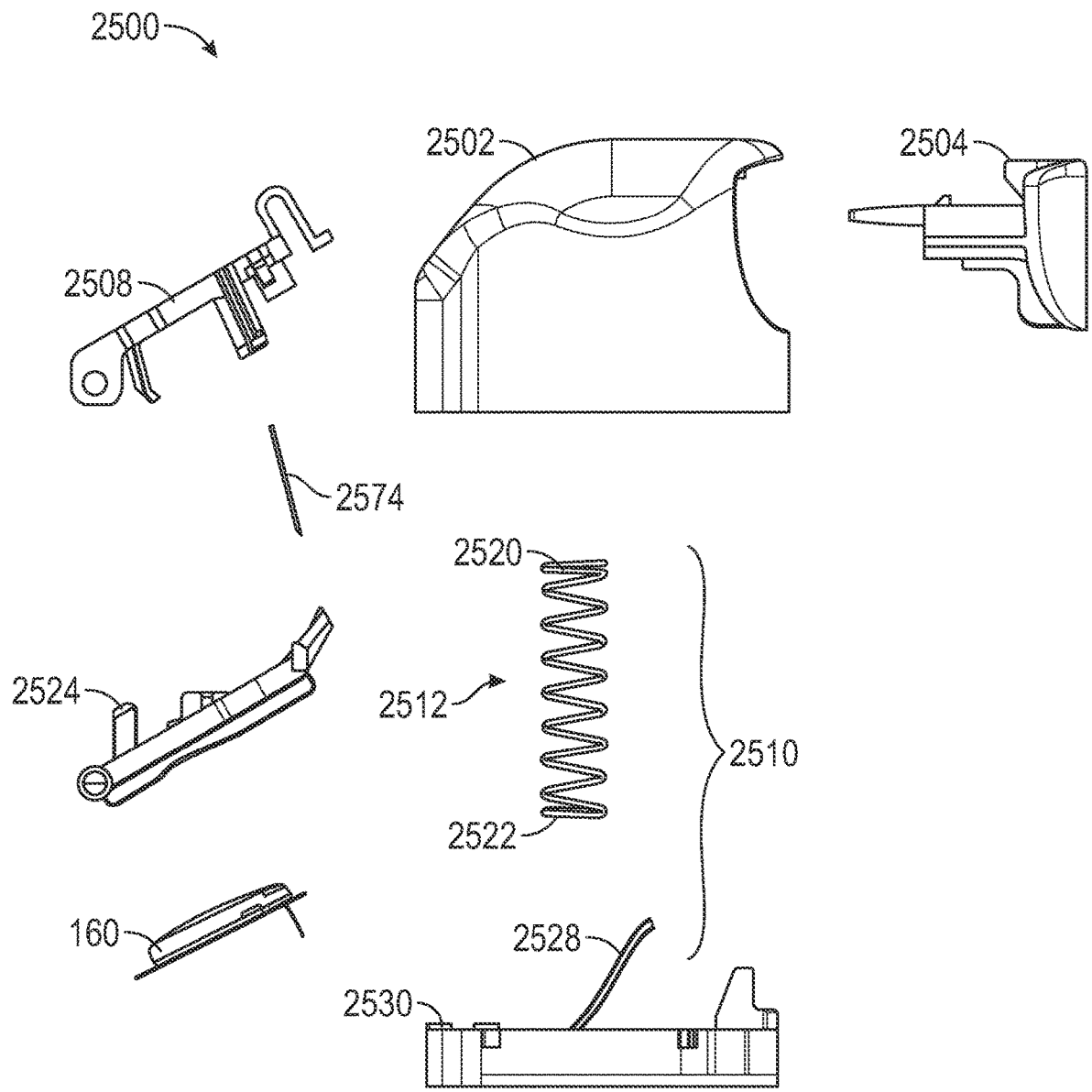
FIG. 25 illustrates an exploded perspective view of yet another applicator for an on-skin sensor assembly of an analyte sensor system, according to some embodiments.

FIG. 25 illustrates an exploded perspective view of yet another applicator 2500 for on-skin sensor assembly 160 of an analyte sensor system, according to some embodiments. Applicator 2500 may include an applicator housing 2502 configured to house one or more mechanisms for applying on-skin sensor assembly 160 to skin 130 of a host. Applicator housing 2502 may be formed of any suitable material, e.g., a polymer, polycarbonate, ABS, nylon, polyethylene, polypropylene, etc.

Applicator 2500 includes an activation element 2504 configured to activate a drive assembly of applicator 2500. In some embodiments, activation element 2504 may be a button, a switch, a toggle, a slide, a trigger, a knob, a rotating member, a component that deforms and/or flexes or any other suitable mechanism for activating a drive assembly of applicator 2500. Applicator 2500 may further comprise a needle carrier assembly 2508, including an insertion element 2574 configured to insert sensor 138 (e.g., FIG. 1) of on-skin sensor assembly 160 (e.g., FIG. 1) into skin 130 (e.g., FIG. 1) of the host. In some embodiments, insertion element 2574 comprises a needle, for example, an open sided-needle, a needle with a deflected-tip, a curved needle, a polymer-coated needle, a hypodermic needle, or any other suitable type of needle or structure, as will be described in more detail in connection with at least FIGS. 47-50 and 80A-B. In yet other embodiments, insertion element may comprise sensor 138, sufficiently rigid to be inserted partially into skin 130 of the host with minimal or no structural support.

Applicator 2500 may further comprise a drive assembly 2510 configured to drive insertion element 2574 of needle carrier assembly 2508 in a distal direction to a distal insertion position and in a proximal direction from the distal insertion position to a proximal retraction position.

Applicator 2500 may further include a holder 2524 releasably coupled to needle carrier assembly 2508 and configured to guide on-skin sensor assembly 160 while coupled to needle carrier assembly 2508. As will be described in more detail below, on-skin sensor assembly 160 may be stripped from holder 2524 and needle carrier assembly 2508 once on-skin sensor assembly 160 is disposed on skin 130 of the host.

Drive assembly 2510 may include a spring 2512, which may be any suitable type of spring, e.g., a compression spring, extension spring, leaf spring, flex arm spring, etc. Spring 2512 may have a first end 2520 coupled to applicator housing 2502 and a second end coupled to needle carrier assembly 2508. Spring 2520 may be configured to, upon activation of drive assembly 2510, drive needle carrier assembly 2508 in the distal direction. In some embodiments, spring 2512 may be pre-loaded, e.g., at the factory. In some other embodiments, spring 2512 may be loaded by an action of the user of applicator 2500.

Drive assembly 2510 further includes a spring 2528 that may be coupled to an applicator base 2530 of applicator 2500. In some embodiments, spring 2528 may be a compression spring, extension spring, leaf spring, flex arm spring, etc. In some embodiments, spring 2528 may be pre-loaded, e.g., at the factory. In some other embodiments, spring 2528 may be loaded by an action of the user. In yet other embodiments, spring 2528 may be loaded by unloading of spring 2512. Spring 2528 may comprise one or more portions configured to drive needle carrier assembly 2508 in the proximal direction from the distal insertion position, as will be described in more detail below.

Figure 26A:
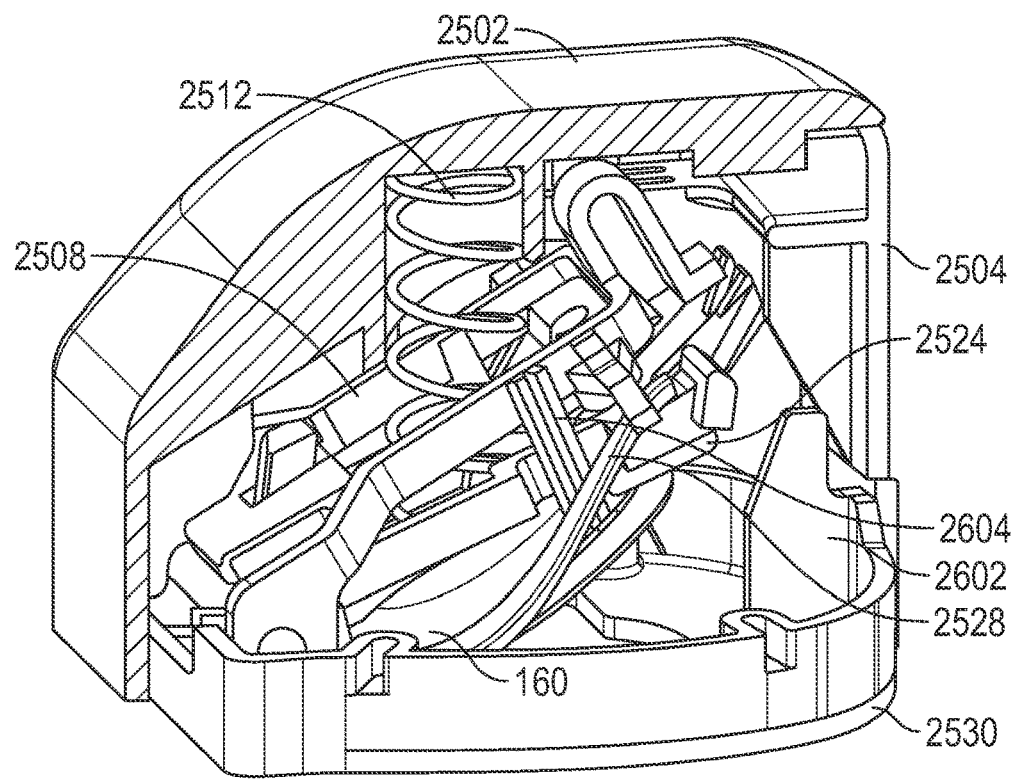
FIG. 26A-26D illustrate several cutaway perspective views and a bottom view of several features of the applicator of FIG. 25, according to some embodiments.

FIG. 26A-26D illustrate several cutaway views and a bottom view of several features of applicator 2500 of FIG. 25, according to some embodiments. FIG. 26A illustrates a perspective cutaway view of applicator 2500 including applicator housing 2502, activation element 2504, applicator base 2530 including protrusion 2602, spring 2512, leaf spring(s) 2528, needle carrier assembly 2508, holder 2524, and on-skin sensor assembly 160. Each of these components may have functionality as previously described in connection with at least FIG. 25.

Figure 26B:
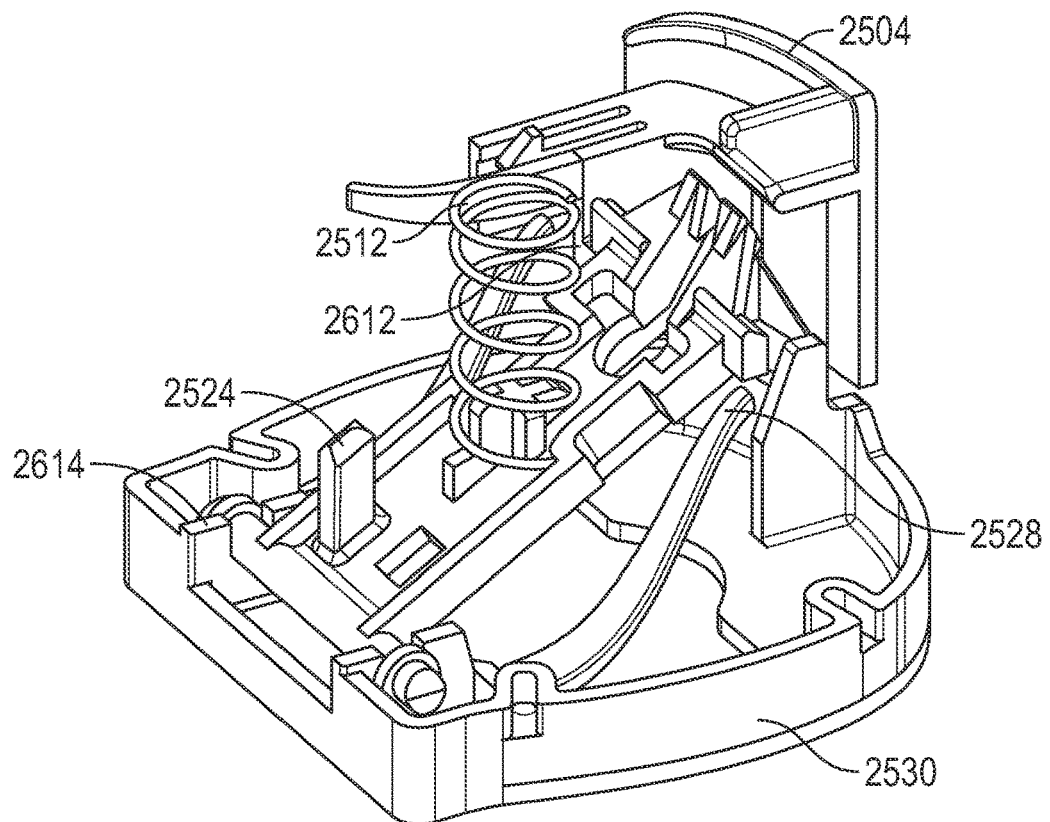

FIG. 26B illustrates a perspective view of several features of holder 2524, applicator base 2530 and activation element 2504. Spring 2512 is configured to be coupled to applicator housing 2502 at a first end and to holder 2524 at a second end. In a pre-activation state, spring 2512 may be configured to store energy for driving holder 2512 (and needle carrier assembly 2508) in the distal direction to the distal insertion position upon activation. Holder 2524 comprises an axle 2614 configured to snap into applicator base 2530 such that holder 2524 is configured to pivot in a substantially circular arc about axle 2614. In FIG. 26B, activation element 2504 is illustrated as comprising a protrusion 2612 configured to guide holder 2524 in the pre-activation position shown until activation element 2504 is activated, thereby displacing protrusion 2612 from its pre-activation orientation relative to holder 2524 and releasing holder 2524. FIG. 26B further illustrates that leaf spring(s) 2528 are not coupled to holder 2524. Instead, leaf spring(s) 2528 are coupled to needle carrier assembly 2508 and are configured to drive needle carrier assembly 2508 in the proximal direction from the distal insertion position. Although activation element 2504 is shown as a button, the present disclosure further contemplates activation element 2504 as a switch, a toggle, a slide, a trigger, a knob, a rotating member, a component that deforms and/or flexes or any other suitable mechanism for activating a drive assembly of applicator 2500. Moreover, although activation element 2504 is illustrated as being disposed on a side of applicator housing 2502, the present disclosure contemplates any other location, e.g., on a top, bottom, or other side location of applicator housing 2502, and/or any other angle of disposition with respect to applicator housing 2502.

Figure 26C:
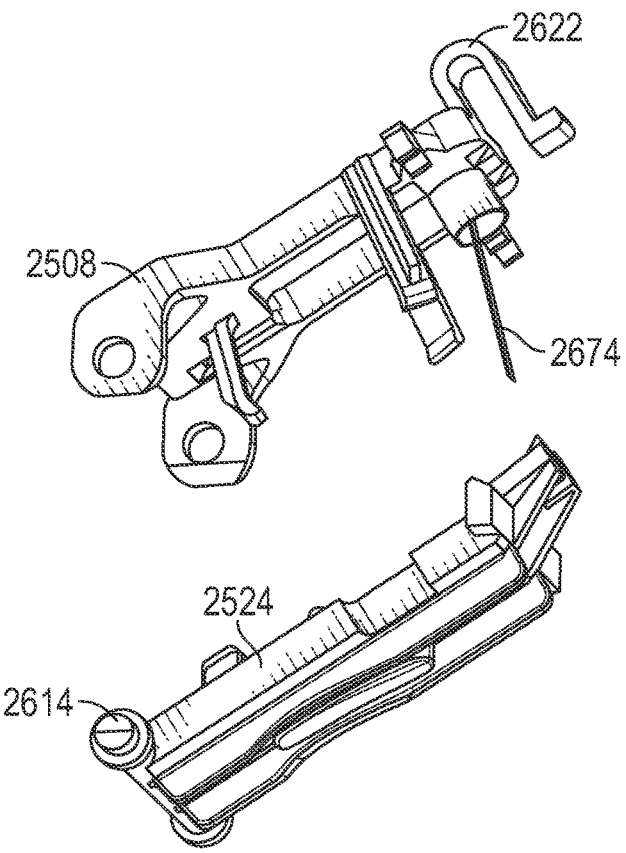

FIG. 26C illustrates an exploded perspective view of needle carrier assembly 2508, insertion element 2674, and holder 2524. Insertion element 2674 is coupled to needle carrier assembly 2508. In some embodiments, insertion element 2674 comprises an open-sided needle configured to guide and insert sensor 138 of on-skin sensor assembly 160 (e.g., FIG. 1) into skin 130 of the host. Insertion assembly 2508 is coupled at a first end to axle 2614 of holder 2524. Insertion assembly 2508 further comprises a retention element 2622 configured to releasably couple a second end of needle carrier assembly 2508 to holder 2524. Insertion assembly 2508 further comprises a retention element 2604 configured to releasably couple on-skin sensor assembly 160 to needle carrier assembly 2508 and holder 2524. In some embodiments, retention element 2604 may comprise a snap fit, friction fit, interference feature, elastomeric grip and/or adhesive configured to couple on-skin sensor assembly 160 with needle carrier assembly 2508 and/or holder 2524. Spring 2512 is configured to, upon activation of applicator 2500, drive needle carrier assembly 2508 and holder 2524 in the distal direction along a circular arc defined by axle 2614 to the distal insertion position. Spring 2512 transfers at least a portion of its stored energy to leaf spring(s) 2528 as needle carrier assembly 2508 is driven in the distal direction along the circular arc. In some other embodiments, leaf spring(s) 2528 may be pre-loaded such that spring 2512 does not transfer stored energy to leaf spring(s) 2528. As needle carrier assembly 2508 is driven in the distal direction, a protrusion 2602 of applicator base 2530 is configured to deflect retention element 2622 sufficiently to separate needle carrier assembly 2508 from holder 2524 substantially at the distal insertion position, thereby uncoupling the second end of needle carrier assembly 2508 from holder 2524. Accordingly, from the distal insertion position, leaf spring(s) 2528, now loaded, are configured to drive needle carrier assembly 2508 in the proximal direction from the distal insertion position, along the circular arc, to the proximal retraction position.

Figure 26D:
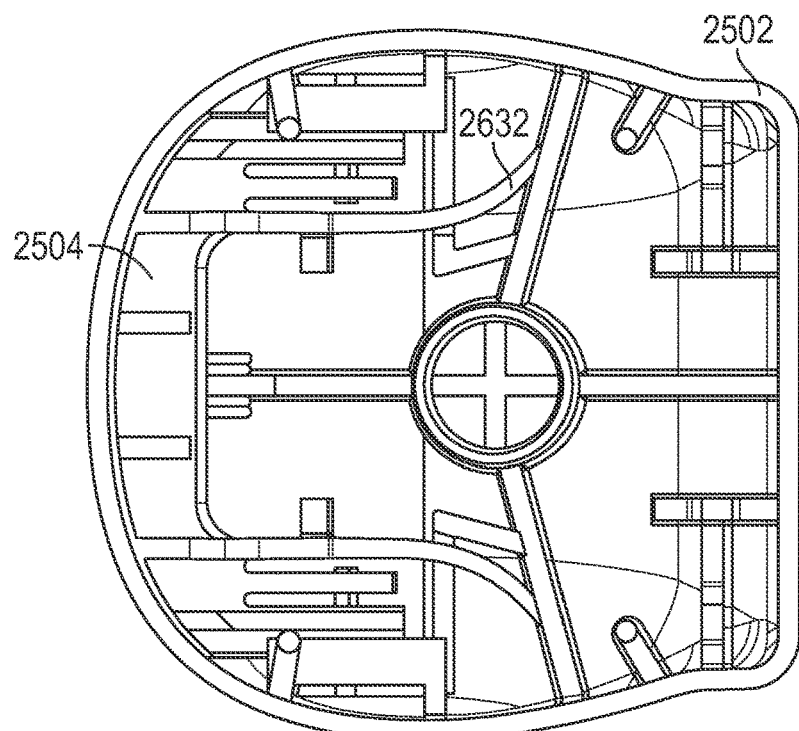

FIG. 26D illustrates a portion 2632 of activation element 2504 coupled to applicator housing 2502 and configured to act as a return spring, returning activation element 2504 to its pre-activation position after activation. For example, as activation element 2504 is pressed to the right as shown in FIG. 26D, portion 2632 is deformed against applicator housing 2502, thereby functioning substantially as a spring, which when unloaded, returns activation element 2504 to its pre-activation position.

Figure 27A:
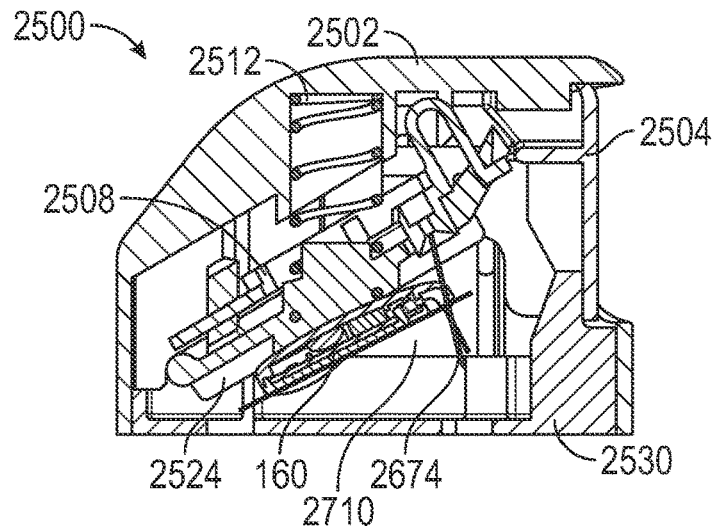
FIGS. 27A-27E illustrate several cross-sectional views of the applicator of FIG. 25 during operation, according to some embodiments.
Figure 86:
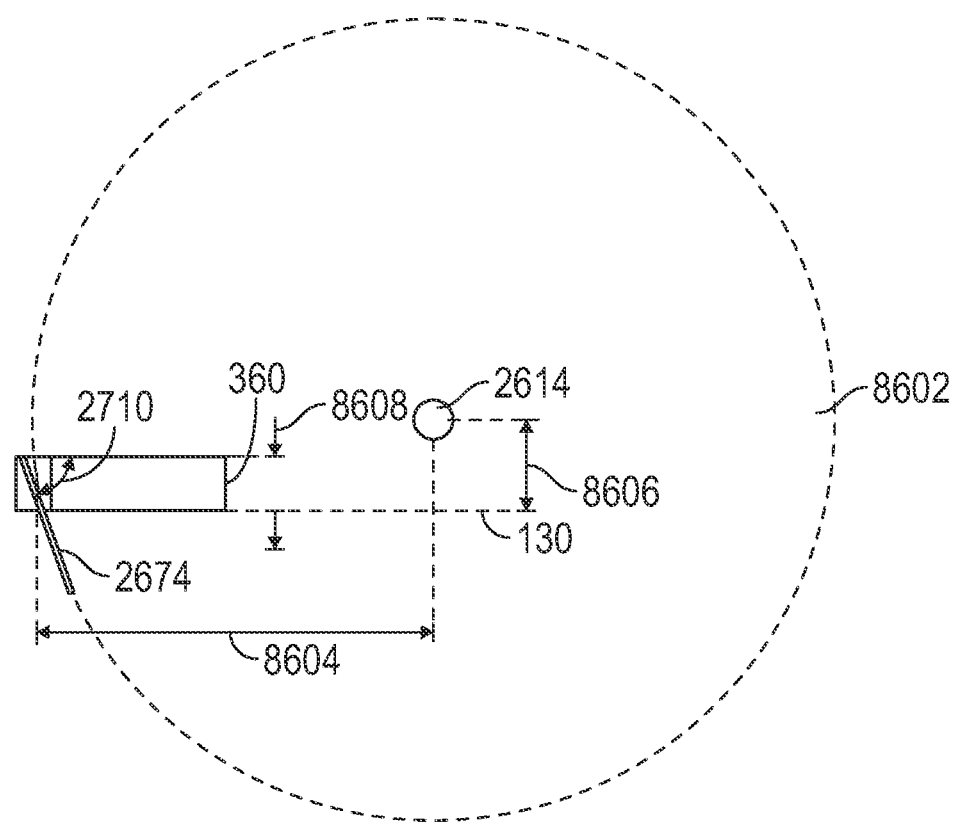
FIG. 86 illustrates relationships between the axle, insertion element, and a circular arc travelled by the insertion element of at least FIG. 26C during insertion and retraction, according to some embodiments.

FIGS. 27A-27E illustrate several cross-sectional views of applicator 2500 of FIG. 25 during operation, according to some embodiments. FIG. 86 illustrates relationships between axle 2614, insertion element 2674, and a circular arc 8602 travelled by insertion element 2674 during insertion and retraction, according to some embodiments. FIG. 27A illustrates applicator 2500 at the time of activation. For example, activation element 2504 is illustrated in an activated position, e.g., pushed inwardly, which releases holder 2524 from its immobilized, pre-activation state. Spring 2512, needle carrier assembly 2508, insertion element 2674, holder 2524, and on-skin sensor assembly 160 are all shown in their pre-activation positions.

Figure 27B:
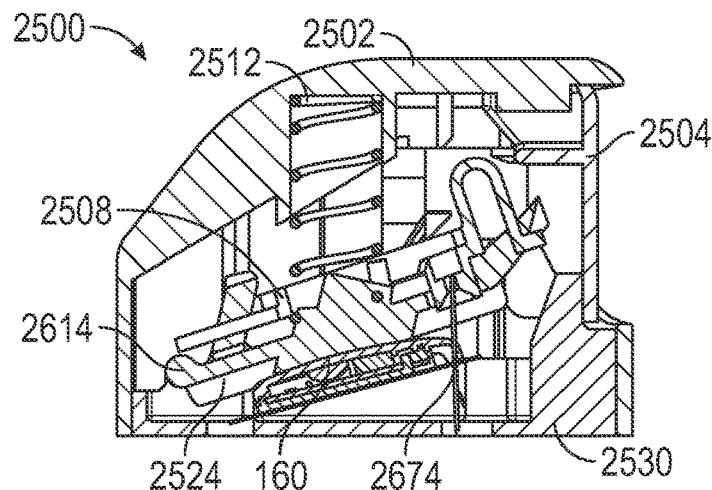

FIG. 27B illustrates applicator 2500 during activation. Spring 2512 is driving holder 2524, and so releasably coupled needle carrier assembly 2508, insertion element 2674, and on-skin sensor assembly 160, in the distal direction along the circular arc 8602 (see FIG. 86) defined by axle 2614. In some embodiments, a radius 8604 (see FIG. 86) of the circular arc 8602 may be between 20 millimeters (mm) and 80 mm, inclusive, although radiuses larger or smaller than this range are also contemplated.

With respect to FIG. 86, the radius 8604 of this circular arc 8602 may depend on one or more of a distance 8606 from the skin 130 of the host to axle 2614, a height 8608 of the on-skin sensor assembly 160 from a bottom opening or surface of applicator 2500 or from axle 2614, and/or a location of sensor 138 within on-skin sensor assembly 160. Selection of a radius 8604 may be made at least in part to minimize tissue trauma, optimize deployment of sensor 138, and to minimize insertion and/or retraction friction between the insertion member and the tissue of the host.

For example, with respect to FIGS. 27A and 86, an angle 2710 between a needle axis and a bottom plane of on-skin sensor assembly may be calculated such that a minimum offset is achieved between the straight needle path and the ideal curved profile 8602. In some embodiments, it has been determined that an approximately 71 degree angle between the needle axis and the bottom plane of on-skin sensor assembly produces less lateral motion of the tip of the insertion element 2674 within the skin of the host compared to an approximately 90 degree angle between the needle axis and the bottom plane of on-skin sensor assembly. However, this angle may depend on at least some of the same factors affecting an ideal radius of the circular arc.

Moreover, various needle geometries may be utilized, including, but not limited to, straight needle geometries, kinked needle geometries (e.g., two or more substantially straight portions with one or more bends disposed therebetween), and fully or partially curved needle geometries (e.g., a curved distal portion configured to at least partially pierce the skin of the host with or without a straight proximal portion), as described in more detail in connection with at least FIGS. 47-50 and 80A-B.

Figure 27C:
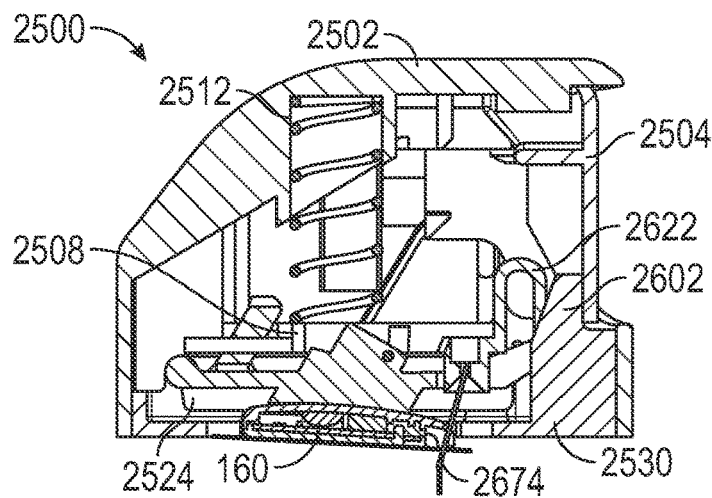

FIG. 27C illustrates applicator 2500 in the distal insertion position. Spring 2512 has driven holder 2524, and so releasably coupled needle carrier assembly 2508, insertion element 2674, and on-skin sensor assembly 160, in the distal direction to the distal insertion position. In addition, protrusion 2602 of applicator base 2530 has deflected retention arm 2622 sufficiently to release the second end of needle carrier assembly 2508 from holder 2524 in preparation for movement in the proximal direction from the distal insertion position.

Figure 27D:
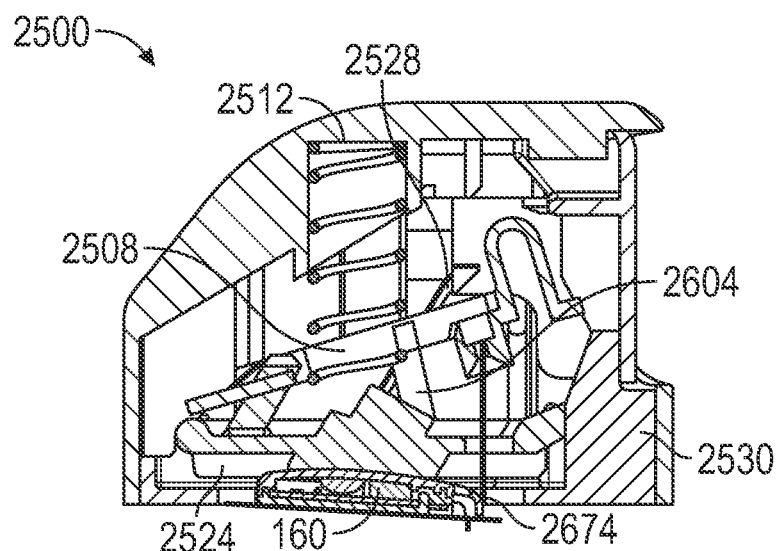

FIG. 27D illustrates applicator 2500 during retraction. Spring 2512 remains unloaded, pinning holder 2524 in the distal insertion position. However, leaf spring(s) 2528, still in contact with now-released needle carrier assembly 2508, drive needle carrier assembly 2508 and coupled insertion element 2674 in the proximal direction from the distal insertion position to the proximal retraction position. Retention element(s) 2604 are released from on-skin sensor assembly 160 by virtue of spring 2512 pinning holder 2524, and so on-skin sensor assembly 160 disposed thereunder, in the distal insertion position. In some embodiments, retention element(s) 2604 may comprise snap fits, friction fits, interference features, elastomeric grips and/or adhesives.

Figure 27E:
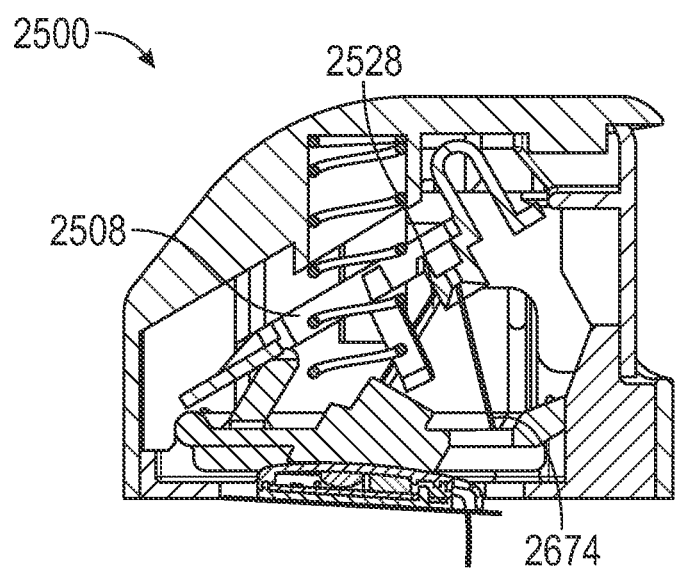

FIG. 27E illustrates applicator 2500 in the proximal retraction position. Leaf spring(s) 2528 have driven needle carrier assembly 2508 and insertion element 2674 in the proximal direction to the proximal retraction position. Applicator 2500 may then be released from the skin of the host, whereby all portions of the applicator 2500 will be removed from the skin of the host except the on-skin sensor assembly 160 and the sensor 138 (e.g., FIG. 1) which is now at least partially inserted into the skin of the host.

Figure 28C:
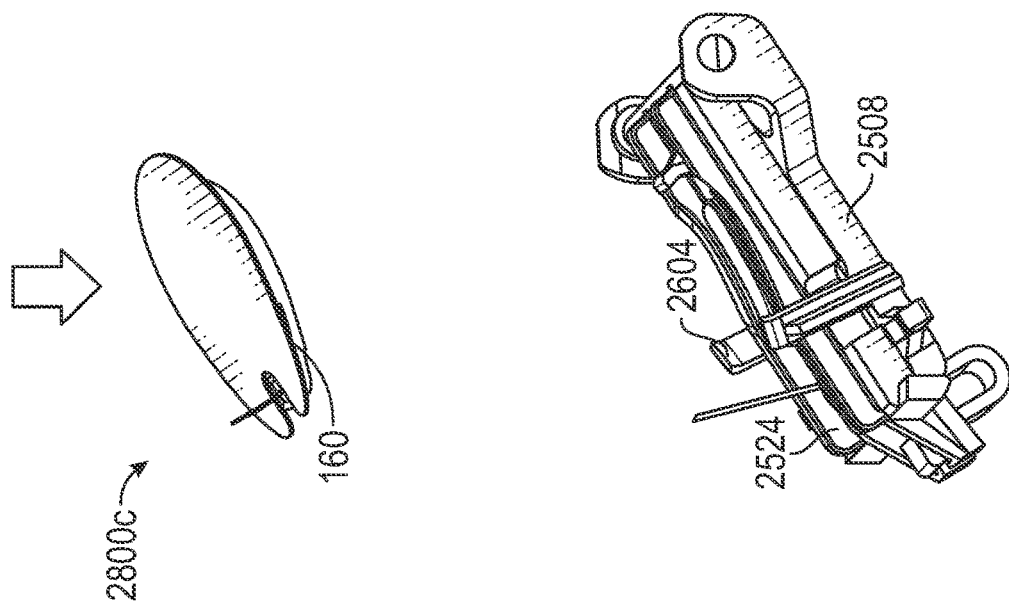
Figure 28B:
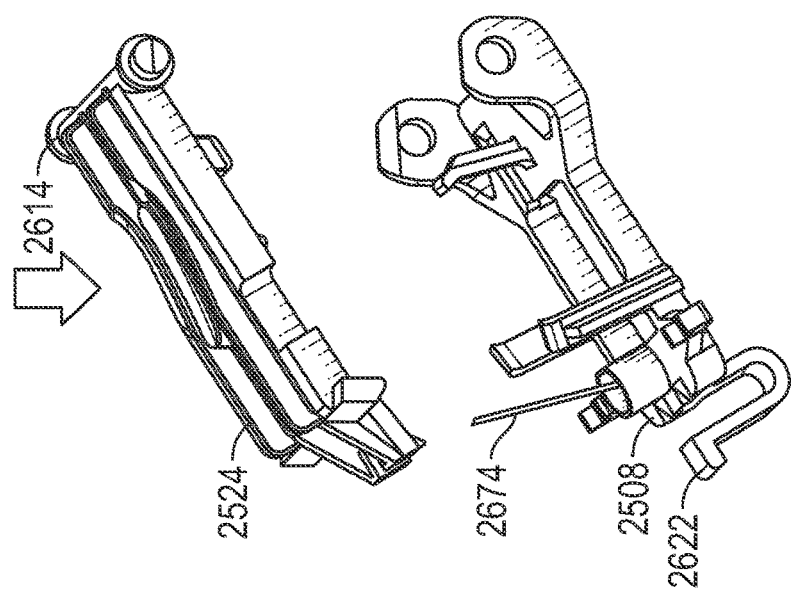
Figure 28A:
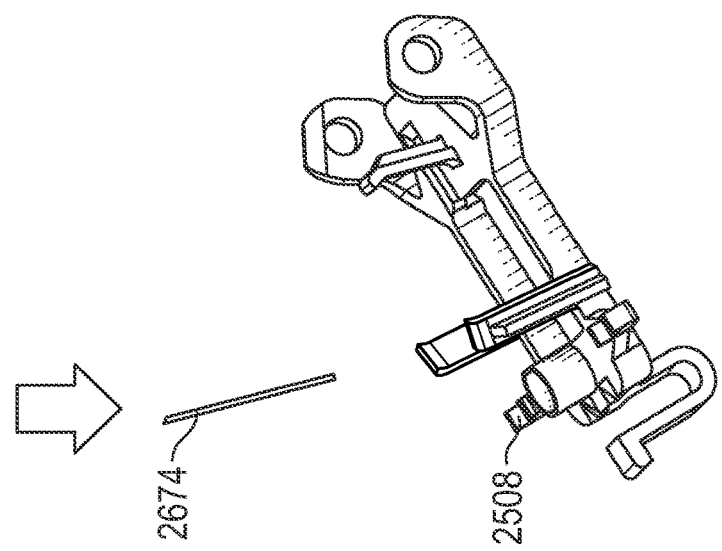

FIGS. 28A-28H illustrate steps to assemble applicator 2500 of FIG. 25, according to some embodiments. FIG. 28A illustrates coupling insertion element 2674 to needle carrier assembly 2508. In some embodiments, insertion element 2674 may be coupled to needle carrier assembly 2508 at an angle that substantially coincides with the circular path insertion element 2674 and needle carrier assembly 2508 traverse during activation. FIG. 28B illustrates coupling holder 2524 to needle carrier assembly 2508 by coupling needle carrier assembly 2508 to axle 2614 of holder 2524 and retention element 2622 to holder 2524. FIG. 28C illustrates coupling on-skin sensor assembly 160 to holder 2524 and needle carrier assembly 2508 by engaging retention element(s) 2604 of needle carrier assembly 25089 with on-skin sensor assembly 160.

FIG. 28D illustrates inserting activation element 2504 into applicator housing 2502. FIG. 28E illustrates coupling a first end of spring 2512 with applicator housing 2502 through an opening in the bottom of applicator housing 2502. FIG. 28F illustrates inserting the assembly 2800c resulting from the step(s) illustrated by FIG. 28C into applicator housing 2502. In assembly 2800c, shown in FIG. 28F, spring 2512 is placed in contact with holder 2524 and holder 2524 is secured by protrusion 2612 of activation element 2504.

Figure 28H:
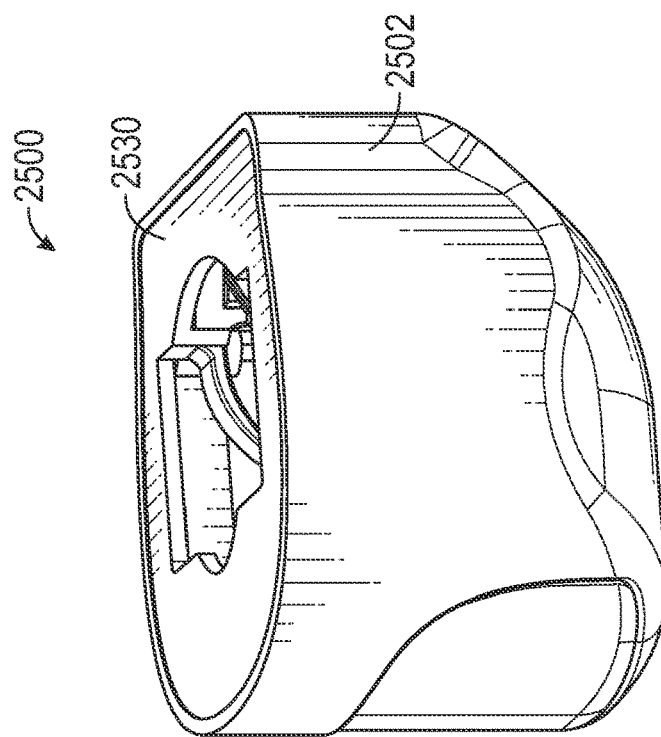
Figure 28G:
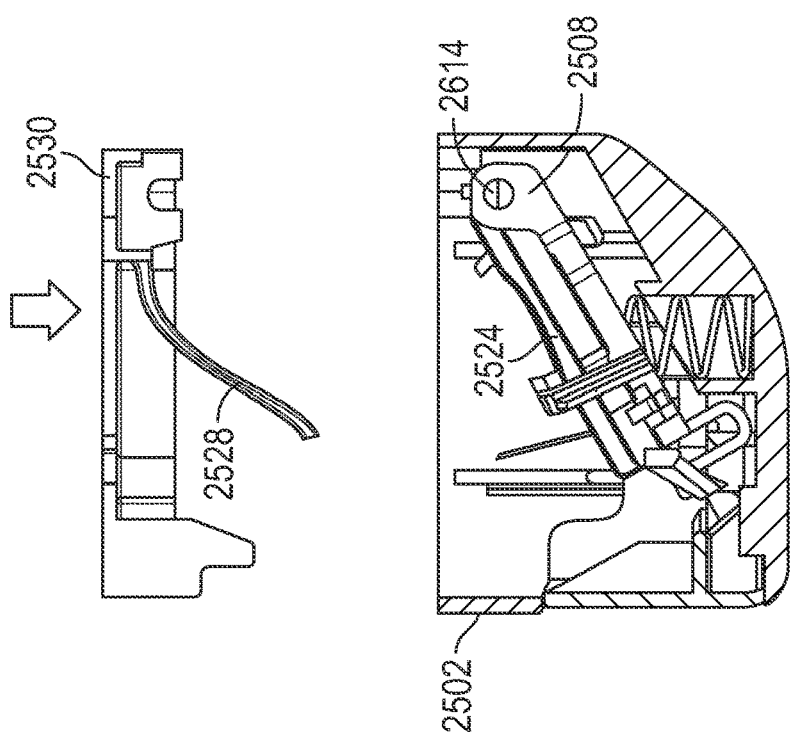

FIG. 28G illustrates coupling applicator base 2530 to applicator housing 2502. Axle 2614 of holder 2524 is coupled to applicator base 2530 and leaf spring(s) 2528 are placed in contact with needle carrier assembly 2508. FIG. 28H illustrates applicator 2500 in assembled form. At this step, applicator base 2530 may be coupled to applicator housing 2502, for example, via sonic welding, press-fit, snap-fit, adhesive, or any other suitable method of securing plastic materials together.

Figure 29:
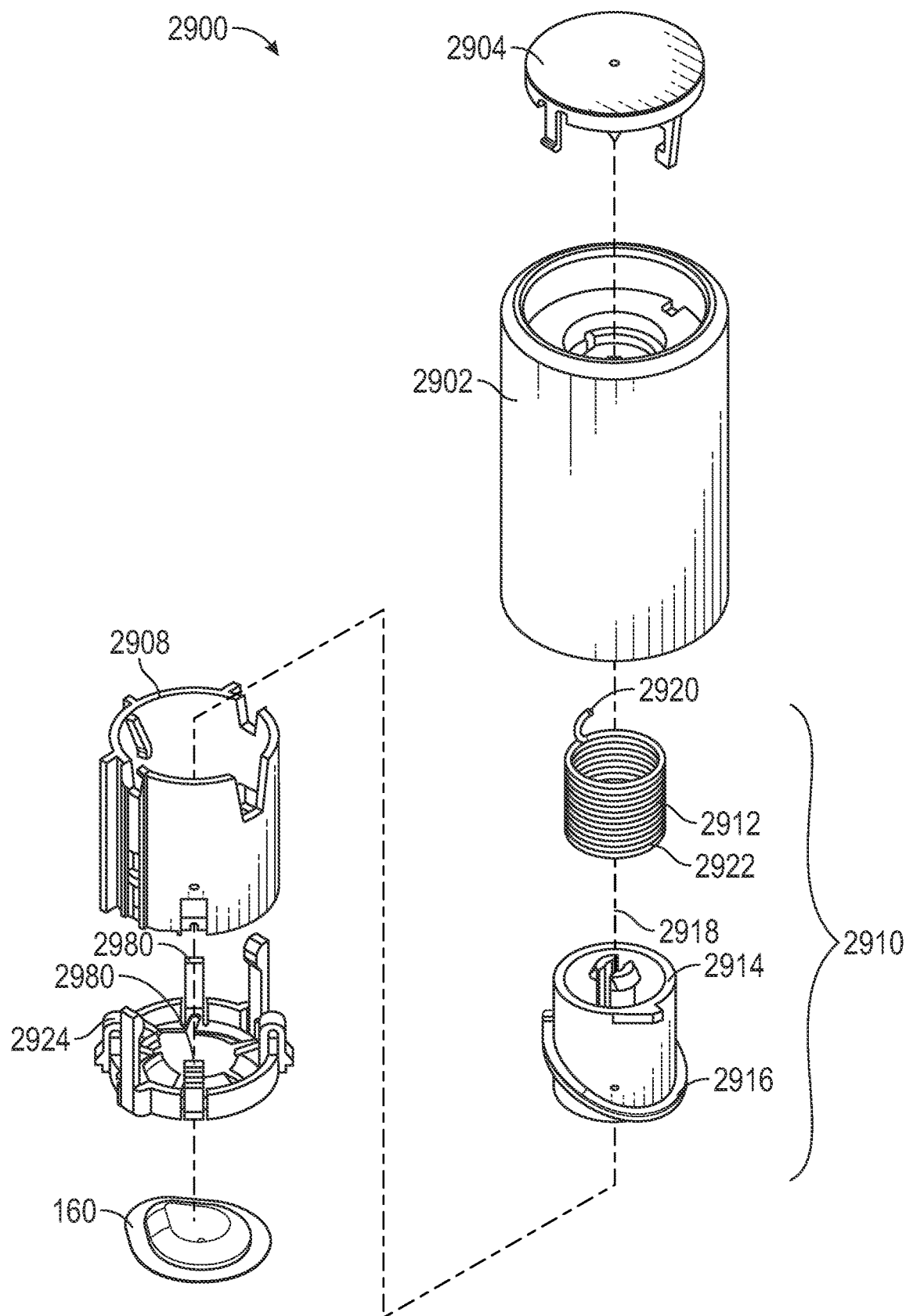
FIG. 29 illustrates an exploded perspective view of an applicator for an on-skin sensor assembly of an analyte sensor system, according to some embodiments.

FIG. 29 illustrates an exploded perspective view of yet another applicator 2900 for applying an on-skin sensor assembly to skin 130 of a host, according to some embodiments. Applicator 2900 may include an applicator housing 2902 having an opening at its bottom and configured to house at least one or more mechanisms utilized to apply on-skin sensor assembly 160 to skin 130 of a host.

Applicator 2900 includes an activation element 2904 configured to activate a drive assembly of applicator 2900. In some embodiments, activation element 2904 may be a button, a switch, a toggle, a slide, a trigger, a knob, a rotating member, a component that deforms and/or flexes or any other suitable mechanism for activating a drive assembly of applicator 2900. Applicator 2900 may further comprise a needle carrier assembly 2908, including an insertion element (see FIG. 30) configured to insert sensor 138 of on-skin sensor assembly 160 (e.g., FIG. 1) into skin 130 of the host. In some embodiments, the insertion element comprises a needle, for example, an open sided-needle, a needle with a deflected-tip, a curved needle, a polymer-coated needle, a hypodermic needle, or any other suitable type of needle or structure, as will be described in more detail in connection with at least FIGS. 47-50 and 80A-B. In yet other embodiments, insertion element may comprise sensor 138 itself, sufficiently rigid to be inserted partially into skin 130 of the host with minimal or no structural support.

Applicator 2900 may further comprise a drive assembly 2910 configured to drive the insertion element of needle carrier assembly 2908 in a distal direction to a distal insertion position and in a proximal direction from the distal insertion position to a proximal retraction position. A distal direction may be defined as extending towards an open-ended side of applicator 2900 along a path needle carrier assembly 2908 is configured to travel. The distal direction may also be defined as towards the skin of a user. A proximal direction may be defined as a direction extending in a substantially opposite direction from the distal direction. In some embodiments, the distal direction and the proximal direction extend along an insertion axis of the insertion element and of needle carrier assembly 2908.

Drive assembly 2910 may include a rotating drive element 2914 disposed within needle carrier assembly 2908 and configured to rotate with respect to needle carrier assembly 2908 about an axis of rotation 2918 parallel with a centerline of needle carrier assembly 2908. In some embodiments, rotating drive element 2914 is configured to rotate in a plane substantially perpendicular to the proximal direction and the distal direction. In some embodiments, rotating drive element 2914 may comprise a barrel cam. Rotating drive element 2914 comprises a ridge 2916 that defines a variable cam path around at least a portion of a circumference of the rotating drive element. Ridge 2916 is configured to slide along a channel (see FIG. 30) on an inside surface of needle carrier assembly 2908 as rotating drive element 2914 rotates, thereby driving needle carrier assembly 2908 in the distal direction to the distal insertion position and then in the proximal direction to the proximal retraction position as defined by the variable cam path of ridge 2916.

Drive assembly 2910 may further include a spring 2912 disposed within rotating drive element 2914. Spring 2912 may be a torsion spring, or any suitable type of spring. Spring 2912 may have a first end 2920 coupled to applicator housing 2902 and a second end 2922 coupled to rotating drive element 2914. Spring 2912 may be disposed coaxially with rotating drive element 2914 and needle carrier assembly 2908. Spring 2920 may be configured to, upon activation of drive assembly 2910, rotate rotating drive element 2914 in a single direction with respect to needle carrier assembly 2908.

Figure 30:
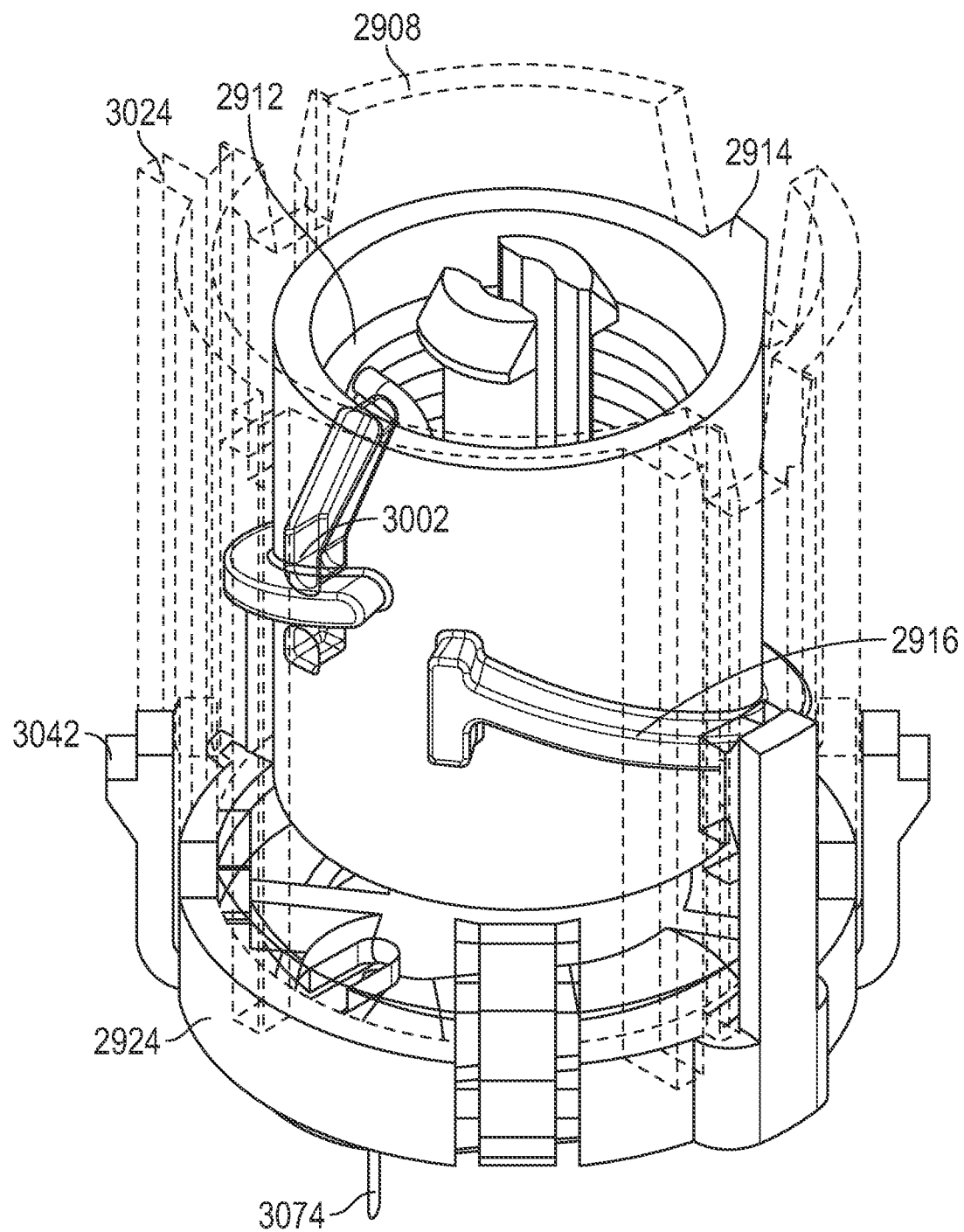
FIG. 30 illustrates a cutaway view of a portion of the applicator of FIG. 29, according to some embodiments.

By virtue of rotating drive element 2914 being configured to rotate with respect to needle carrier assembly 2908, about axis of rotation 2918, and ridge 2916 being restrained to travel in the channel of needle carrier assembly 2908, rotational motion of rotating drive element 2914, caused by spring 2912, is converted into linear, reciprocating motion of needle carrier assembly 2908 and, therefore, insertion element (see FIG. 30). More specifically, rotation of rotating drive element 2914 drives insertion element 2908 in the distal direction to the distal insertion position and in the proximal direction from the distal insertion position to the proximal retraction position.

Applicator 2900 may further include a holder 2924 releasably coupled to needle carrier assembly 2908 via retention element(s) 2980 and configured to guide on-skin sensor assembly 160 while coupled to needle carrier assembly 2908. In some embodiments, retention element(s) 2980 may comprise snap fits, friction fits, interference features, elastomeric grips and/or adhesives configured to couple on-skin sensor assembly 160 with needle carrier assembly 2908 and/or holder 2924. On-skin sensor assembly 160 may be stripped from holder 2924 and/or needle carrier assembly 2908 once on-skin sensor assembly 160 is disposed on skin 130 of the host.

FIG. 30 illustrates a perspective cutaway view of a portion of applicator 2900 of FIG. 29, according to some embodiments. FIG. 30 illustrates at least one protrusion 3024 of needle carrier assembly 2908 configured to slide within tracks (not shown in FIG. 30) on an inside surface of applicator housing 2902 (similar to tracks 622a-622c in FIG. 6) that define a linear path of travel for needle carrier assembly 2908. FIG. 30 further illustrates channel 3002 in which ridge 2916 of rotating drive element 2914 is configured to slide as spring 2912 rotates rotating drive element 2914 with respect to needle carrier assembly 2908. FIG. 30 further illustrates insertion element 3074 coupled to needle carrier assembly 2908.

In some embodiments, holder 2924 further includes a retention element 3042 configured to engage with a retention element (not shown in FIG. 30) of applicator housing 2902, similar to stop element 644 of applicator housing 462 of FIG. 6, and immobilize holder 2924 to applicator housing 2902 upon needle carrier assembly 2908 reaching the distal insertion position. Although not shown in FIG. 30, holder 2928 may further comprise a protrusion and applicator housing 2902 may further comprise a protrusion configured to prevent holder 2924 from travelling beyond the distal insertion position in the distal direction, similar to protrusion 652 and protrusion 654 as previously described in connection with FIG. 6F.

Figure 31:
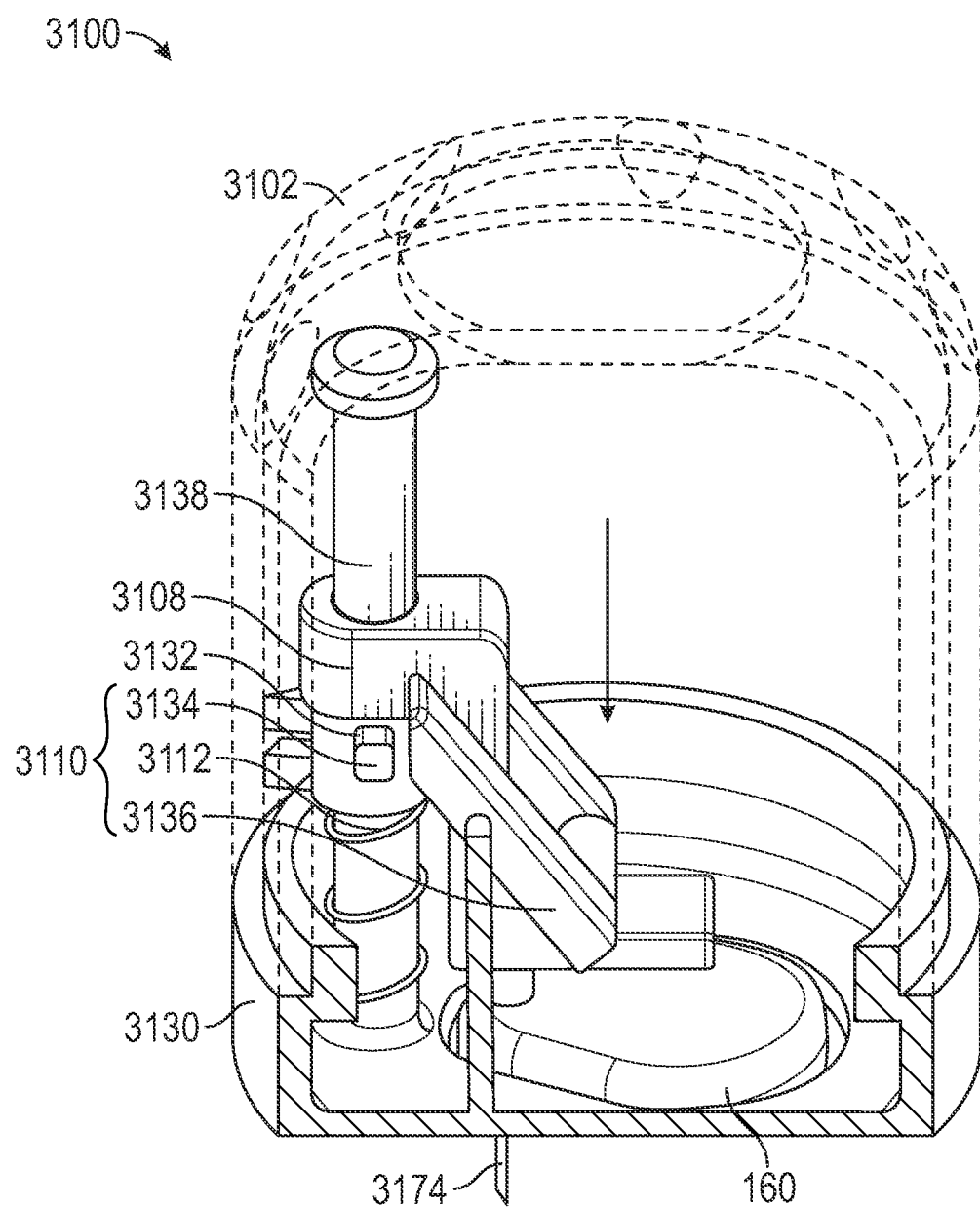
FIG. 31 illustrates a cutaway view of yet another applicator for an on-skin sensor assembly of an analyte sensor system, according to some embodiments.

FIG. 31 illustrates a cutaway view of yet another applicator 3100 for an on-skin sensor assembly of an analyte sensor system, according to some embodiments. In some embodiments, applicator 3100 may include an applicator housing 3102 configured to house one or more mechanisms for applying on-skin sensor assembly 160 to skin 130 of a host. Applicator 3100 may further comprise a base 3130 coupled to applicator housing 3102 and configured to form a bottom of applicator 3100.

Applicator 3100 further includes an activation element (not shown in FIG. 31) configured to activate a drive assembly 3110 of applicator 3100. In some embodiments, the activation element may be a button, a switch, a toggle, a slide, a trigger, a knob, a rotating member, a component that deforms and/or flexes or any other suitable mechanism for activating a drive assembly of applicator 3100. In addition, the activation element of applicator 3100 may be disposed in any location and orientation with respect to applicator housing 3102, e.g., a top, any portion of a side, or bottom of applicator housing 3102 and/or at any angle with respect to the portion of applicator housing 2102 in which the activation element is disposed. Applicator 3100 may further comprise a needle carrier assembly 3108, including an insertion element 3174 releasably coupled to on-skin sensor assembly 160 and configured to insert sensor 138 of on-skin sensor assembly 160 (e.g., FIG. 1) into skin 130 of the host. In some embodiments, the insertion element comprises a needle, for example, an open sided-needle, a needle with a deflected-tip, a curved needle, a polymer-coated needle, a hypodermic needle, deflected-tip or any other suitable type of needle or structure, as will be described in more detail in connection with at least FIGS. 47-50 and 80A-B. In yet other embodiments, insertion element may comprise sensor 138 itself, sufficiently rigid to be inserted partially into skin 130 of the host with minimal or no structural support, Drive assembly 3110 may be configured to drive insertion element 3174 of needle carrier assembly 3108 in a distal direction to a distal insertion position and in a proximal direction from the distal insertion position to a proximal retraction position. Drive assembly 3110 may include a guide member 3138, a spring 3112, a hub 3132 and a reverse toggling element 3136. guide member 3138 may be coupled to at least one of applicator housing 3102 and base 3130 at a first end and/or a second end, respectively. Spring 3112 may be disposed around guide member 3138 such that guide member 3138 extends substantially along a centerline of spring 3112. Spring 3112 may be any suitable type of spring, e.g., a compression spring, and may have a first end coupled to base 3130 and a second end coupled to a hub 3132, which is disposed on and configured to travel along guide member 3138. Spring 3120 may be configured to, upon activation of drive assembly 3110, drive hub 3132 in the proximal direction along guide member 3138, as shown by the arrow. Reverse toggling element 3136 may function substantially as a lever with a fulcrum at or near its midpoint, rotatably coupled to base 3130 or applicator housing 3102. A first end of reverse toggling element 3136 may be in contact with a protrusion 3134 of hub 3132 for at least a first portion of travel of hub 3132 in the proximal direction and a second end of reverse toggling element 3136 may be in contact with needle carrier assembly 3108. Insertion assembly 3108 may be slideably coupled to guide member 3138 on the side of hub 3132 opposite spring 3112.

In operation, upon activation of drive assembly 3110, spring 3112 drives hub 3132 along guide member 3138 in the proximal direction. For a first portion of travel along guide member 3138, protrusion 3134 of hub 3132 is in contact with the first end of reverse toggling element 3136, causing the second end of reverse toggling element 3136 to drive needle carrier assembly 3138, and so insertion element 3174 and on-skin sensor assembly 160, in the distal direction. After the first portion of travel along guide member 3138, protrusion 3134 of hub 3132 will clear the first end of reverse toggling element 3136 and make contact with the portion of needle carrier assembly 3138 slideably coupled with guide member 3138. At this point, needle carrier assembly 3108, insertion element 3174 and on-skin sensor assembly 160 are in the distal insertion position. For a second portion of travel along guide member 3138 in the proximal direction, hub 3132, still driven by spring 3112, drives needle carrier assembly 3108, and so insertion element 3174, in the proximal direction from the distal insertion position to the proximal retraction position. In this way, drive assembly 3110 converts linear motion of spring 3112 in a single direction, e.g., the proximal direction, into reciprocating linear motion in the distal direction and then the proximal direction.

FIG. 32A illustrates an exploded perspective view of yet another applicator 3200 for an on-skin sensor assembly of an analyte sensor system, according to some embodiments. Applicator 3200 may include an applicator housing 3202 configured to house at least one or more mechanisms utilized to apply the on-skin sensor assembly 160 to skin 130 of a host. Applicator 3200 may further include a base 3230 coupled to a bottom opening of applicator housing 3202. Base 3230 defines a bottom surface of applicator 3200 and a plane for application of on-skin sensor assembly 160 to skin 130 of a host.

Applicator 3200 includes an activation element 3204 configured to activate a drive assembly of applicator 3200. In some embodiments, activation element 3204 may be a button, a switch, a toggle, a slide, a trigger, a knob, a rotating member, a component that deforms and/or flexes or any other suitable mechanism for activating a drive assembly of applicator 460.

Applicator 3200 may further comprise a needle carrier assembly 3208, including an insertion element 3274 configured to insert sensor 138 of on-skin sensor assembly 160 into skin 130 of the host (e.g., FIG. 1). In some embodiments, the insertion element comprises a needle, for example, an open sided-needle, a needle with a deflected-tip, a curved needle, a polymer-coated needle, a hypodermic needle, or any other suitable type of needle or structure, as will be described in more detail in connection with at least FIGS. 47-50 and 80A-B. In yet other embodiments, insertion element may comprise sensor 138, sufficiently rigid to be inserted partially into skin 130 of the host with minimal or no structural support.

Applicator 3200 may further include a holder 3224 releasably coupled to needle carrier assembly 3208 and configured to guide on-skin sensor assembly 160 while coupled to needle carrier assembly 3208. As will be described in more detail below, on-skin sensor assembly 160 may be stripped from holder 3224 and needle carrier assembly 3208 once on-skin sensor assembly 160 is disposed on skin 130 of the host.

Applicator 3200 may further comprise a drive assembly configured to drive insertion element 3274 and needle carrier assembly 3208 in the distal direction to the distal insertion position and in the proximal direction from the distal insertion position to the proximal retraction position. Drive assembly 3210 may include a first spring 3212 and a second spring 3228. First spring 3212 may be a compression spring, or any suitable type of spring, and may have a first end coupled to applicator housing 3202 and a second end coupled to holder 3224. First spring 3212 is configured to, upon activation of drive assembly 3210, drive holder 3224, and also coupled needle carrier assembly 3208, insertion element 3274 and on-skin sensor assembly 160, in the distal direction to the distal insertion position. Substantially at the distal insertion position, needle carrier assembly 3208 may decouple from holder 3224 and on-skin sensor assembly 160.

Second spring 3228 may be a compression spring, or any suitable type of spring, and may have a first end coupled to holder 3224 and a second end coupled to needle carrier assembly 3208. Second spring 3228 is configured to drive needle carrier assembly 3208, and also insertion element 3274, in the proximal direction from the distal insertion position to the proximal retraction position. In some embodiments, first spring and/or second spring can be preloaded, partially loaded, or unloaded.

FIG. 32B illustrates an exploded perspective view 3250 of needle carrier assembly 3208 coupled to insertion element 3274, second spring 3228, holder 3224 and on-skin sensor assembly 160.

Figure 33A:
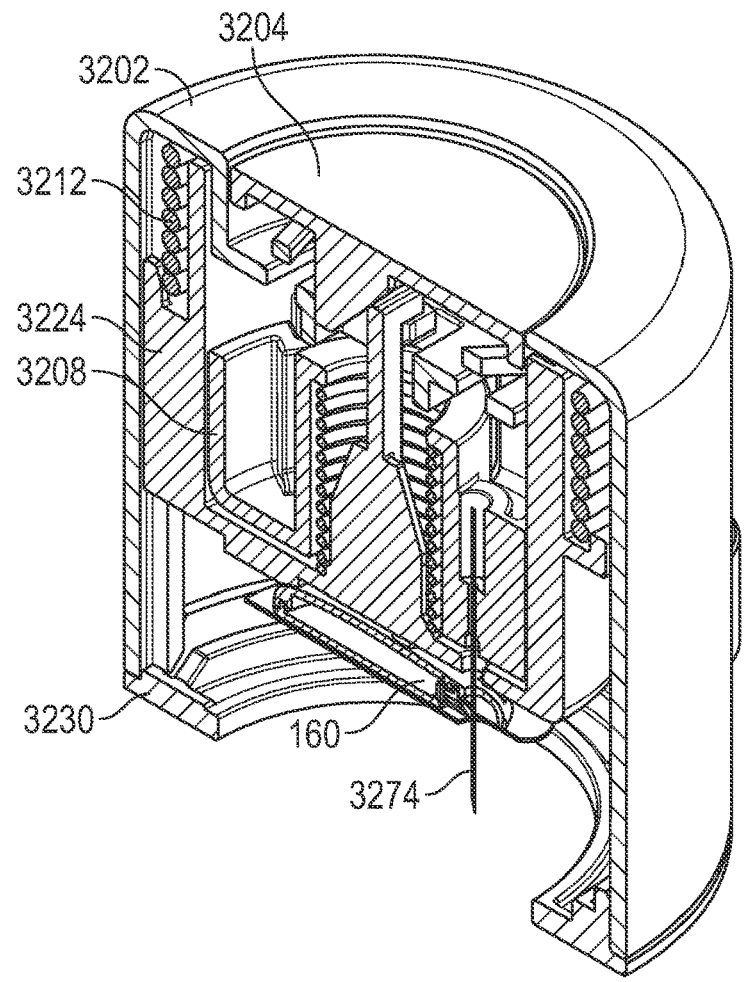
FIGS. 33A-33E illustrate several perspective cutaway views of several features of the applicator of FIG. 32, according to some embodiments.

FIG. 33A-33E illustrate perspective cutaway views of several features of applicator 3200 of FIGS. 32A-32B, according to some embodiments. FIG. 33A illustrates a perspective cutaway view of the entire applicator 3200, including applicator housing 3202, activation element 3204, first spring 3212, needle carrier assembly 3208 coupled to insertion element 3274, holder 3224 coupled to on-skin sensor assembly 160, and base 3230. Each of these components may have functionality as previously described in connection with at least FIGS. 32A-32B.

Figure 33B:
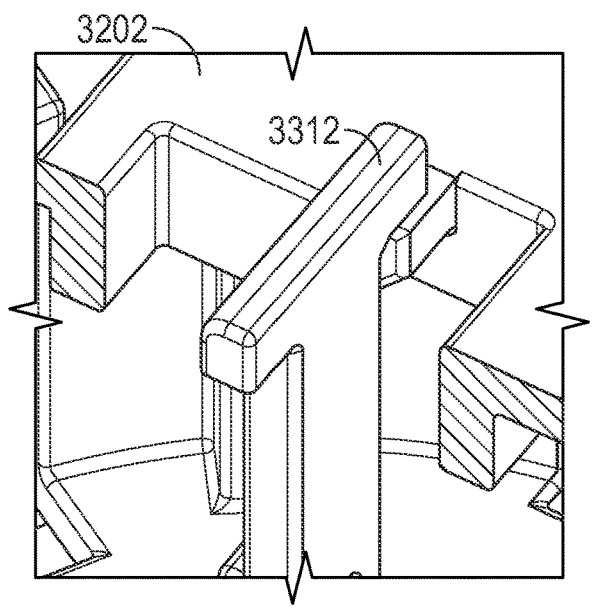

FIG. 33B illustrates a magnified perspective cutaway view of a retention element 3312 of holder 3224 releasably coupled to application housing 3202. Retention element 3312 is configured to prevent holder 3224 from traveling in the distal direction and, therefore, spring 3212 from unloading. Activation mechanism 3204, when activated, is configured to deflect retention element 3312 sufficiently to decouple it from applicator housing 3202, thereby freeing holder 3224 to travel in the distal direction, driven by spring 3212.

Figure 33C:
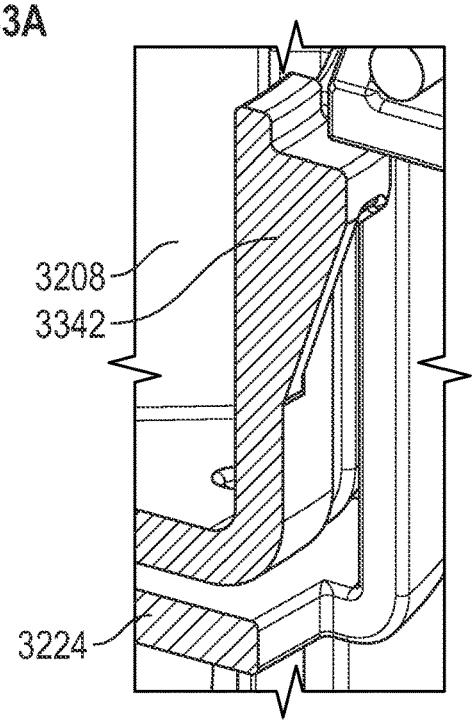

FIG. 33C illustrates a magnified perspective cutaway view of a retention element 3342 of needle carrier assembly 3208 configured to releasably couple needle carrier assembly 3208 to holder 3224. As shown, retention element 3342 may have a sloped surface configured to come in contact with a protrusion (not shown in FIG. 33) of the applicator housing 3202 or base 3230 (not shown in FIG. 33) that is configured to deflect retention element 3342 sufficiently to decouple needle carrier assembly 3208 from holder 3224 when needle carrier assembly 3208 is at or near the distal insertion position.

Figure 33D:
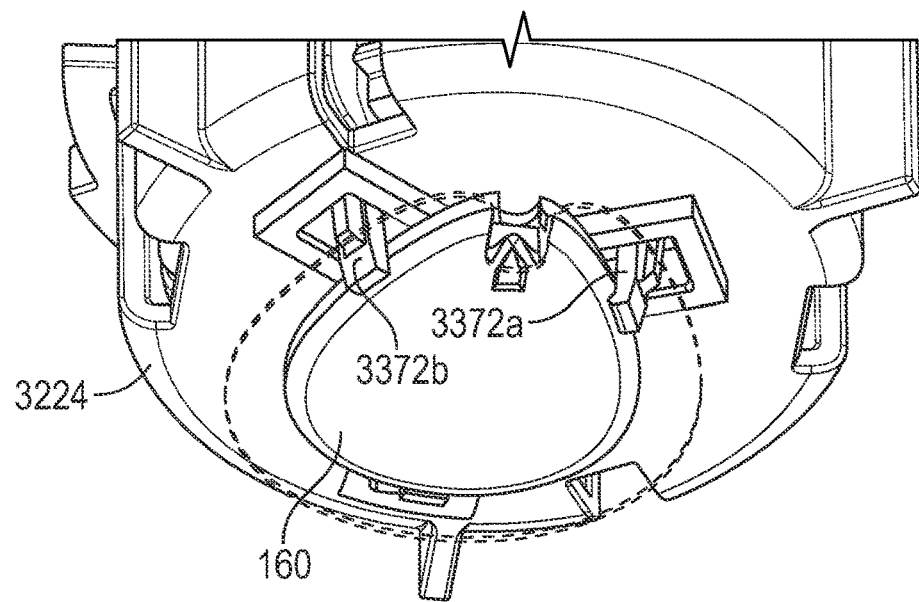

FIG. 33D illustrates a perspective view of a plurality of retention elements 3372a, 3372b of needle carrier assembly 3208 configured to pass through holder 3224 and releasably couple on-skin sensor assembly 160 to holder 3224 and to needle carrier assembly 3208. As previously described, at the distal insertion position, deflected retention element 3342 decouples needle carrier assembly 3208 from holder 3224, allowing second spring 3228 to drive needle carrier assembly 3208 in the proximal direction. As needle carrier assembly 3208 is driven in the proximal direction, retention elements 3372a, 3372b detach from on-skin sensor assembly 160. Although two retention elements are illustrated, any number of retention elements are contemplated. In some embodiments, retention element(s) 3372a, 3372b may comprise snap fits, friction fits, interference features, elastomeric grips and/or adhesives configured to couple on-skin sensor assembly 160 with needle carrier assembly 3208 and/or holder 3224. Moreover, alternative mechanisms that may perform such retention and release actions are further described in connection with at least FIGS. 35A-37C below.

Figure 33E:
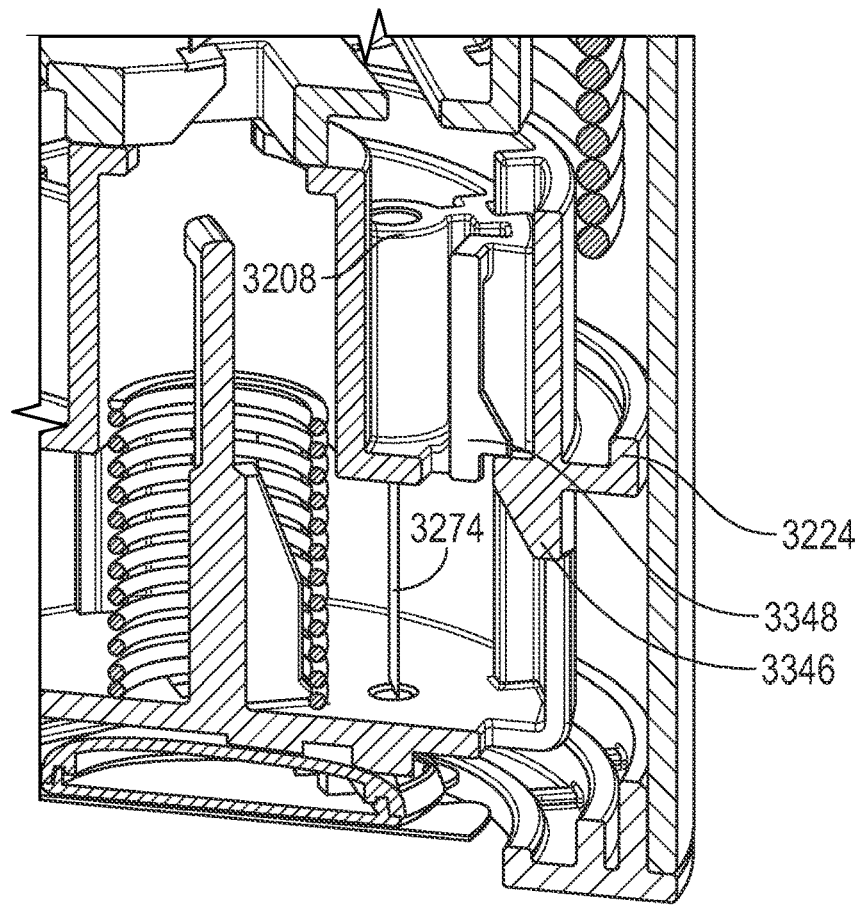

FIG. 33E illustrates a perspective cutaway view of a retention element 3346 of holder 3224 and a retention element 3348 of applicator housing 3202 configured to immobilize needle carrier assembly 3208 to holder 3346 upon needle carrier assembly 3208 reaching the distal insertion position. This interaction immobilizes insertion element 3274 in the proximal retraction position, thereby ensuring the end of insertion element 3274 is not exposed out the bottom of applicator 3200.

A brief description of the operation of applicator 3200 follows with respect to FIGS. 34A-34F, which illustrate several perspective views of the applicator of FIG. 32 during operation, according to some embodiments.

Figure 34B:
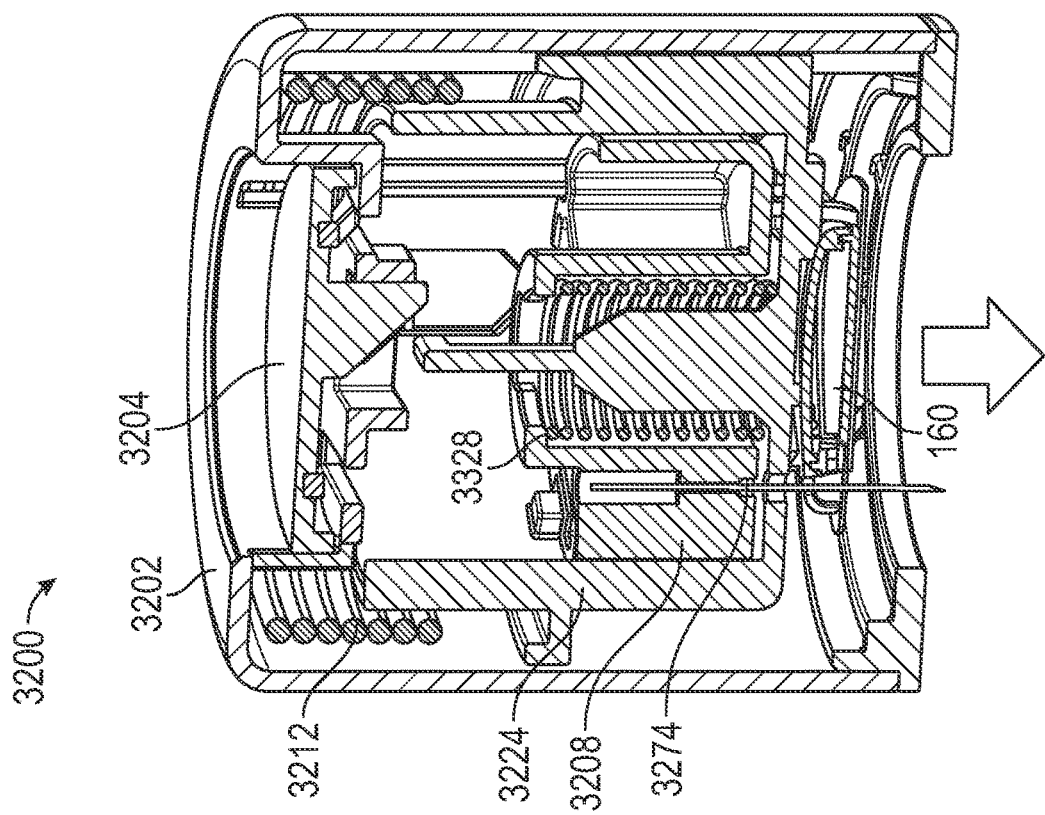
Figure 34A:
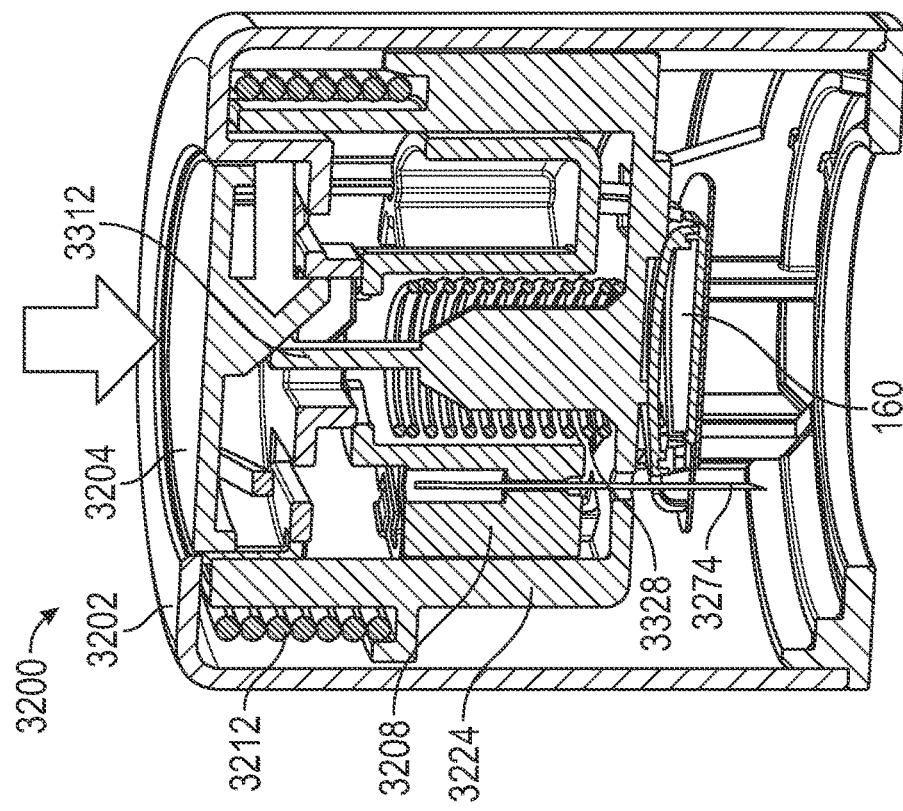

FIG. 34A illustrates a state of applicator 3200 at activation. Activation element 3204 is illustrated in the process of being activated, having been pushed down by a user, for example. Activation element 3204 deflects retention element 3312 such that holder 3224 is not prevented from traveling in the distal direction. Holder 3224, needle carrier assembly 3208, insertion element 3274, first spring 3212 and second spring 3228 are all shown in pre-activation positions.

FIG. 34B illustrates applicator 3200 during activation. Activation element 3204 is illustrated in the activated position. Spring 3212 is driving holder 3224, and also needle carrier assembly 3208, insertion element 3274, and on-skin sensor assembly 160, in the distal direction toward the distal insertion position.

Figure 34D:
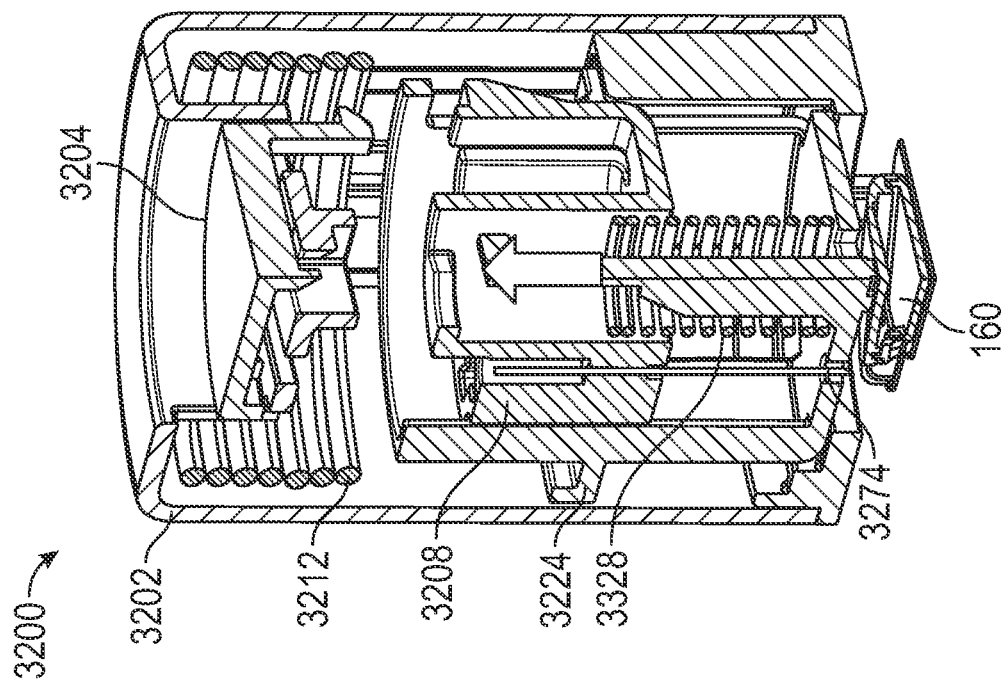
Figure 34C:
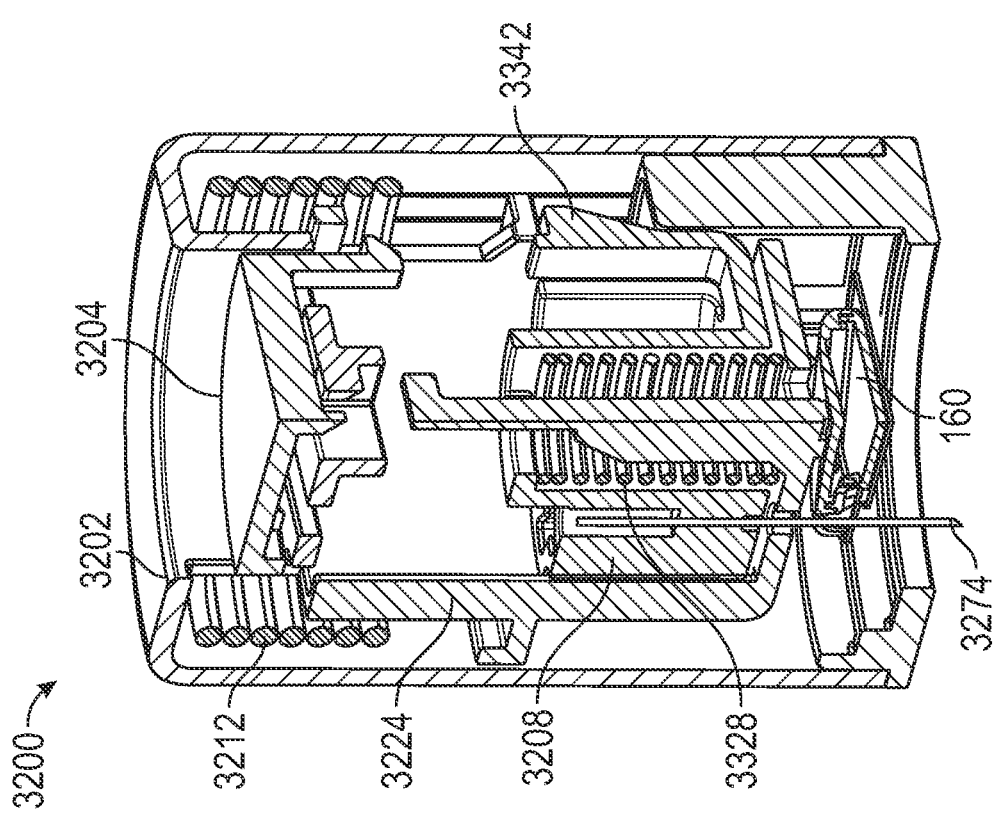

FIG. 34C illustrates applicator 3200 during activation, as needle carrier assembly 3208 approaches the distal insertion position. Activation element 3204 is illustrated in the activated position. Insertion assembly 3208, insertion element 3274, holder 3224 and on-skin sensor assembly 160 are driven in the distal direction to the distal insertion position. At or near this distal insertion position, at least a portion of insertion element 3274 as well as at least a portion of sensor 138 of on-skin sensor assembly 160 may be inserted into the skin of the host. At this position, retention element 3342 is deflected by a portion of applicator housing 3302 or base 3230, thereby decoupling needle carrier assembly 3208 from holder 3224.

FIG. 34D illustrates applicator 3200 during activation. Activation element 3204 is illustrated in the activated position. Second spring 3228 drives needle carrier assembly 3208 and insertion element 3274 in the proximal direction from the distal insertion position. Although not shown in FIG. 34D, once needle carrier assembly reaches the proximal retraction position, retention elements 3346 and 3348 may be engaged with one another immobilizing needle carrier assembly 3208 and insertion element 3274 in the proximal retraction position, thereby maintaining insertion element 3274 in a locked, retracted position.

FIG. 35A-35C illustrate several cross-sectional views of an on-skin sensor assembly retention mechanism of applicator 3200 of FIG. 32, according to some embodiments. The retention mechanism described in connection with FIGS. 35A-35C is similar to the retention mechanism previously described in connection with FIGS. 6A-6H. FIG. 35A illustrates the retention mechanism while applicator 3200 is in the pre-activated state. Retention element 3372a is illustrated as a portion of holder 3224 and configured to releasably couple on-skin sensor assembly 160 to holder 3224 as needle carrier assembly 3208 travels in the distal direction to the distal insertion position, and to decouple on-skin sensor assembly 160 from holder 3224 as needle carrier assembly 3208 travels in the proximal direction from the distal insertion position towards the proximal retraction position. Specifically, retention element 3372a may comprise a first end 3376a and a second end 3378a. The second end may be releasably coupled to on-skin sensor assembly 160 in the pre-activation state. As previously stated, retention element(s) 3372a, 3372b may comprise snap fits, friction fits, interference features, elastomeric grips and/or adhesives configured to couple on-skin sensor assembly 160 with needle carrier assembly 3208 and/or holder 3224. FIG. 35A further illustrates applicator housing 3202 comprising an optional reinforcing element 3510 configured to prevent lateral motion of retention element 3372a in the proximal starting position, thereby supporting releasable coupling of second end 3378a of retention element 3372a with on-skin sensor assembly 160.

FIG. 35B illustrates applicator 3200 in the distal insertion position after activation. As needle carrier assembly 3208 travels in the distal direction to the distal insertion position, retention element 3342 of needle carrier assembly 3208 is released from holder 3224. The second end of retention element 3372a may still be releasably coupled to on-skin sensor assembly 160. FIG. 35B further illustrates optional reinforcing element 3510 as no longer being in physical contact with retention element 3372a in the distal insertion position, thereby allowing for the uncoupling of second end 3378a of retention element 3372a from on-skin sensor assembly 160.

FIG. 35C illustrates applicator 3200 where needle carrier assembly 3208 is moving in the proximal direction from the distal insertion position. Since retention element 3342 of needle carrier assembly 3208 was uncoupled from holder 3224 at the distal insertion position, as needle carrier assembly 3208 travels back in the proximal direction, needle carrier assembly 3208 separates from holder 3224. As needle carrier assembly 3208 travels in the proximal direction, first end 3376a of retention element 3372a is deflected by needle carrier assembly 3208, thereby decoupling second end 3378a of retention element 3372a from on-skin sensor assembly 160. FIG. 35C further illustrates optional reinforcing element 3510 as no longer being in physical contact with retention element 3372a in the distal insertion position.

Figure 36A:
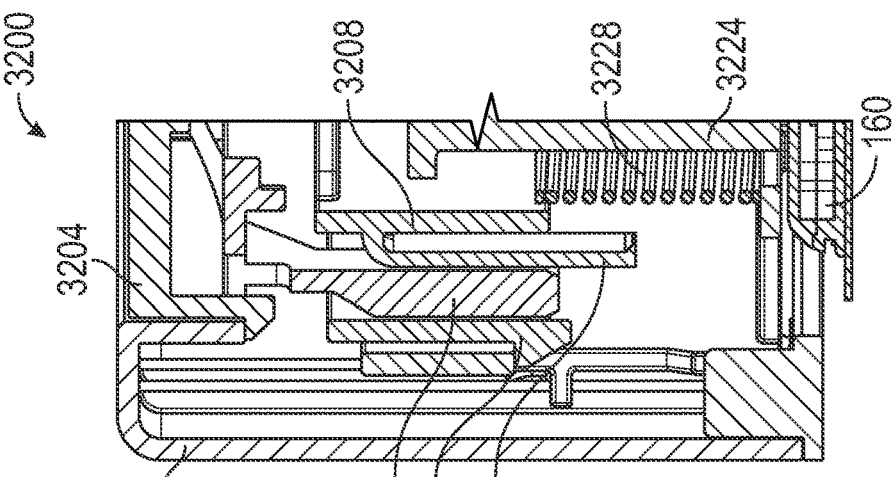
FIG. 36A-36C illustrate cross-sectional views of another on-skin sensor assembly retention mechanism of the applicator of FIG. 32, according to some embodiments.
Figure 36B:
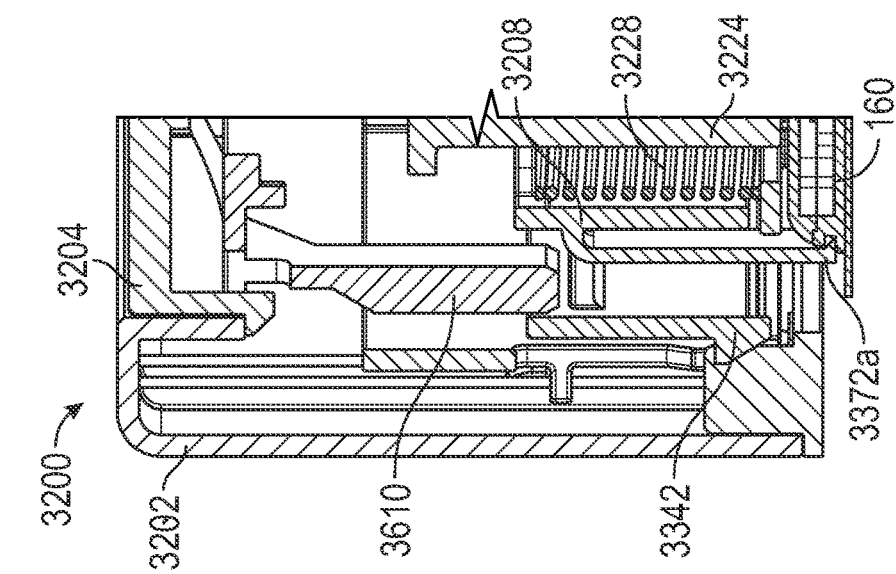
Figure 36C:
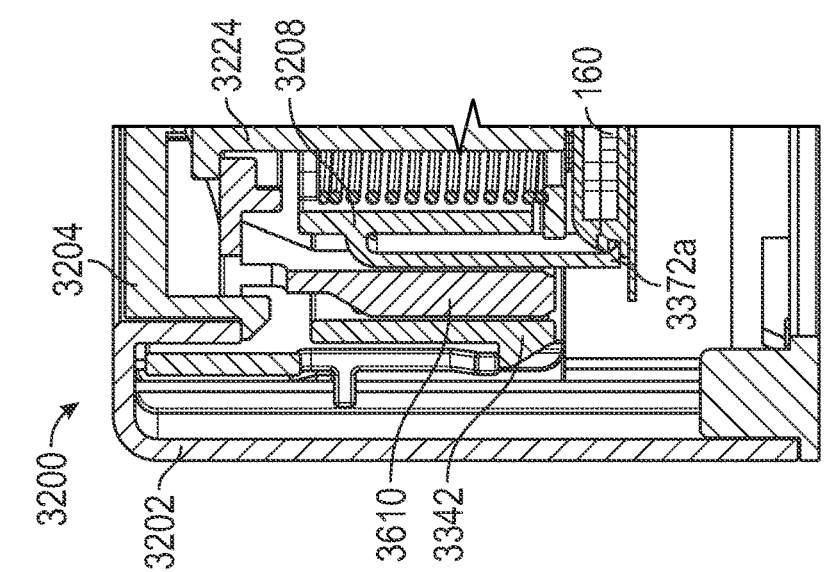

FIG. 36A-36C illustrate several cross-sectional views of another on-skin sensor assembly retention mechanism of applicator 3200 of FIG. 32, according to some embodiments. FIG. 36A illustrates the retention mechanism while applicator 3200 is in the pre-activated state. Retention element 3372a is illustrated as a portion of needle carrier assembly 3208 and is configured to releasably couple on-skin sensor assembly 160 to holder 3224 as needle carrier assembly 3208 travels in the distal direction to the distal insertion position, and to decouple on-skin sensor assembly 160 from holder 3224 as needle carrier assembly 3208 travels in the proximal direction from the distal insertion position towards the proximal retraction position. Specifically, retention element 3372a may releasably couple on-skin sensor assembly 160 as needle carrier assembly 3208 travels in the distal direction to the distal insertion position. FIG. 36A further illustrates applicator housing 3202 comprising an optional reinforcing element 3610 configured to prevent lateral motion of retention element 3372a and/or retention element 3342 in the proximal starting position, thereby supporting releasable coupling of retention element 3372a with on-skin sensor assembly 160.

FIG. 36B illustrates applicator 3200 at the distal insertion position. Retention element 3342 of needle carrier assembly 3208 is uncoupled from holder 3224 at the distal insertion position, retention element 3224 being deflected by a portion of applicator housing 3202 or an applicator base of applicator housing 3202 sufficient for retention element 3224 to clear a stop element of needle carrier assembly. Accordingly, needle carrier assembly 3208 separates from holder 3224 as needle carrier assembly 3208 travels back in the proximal direction by a force provided by spring 3228. Rather than being physically deflected in orientation as needle carrier assembly 3208 travels in the proximal direction, retention element 3372a is formed to be easily deflected or deformed simply by the separation of holder 3224 from needle carrier assembly 3208. FIG. 36B further illustrates optional reinforcing element 3610 as no longer being in physical contact with retention element 3372a and/or retention element 3342 in the distal insertion position, thereby allowing for the uncoupling of retention element 3372a from on-skin sensor assembly 160 and/or the uncoupling of holder 3224 from needle carrier assembly 3208.

FIG. 36C illustrates needle carrier assembly 3208 moving in the proximal direction from the distal insertion position of FIG. 36B. As shown, retention element 3372a has been released from on-skin sensor assembly 160 by separation of needle carrier assembly 3208 from holder 3224, and needle carrier assembly 3208 is driven in the proximal direction by a force provided by spring 3228. FIG. 36C further illustrates optional reinforcing element 3610 as no longer being in physical contact with retention element 3372a and/or retention element 3342 in the proximal retracted position.

FIG. 37A-37C illustrate several cross-sectional views of yet another on-skin sensor assembly retention mechanism of applicator 3200 of FIG. 32, according to some embodiments. FIG. 37A illustrates applicator 3200 in the pre-activated position. Retention element 3372a is illustrated in FIG. 37A as an integral portion of holder 3208 and is configured to releasably couple on-skin sensor assembly 160 to holder 3224 as needle carrier assembly 3208 travels in the distal direction to the distal insertion position, and to decouple on-skin sensor assembly 160 from holder 3224 as needle carrier assembly 3208 travels in the proximal direction from the distal insertion position towards the proximal retraction position. Specifically, retention element 3372a may releasably couple on-skin sensor assembly 160 as needle carrier assembly 3208 travels in the distal direction to the distal insertion position. FIG. 37A further illustrates applicator housing 3202 comprising an optional first reinforcing element 3710 configured to prevent lateral motion of retention element 3342 in the proximal retracted position. FIG. 37A further illustrates needle carrier assembly 3208 comprising an optional second reinforcing element 3712 configured to prevent lateral motion of retention element 3372a, thereby supporting releasable coupling of retention element 3372a with on-skin sensor assembly 160.

FIG. 37B illustrates needle carrier assembly 3208 in the distal insertion position. Retention element 3342 of needle carrier assembly 3208 is uncoupled from holder 3224 at the distal insertion position. Accordingly, needle carrier assembly 3208 separates from holder 3224 as needle carrier assembly 3208 travels back in the proximal direction under influence of a force provided by spring 3228 as spring 3228 unloads, pushing against holder 3224 and needle carrier assembly 3208. FIG. 37B further illustrates optional first reinforcing element 3710 as no longer being in physical contact with retention element 3342 in the distal insertion position, thereby allowing for the uncoupling of holder 3224 from needle carrier assembly 3208. Optional second reinforcing element 3712 is still illustrated as being in physical contact with retention element 3372a in the distal insertion position.

FIG. 37C illustrates needle carrier assembly as it begins to travel in the proximal direction, after retention element 3372a of needle carrier assembly 3208 is uncoupled from holder 3224. Rather than being physically deflected in orientation as needle carrier assembly 3208 travels in the proximal direction, as in FIGS. 35A-35C, retention element 3372a detaches from on-skin sensor assembly 160 simply by the user removing applicator 3200 from the skin. In some embodiments, an adhesive patch that holds on-skin sensor assembly 160 to the skin of the host provides sufficient bonding strength to decouple on-skin sensor assembly 160 from the skin of the host when applicator 3200 is removed from the skin. FIG. 37C further illustrates optional first reinforcing element 3710 as no longer being in physical contact with retention element 3372a in the proximal retracted position, thereby supporting uncoupling of retention element 3372a from on-skin sensor assembly 160.

Figure 38:
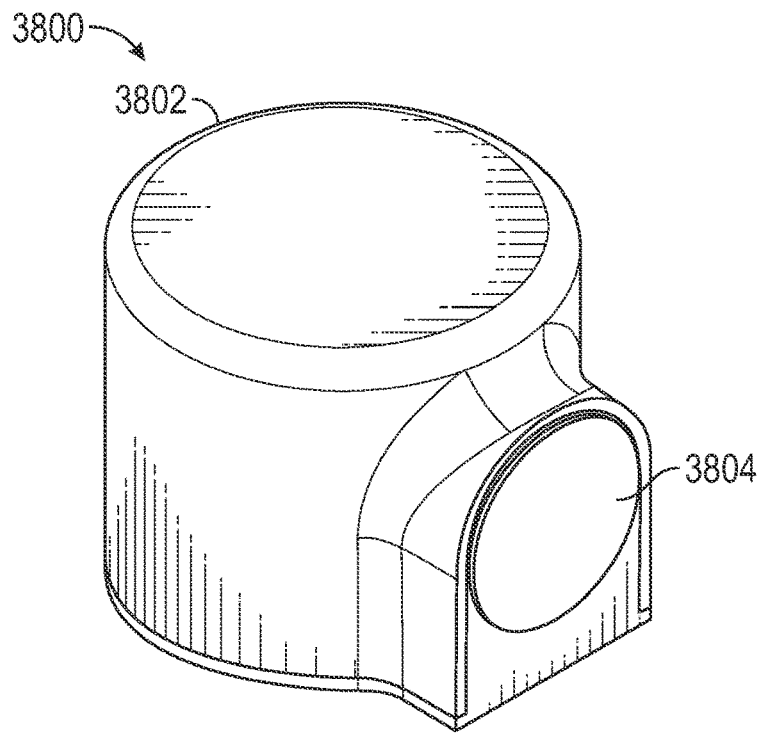
FIG. 38 illustrates a perspective view of an applicator similar to those shown in FIG. 32, including an activation element on a side of the housing, according to some embodiments.

FIG. 38 illustrates a perspective view of an applicator 3800 similar to those shown in FIG. 32, including an activation element 3804 on a side of an applicator housing 3802, according to some embodiments. Applicator 3800 may have substantially the same features as either applicator 3200 of FIG. 32, except that activation element 3804 is located on a side of applicator housing 3802, rather than on a top of the applicator housing. Such an arrangement may provide for an applicator having a reduced height compared to top-activated applicators, though potentially having an increased width or diameter compared to the top-activated applicators.

Figure 39:
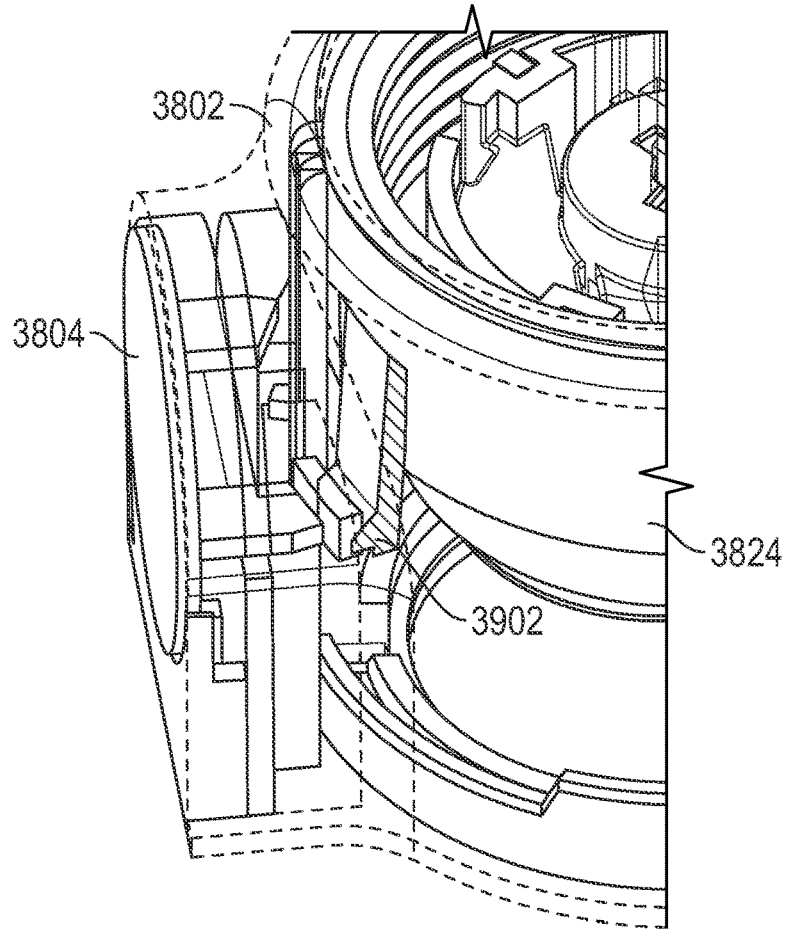
FIG. 39 illustrates a cutaway perspective view of a portion of the applicator of FIG. 38, according to some embodiments.

FIG. 39 illustrates a cutaway view of a portion of applicator 3800 of FIG. 38, according to some embodiments. Activation element 3804 may be configured to, upon activation, deflect a retention element 3902 of holder 3824 configured to prevent holder 3824 from traveling in the distal direction. All other features of applicator 3800 not discussed may be substantially as previously described for either applicator 3200 of FIG. 32.

Figure 40C:
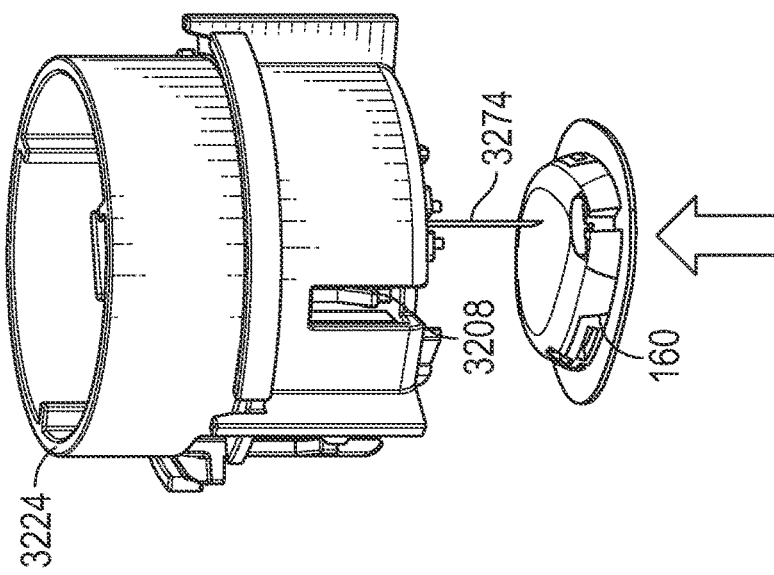
FIGS. 40A-40G illustrate several perspective views of steps for assembling the applicator of FIG. 32, according to some embodiments.
Figure 40B:
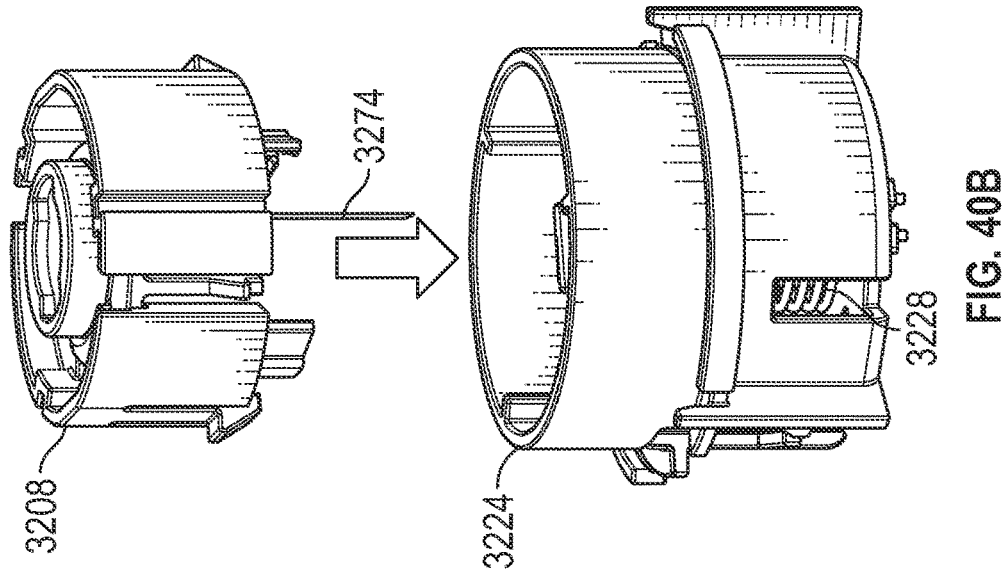
Figure 40A:
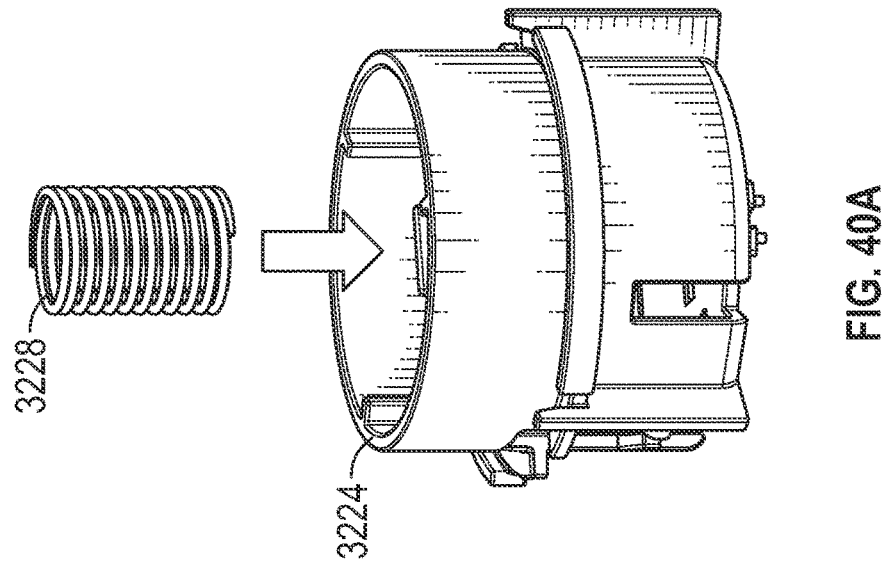

FIGS. 40A-40G illustrate several perspective views of an assembly process for the applicator of FIG. 32, according to some embodiments. FIG. 40A illustrates inserting second spring 3228 into holder 3224. FIG. 40B illustrates next inserting insertion element 3274 into needle carrier assembly 3208 and then inserting insertion element 3274 into needle carrier assembly 3208 into holder 3224. In some embodiments, inserting insertion element 3274 into needle carrier assembly 3208 into holder 3224 pre-compresses second spring 3228. FIG. 40C illustrates coupling on-skin sensor assembly 160 to at least one of holder 3224 and needle carrier assembly 3208 by coupling retention elements (not shown in FIG. 40C) of holder 3224 or of needle carrier assembly 3208 to attachment points (not shown in FIG. 40C) of on-skin sensor assembly 160.

Figure 40E:
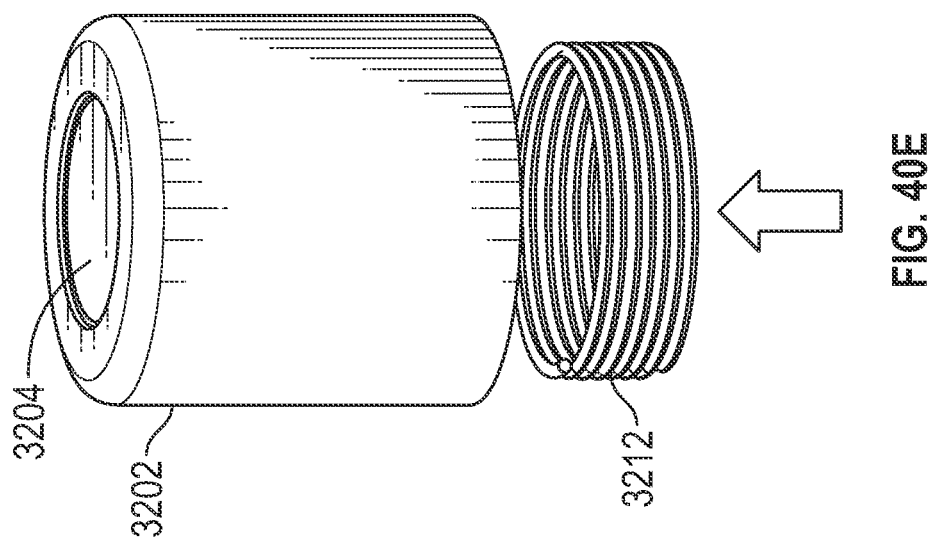
Figure 40D:
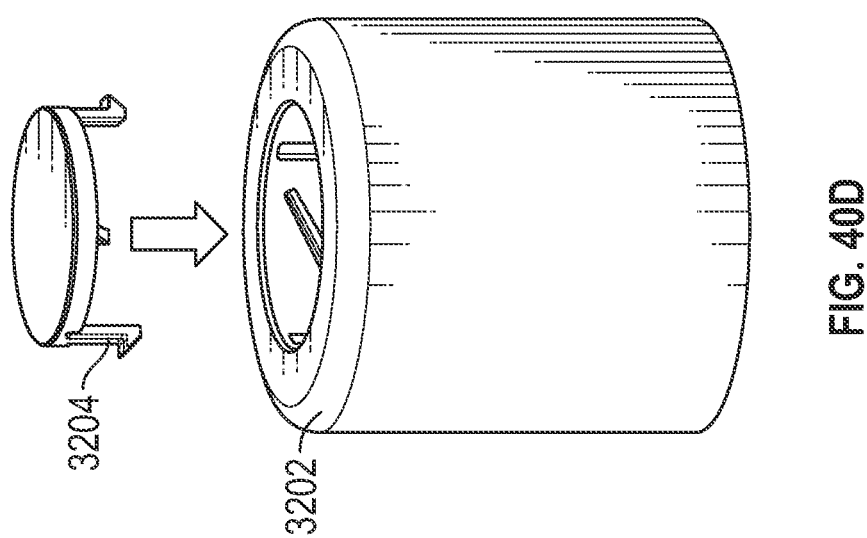
Figure 40G:
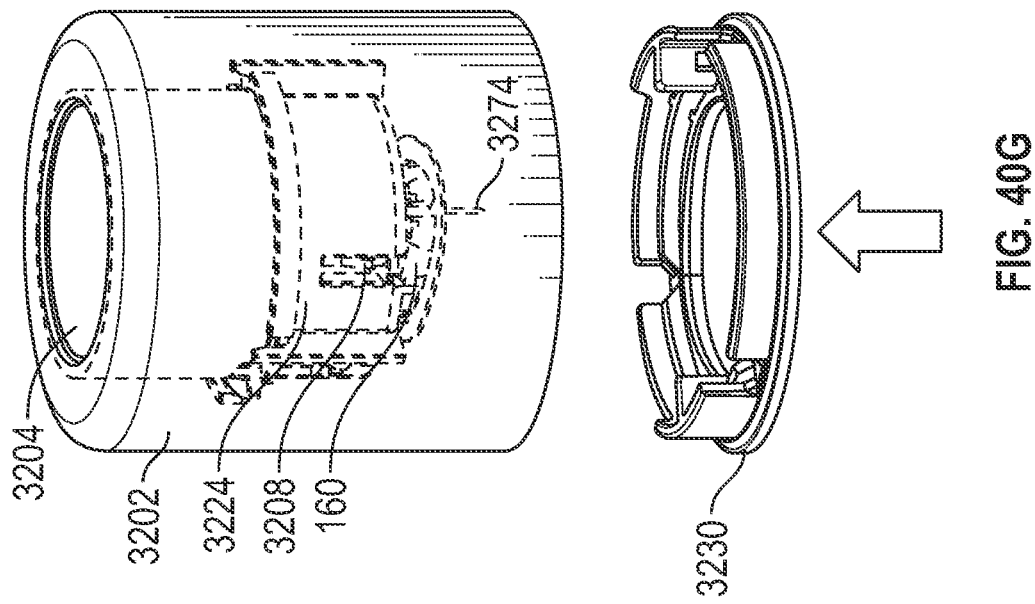
Figure 40F:
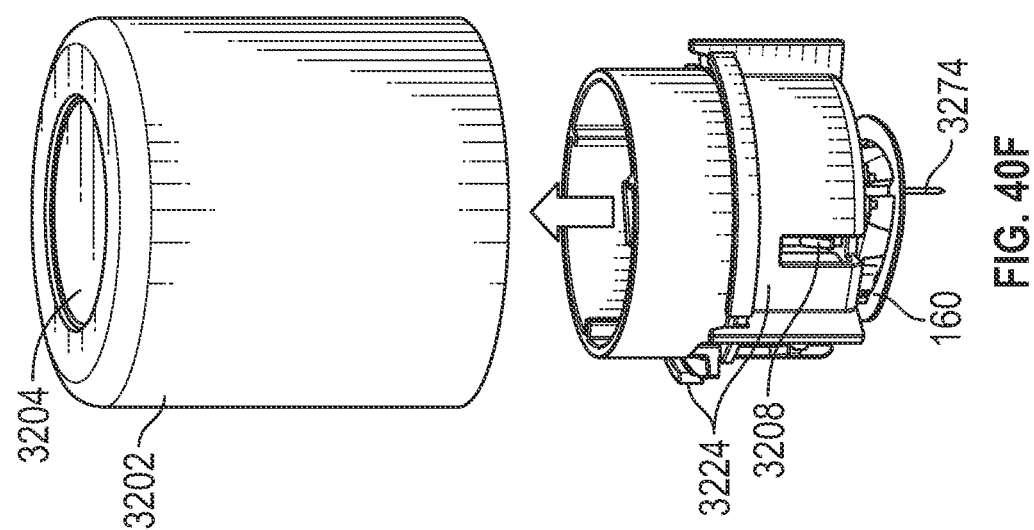

FIG. 40D illustrates coupling activation element 3204 to applicator housing 3202. In FIG. 40D, activation element 3204 is coupled on a top of applicator housing 3202. In some embodiments, activation element 3204 may be pressed into an opening of applicator housing 3202 configured to receive activation element 3204. However, in other embodiments, applicator housing 3202 may accommodate activation element 3204 in other locations, for example, an upper, medial or lower side of applicator housing. FIG. 40E illustrates inserting first spring 3212 into applicator housing 3202. FIG. 40F illustrates inserting the assembly described in FIG. 40C (comprising holder 3224, second spring 3228, needle carrier assembly 3208, insertion element 3274 and on-skin sensor assembly 160) into applicator housing 3202. In some embodiments, the act of inserting the assembly described in FIG. 40C pre-compresses first spring 3212. FIG. 40G illustrates coupling base 3230 to applicator housing 3202.

On-Skin Sensor Assembly Retention Mechanisms

In some embodiments of applicators described herein, on-skin sensor assembly 160 is held in place during at least travel in the distal direction to the distal insertion position. In some such embodiments, on-skin sensor assembly 160 is then released or decoupled from a portion of the applicator during application to the skin of the host so that a needle carrier assembly and insertion element may travel back in the proximal direction. FIGS. 41A-45 illustrate several alternative retention mechanisms that may be utilized in any of the applicators described herein.

Figure 41A:
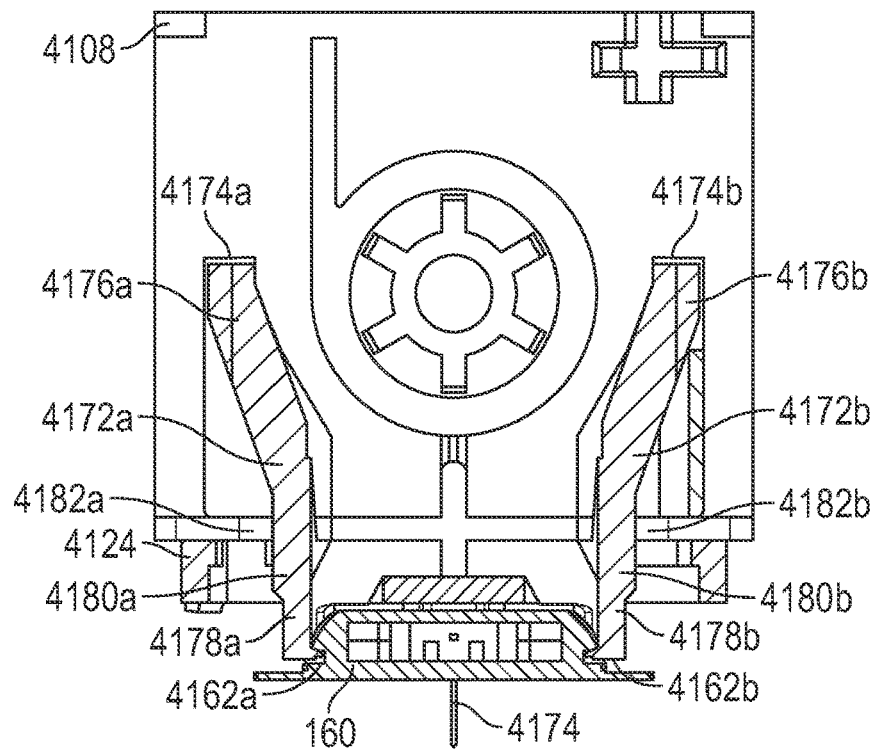
FIGS. 41A-41B illustrate cross-sectional views an exemplary on-skin sensor assembly retention mechanism of an applicator for an analyte sensor system, according to some embodiments.
Figure 41B:
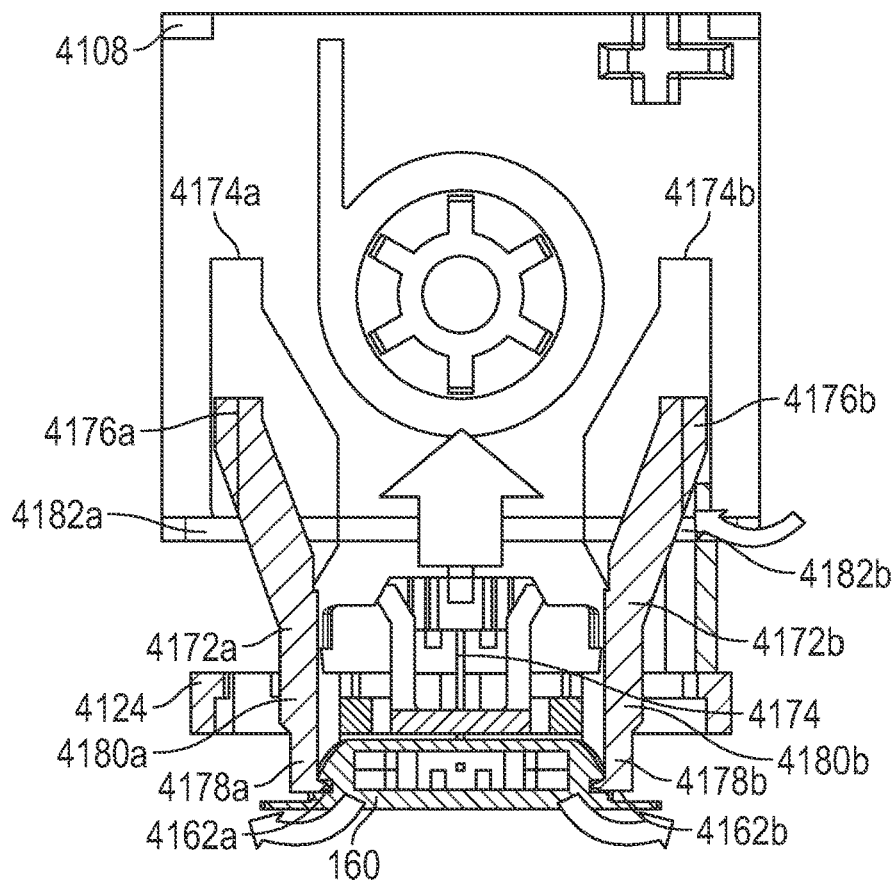

FIGS. 41A-41B illustrate an exemplary on-skin sensor assembly retention mechanism of an applicator for an analyte sensor system, according to some embodiments. The retention mechanism illustrated by FIGS. 41A-41B may be considered a first on-skin sensor assembly retention configuration, and is similar to the retention mechanism previously described in connection with FIG. 5.

FIG. 41A illustrates a retention mechanism in a state where on-skin sensor assembly 160 is retained, while FIG. 41B illustrates the retention mechanism in a state where on-skin sensor assembly 160 is decoupled.

FIG. 41A illustrates retention elements 4172a, 4172b of a holder 4124 configured to releasably couple on-skin sensor assembly 160 to holder 4124 as needle carrier assembly 4108 (and so insertion element 4172, holder 4124, and on-skin sensor assembly 160) travels in the distal direction to the distal insertion position. Specifically, retention elements 4172a, 4172b may each comprise a first end 4176a, 4176b, a second end 4178a, 4178b, and a pivot point 4180a, 4180b. First end 4176a, 4176b is immobilized in a respective guide 4174a, 4174b of needle carrier assembly 4108 and each of retention elements 4172a, 4172b is immobilized against interference points 4182a, 4182b of needle carrier assembly 4108, thereby releasably coupling and immobilizing second end 4178a, 4178b to attachment points 4162a, 4162b of on-skin sensor assembly 160 as needle carrier assembly 4108 travels in the distal direction to the distal insertion position. In some embodiments, the profile of slots 4174a, 4174b may be such that the sides of slots 4174a, 4174b exert a force on first ends 4176a, 4176b of retention elements 4172a, 4172b sufficient to hold second ends 4178a, 4178b of retention elements 4172a, 4172b in engagement with attachment points 4162a, 4162b of on-skin sensor assembly 160. Although two retention elements are illustrated, any number of retention elements are contemplated.

FIG. 41B illustrates the retention mechanism as needle carrier assembly 4108 and insertion element 4174 travel in the proximal direction from the distal insertion position to the proximal retraction position. As needle carrier assembly 4108 travels back in the proximal direction, needle carrier assembly 4108 separates from holder 4124, thereby removing first ends 4176a, 4176b of retention elements 4172a, 4172b from respective slots 4174a, 4174b, allowing first ends 4176a, 4176b to deflect inward and second ends 4178a, 4178b of retention elements 4172a, 4172b to deflect outward from attachment points 4162a, 4162b of on-skin sensor assembly 160 as retention elements 4172a, 4172b rotate about pivot points 4180a, 4180b.

Figure 42A:
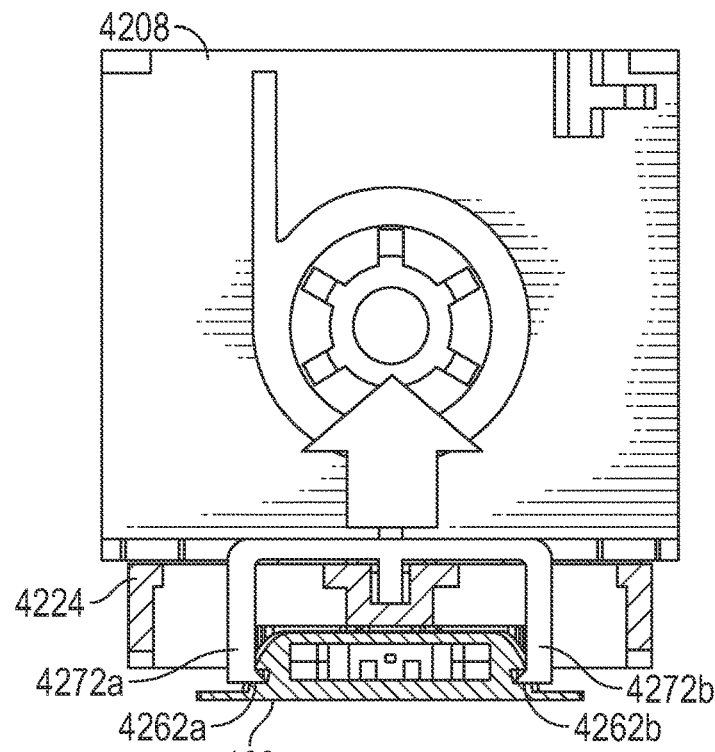
FIGS. 42A-42B illustrate cross-sectional views of another exemplary on-skin sensor assembly retention mechanism of an applicator for an analyte sensor system, according to some embodiments.
Figure 42B:
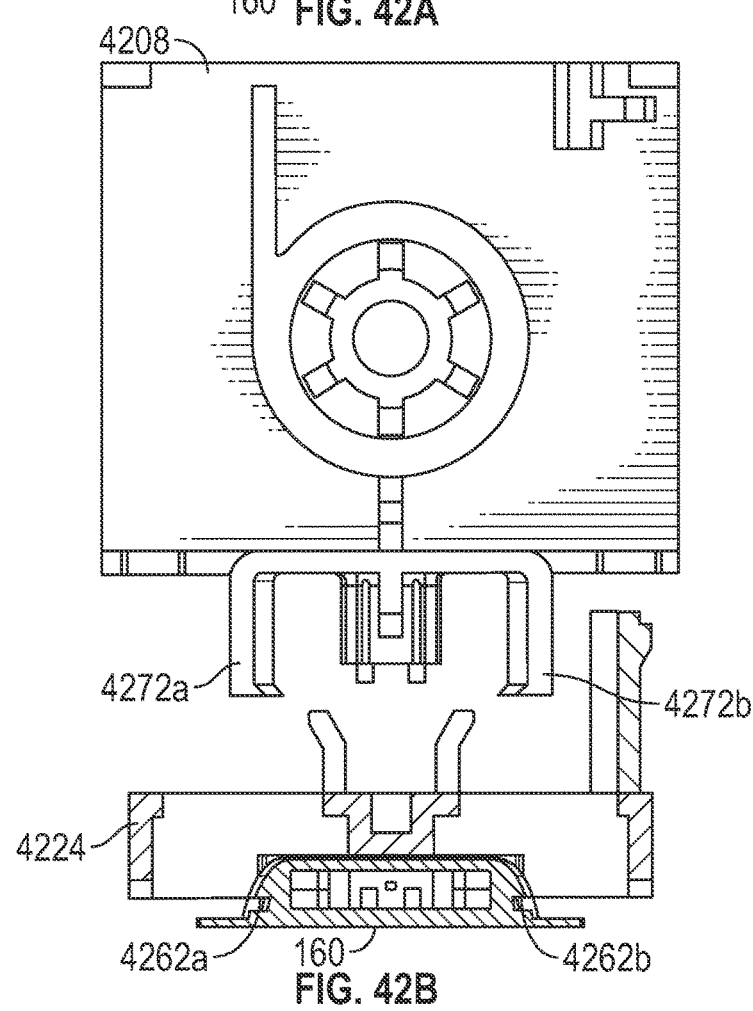

FIGS. 42A-42B illustrate an exemplary on-skin sensor assembly retention mechanism of an applicator for an analyte sensor system, according to some embodiments. The retention mechanism illustrated by FIGS. 42A-42B may be considered a second on-skin sensor assembly retention configuration, and is similar to the retention mechanism previously described in connection with FIG. 36. FIG. 42A illustrates a retention mechanism in a state where on-skin sensor assembly 160 is retained, while FIG. 42B illustrates the retention mechanism in a state where on-skin sensor assembly 160 is decoupled.

FIG. 42A illustrates retention elements 4272a, 4272b as portions of needle carrier assembly 4208 that pass through or around needle carrier assembly 4208, rather than as portions of holder 4224. Retention elements 4272a, 4272b are configured to releasably couple on-skin sensor assembly 160 to holder 4228 as needle carrier assembly 4208 (and so an insertion element, holder 4224, and on-skin sensor assembly 4224) travels in the distal direction to the distal insertion position.

FIG. 42B illustrates the retention mechanism as needle carrier assembly 4208 and insertion element 4274 travel in the proximal direction from the distal insertion position to the proximal retraction position. As needle carrier assembly 4208 travels in the proximal direction, needle carrier assembly 2508 separates from holder 4224 and retention elements 4272a, 4272b are uncoupled from respective attachment points 4262a, 4262b of on-skin sensor assembly 160. Rather than being physically deflected in orientation as needle carrier assembly 4208 travels in the proximal direction, as described for retention elements 4172a, 4172b of FIGS. 41A-41B, retention elements 4272a, 4272b are pulled out of attachment points 4262a, 4262b by the energy of the retraction.

Figure 43A:
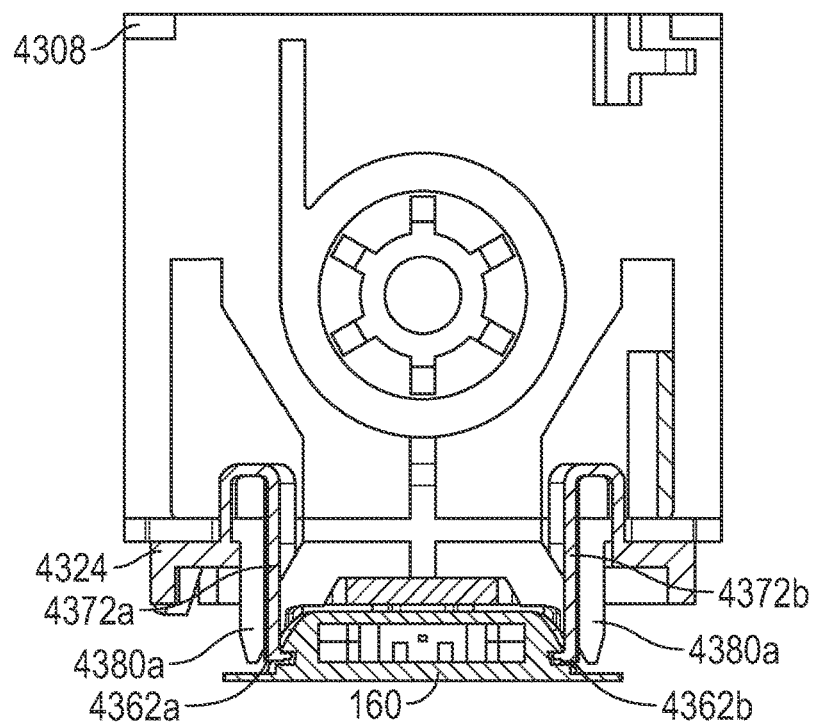
FIGS. 43A-43B illustrate cross-sectional views of yet another exemplary on-skin sensor assembly retention mechanism of an applicator for an analyte sensor system, according to some embodiments.
Figure 43B:
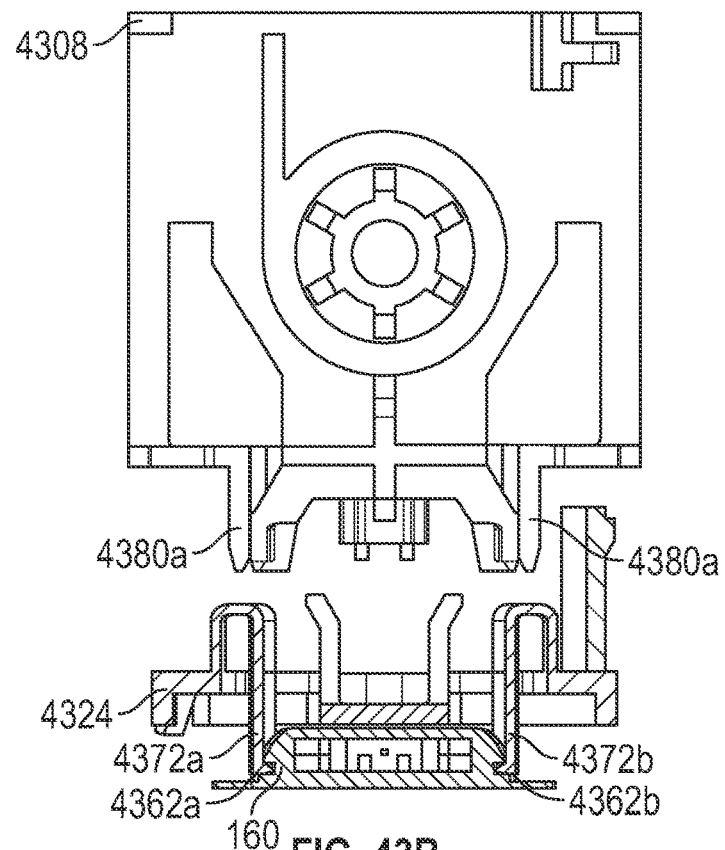

FIGS. 43A-43B illustrate an exemplary on-skin sensor assembly retention mechanism of an applicator for an analyte sensor system, according to some embodiments. The retention mechanism illustrated by FIGS. 43A-43B may be considered a passive snap design. FIG. 43A illustrates a retention mechanism in a state where on-skin sensor assembly 160 is retained, while FIG. 43B illustrates the retention mechanism in a state where on-skin sensor assembly 160 is decoupled.

FIG. 43A illustrates retention elements 4372a, 4372b as portions of a holder 4324. Retention elements 4372a, 4372b are configured to releasably couple on-skin sensor assembly 160 to holder 4324 as needle carrier assembly 4308 (and so an insertion element, holder 4324, and on-skin sensor assembly 4324) travels in the distal direction to the distal insertion position. FIG. 43A further illustrates protrusions 4380a, 4380b of needle carrier assembly 4308 configured to physically contact retention elements 4372a, 4372b of holder 4324 thereby preventing retention elements 4372a, 4372b from disengaging from on-skin sensor assembly 4324 while needle carrier assembly 4308 is in contact with holder 4324.

FIG. 43B illustrates the retention mechanism as needle carrier assembly 4308 travels in the proximal direction from the distal insertion position to the proximal retraction position. As needle carrier assembly 4308 travels in the proximal direction, needle carrier assembly 4308 separates from holder 4324. Although not shown in FIGS. 43A-43B, holder 4324 may be immobilized to an applicator housing or base by one or more retention elements, similar to retention elements 642, 644 of FIG. 6E. Accordingly, retention elements 4372a, 4372b may be uncoupled from respective attachment points 4362a, 4362b of on-skin sensor assembly 160 as the applicator is removed from the skin of the host. In some embodiments, an adhesive patch that holds on-skin sensor assembly 160 to the skin of the host provides sufficient bonding strength to decouple on-skin sensor assembly 160 from the skin of the host when the applicator is removed from the skin.

Figure 44:
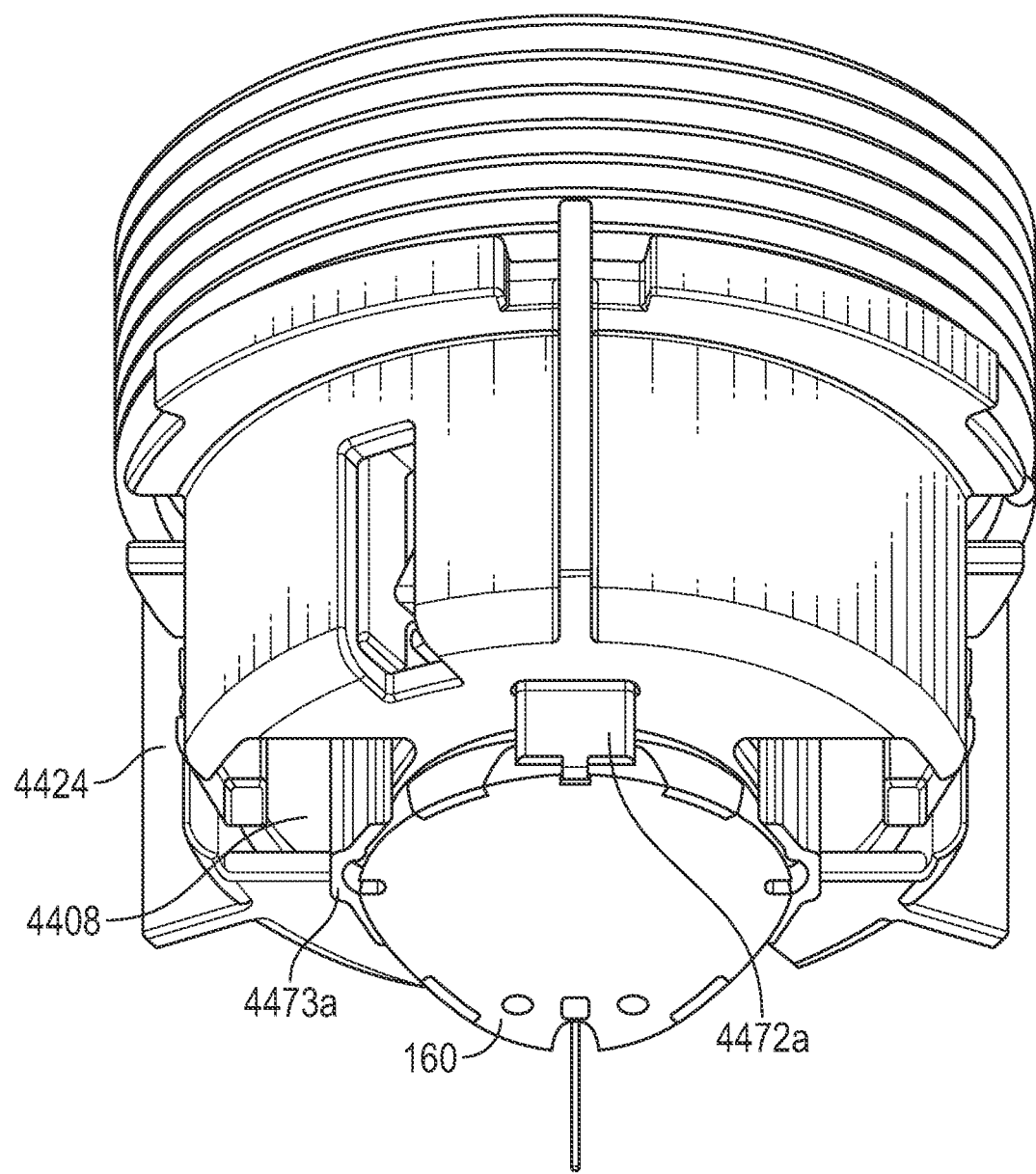
FIG. 44 illustrates a perspective view of a portion of another exemplary on-skin sensor assembly retention mechanism of an applicator for an analyte sensor system, according to some embodiments.

FIG. 44 illustrates another portion of an exemplary on-skin sensor assembly retention mechanism of an applicator for an analyte sensor system, according to some embodiments. FIG. 44 illustrates a needle carrier assembly 4408, a holder 4424, and on-skin sensor assembly 160. Contrary to several previous embodiments of retention mechanisms for on-skin sensor assembly 160, needle carrier assembly 4408 comprises at least one retention element 4472a and holder 4424 comprises at least one alignment element 4473a, in which retention element 4472a is configured to releasably couple to on-skin sensor assembly 160, and alignment element 4473a is configured to align on-skin sensor assembly 160 within the applicator. This distribution of retention elements between both a needle carrier assembly and a holder may be implemented for any on-skin sensor assembly retention mechanism described herein.

Figure 45:
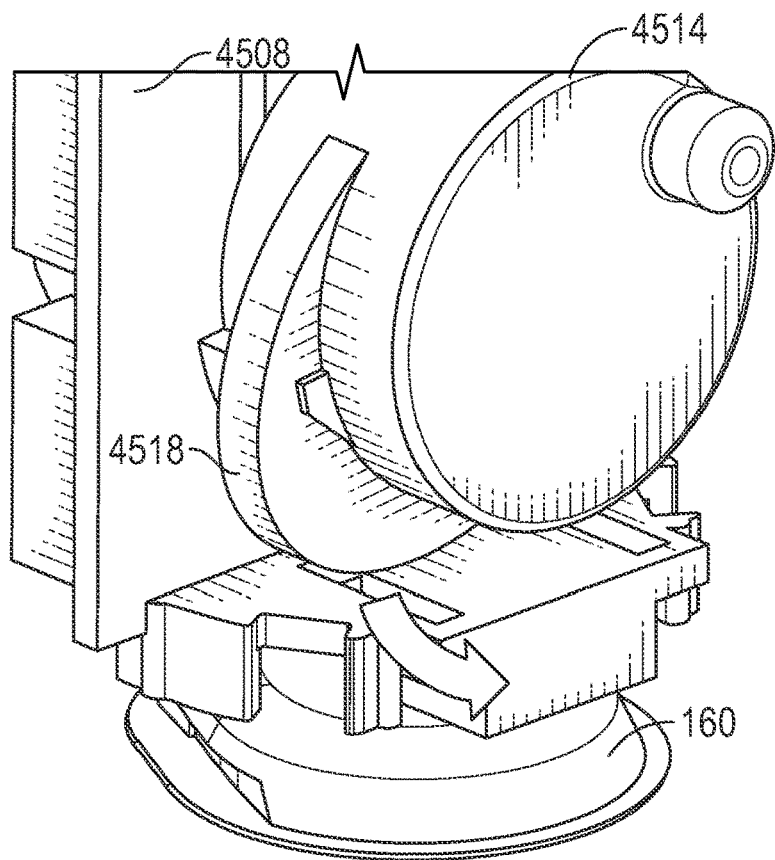
FIG. 45 illustrates a perspective view of portion of an exemplary on-skin sensor assembly retention mechanism of an applicator for an analyte sensor system, according to some embodiments.
Figure 46:
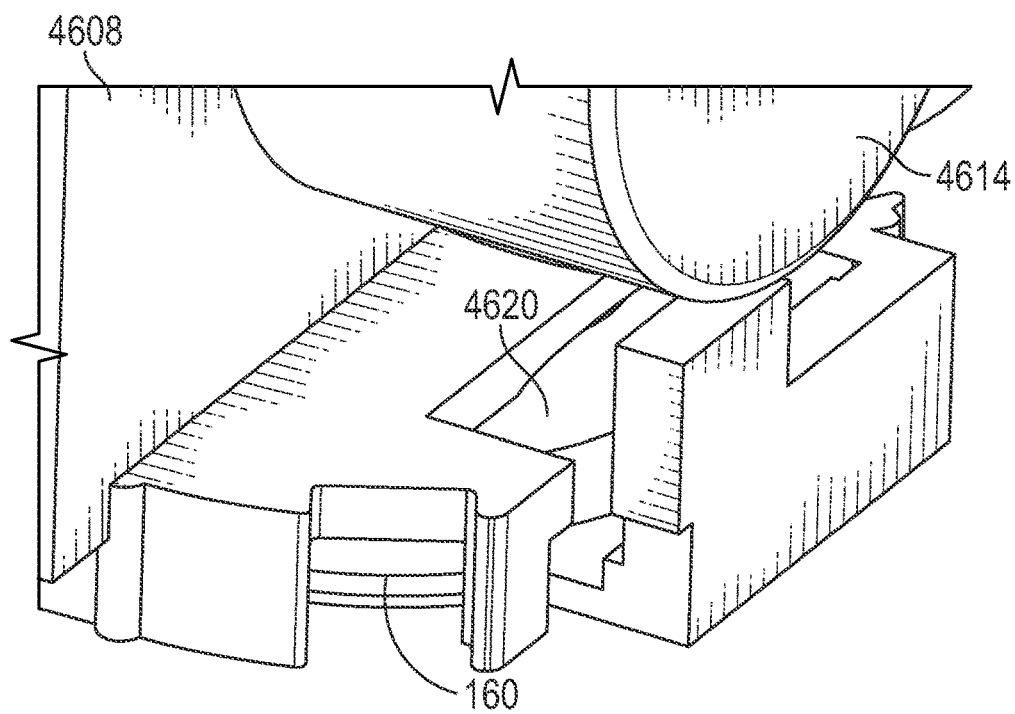
FIG. 46 illustrates a perspective view of a portion of an exemplary on-skin sensor assembly retention mechanism of an applicator for an analyte sensor system, according to some embodiments.

FIGS. 45 and 46 illustrate portions of exemplary on-skin sensor assembly retention mechanisms of an applicator for an analyte sensor system, according to some embodiments. FIGS. 45 and 46 illustrate a needle carrier assembly 4508, 4608, a rotating drive element 4514, 4614 similar to that previously described in connection with FIG. 5, and on-skin sensor assembly 160. Accordingly, the retention mechanisms of FIGS. 45 and 46 may function similarly to that described in FIG. 5. Rotating drive element 4514, 4614 may be a wheel cam and may comprise a cam lobe 4518 (e.g., a ramp or protrusion, not shown in FIG. 46, see FIG. 45) disposed along at least a portion of a circumference of rotating drive element 4514, 4614. In FIG. 45, as rotating drive element 4514 is rotated, protrusion 4518 may travel alongside needle carrier assembly 4508 and come into contact with and increasingly apply a force to on-skin sensor assembly 160 such that on-skin sensor assembly 160 decouples from needle carrier assembly 4508. In FIG. 46, as rotating drive element 4614 is rotated, the protrusion may travel at least partially through a guide or slot 4620 in needle carrier assembly 4608 and come into contact with and increasingly apply a force to on-skin sensor assembly 160 such that on-skin sensor assembly 160 decouples from needle carrier assembly 4608. In this way, rotating drive element 4514, 4614 may serve both to drive needle carrier assembly 4508, 4608 in the distal and proximal directions, as previously described in connection with FIG. 5, and to release on-skin sensor assembly 160 upon deposition to the skin of the host.

In some embodiments, on-skin sensor assembly retention mechanisms may incorporate features to couple an on-skin sensor assembly to the needle carrier assembly and/or the holder. Methods of coupling on-skin sensor assembly are described in U.S. patent application Ser. No. 15/387,088, which is incorporated herein by reference it its entirety. For non-limiting example, on-skin sensor assembly retention mechanisms may include a frangible release (e.g. FIGS. 137-140), a frangible elastomer (e.g. FIGS. 134-136), a releasable adhesive (e.g. FIG. 123-125), or a releasable friction-fit coupling (e.g. FIG. 126-133).

For example, a frangible release can be implemented in the current embodiments by a structure attached between an on-skin sensor assembly (e.g. 160), a holder (e.g. 524), a needle carrier (e.g. 508), and/or an applicator housing (e.g. 502). The frangible component may include features such has a weakened portion or a portion designated to fracture during release of the on-skin sensor assembly from the applicator. Frangible components configured to fracture may include patch material (e.g. spun lace) or molded components (e.g. ABS, PC, polymer, elastomeric polymer, etc.).

For example, a releasable adhesive can be implemented in the current embodiments by a releasable adhesive releasably attached between an on-skin sensor assembly (e.g. 160), a holder (e.g. 524), a needle carrier (e.g. 508), and/or an applicator housing (e.g. 502). The releasable adhesive may consist of a double sided adhesive tape, a glue, or a hot melt polymer. The releasable adhesive is configured to detach during release of the on-skin sensor assembly from the applicator via an applicator mechanism (e.g. retraction mechanism) or user force.

For example, a releasable friction-fit coupling can be implemented in the current embodiments by a surface contact between an on-skin sensor assembly (e.g. 160), a holder (e.g. 524), a needle carrier (e.g. 508), and/or an applicator housing (e.g. 502). The releasable friction-fit coupling may consist of a rigid or elastomeric material (e.g. silicone, TPE, TPU, rubber, etc.) or a combination thereof. The coupled components (e.g. on-skin sensor assembly 160 and holder 524) have a frictional material interaction (e.g. interference fit, deformable fit, etc.). The releasable friction-fit coupling is configured to detach during release of the on-skin sensor assembly from the applicator via an applicator mechanism (e.g. retraction mechanism) or user force.

Discussion with respect to FIGS. 71-89 below may be directed to, among other aspects, applicators that account for skin tenting (e.g., the skin bowing in a substantially convex fashion as the host pushes the applicator against the skin). FIGS. 71-89 may be further directed to preventing an insertion mechanism, assembly or spring from stalling due to such skin tenting by, among other aspects, initiating retraction, after insertion, based on an on-skin sensor assembly and/or other features of the applicator pushing against the skin of the host with a force sufficient to initiate the retraction, as opposed to retraction being triggered by the on-skin sensor assembly and/or other features of the applicators reaching a predetermined physical displacement in the distal direction. It is contemplated that such force-based retraction trigger allows the transition from insertion to retraction at a variety of distally displaced positions based at least in part on the location of the surface of the skin of the host during application.

Figures 71, 72:
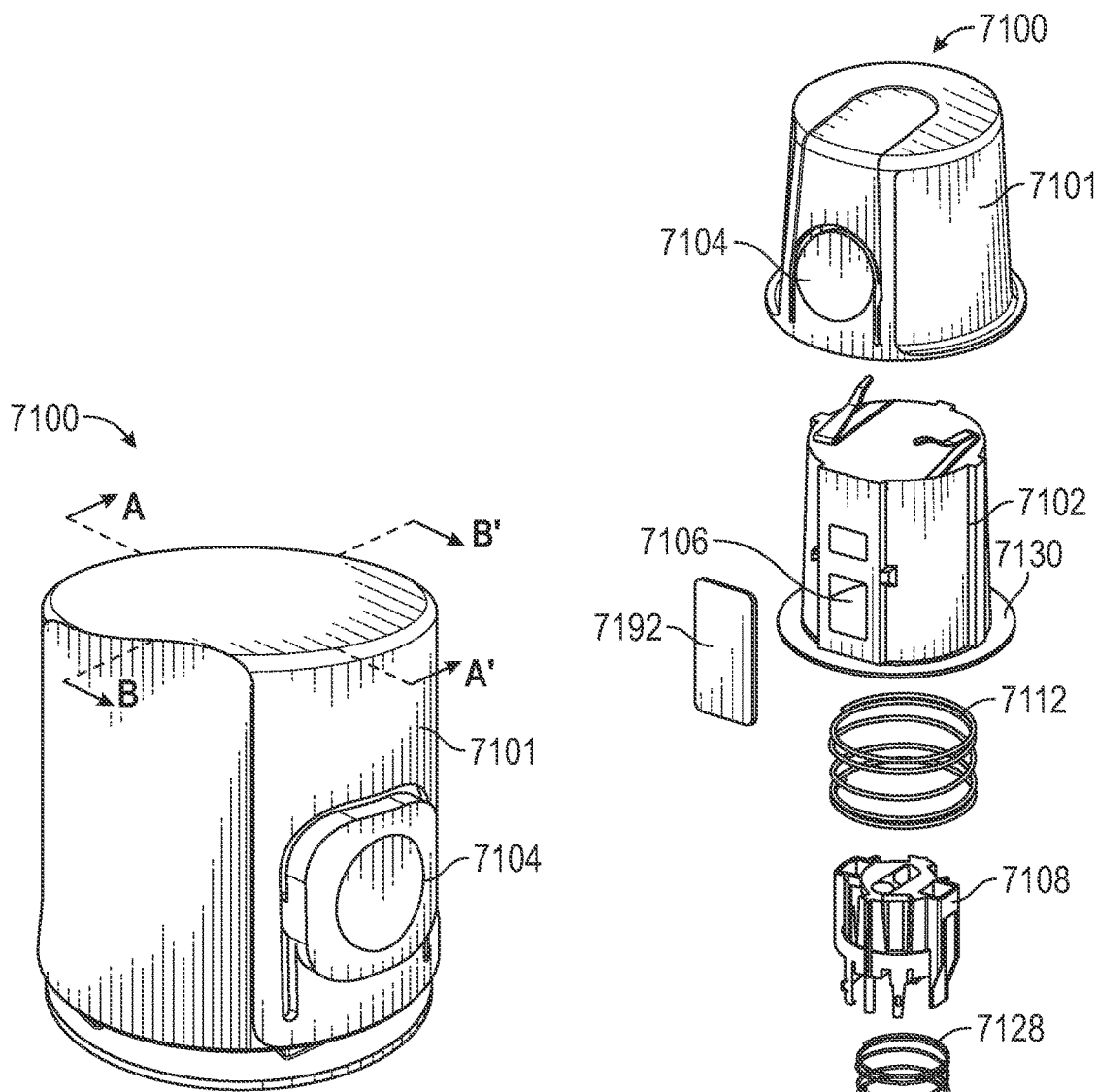
FIG. 71 illustrates yet another applicator for an on-skin sensor assembly of an analyte sensor system, according to some embodiments.
FIG. 72 illustrates an exploded perspective view of the applicator of FIG. 71, according to some embodiments.

FIG. 71 illustrates an applicator 7100 for an on-skin sensor assembly of an analyte sensor system, according to some embodiments. As will be described below, applicator 7100 may comprise an activation element 7104 disposed on a side of applicator 7100, for example, on a side of an outer housing 7101 of applicator 7100. In some embodiments, activation element 7104 may be a button, a switch, a toggle, a slide, a trigger, a knob, a rotating member, a portion of applicator 7100 that deforms and/or flexes or any other suitable mechanism for activating an insertion and/or retraction assembly of applicator 7100. In some embodiments, activation element 7104 may be disposed in any location, e.g., a top, upper side, lower side, or any other location of applicator 7100. Applicator 7100 may be large enough for a host to grasp with a hand and push, or otherwise activate, activation element 7104 with, for example, a thumb, or with an index finger and/or a middle finger.

Applicator 7100 may be configured with one or more safety features such that applicator 7100 is prevented from activating until the safety feature is deactivated. In one example, the one or more safety features prevents applicator 7100 from activating unless applicator 7100 is pressed against the skin of a host with sufficient force. Moreover, as will be described in more detail in connection with one or more of FIGS. 72-80B below, applicator 7100 may be further configured such that one or more components therein retract based at least in part on the one or more components pushing against the skin of the host with a force exceeding a predetermined threshold, rather than based on the one or more components translating beyond a predetermined and static distal position. In other words, applicator 7100 may implement force-based retraction triggering rather than being limited to displacement-based retraction triggering.

FIG. 72 illustrates an exploded perspective view of applicator 7100 of FIG. 71, according to some embodiments. Applicator 7100 may include outer applicator housing 7101 comprising activation element 7104. Outer applicator housing 7101 may be configured to translate in a distal direction by a force applied by a host to applicator 7100, specifically to inner housing 7102, thereby aligning activation element 7104 in a position that allows applicator 7100 to fire. Further explanation of the alignment process will be explained below.

Applicator 7100 further comprises inner housing 7102, configured to house at least one or more mechanisms utilized to apply on-skin sensor assembly 360 to skin 130 of a host. A distal surface 7130 of a bottom opening of inner housing 7102 may define a bottom surface of applicator 7100. In some embodiments, upon pressing applicator 7100 against skin 130 of the host, skin 130 may deform in a substantially convex shape at distal surface 7130 such that at least a portion of a surface of skin 130 disposed at the bottom opening of applicator housing 7102 extends into the bottom opening of inner housing 7102 beyond a plane defined by distal surface 7130 in a proximal direction.

In some embodiments, a first barrier layer 7192 may be disposed over one or more apertures in inner housing 7102, for example, an aperture 7106 through which at least a portion of activation element 7104 may be configured to extend through during activation of applicator 7100. In such embodiments, a portion of activation element 7104 may be configured to pierce or deform first barrier layer 7192 upon activation of applicator 7100. First barrier layer 7192 may comprise a gas permeable material such as Tyvek, or a non-gas permeable material such as metallic foil, polymer film, elastomer, or any other suitable material.

Applicator 7100 may further comprise a needle carrier assembly 7108, including a needle hub 7150 configured to couple an insertion element 7174 to needle carrier assembly 7108. In some other embodiments, insertion element 7174 may be directly coupled to needle carrier assembly 7108. Insertion element 7174 is configured to insert sensor 338 of on-skin sensor assembly 360 (see FIGS. 3A-4) into skin 130 of the host (e.g., FIG. 1). In some embodiments, the insertion element comprises a needle, for example, an open sided-needle, a needle with a deflected-tip, a curved needle, a polymer-coated needle, a hypodermic needle, or any other suitable type of needle or structure, as described in connection with at least FIGS. 47-50 and 80A-B. In yet other embodiments, insertion element 7174 may be integrally formed with sensor 338 and may be sufficiently rigid to be inserted partially into skin 130 of the host with minimal or no structural support.

Applicator 7100 may further include a holder 7124 releasably coupled to needle carrier assembly 7108 and configured to guide needle carrier assembly 7108 and on-skin sensor assembly 360 while coupled to needle carrier assembly 7108, e.g., at least during translation from a proximal position to a distal insertion position. As will be described in more detail below, on-skin sensor assembly 360 may be stripped or released from holder 7124 and/or needle carrier assembly 7108 once on-skin sensor assembly 360 is disposed on skin 130 of the host.

Applicator 7100 may further comprise an insertion assembly configured to translate insertion element 7174, needle hub 7150, needle carrier assembly 7108, and on-skin sensor assembly 360 from a proximal position, in the distal direction, to a distal insertion position. Such an insertion assembly may include a first spring 7112. First spring 7112 may be a compression spring, or any suitable type of spring, and may have a first end in contact with or coupled to inner applicator housing 7102 and a second end in contact with or coupled to holder 7124. First spring 7112 is configured to, upon activation of the insertion assembly, translate holder 7124, needle carrier assembly 7108, needle hub 7150, insertion element 7174 and on-skin sensor assembly 360, in the distal direction to the distal insertion position. Substantially at the distal insertion position, needle carrier assembly 7108 may decouple from holder 7124 and on-skin sensor assembly 360.

Applicator 7100 may further comprise a retraction assembly configured to translate needle carrier assembly 7108, needle hub 7150 and insertion element 7174, in the proximal direction, from the distal insertion position to a proximal retracted position. In some embodiments the initial proximal position may be the same as the proximal retracted position. In other embodiments, the initial proximal position may be different from the proximal retracted position. Such a retraction assembly may include a second spring 7128. Second spring 7128 may be a compression spring, or any suitable type of spring, and may have a first end contacting or coupled to holder 7124 and a second end in contact with or coupled to at least one spring retention element (e.g., 7442a, 7442b in FIGS. 74A-75B), at least until retraction. Second spring 7128 is configured to translate needle carrier assembly 7108, needle hub 7150, and insertion element 7174 in the proximal direction from the distal insertion position to the proximal retracted position in response to on-skin sensor assembly 360 contacting skin 130 of the host, and/or reaching a limit of travel with a force exceeding a predetermined threshold sufficient to cause first end of second spring 7128 to overcome the at least one spring retention element (e.g., 7442a, 7442b in FIGS. 74A-75B). In some embodiments, a stop feature (not shown) may be disposed at a bottom of applicator 7100, e.g., on a distal portion of inner housing 7102. Such a stop feature may be configured to contact one or more of on-skin sensor assembly 360, needle carrier 7108, or holder 7124 in the distal insertion position.

In some embodiments, transfer of on-skin sensor assembly 360 between insertion and retraction may occur as previously described in connection with, for example, any of FIGS. 35A-37C.

In some embodiments, a second barrier layer 7194 may be disposed over the bottom opening of inner housing 7102. Second barrier layer 7194 may comprise a gas permeable material such as Tyvek, or a non-gas permeable material such as metallic foil, film. In some embodiments, second barrier layer 7194 may be removed by the host prior to use of applicator 7100. In embodiments comprising one or both of first and second barrier layers 7192, 7194, such layers may provide a sterile environment between applicator 7100 and the outside environment and/or may allow ingress and egress of gas such as during sterilization.

Although not shown in FIGS. 71-72, in some embodiments, applicator 7100 may comprise a cap configured to be secured to distal surface 7130 of inner housing 7102 and that may be removed before use. In some embodiments, such a cap may also function as a sterile barrier, as previously described in U.S. patent application Ser. No. 16/011,527, hereby incorporated by reference in its entirety.

Figure 73A:
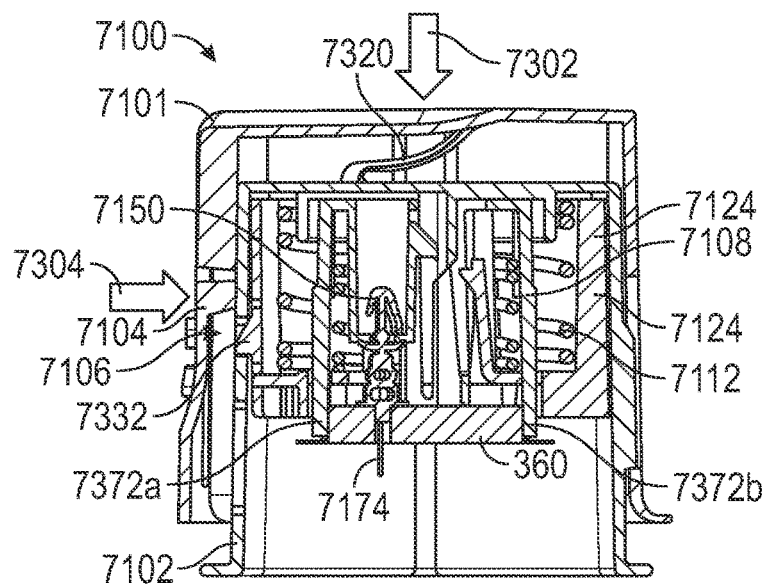
FIGS. 73A-73C illustrate several cross-sectional views of the applicator of FIGS. 71 and 72, taken along the section line A-A' of FIG. 71, during operation, according to some embodiments.
Figure 73B:
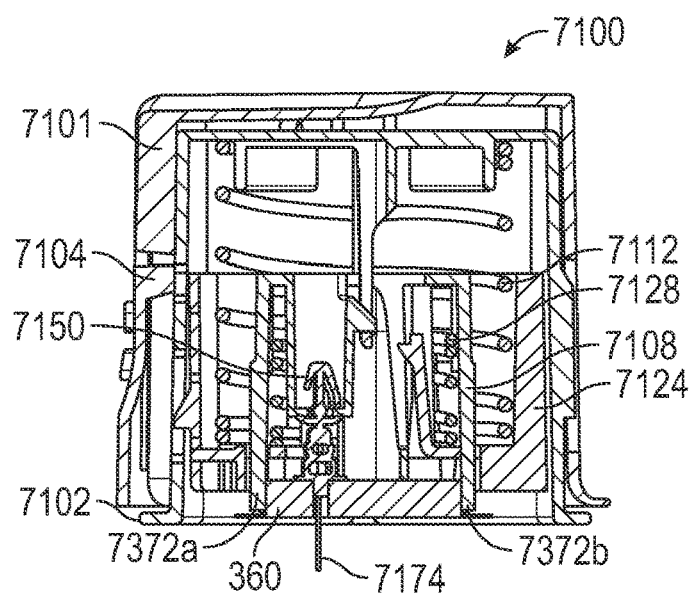
Figure 73C:
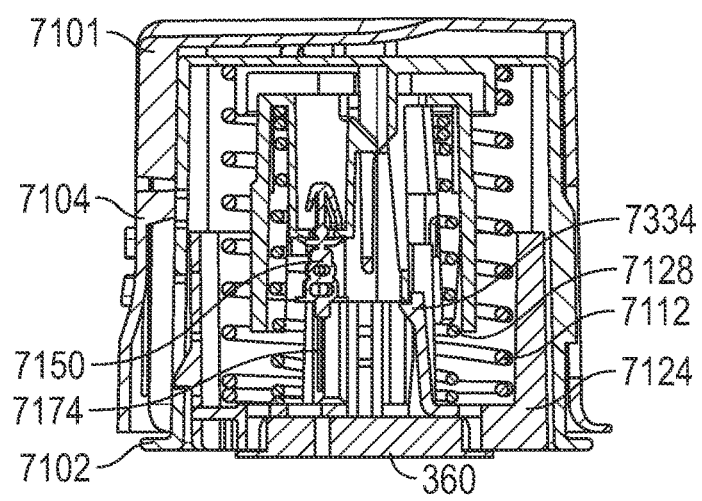

A brief description of some aspects of the operation of applicator 7100 follows with respect to FIGS. 73A-73C, which illustrate several cross-sectional views of applicator 7100 of FIGS. 71 and 72 during operation, according to some embodiments. FIGS. 73A-73C may correspond to applicator 7100 cut along the section line A-A' shown in FIG. 71, for example.

FIG. 73A illustrates a state of applicator 7100 prior to activation. Holder 7124 comprises an insertion assembly retention element 7332 configured to contact inner housing 7102, thereby immobilizing holder 7124, needle carrier assembly 7108, needle hub 7150, insertion element 7174 and on-skin sensor assembly 360, in the pre-activated state.

Needle carrier assembly 7108 comprises a plurality of wearable retention and/or alignment elements 7372a, 7372b configured to extend through holder 7124 and releasably couple on-skin sensor assembly 360 to holder 7124 and/or to needle carrier assembly 7108. Wearable retention elements 7372a, 7372b may comprise, e.g., arms, deflection element, tabs, detents, snaps or any other features capable of a retaining function. In some embodiments, wearable retention elements 7372a, 7372b may extend around rather than through holder 7124. Although two wearable retention elements are illustrated, any number of wearable retention elements are contemplated. In some embodiments, wearable retention element(s) 7372a, 7372b may comprise snap fits, friction fits, interference features, elastomeric grips and/or adhesives configured to couple on-skin sensor assembly 360 with needle carrier assembly 7108 and/or holder 7124.

Inner housing 7102 may comprise a spring 7320 configured to contact outer housing 7101 and maintain a predetermined spacing between outer housing 7101 and inner housing 7102 in the pre-activation orientation of FIG. 73A. Spring 7320 may be a compression spring, leaf spring, flex arm spring, a piece of foam or rubber, etc. In some other embodiments, outer housing 7101 may comprise spring 7320 and spring 7320 may be configured to contact inner housing 7102, in a reverse fashion from that shown in FIG. 73A.

Activation of applicator 7100 may include a host pressing applicator 7100 against their skin with sufficient force to translate outer housing 7101 in a distal direction, as shown by arrow 7302, toward and with respect to inner housing 7102 until activation element 7104 is aligned with aperture 7106 of inner housing 7102 and insertion assembly retention element 7332 of holder 7124. Insertion assembly retention element 7332 may comprise, e.g., an arm, a deflection element, a tab, a detent, a snap or any other feature capable of a retaining function. Once such an alignment is achieved, a host may initiate (e.g. pushing) activation element 7104, as shown by arrow 7304, thereby deflecting insertion assembly retention element 7332 sufficiently to release holder 7124 from inner housing 7102. In some other embodiments, applicator 7100 may be configured such that activation element 7104 may be activated first, but that actual insertion is not triggered until outer housing 7101 is translated sufficiently in the distal direction toward and with respect to inner housing 7102. In yet other embodiments, activation element 7104 may be biased toward a center of applicator 7100 such that activation element 7104 need not be explicitly activated by the host but, instead, activation element 7104 may be configured to automatically initiate insertion upon outer housing 7101 being translated sufficiently in the distal direction toward and with respect to inner housing 7102.

Such configurations provide several benefits. First, translation of outer housing 7101 with respect to inner housing 7102 before activation provides a measure of drop protection such that if applicator 7100 is accidentally dropped, it may not prematurely fire. Second, spring 7320 provides a force bias that the host has to affirmatively overcome by pressing applicator 7100 into their skin prior to firing, thereby reducing the probability of activating applicator 7100 before it is properly positioned. Further, the host may decide to not fire applicator 7100 and discontinue pressing applicator 7100 against their skin, in which spring 7320 will bias against outer housing 7101 and allow outer housing 7101 to return to its initial state.

Holder 7124, needle carrier assembly 7108, needle hub 7150, insertion element 7174, on-skin sensor assembly 360, first spring 7112 and second spring 7128 are all shown in pre-activation positions in FIG. 73A.

FIG. 73B illustrates applicator 7100 during insertion of on-skin sensor assembly 360 but before retraction of needle carrier assembly 7108. First spring 7112 drives holder 7124, needle carrier assembly 7108, needle hub 7150, insertion element 7174, and on-skin sensor assembly 360, in the distal direction toward the distal insertion position. FIG. 73B illustrates a position where on-skin sensor assembly 360 is in contact with skin 130 of the host but where holder 7124 is not yet fully driven, by first spring 7112, into contact with on-skin sensor assembly 360 or skin 130 of the host.

In some embodiments, masses of each of holder 7124, needle carrier assembly 7108, needle hub 7150, insertion element 7174, and on-skin sensor assembly 360 may be specifically designed to reduce or substantially eliminate a tendency of needle carrier assembly 7108, needle hub 7150, insertion element 7174, and on-skin sensor assembly 360 to detach due to inertial forces from holder 7124 while being driven in the distal direction during insertion. In some embodiments, a force exerted by first spring 7112 may be selected to be sufficient for proper operation of applicator 7100, while not so large as to further exacerbate such above-described inertially triggered detachment. In some embodiments, a spring (not shown) may be configured to exert a force against a portion of needle carrier assembly 7108, for example in a distal direction, sufficient to prevent needle carrier assembly 7108 from inertially triggered detaching from holder 7124 during insertion.

FIG. 73C illustrates applicator 7100 during activation, as needle carrier assembly 7108, needle hub 7150 and insertion element 7174 are retracted in the proximal direction by second spring 7128. In FIG. 73C, first spring 7112 has fully driven on-skin sensor assembly 360 to the skin of the host. In this position, second spring 7128 is released from spring retention elements (e.g., 7442a, 7442b in FIGS. 74A-75B) and drives needle carrier assembly 7108, needle hub 7150, and insertion element 7174 in the proximal direction from the distal insertion position. Upon needle carrier assembly 7108 reaching the proximal retraction position, needle carrier retention element 7334 of holder 7124 engages with needle carrier assembly 7108, thereby maintaining needle carrier assembly 7108, needle hub 7150 and insertion element 7174 in a locked, retracted position limiting access to insertion element 7174. Needle carrier retention element 7334 may comprise, e.g., an arm, a deflection element, a tab, a detent, a snap or any other feature capable of a retaining function. In this retracted position, needle carrier assembly 7108, needle hub 7150, and insertion element 7174 is prevented from travelling in a distal direction.

Figure 74A:
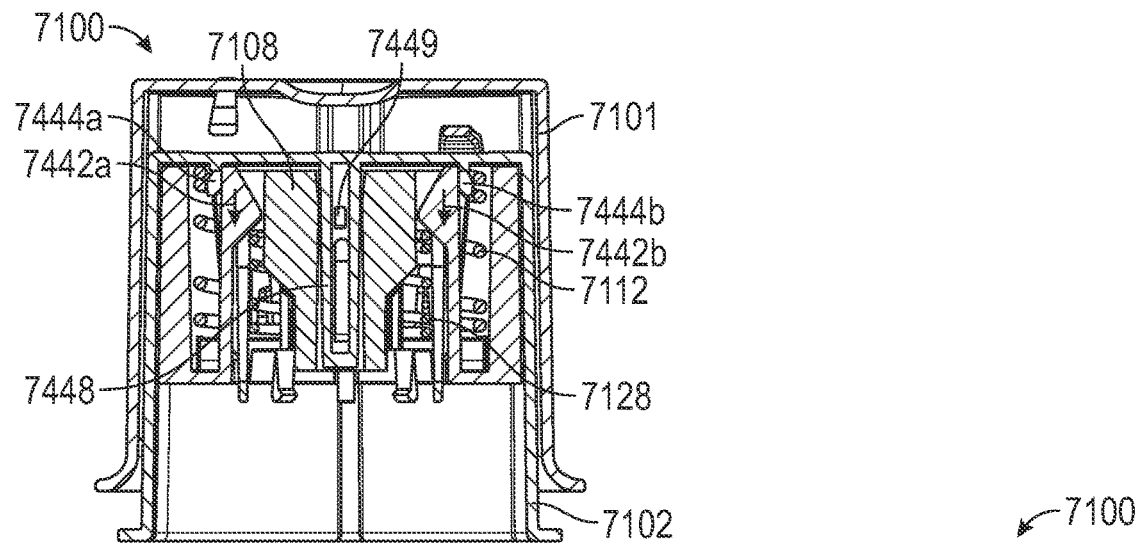
FIGS. 74A-74C illustrate several cross-sectional views of the applicator of FIGS. 71 and 72, taken along the section line B-B' of FIG. 71, during operation, according to some embodiments.
Figure 74B:
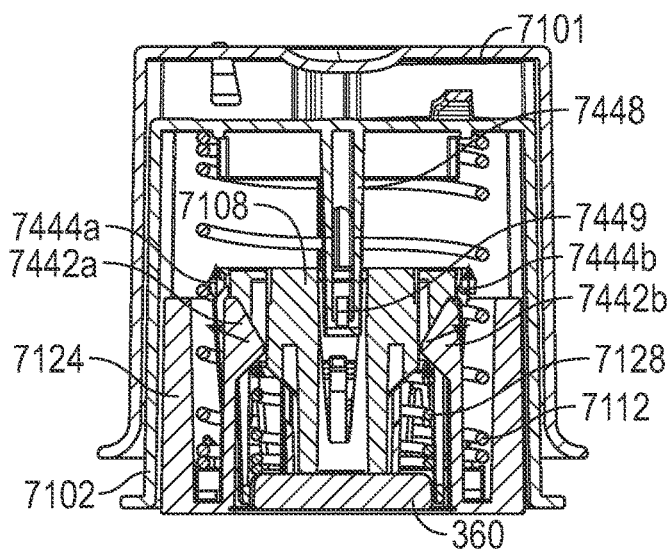
Figure 74C:
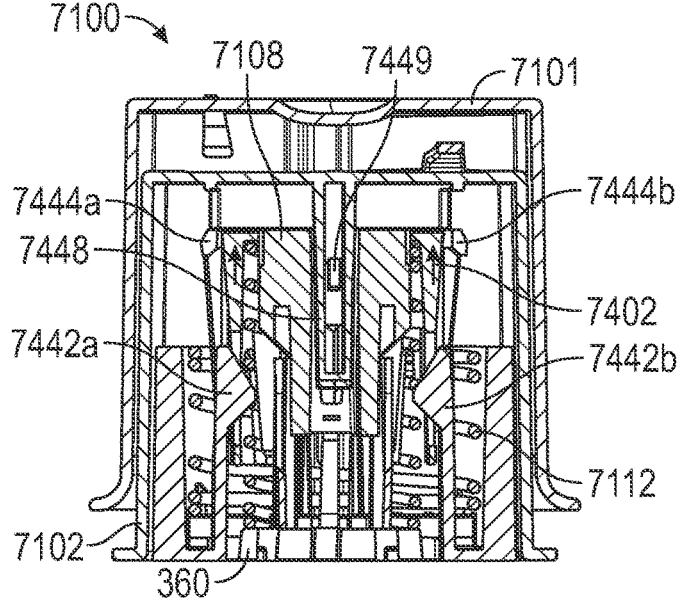

A further description of some aspects of the operation of applicator 7100 follows with respect to FIGS. 74A-74C, which illustrate several cross-sectional views of applicator 7100 of FIGS. 71 and 72 during operation, according to some embodiments. FIGS. 74A-74C may correspond to applicator 7100 cut along the section line B-B' shown in FIG. 71, for example. For ease of illustration, needle hub 7150 and insertion element 7174 are not shown in FIGS. 74A-74C.

FIG. 74A illustrates a state of applicator 7100 prior to activation. For ease of illustration, on-skin sensor assembly 360 is not illustrated in FIG. 74A. Holder 7124 comprises spring retention elements 7442a, 7442b configured to contact and retain a first end of second spring 7128 in the pre-activated state, e.g., during insertion, while a second end of spring 7128 is in contact with needle carrier assembly 7108. Spring retention elements 7442a, 7442b may comprise, e.g., arms, deflection element, tabs, detents, snaps or any other features capable of a retaining function. Although two spring retention elements 7442a, 7442b are shown, at least one spring retention element is contemplated. In some embodiments, applicator 7100 may include one spring retention element, as shown in FIGS. 81A-81D. In some embodiments, applicator 7100 may include three spring retention elements. In some embodiments, applicator 7100 may include four spring retention elements. In some embodiments, spring retention elements 7442a, 7442b are deflectable arms, rigid arms, deformable features, snaps, catches, or hooks. In some embodiments, spring retention elements

7442*a*, 7442*b* may be actively deflected by one or more features within applicator 7100.

Needle carrier assembly 7108 comprises backstop features 7444*a*, 7444*b*, configured to prevent lateral deflection of spring retention elements 7442*a*, 7442*b* in the proximal starting position, e.g., at least during insertion, thereby supporting retention of second spring 7128 between spring retention elements 7442*a*, 7442*b* and holder 7124 until retraction. Although two backstop features are illustrated, any number of backstop features are contemplated. The number of backstop features may equal the number of spring retention elements.

Figure 75A:
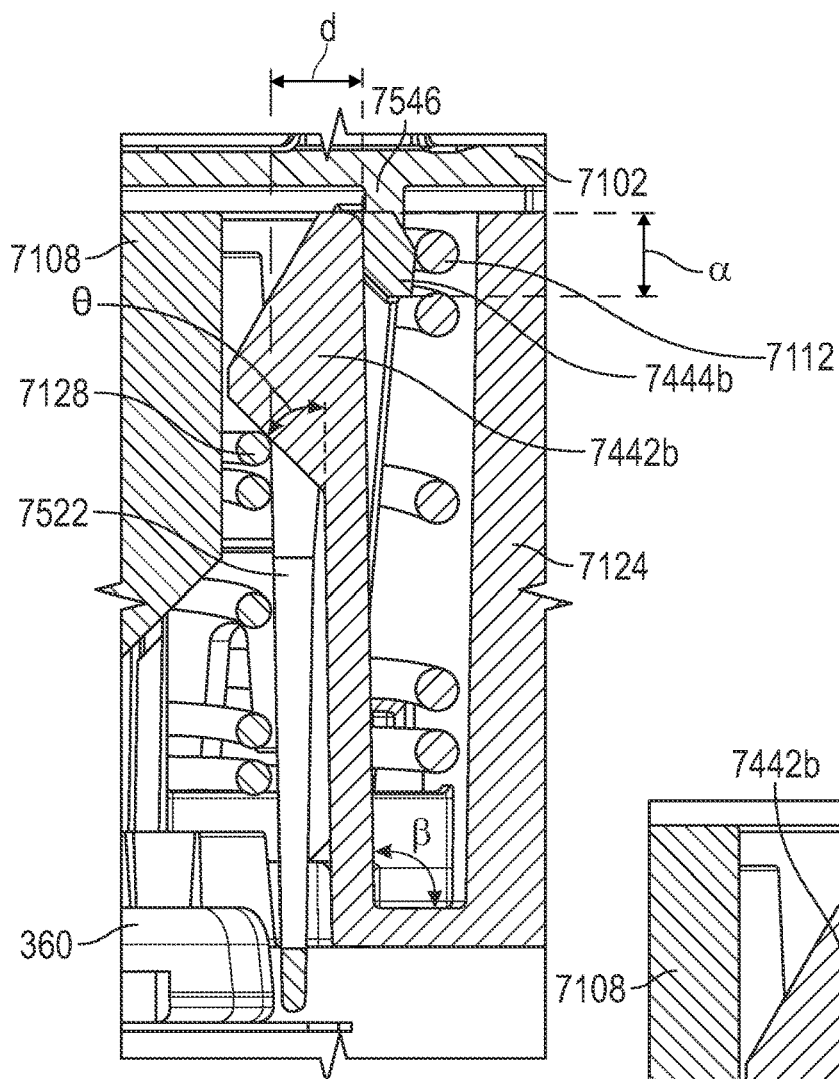
FIGS. 75A and 75B illustrate magnified views of some features of the applicator of FIGS. 71 and 72, according to some embodiments.

FIG. 75A illustrates a magnified view of spring retention element 7442*b* and backstop feature 7444*b*. In FIG. 75A, first spring 7112 is driving holder 7124, needle carrier assembly 7108 and on-skin sensor assembly 360, in the distal direction toward the distal inserted position. Backstop feature 7444*b* is shown engaged to spring retention element 7442*b*, preventing spring retention element 7442*b* from deflecting laterally, thereby preventing second spring 7128 from releasing. As shown in FIG. 75A, a proximal end of spring retention element 7442*b* may be offset from a distal end of backstop feature 7444*b* by a distance a. In some embodiments, distance a is the length required for spring retention element 7442*b* to traverse along backstop feature 7444*b* such that spring retention element 7442*b* clears past backstop feature 7444*b*. Backstop feature 7444*b* may feature a ramp to guide spring retention element 7442*b*. A distal end of needle carrier assembly 7108 and a distal end of holder 7124 may be offset from each other at least the same distance a to allow for spring retention element 7442*b* to traverse distally past backstop feature 7444*b*.

It may be appreciated that the frictional force between corresponding contacting surfaces of backstop feature 7444*b* and spring retention element 7442*b* may at least partly determine an amount of force to release spring retention element 7442*b* from backstop feature 7444*b*. This force may allow for lateral deflection of spring retention element 7442*b* and thus allow the expansion of second spring 7128. In some embodiments, the amount of force is at least 0.1 pounds. In some embodiments, the amount of force is at least 0.5 pounds. In some embodiments, the amount of force is at least 1 pound. In some embodiments, the amount of force is at least 2 pounds. In some embodiments, the amount of force is at least 3 pounds. In some embodiments, the amount of force is at least 4 pounds. In some embodiments, the amount of force is at least 5 pounds.

Although the figure shows backstop feature 7444*b* preventing lateral deflection of spring retention element 7442*b* in a radially outward direction, it is contemplated that an inverse structural relationship can be achieved. For instance, the ramped surface of spring retention element 7442*b* can be reversed to face the opposite direction as shown in FIG. 75A. Further, the ramped surface of spring retention element 7442*b* may be biased in a radially inward direction by second spring 7128 against backstop feature 7444*b*. In such embodiments, backstop feature 7444*b* may be located radially inward of spring retention element 7442*b*.

Accordingly, in some embodiments, materials utilized to form holder 7124 and needle carrier assembly 7108 may be selected based on a desired amount of force to release spring retention element 7442*b* for lateral deflection. Examples of such materials may include Polycarbonate, ABS, PC/ABS, Polypropylene, HIPS (High impact polystyrene), Polybutylene Terephthalate (PBT), Polyoxymethylene (POM), Acetal, polyacetal, polyformaldehyde, PTFE, High density polyethylene (HDPE), Nylon, Polyethylene terephthalate (PET), Thermoplastic elastomer (TPE), Thermoplastic polyurethane (TPU), TPSiv, Cyclo olefin polymer (COP), Cyclo olefin copolymer (COC), and/or Liquid-crystal polymer (LCP).

An angle $\theta$ of a portion of spring retention element 7442*b* in contact with second spring 7128 may also affect the amount of frictional force to laterally deflect spring retention element 7442*b* and so to release second spring 7128. Accordingly, the angle $\theta$ may be selected based on a desired amount of force to laterally deflect spring retention element 7442*b* sufficiently to release second spring 7128. In some embodiments, the angle $\theta$ is at least 1 degree with respect to a vertical axis of the spring retention element 7442*b*. In some embodiments, the angle $\theta$ is at least 5 degrees. In some embodiments, the angle $\theta$ is at least 10 degrees. In some embodiments, the angle $\theta$ is at least 15 degrees. In some embodiments, the angle $\theta$ is at least 20 degrees. In some embodiments, the angle $\theta$ is about 30 to 45 degrees. In addition, the force profile of second spring 7128 may affect a target amount of frictional force to laterally deflect spring retention element 7442*b*. Accordingly, in some embodiments, the force profile of second spring 7128 may be taken into account when selecting one or both of the materials for forming holder 7124 and needle carrier assembly 7108 and the angle $\theta$ of the portion of spring retention element 7442*b* in contact with second spring 7128.

An angle ß of spring retention element 7442*b* with respect to a vertical axis may also affect the amount of frictional force to laterally deflect spring retention element 7442*b* and so to release second spring 7128. By contacting spring retention element 7442*b*, second spring 7128 may exert a force on spring retention element 7442*b* at a distance d from a bottom of spring retention element 7442*b* that causes a torque moment sufficient to induce a lateral deflection of spring retention element 7442*b*.

Figure 75B:
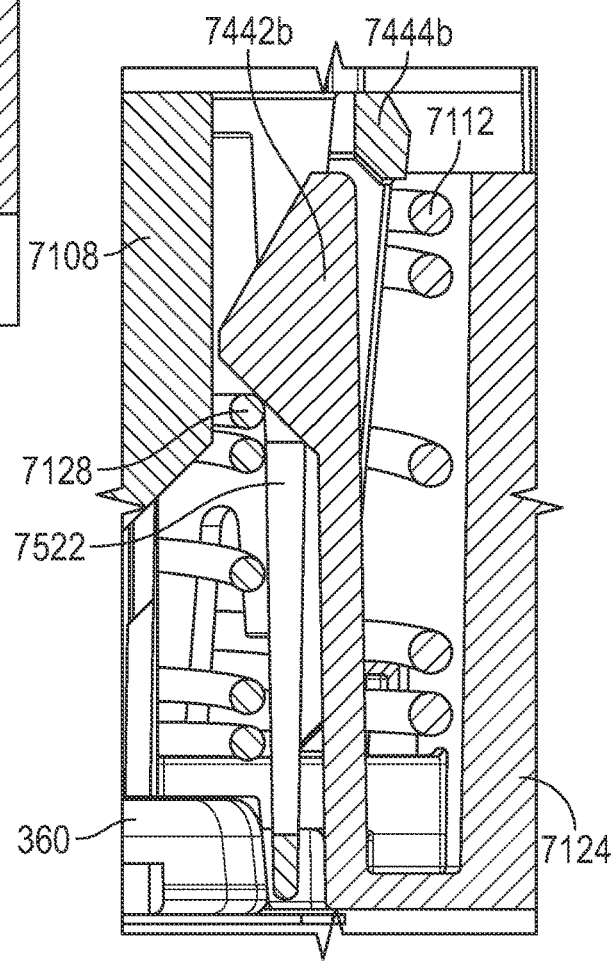

FIG. 75A further illustrates needle carrier assembly 7108 comprising a deflecting element 7522 configured to contact spring retention element 7442*b* and maintain spring retention element 7442*b* in a laterally deflected orientation once second spring 7128 has initially deflected spring retention element 7442*b* and sufficiently driven needle carrier assembly 7108 in the proximal direction, as will be shown in more detail in FIG. 75B. Deflecting element 7522 may prevent spring retention element 7442*b* from contacting the windings of second spring 7128 while second spring 7128 is extending, smoothing the operation of applicator 7100 and preventing energy released by second spring 7128 and designed for driving needle carrier assembly 7128 in the proximal direction from being absorbed by undesired contact with spring retention element 7442*b* during the release of second spring 7128.

In some embodiments, the angle $\theta$ of the portion of spring retention element 7442*b* in contact with second spring 7128 may be substantially 90° (e.g., flat) and deflecting element 7522 may have a ramped or angled surface in contact with spring retention element 7442*b* in the position illustrated in FIG. 75A. In such embodiments, deflecting element 7522, in addition to the above-described functionality, may be configured to initially deflect spring retention element 7442*b* as first spring 7112 drives holder 7124 from the position illustrated in FIG. 75A to the position illustrated in FIG. 75B.

In some embodiments, inner housing 7102 may comprise a protrusion 7546 extending from inner housing 7102 in the distal direction. Protrusion 7546 may be configured to contact at least one of spring retention elements 7442*a*, 7442*b* and backstop features 7444*a*, 7444*b* in the pre-activation state such that spring retention elements 7442a, 7442b are prevented from laterally deflecting until holder 7124 and needle carrier assembly 7108 have translated at least a predetermined minimum distance in the distal direction. Accordingly, protrusion 7546 may provide a measure of drop protection such that applicator 7100 may not prematurely fire in response to a concussive shock from being dropped before intentional activation.

Turning back to FIG. 74A, inner housing 7102 may further comprise an engagement element 7448 configured to engage with a protrusion 7449 of needle carrier assembly 7108 upon needle carrier assembly 7108 translating in the distal direction beyond a predetermined threshold, thereby preventing needle carrier assembly 7108 from translating in the distal direction beyond the predetermined threshold. It is contemplated that this may ensure needle carrier assembly retraction in the event of an air firing or dry firing in which applicator 7100 is somehow activated when not held against the skin of the host. In some embodiments, the predetermined threshold may correspond to the distal end of needle carrier assembly 7108 extending beyond a point proximal to the distal end of inner housing 7102, to a point substantially in line with the distal end of inner housing 7102 or to a point distal of the distal end of inner housing 7102. In some embodiments, engagement element 7448 comprises a hook, a U-shaped structure, a loop, a protrusion, or any other structure capable of engaging with protrusion 7449 as described above.

FIG. 74B illustrates applicator 7100 after activation, at a beginning of a force retraction feature process at or near the distal insertion position where on-skin sensor assembly 360 may be in contact with the skin of the host. First spring 7112 has driven holder 7124, needle carrier assembly 7108, needle hub 7150, insertion element, and on-skin sensor assembly 360, in the distal direction toward the distal insertion position. During proper operation, holder 7124 and on-skin sensor assembly 360 should be pressing against the skin of the host. However, FIG. 74B may also illustrate a dry fire condition, where applicator 7100 is not properly pressed against the skin of the host before triggering applicator 7100. Accordingly, upon first spring 7112 driving holder 7124 and needle carrier assembly 7108 in the distal direction beyond the predetermined threshold, engagement element 7448 contacts protrusion 7449, which prevents needle carrier assembly 7108 from traveling further in the distal direction, while holder 7124 is driven sufficiently further in the distal direction such that backstop features 7444a, 7444b of needle carrier assembly 7108 no longer contact spring retention elements 7442a, 7442b in the distal insertion position, thereby releasing the first end of second spring 7128 and initiating retraction even when applicator 7100 is dry fired. The insertion force provided by first spring 7112 may be sufficient to additionally overcome the frictional force between corresponding contacting surfaces of backstop feature 7444b and spring retention element 7442b.

Turning to FIG. 75B, first spring 7112 has driven holder 7124, needle carrier assembly 7108 and on-skin sensor assembly 360 in the distal direction to the skin of the host. As first spring 7112 drives holder 7124, needle carrier assembly 7108 and on-skin sensor assembly 360 against the skin of the host, the skin provides a counter force to the force generated by first spring 7112. The skin may oppose the force of first spring 7112 and bias against the distal end of on-skin sensor assembly 360. Because the distal end of holder 7124 is offset from the distal end of on-skin sensor assembly 360 as shown in FIG. 75A, the counter force provided by the skin is transferred to holder 7124 as first spring 7112 continues to drive holder 7124 towards the skin while on-skin sensor assembly 360 is pressed against the skin. The counter force provided by the skin allows spring retention element 7442b to displace past backstop feature 7444b. Once spring retention element 7442b has cleared distance a past backstop feature 7444b, second spring 7128 can laterally deflect spring retention element 7442b, thereby releasing second spring 7128, which drives needle carrier assembly 7108 in the proximal direction. Alternatively, as described above in connection with FIG. 75A, where the angle θ of the portion of spring retention element 7442b in contact with second spring 7128 is substantially 90° (e.g., flat), the ramped or angled surface of deflecting element 7522 in contact with spring retention element 7444b deflects spring retention element 7442b sufficiently to release second spring 7128, which drives needle carrier assembly 7108 in the proximal direction.

In some embodiments, engagement element 7448 may engage protrusion 7449 even when applicator 7100 is pressed against the skin of a user. In such embodiments, engagement element 7448 engages protrusion 7449 as first spring 7112 drives holder 7124, needle carrier assembly 7108, and on-skin sensor assembly 360 against the skin of the host. As explained above, engagement element 7448 prevents needle carrier assembly 7108 from moving distally when engagement element 7448 engages protrusion 7449. This allows spring retention elements 7442a, 7442b to separate away from backstop features 7444a, 7444b and allow for release of second spring 7128. The engagement of engagement element 7448 and protrusion 7449 may add additional force to the counter force provided by the skin, thus increasing the energy needed to overcome the frictional engagement of spring retention elements 7442a, 7442b and backstop features 7444a, 7444b. In some instances, the engagement of engagement element 7448 and protrusion 7449 provides an immediate impulse force that converts at least some of the initial energy of first spring 7112 into energy needed to overcome the frictional engagement of spring retention elements 7442a, 7442b and backstop features 7444a, 7444b. It is contemplated that such embodiments may benefit users with soft skin or higher body fat percentage.

Turning back to FIG. 74C, which illustrates applicator 7100 during activation, needle carrier assembly 7108 is retracted in the proximal direction by second spring 7128, as indicated by arrow 7402. In FIG. 74C, with backstop features 7444a, 7444b no longer immobilizing spring retention elements 7442a, 7442b, first end of second spring 7128 pushes against spring retention elements 7442a, 7442b with sufficient force to deflect spring retention elements 7442a, 7442b in the distal insertion position when on-skin sensor assembly 360 is in contact with skin 130 of the host, allowing second spring 7128 to clear spring retention elements 7442a, 7442b and drive needle carrier assembly 7108 in the proximal direction, thereby maintaining needle carrier assembly 7108, needle hub 7150 (see FIGS. 73A-73C) and insertion element 7174 (see FIGS. 73A-73C) in a locked, retracted position even in the event of a dry fire.

Figure 76A:
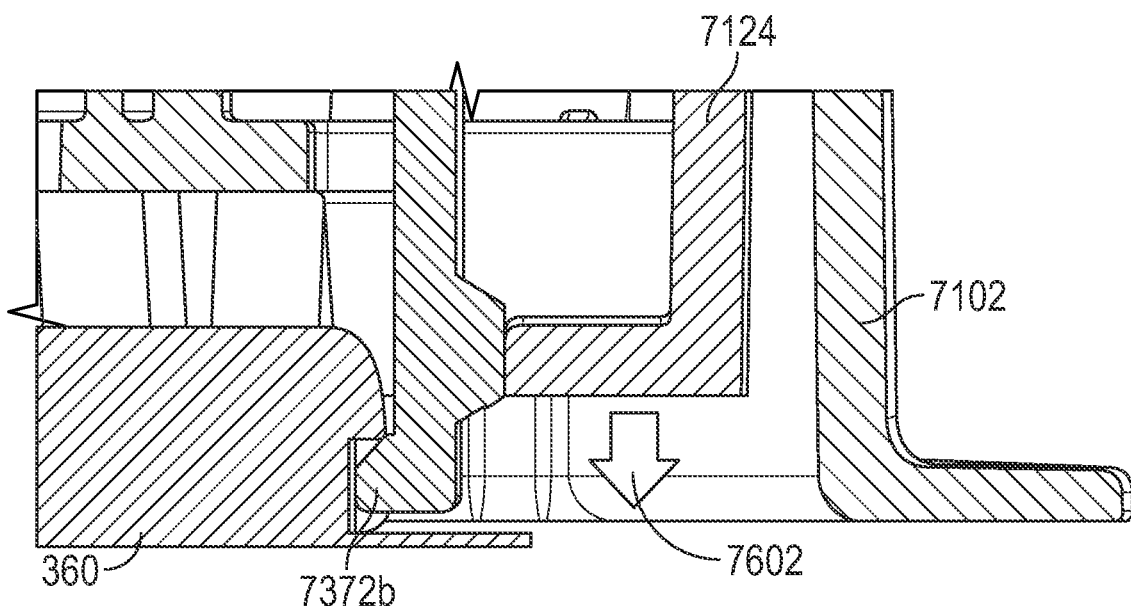
FIGS. 76A and 76B illustrate magnified views of some features of the applicator of FIGS. 71 and 72, according to some embodiments.
Figure 76B:
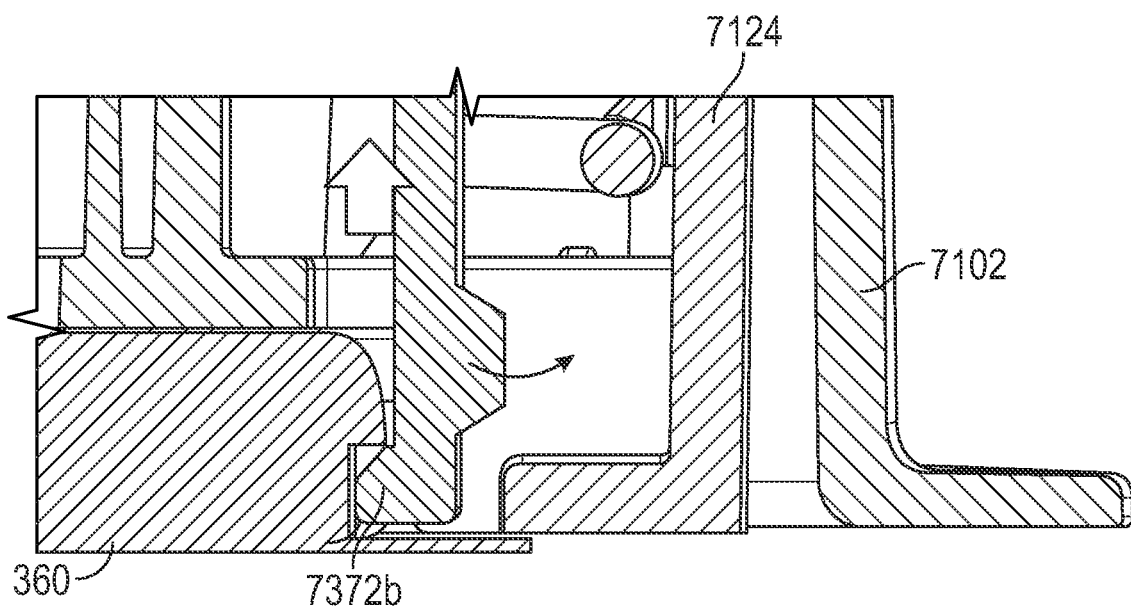

FIGS. 76A and 76B illustrate magnified views of some features of an applicator, such as applicator 7100, according to some embodiments.

In FIG. 76A, first spring 7112 (see FIGS. 72-74C) is driving holder 7124, as well as the needle carrier assembly and on-skin sensor assembly 360 in the distal direction, illustrated by arrow 7602, toward the distal insertion position. Retention element 7372b of the needle carrier assembly is releasably coupled to on-skin sensor assembly 360. As illustrated, during insertion and near the distal inserted position, holder 7124 is in contact with spring retention element 7372*b*, preventing spring retention element 7372*b* from deflecting laterally and thereby rigidly securing on-skin sensor assembly 360 to the needle carrier assembly.

In FIG. 76B, second spring 7128 (see FIGS. 72-74C) is driving needle carrier assembly 7108 in the proximal direction from the distal insertion position. Because holder 7124 has been driven sufficiently in the distal direction, at the distal insertion position, holder 7124 is no longer in contact with wearable retention element 7372*b*. Accordingly, wearable retention element 7372*b* is free to deflect laterally, thereby releasing on-skin sensor assembly 360 from wearable retention element 7372*b* and thus from the needle carrier assembly 7108. Needle carrier assembly 7108 is now driven in the proximal direction by second spring 7128, while on-skin sensor assembly 360 is secured to the skin of the host. Moreover, in some embodiments, because holder 7124 is driven to the distal inserted position and substantially held in that position by first spring 7112, holder 7124 may press against one or both of on-skin sensor assembly 360 or an adhesive patch of on-skin sensor assembly 360, supporting one or both during attachment to the skin of the host.

Figure 90:
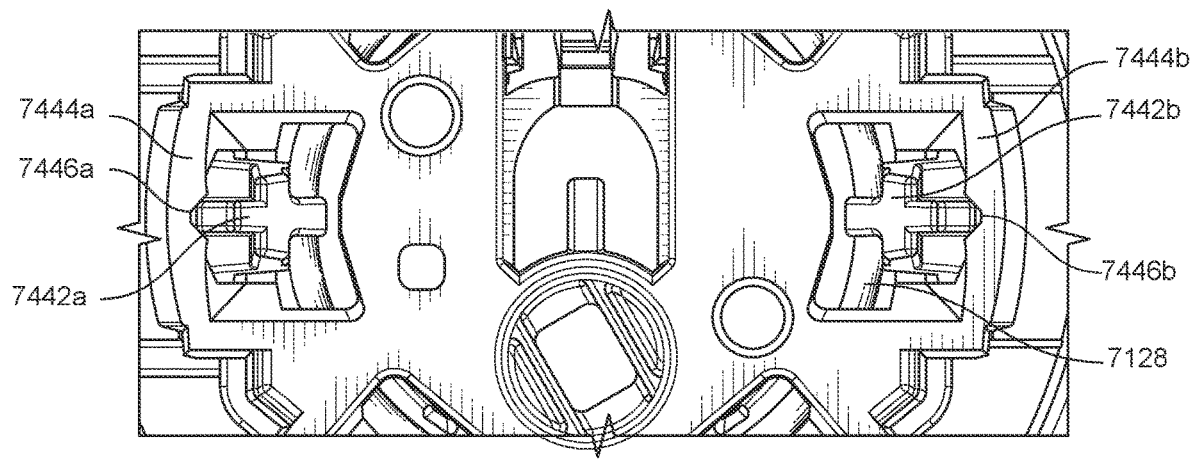
FIG. 90 illustrates a magnified view of some features of the applicator of FIGS. 71 and 72, according to some embodiments.

FIG. 90 illustrates a magnified view of some features of the applicator of FIGS. 71 and 72, according to some embodiments. As shown, applicator 7100 is in a pre-activation state. In this state, spring retention elements 7442*a*, 7442*b* may be retained against backstop features 7444*a*, 7444*b*. Second spring 7128 may be biasing spring retention elements 7442*a*, 7442*b* against backstop features 7444*a*, 7444*b*. As described above, sufficient force is needed to deflect spring retention elements 7442*a*, 7442*b* past backstop features 7444*a*, 7444*b*. The sufficient force may be determined or at least partly determined by the frictional force between spring retention elements 7442*a*, 7442*b* and backstop features 7444*a*, 7444*b*. It may be appreciated that backstop features 7444*a* and 7444*b* may feature a groove 7446*a* and a groove 7446*b*, respectively, to engage with spring retention elements 7442*a*, 7442*b*. Grooves 7446*a*, 7446*b* may increase a drag force between spring retention elements 7442*a*, 7442*b* and backstop features 7444*a*, 7444*b*. In such embodiments, grooves 7446*a*, 7446*b* can increase the force required to deflect spring retention elements 7442*a*, 7442*b* from backstop features 7444*a*, 7444*b* while the materials of spring retention elements 7442*a*, 7442*b* and/or backstop features 7444*a*, 7444*b* have low or lower coefficient of friction. Further, grooves 7446*a*, 7446*b* can increase the force required to deflect spring retention elements 7442*a*, 7442*b* from backstop features 7444*a*, 7444*b* while second spring 7128 has a small or smaller diameter or has a low or lower spring constant. In some embodiments, grooves 7446*a*, 7446*b* may each feature a concave channel. The concave shape of the channel may feature angled surfaces configured to drag against multiple edges of spring retention elements 7442*a*, 7442*b*. In such embodiments, spring retention element 7442*a*, 7442*b* can be wedges configured to drag within grooves 7446*a*, 7446*b*. In some embodiments, applicator 7100 may include as many grooves 7446 as backstop features 7444.

FIG. 77 illustrates a perspective partial cutaway view of needle carrier assembly 7108, needle hub 7150, and on-skin sensor assembly 360 of applicator 7100 of FIGS. 71 and 72, according to some embodiments. FIG. 78 illustrates a cross-sectional view of needle hub 7150 and on-skin sensor assembly 360, according to some embodiments. FIG. 79 illustrates a top view of a portion of needle carrier assembly 7108 and needle hub 7150, according to some embodiments. The following is a description of these features with reference to FIGS. 77-79.

On-skin sensor assembly 360 comprises sensor assembly aperture 396. Hub 7150 is configured to couple insertion element 7174 to needle carrier assembly 7108 and to substantially maintain a desired orientation of insertion element 7174 during insertion of the sensor of on-skin sensor assembly 360 into the skin of the host.

Needle hub 7150 comprises a plurality of upper arms 7156*a*, 7156*b*, a plurality of lower arms 7154*a*, 7154*b*, and a base 7152. Although two upper arms and two lower arms are illustrated, any number of arms, including a single upper and lower arm, are contemplated. In some embodiments, upper arms 7156*a*, 7156*b* and lower arms 7154*a*, 7154*b* may be flexible such that, when needle hub 7150 is coupled to needle carrier assembly 7108, upper arms 7156*a*, 7156*b* and lower arms 7154*a*, 7154*b* secure needle hub 7150 in a desired orientation with respect to needle carrier assembly 7108. For example, upper arms 7156*a*, 7156*b* may be configured to flex radially inward, such that when disposed through a carrier aperture 7712 in needle carrier assembly 7108, upper arms 7156*a*, 7156*b* are in contact with an upper surface of needle carrier assembly 7108 adjacent to carrier aperture 7712 and lower arms 7154*a*, 7154*b* are in contact with a lower surface of needle carrier assembly 7108 adjacent to carrier aperture 7712. Such an arrangement allows a compliant fit between needle carrier assembly 7108 and needle hub 7150 where lower arms 7154*a*, 7154*b* deflect to allow upper arms 7156*a*, 7156*b* to expand after clearing surface of carrier aperture 7712. The lower arms 7154*a*, 7154*b* can partially or fully relax to bias the needle hub in a distal direction and decrease the clearance between the needle hub and the needle carrier that would otherwise exist with a non-compliant fit. In addition, upper arms 7156*a*, 7156*b* and lower arms 7154*a*, 7154*b* also help to maintain contact between base 7152 and a top surface of on-skin sensor assembly 360.

Base 7152 comprises an anti-rotation feature. The anti-rotation feature may comprise a key having a shape complementary to at least a portion of sensor assembly aperture 396 of on-skin sensor assembly 360 and may be configured to substantially prevent needle hub 7150 from rotating about an axis 7702 parallel to insertion element 7174 with respect to on-skin sensor assembly 360, e.g., to prevent rotation of base 7152 within sensor assembly aperture 396. In addition, or the alternative, the upper surface of needle carrier assembly 7108 adjacent to carrier aperture 7712 may comprise a groove 7910 configured to accept upper arms 7156*a*, 7156*b* when upper arms 7156*a*, 7156*b* are disposed through carrier aperture 7712 in an orientation complementary to an orientation of groove 7910, as illustrated in FIG. 79, thereby immobilizing needle hub 7150 with respect to needle carrier assembly 7108.

In some embodiments, base 7152 further comprises a substantially flat surface configured to mate with a top surface of on-skin sensor assembly 360 and maintain insertion element 7174 in a substantially perpendicular orientation to the top surface of on-skin sensor assembly 360, in some cases, when the anti-rotation feature of base 7152 is engaged within sensor assembly aperture 396 of on-skin sensor assembly 360.

Based at least upon the above-described features of needle hub 7150, on-skin sensor assembly 360, and/or needle carrier assembly 7108, base 7152 allows easy assembly during manufacture, including but not limited to proper alignment and preassembly of insertion element 7174 onto on-skin sensor assembly 360, and/or the ability to easily engage an assembly of needle hub 7150, insertion element 7174, sensor 338 and on-skin sensor assembly 360 to other portions of assembled applicator 7100.

Figure 80A:
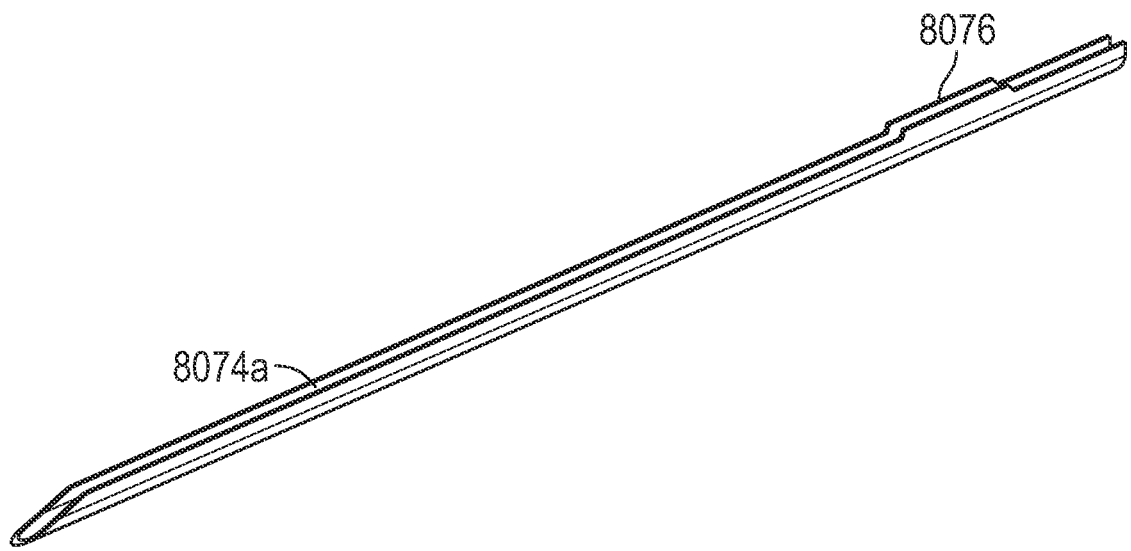
FIGS. 80A and 80B illustrate perspective views of locking features for needles for use in an applicator for an analyte sensor system, according to some embodiments.
Figure 80B:
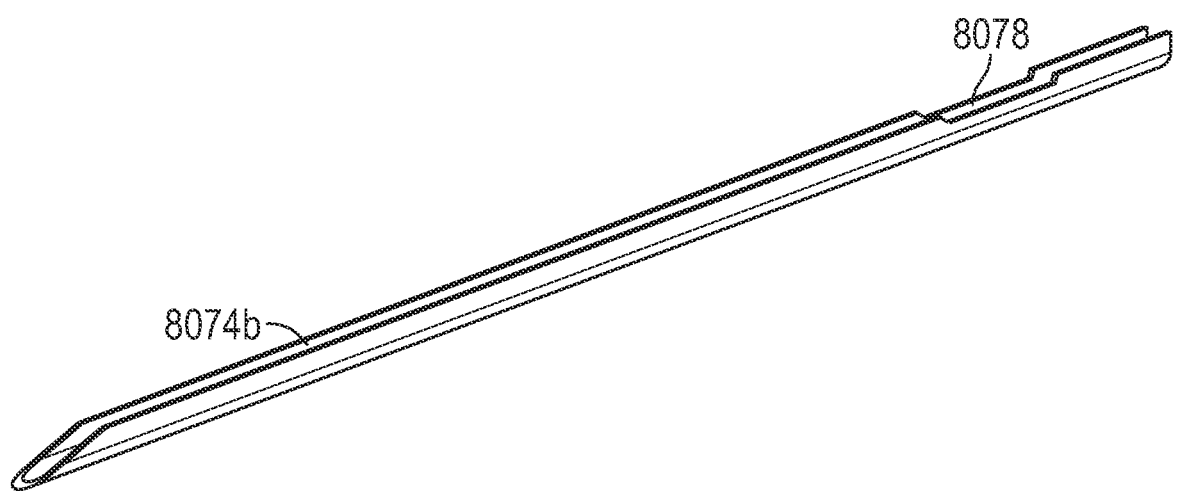

FIGS. 80A and 80B illustrate perspective views of locking features for needles 8074a, 8074b for use in an applicator for an analyte sensor system, according to some embodiments. For example, needle 8074a of FIG. 80A comprises a locking feature comprising a ridge 8076 configured to mate with a complementary-shaped feature within needle hub 7150, for example. In the alternative, needle 8074b of FIG. 80B comprises a locking feature comprising a groove 8078 configured to mate with a complementary-shaped feature within needle hub 7150, for example.

In yet another alternative, any insertion element described in this disclosure may comprise a locking feature that heat stakes the selected insertion element to needle hub 7150, for example. In yet another alternative, any insertion element described in this disclosure may comprise a locking feature comprising one or more friction-fit or snap-fit elements securing the selected insertion element to needle hub 7150, for example. In yet another alternative, any insertion element described in this disclosure may comprise a locking feature comprising complementary clamshell elements on the selected insertion element and needle hub 7150, for example, configured to mate with one another. In yet another alternative, any insertion element described in this disclosure may comprise a locking element comprising one or more inserted molded elements configured to couple the selected insertion element to needle hub 7150, for example.

During manufacture, applicator 7100 may be assembled in stages. For example, and not limitation, if present, first barrier layer 7192 may be affixed to inner housing 7102. Insertion element 7174 may be coupled to needle hub 7150, which may then be coupled to on-skin sensor assembly 360. Second spring 7128 may be placed into holder 7124 or needle carrier assembly 7108 and then needle carrier assembly 7108 may be disposed into holder 7124 and attached to needle hub 7150 and to on-skin sensor assembly 360 via wearable retention elements 7372a, 7372b. First spring 7112 may be disposed in holder 7124, which may then be installed into inner housing 7102. Inner housing 7102 may be inserted into and secured to outer housing 7102. If present, second barrier layer 7194 may be affixed to inner housing 7102. If a separate element, activation element 7104 may then be disposed into outer housing 7101. Any labeling, sterilizing and/or packaging may then be applied to applicator 7100.

Figure 81A:
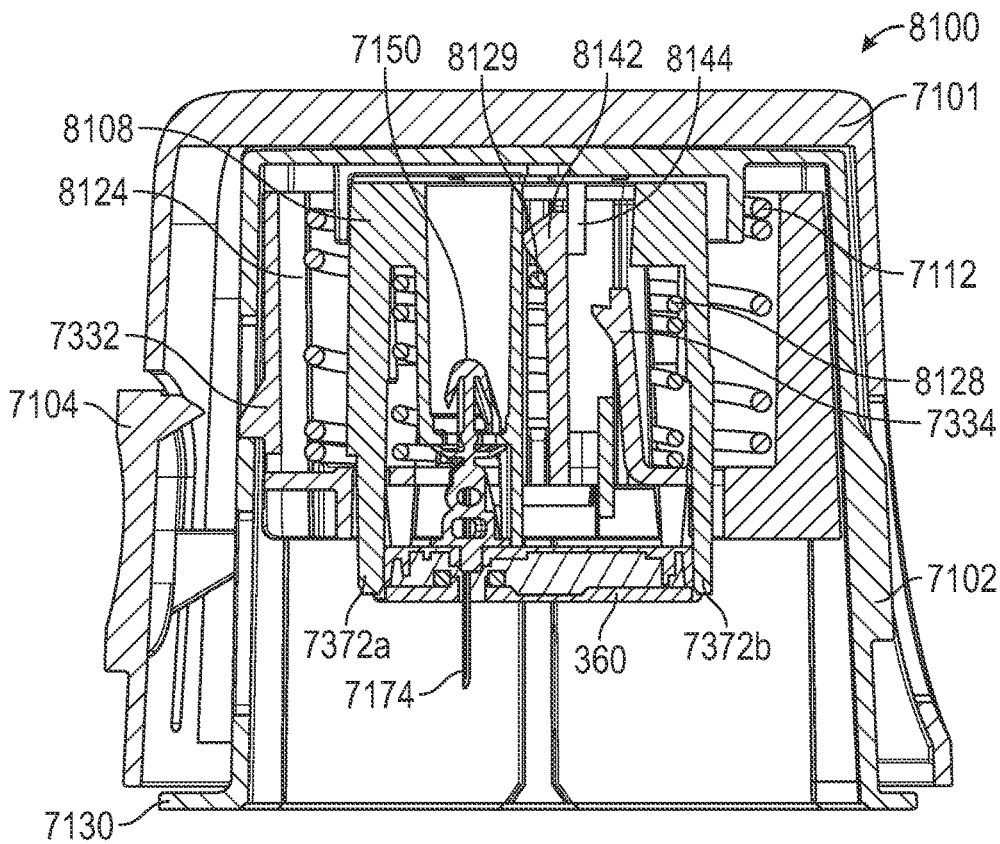
FIGS. 81A-81C illustrate several cross-sectional views, and various features and operating positions, of yet another applicator for an on-skin sensor assembly of an analyte sensor system, according to some embodiments.
Figure 81B:
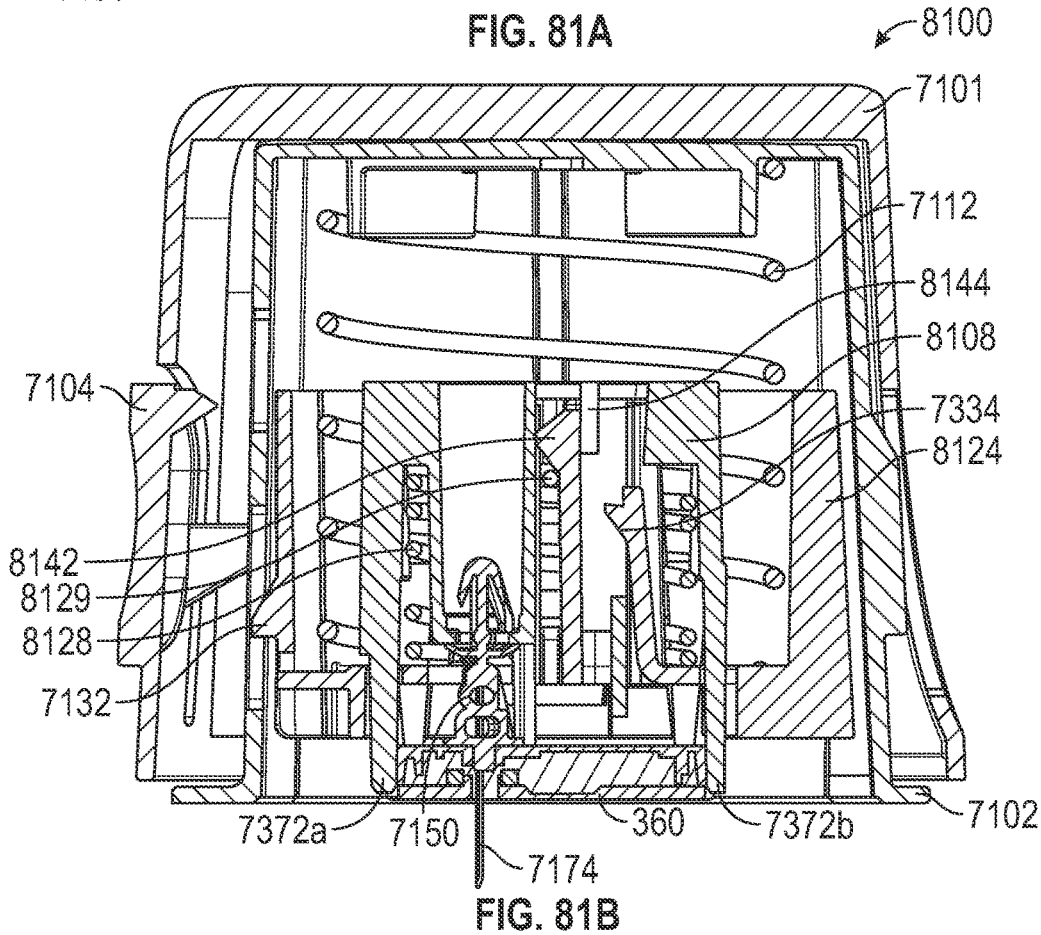
Figure 81C:
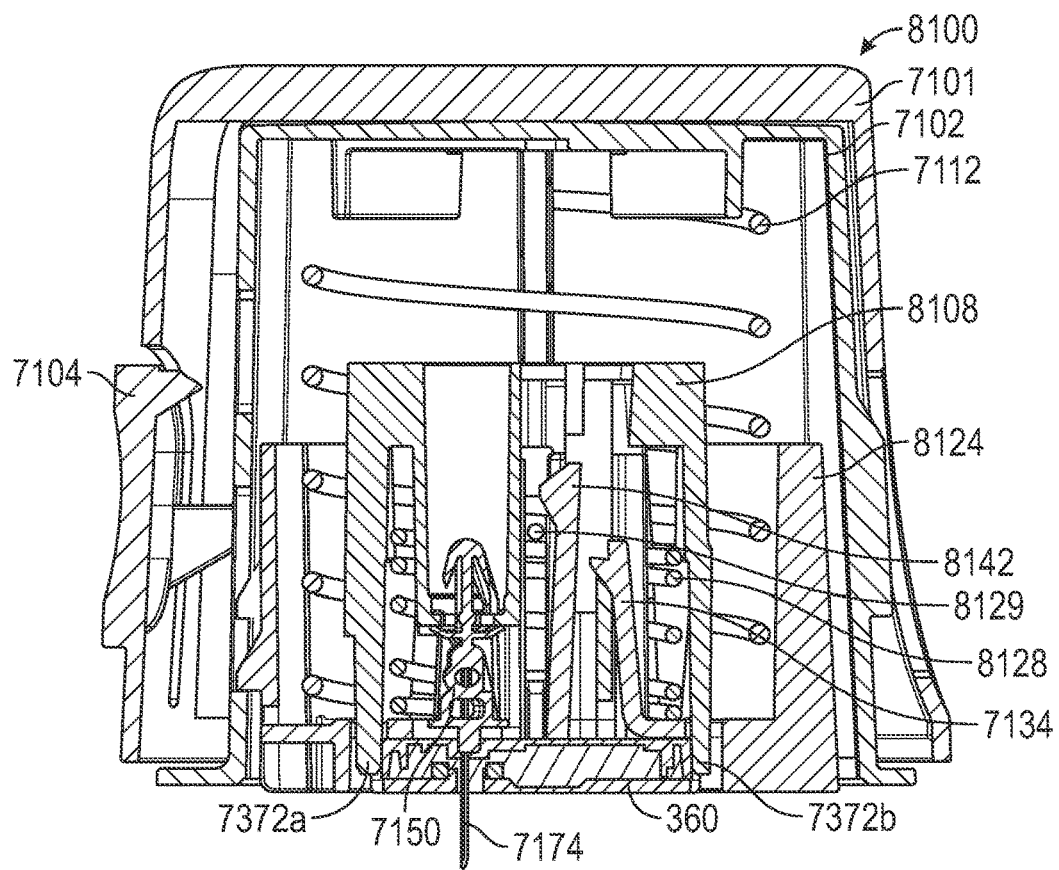

FIGS. 81A-81C illustrate several cross-sectional views, and various features and operating positions, of yet another applicator 8100 for an on-skin sensor assembly of an analyte sensor system, according to some embodiments.

Applicator 8100 may include outer applicator housing 7101 comprising activation element 7104. Outer applicator housing 7101 may be configured to translate in a distal direction under force applied by a host of applicator 8100, thereby aligning activation element 7104 in a position that allows applicator 8100 to fire, an alignment illustrated by FIG. 81A. As previously described in connection with applicator 7100, in some embodiments, activation element 7104 may be disposed in any location, e.g., a top, upper side, lower side, or any other location of applicator 8100.

Applicator 8100 further comprises inner housing 7102, configured to house one or more mechanisms utilized to apply on-skin sensor assembly 360 to skin of a host. Distal surface 7130 of a bottom opening of inner housing 7102 may define a bottom surface of applicator 8100. In some embodiments, upon pressing applicator 8100 against the skin of the host, the skin may deform in a substantially convex shape at distal surface 7130 such that at least a portion of a surface of the skin disposed at the bottom opening of applicator housing 7102 extends into the bottom opening of inner housing 7102, in a proximal direction, beyond a plane defined by distal surface 7130.

Although not illustrated in FIGS. 81A-81C, inner housing 7102 may comprise a spring 7320 configured to contact outer housing 7101 and maintain a predetermined spacing between outer housing 7101 and inner housing 7102 in the pre-activation orientation (see FIG. 73A). Spring 7320 may be a compression spring, leaf spring, flex arm spring, a piece of foam or rubber, etc. In some other embodiments, outer housing 7101 may comprise spring 7320 and spring 7320 may be configured to contact inner housing 7102.

Applicator 8100 may further comprise a needle carrier assembly 8108. Needle carrier assembly 8108 comprises wearable retention and/or alignment elements 7372a, 7372b configured to pass through holder 8124 and releasably couple on-skin sensor assembly 360 to holder 8124 and/or to needle carrier assembly 8108. Although two wearable retention and/or alignment elements are illustrated, any number of wearable retention and/or alignment elements are contemplated.

Applicator 8100 further comprises needle hub 7150 configured to couple insertion element 7174 to needle carrier assembly 8108. Insertion element 7174 is configured to insert sensor 338 of on-skin sensor assembly 360 into skin 130 of the host (e.g., FIGS. 3A-4). In some embodiments, insertion element 7174 comprises a needle, for example, an open sided-needle, a needle with a deflected-tip, a curved needle, a polymer-coated needle, a hypodermic needle, or any other suitable type of needle or structure, as described in connection with at least FIGS. 47-50 and 80A-B. In yet other embodiments, insertion element 7174 may be integrally formed with sensor 338, in which insertion element 7174 may be sufficiently rigid to be inserted partially into skin 130 of the host with minimal or no structural support.

Applicator 8100 may further include holder 8124 releasably coupled to needle carrier assembly 8108 and configured to guide on-skin sensor assembly 360 while coupled to needle carrier assembly 8108, e.g., at least during translation from a proximal position to a distal insertion position. As previously described in connection with applicator 7100, on-skin sensor assembly 360 may be stripped or released from holder 8124 and/or needle carrier assembly 8108 once on-skin sensor assembly 360 is disposed on the skin of the host.

Applicator 8100 may further comprise an insertion assembly configured to translate insertion element 7174, needle hub 7150, and needle carrier assembly 8108 from a proximal position, in the distal direction, to a distal insertion position. Such an insertion assembly may include first spring 7112. First spring 7112 may be a compression spring, or any suitable type of spring, and may have its first end in contact with or coupled to inner applicator housing 7102 and its second end in contact with or coupled to holder 8124. First spring 7112 is configured to, upon activation of the insertion assembly, translate holder 8124, needle carrier assembly 8108, needle hub 7150, insertion element 7174 and on-skin sensor assembly 360, in the distal direction to the distal insertion position. Substantially at the distal insertion position, needle carrier assembly 8108 may decouple from holder 8124 and on-skin sensor assembly 360.

Applicator 8100 may further comprise a retraction assembly configured to translate needle carrier assembly 8108, needle hub 7150 and insertion element 7174, in the proximal direction, from the distal insertion position to a proximal retracted position. In some embodiments the initial proximal position may be the same as the proximal retracted position. In other embodiments, the initial proximal position may be different from the proximal retracted position. Such a retraction assembly may include a second spring 8128. Second spring 8128 may be a compression spring, or any suitable type of spring, and may have a first end contacting or coupled to holder 8124 and a second end, comprising a tang 8129 (e.g., a spring portion or spring end) disposed substantially along a diameter of second spring 8128, in contact with or coupled to a spring retention element 8142 of holder 8124, at least until retraction. Spring retention element 8142 may comprise, e.g., an arm, a deflection element, a tab, a detent, a snap or any other feature capable of a retaining function. Spring retention element 8142 may have substantially the same form and function as spring retention elements 7442a, 7442b of applicator 7100 except as described below. Second spring 8128 is configured to translate needle carrier assembly 8108, needle hub 7150, and insertion element 7174 in the proximal direction from the distal insertion position to the proximal retracted position. Tang 8129 of second spring 8128 is released from spring retention element 8142 in the distal insertion position when spring retention element 8142 is not backed up by backstop element 8144 and in response to tang 8129 of second spring 8128 pushing against spring retention element 8142 with a force exceeding a predetermined threshold sufficient to overcome and deflect spring retention element 8142.

In some embodiments, transfer of on-skin sensor assembly 360 between insertion and retraction may occur as previously described in connection with, for example, any of FIGS. 35A-37C.

Needle carrier assembly 8108 further comprises a backstop feature 8144, configured to prevent lateral motion of spring retention element 8142 of holder 8124 in at least the proximal pre-activation position, thereby supporting retention of second spring 8128 between spring retention element 8142 and holder 8124 until retraction. In the orientation shown in FIG. 81A, second spring 8128 is exerting a force against spring retention element 8142 but backstop feature 8144 prevents lateral deflection of retention element 8142.

Holder 8124 further comprises needle carrier retention element 7334, which may comprise a deflectable arm, rigid arm, deformable feature, snap, catch, or hook. Upon needle carrier assembly 8108 reaching the proximal retraction position after activation, needle carrier retention element 7334 is configured to engage with needle carrier assembly 8108, thereby maintaining needle carrier assembly 8108, needle hub 7150 and insertion element 7174 in a locked, retracted position, limiting access to insertion element 7174.

Although not illustrated in FIGS. 81A-81C, inner housing 7102 of applicator 8100 may further comprise engagement element 7448 and needle carrier assembly 8108 may further comprise protrusion 7449 and may function substantially as previously described in connection with at least FIGS. 74A-74C.

Although not illustrated in FIGS. 81A-81C, inner housing 7102 of applicator 8100 may further comprise a protrusion extending from inner housing 7102 in the distal direction, substantially as previously described protrusion 7546. Similar to that previously described in connection with FIG. 75A, this protrusion may be configured to contact at least one of spring retention element 8142 and backstop feature 8144 in the pre-activation state such that spring retention element 8142 is prevented from laterally deflecting until holder 8124 and needle carrier assembly 8108 have translated at least a predetermined minimum distance in the distal direction. Accordingly, the protrusion may provide a measure of drop protection such that applicator 8100 may not prematurely fire in response to a concussive shock from being dropped before activation.

Applicator 8100 functions substantially similarly to applicator 7100 with the exception that instead of utilizing spring retention elements 7442a, 7442b, which are disposed along an outside of second coil 7128 and are configured to contact and retain a coil of second spring 7128, applicator 8100 utilizes spring retention element 8142, which is disposed along an inside of second spring 8128 and is configured to contact and retain tang 8129 of second spring 8128 along a diameter of second spring 8128. Disposing spring retention element 8142 within and substantially along a center of second spring 8128, as opposed to along an outside of second spring 8128, further ensures that spring retention element 8142 does not contact the coils of second spring 8128 as second spring 8128 extends during retraction, thereby smoothing the operation of applicator 8100. In addition, the arrangement including spring retention element 8142, as opposed to spring retention elements 7442a, 7442b mitigates the risk of, and difficulty ensuring that, multiple spring retention elements trigger or are overcome at substantially the same time.

Although not shown in FIGS. 81A-81C, in some embodiments, applicator 8100 may comprise a cap configured to be secured to distal surface 7130 of inner housing 7102, which may be removed before use. In some embodiments, such a cap may also function as a sterile barrier, as previously described in U.S. patent application Ser. No. 16/011,527, hereby incorporated by reference in its entirety.

FIG. 81A illustrates a state of applicator 8100 prior to activation, according to some embodiments. Holder 8124, needle carrier assembly 8108, needle hub 7150, insertion element 7174, on-skin sensor assembly 360, first spring 7112 and second spring 7128 are all shown in pre-activation positions.

Retention element 7332 of holder 8124 is in contact with inner housing 7102, thereby immobilizing holder 8124, and therefore also needle carrier assembly 8108, needle hub 7150, insertion element 7174 and on-skin sensor assembly 360, in the pre-activated state.

Backstop feature 8144 of needle carrier assembly 8108 is in contact with and prevents spring retention element 8142 from deflecting laterally, thereby ensuring spring retention element 8142 retains tang 8129 of second spring 8128 in the loaded or pre-activation position shown.

Activation of applicator 8100 may include a host pressing applicator 8100 against their skin with sufficient force to translate outer housing 7101 in a distal direction toward and with respect to inner housing 7102 until activation element 7104 is aligned with insertion assembly retention element 7332 of holder 8124, as shown in FIG. 81A. Once such an alignment is achieved, a host may initiate activation element 7104, thereby deflecting insertion assembly retention element 7332 sufficiently to release holder 8124 from inner housing 7102. In some other embodiments, applicator 8100 may be configured such that activation element 7104 may be activated first, but that actual insertion is not triggered until outer housing 7101 is translated sufficiently in the distal direction toward and with respect to inner housing 7102. In yet other embodiments, activation element 7104 may be biased toward a center of applicator 8100 such that activation element 7104 need not be explicitly activated by the host but, instead, activation element 7104 may be configured to automatically initiate insertion upon outer housing 7101 being translated sufficiently in the distal direction toward and with respect to inner housing 7102.

FIG. 81B illustrates applicator 8100 after activation and during insertion, according to some embodiments. First spring 7112 drives holder 8124, and so needle carrier assembly 8108, needle hub 7150, insertion element 7174, and on-skin sensor assembly 360, in the distal direction toward the distal insertion position. FIG. 81B illustrates on-skin sensor assembly 360 in contact with skin 130 of the host but where holder 8124 is not yet fully driven, by first spring 7112, into contact with on-skin sensor assembly 360 or skin 130 of the host.

In some embodiments, masses of each of holder 8124, needle carrier assembly 8108, needle hub 7150, insertion element 7174, and on-skin sensor assembly 360 may be specifically designed to reduce or substantially eliminate a tendency of needle carrier assembly 8108, needle hub 7150, insertion element 7174, and on-skin sensor assembly 360 to detach from holder 8124 while being driven in the distal direction during insertion. In some embodiments, a force exerted by first spring 7112 may further be selected to be sufficient for proper operation of applicator 7100, while not so large as to further exacerbate such above-described inertially triggered detachment. In some embodiments, a spring (not shown) may be configured to exert a force against a portion of needle carrier assembly 8108, for example in the distal direction, sufficient to prevent needle carrier assembly 7108 from inertially triggered detaching from holder 8124 during insertion.

FIG. 81C illustrates applicator 8100 after activation and at or near the distal insertion position, according to some embodiments. First spring 7112 has driven holder 8124, needle carrier assembly 8108 and on-skin sensor assembly 360 in the distal direction to the distal inserted position. Since first spring 7112 has driven holder 8124 a short distance farther in the distal direction than needle carrier assembly 8108, backstop feature 8144 is no longer in contact with spring retention element 8142, allowing second spring 8128 (e.g. tang 8129) to laterally deflect spring retention element 8142, thereby releasing second spring 8128, which drives needle carrier assembly 8108 in the proximal direction. Alternatively, similar to that described above in connection with applicator 7100 in FIG. 75A, where the angle θ of the portion of spring retention element 8142 in contact with tang 8129 of second spring 7128 is substantially 90° (e.g., flat), spring retention element 8142 may be biased to automatically deflect sufficiently to release second spring 7128 once backstop feature 8144 is no longer in contact with spring retention element 8142, thereby freeing second spring 8128 to drive needle carrier assembly 8108 in the proximal direction. Although not shown in FIGS. 81A-81C, inner housing 7102 may further comprise engagement element 7448 configured to engage with a protrusion 7449 of needle carrier assembly 8108, and to function substantially as previously described in connection with at least FIGS. 74A-74C. In some embodiments, a stop feature (not shown) may be disposed at a bottom of applicator 8100, e.g., on a distal portion of inner housing 7102. Such a stop feature may be configured to contact one or more of on-skin sensor assembly 360, needle carrier 8108, or holder 8124 in the distal insertion position.

Upon release of second spring 8128, second spring 8128 is configured to drive needle carrier assembly 8108, needle hub 7150 and insertion element 7174 in the proximal direction. Although not shown in FIG. 81C, as needle carrier assembly 8108 travels to the proximal retracted position, needle carrier retention element 7134 may engage with needle carrier assembly 8108, thereby retention needle carrier assembly 8108, needle hub 7150 and insertion element 7174, in a locked, retracted position limiting access to insertion element 7174.

Figure 81D:
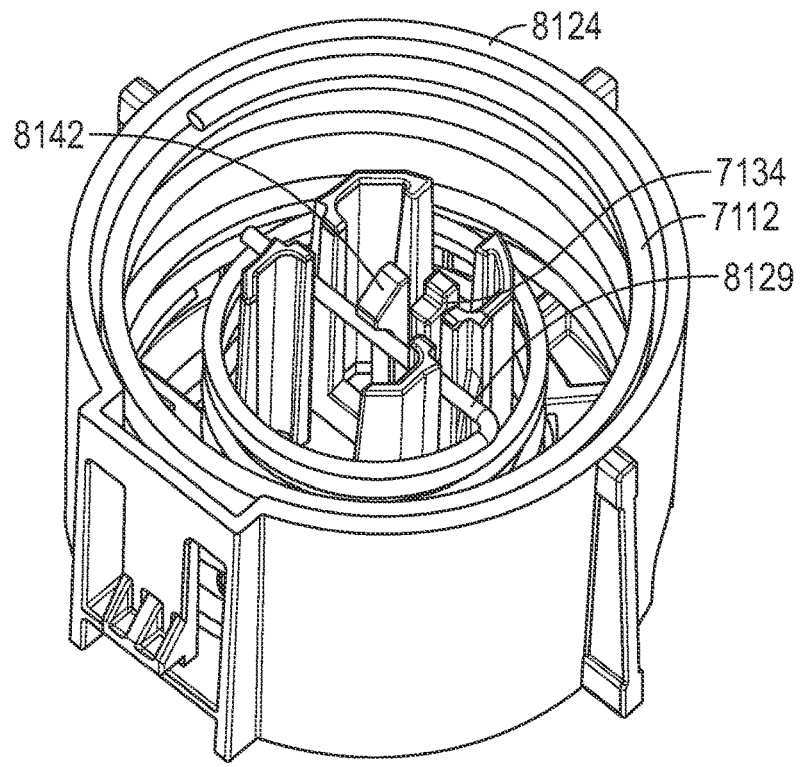
FIG. 81D illustrates a perspective view of various features of the applicator of FIGS. 81A-81D, according to some embodiments.

FIG. 81D illustrates a perspective view of holder 8124, first spring 7112 and second spring 8128 of applicator 8100, according to some embodiments. FIG. 81D illustrates spring retention element 8142, retention tang 8129 of second spring 8128 in an orientation within applicator 8100 before retraction.

During manufacture, applicator 8100 may be assembled in stages. For example, and not limitation, if present, as previously described in connection with applicator 7100, first barrier layer 7192 (see FIG. 72) may be affixed to inner housing 7102. Insertion element 7174 may be coupled to needle hub 7150, which may then be coupled to on-skin sensor assembly 360. Second spring may be placed into holder 8124 or needle carrier assembly 8108 and then needle carrier assembly 8108 may be disposed into holder 8124 and attached to needle hub 7150 and to on-skin sensor assembly via wearable retention elements 7372a, 7372b. First spring 7112 may be disposed in holder 8124, which may then be installed into inner housing 7102. Inner housing 7102 may be inserted into and secured to outer housing 7102. If present, as previously described in connection with applicator 7100, second barrier layers 7194 (see FIG. 72) may be affixed to inner housing 7102. If a separate element, activation element 7104 may then be disposed into outer housing 7101. Any labeling, sterilizing and/or packaging may then be applied to applicator 8100.

FIGS. 82A-82D illustrate several cutaway views, and various features and operating positions, of yet another applicator 8200 for an on-skin sensor assembly of an analyte sensor system, according to some embodiments. In contrast to applicators 7100 and 8100, applicator 8200 utilizes a single spring for both insertion and retraction of an insertion element 8274 for placing an associated sensor 338 and on-skin sensor assembly 360.

Applicator 8200 comprises a housing 8202 and an activation element 8204 disposed on a top of applicator 8200. However, activation element 8204 may be disposed on a side or any other location on applicator 8200.

Applicator 8200 may further comprise a needle carrier assembly 8208. Needle carrier assembly 8208 comprises wearable retention and/or alignment elements 8272a, 8272b configured to pass through holder 8224 and releasably couple on-skin sensor assembly 360 to holder 8224 and/or to needle carrier assembly 8208. In some embodiments, wearable retention elements 8272a, 8272b may extend around rather than through holder 8224. Wearable retention elements 8272a, 8272b may comprise, e.g., arms, deflection element, tabs, detents, snaps or any other features capable of a retaining function. Although two wearable retention and/or alignment elements are illustrated, any number of wearable retention and/or alignment elements are contemplated. Needle carrier assembly 8208 further comprises a protrusion 8266 configured to contact or hook a deployment sleeve 8206 during retraction, thereby causing needle carrier assembly 8208 to translate in a proximal direction during retraction, as will be described in more detail below.

Applicator 8200 further comprises an insertion element 8274 configured to insert sensor 338 of on-skin sensor assembly 360 into skin 130 of the host (e.g., FIG. 1). In some embodiments, insertion element 8274 comprises a needle, for example, an open sided-needle, a needle with a deflected-tip, a curved needle, a polymer-coated needle, a hypodermic needle, or any other suitable type of needle or structure, as described in connection with at least FIGS. 47-50 and 80A-B. In yet other embodiments, insertion element 8274 may comprise sensor 338, sufficiently rigid to be inserted partially into skin 130 of the host with minimal or no structural support.

Although not illustrated in FIGS. 82A-82D, in some embodiments, applicator 8200 may further comprise needle hub 7150, configured to couple insertion element 8274 to needle carrier assembly 8208, as previously described in connection with at least FIGS. 77-79. In some other embodiments, insertion element 8274 may be directly coupled to needle carrier assembly 8208 as shown in FIGS. 82A-82D.

Applicator 8200 may further include holder 8224 releasably coupled to deployment sleeve 8206 via holder retention elements 8232a, 8232b and to needle carrier assembly 8208. Holder retention elements 8232a, 8232b may comprise, e.g., arms, deflection elements, tabs, detents, snaps or any other features capable of a retaining function. Holder 8224 is configured to guide on-skin sensor assembly 360 while coupled to needle carrier assembly 8208 during insertion, e.g., at least during translation from a proximal position to a distal insertion position. As previously described in connection with applicators 7100 and 8100, on-skin sensor assembly 360 may be stripped or released from holder 8224 and/or needle carrier assembly 8208 once on-skin sensor assembly 360 is disposed on the skin of the host.

Applicator 8200 may further comprise an insertion assembly configured to translate holder 8224, insertion element 8274 and needle carrier assembly 8208, in the distal direction, from a proximal position to a distal insertion position. Such an insertion assembly may include a spring 8212. First spring 8212 may be a compression spring, or any suitable type of spring, and may have a first end in contact with or coupled to deployment sleeve 8206 and a second end in contact with or coupled to holder 8224. First spring 8212 is configured to, upon activation of the insertion assembly, translate holder 8224, needle carrier assembly 8208, insertion element 8274 and on-skin sensor assembly 360 in the distal direction to the distal insertion position. Substantially at the distal insertion position, needle carrier assembly 8208 may decouple from holder 8224 and on-skin sensor assembly 360.

Applicator 8200 may further comprise a retraction assembly configured to translate needle carrier assembly 8208 and insertion element 8274, in the proximal direction, from the distal insertion position to a proximal retracted position. In some embodiments the initial proximal position may be the same as the proximal retracted position. In other embodiments, the initial proximal position may be different from the proximal retracted position. Such a retraction assembly may also include spring 8212. First spring 8212 is also configured to translate deployment sleeve 8206, needle carrier assembly 8208 and insertion element 8274 in the proximal direction from the distal insertion position to the proximal retracted position in response to on-skin sensor assembly 360 contacting skin 130 of the host and/or reaching a limit of travel with a force exceeding a predetermined threshold. For example, although not illustrated, housing 8202 may further comprise engagement element 7448 configured to engage with a protrusion 7449 of needle carrier assembly 8208, and to function substantially as previously described in connection with at least FIGS. 74A-74C. In some embodiments, a stop feature (not shown) may be disposed at a bottom of applicator 8200, e.g., on a distal portion of housing 8202. Such a stop feature may be configured to contact one or more of on-skin sensor assembly 360, needle carrier 8208, holder 8224 or deployment sleeve 8206 in the distal insertion position. Spring 8212 is configured to exert a force sufficient to deflect deployment sleeve retention elements 8262a, 8262b of deployment sleeve 8206 when on-skin sensor assembly 360 is in contact with skin 130 of the host, thereby freeing deployment sleeve retention elements 8262a, 8262b of deployment sleeve 8206 from protrusions 8264a, 8264b of housing 8202 (see FIGS. 82C-82D), thereby allowing spring 8212 to translate deployment sleeve 8206, and thus needle carrier assembly 8208 and insertion element 8274, in the proximal direction from the distal inserted position. Deployment sleeve retention elements 8262a, 8262b may comprise, e.g., arms, deflection elements, tabs, detents, snaps or any other features capable of a retaining function.

In some embodiments, transfer of on-skin sensor assembly 360 between insertion and retraction may occur as previously described in connection with any prior figure, for example, any of FIGS. 35A-37C.

Such dual insertion/retraction operability of spring 8212 is possible because, during insertion, deployment sleeve 8206 is immobilized by deployment sleeve retention elements 8262a, 8262b, being in contact with respective protrusions 8264a, 8264b of housing 8202. Thus, when spring 8212 exerts force between deployment sleeve 8206 and holder 8224, spring 8212 drives holder 8224, and coupled needle carrier assembly 8208, insertion element 8274 and on-skin sensor assembly 360, in the distal direction to the distal deployed position, where on-skin sensor assembly 360 is in contact with the skin 130 of the host. Once on-skin sensor assembly 360 is in contact with the host, holder 8224 is immobilized against on-skin sensor assembly 360, a travel-limiting feature of applicator 8200, and/or the skin of the host. Accordingly, with holder 8224 immobilized, the force exerted by spring 8212 between immobilized holder 8224 and deployment sleeve 8206 now acts to push deployment sleeve 8206 in the proximal direction with sufficient force to deflect deployment sleeve retention elements 8262a, 8262b sufficiently to clear protrusions 8264a, 8264b of housing 8202, thereby freeing deployment sleeve 8206 to be driven further in the proximal direction by spring 8212. Since protrusion 8266 of needle carrier assembly 8208 is configured to contact, couple or hook deployment sleeve 8206 as deployment sleeve 8206 translates in the proximal direction, the action of spring 8212 translating deployment sleeve 8206 in the proximal direction also translates needle carrier assembly 8208, and coupled insertion element 8274, in the proximal direction to the proximal retracted position. Positions of the above-described features will now be discussed with respect to FIGS. 82A-82D.

Although not shown in FIGS. 82A-82D, in some embodiments, applicator 8200 may comprise a cap configured to be secured to a distal surface of inner housing 8202 or activation element 8204, which may be removed before use. In some embodiments, this cap may create a sealed volume that provides a sterile barrier, as previously described in U.S. patent application Ser. No. 16/011,527, hereby incorporated by reference in its entirety.

Figure 82A:
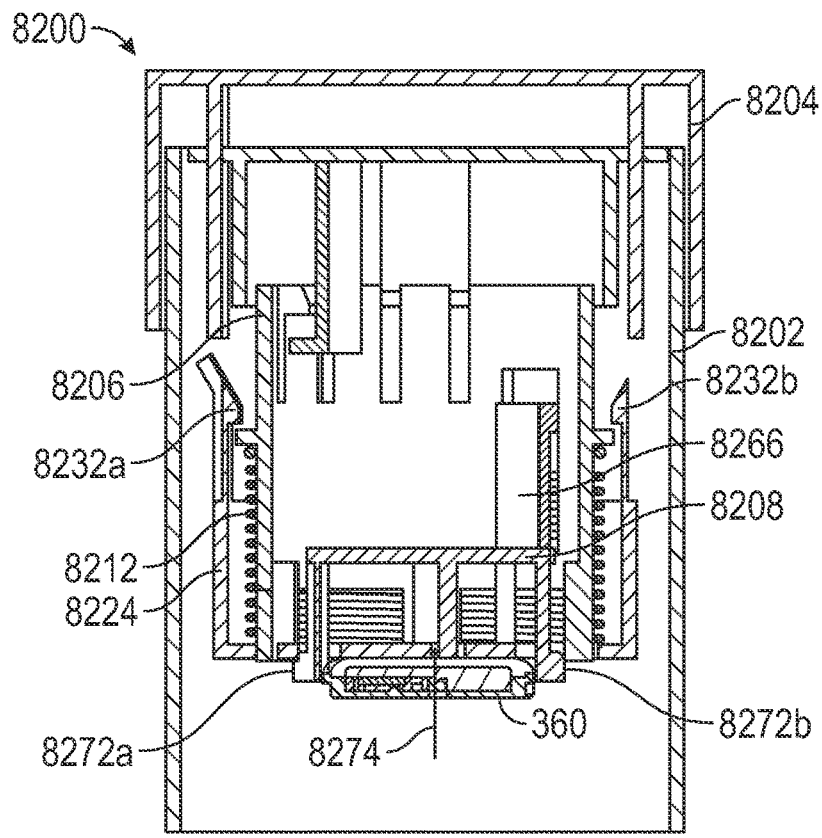
FIGS. 82A-82D illustrate several cross-sectional views, and various features and operating positions, of yet another applicator for an on-skin sensor assembly of an analyte sensor system, according to some embodiments.

FIG. 82A illustrates a state of applicator 8200 prior to activation, according to some embodiments. Prior to activation, holder retention elements 8232a, 8232b immobilize holder 8224 to deployment sleeve 8206. Holder retention elements 8232a, 8232b may comprise, e.g., arms, deflection elements, tabs, detents, snaps or any other features capable of a retaining function. Needle carrier assembly 8208 is coupled to holder 8224. Insertion element 8274 is coupled to needle carrier assembly 8208. And on-skin sensor assembly 360 is coupled to needle carrier assembly 8208 via wearable retention elements 8272a, 8272b. The positions illustrated may correspond to the proximal position.

Figure 82B:
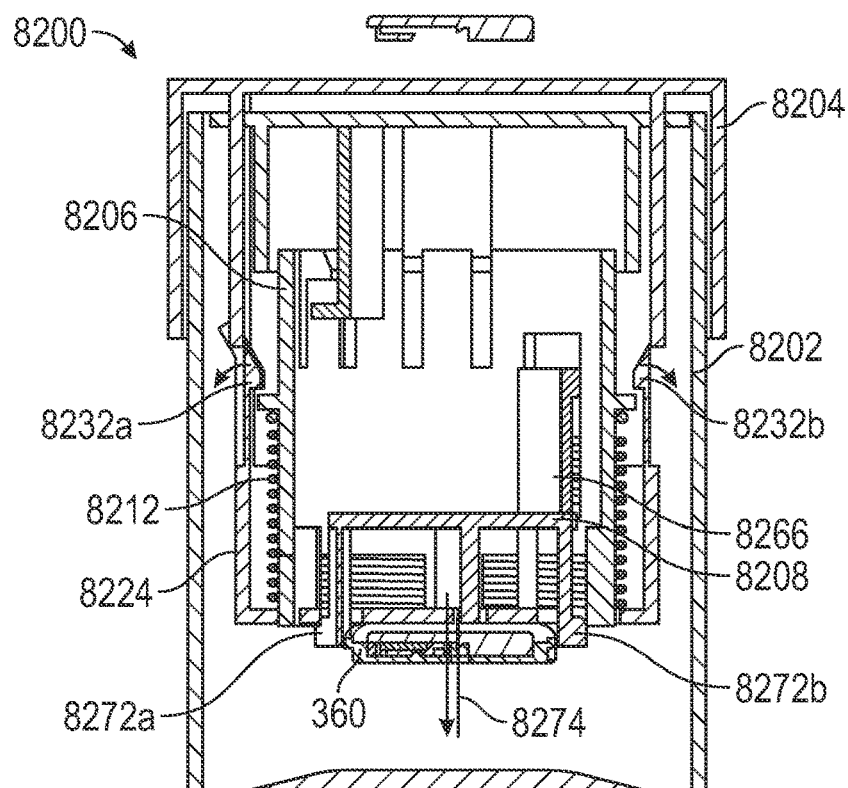

FIG. 82B illustrates a state of applicator 8200 at activation, according to some embodiments. Activation element 8204 is shown as activated (e.g., pressed down) such that protrusions 8264a, 8264b translate in the distal direction sufficiently to laterally deflect holder retention elements 8232a, 8232b, thereby decoupling holder 8224 from deployment sleeve 8206 and freeing spring 8212 to drive holder 8224, needle carrier assembly 8208, insertion element 8274 and on-skin sensor assembly 360. As in FIG. 82A, the illustrated positions of deployment sleeve 8206, holder 8224, needle carrier assembly 8208, insertion element 8274 and on-skin sensor assembly 360 may correspond to the initial proximal position.

Figure 82C:
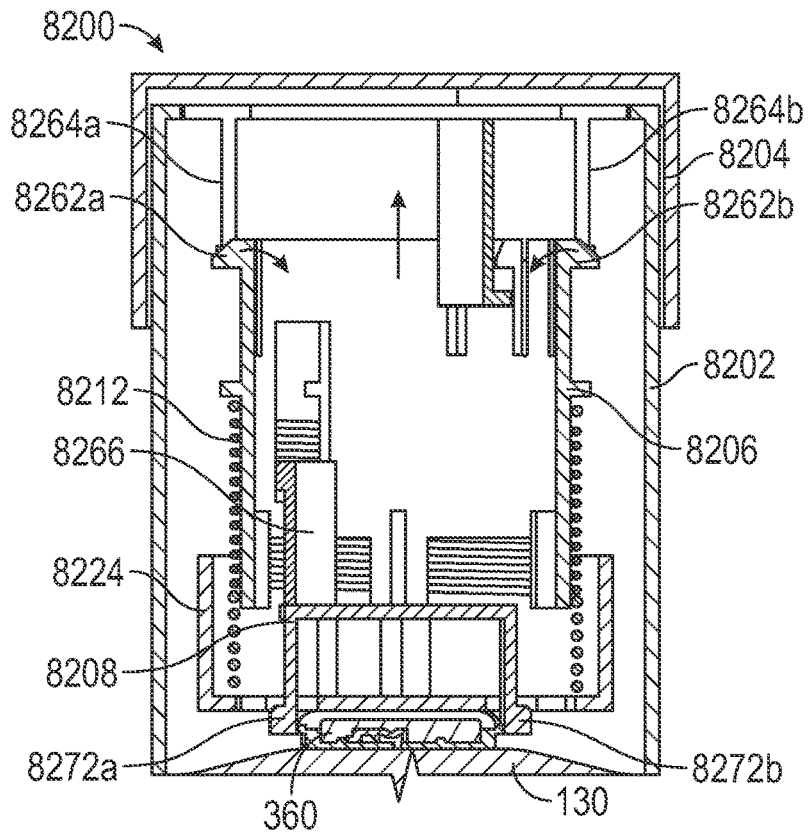

FIG. 82C illustrates a state of applicator 8200 at the end of insertion, according to some embodiments. First spring 8212 has translated holder 8224, needle carrier assembly 8208, insertion element 8274 and on-skin sensor assembly 360 in the distal direction to the distal insertion position. On-skin sensor assembly 360 is shown in contact with skin 130 of the host, insertion element 8274 is inserted into skin 130 of the host, and holder 8224 is being pressed against on-skin sensor assembly 360 by spring 8212. In the illustrated positions, spring 8212 is exerting a force on deployment sleeve 8206 sufficient to laterally deflect deployment sleeve retention elements 8262a, 8262b, thereby freeing deployment sleeve 8206 to be translated in the proximal direction by spring 8212. The illustrated positions of holder 8224, needle carrier assembly 8208, insertion element 8274 and on-skin sensor assembly 360 may correspond to the distal inserted position.

In some embodiments, masses of each of holder 8224, needle carrier assembly 8208, insertion element 8274, and on-skin sensor assembly 360 may be specifically designed to reduce or substantially eliminate a tendency of needle carrier assembly 8208, insertion element 8274, and on-skin sensor assembly 360 to prematurely detach from holder 8224 while being driven in the distal direction during insertion. In some embodiments, a force exerted by spring 8212 may further be selected to be sufficient for proper operation of applicator 8200, while not so large as to further exacerbate such above described inertially triggered detachment. In some embodiments, a spring (not shown) may be configured to exert a force, in the distal direction for example, against a portion of needle carrier assembly 8208 sufficient to prevent needle carrier assembly 8208 from inertially triggered detaching from holder 8224 during insertion.

Figure 82D:
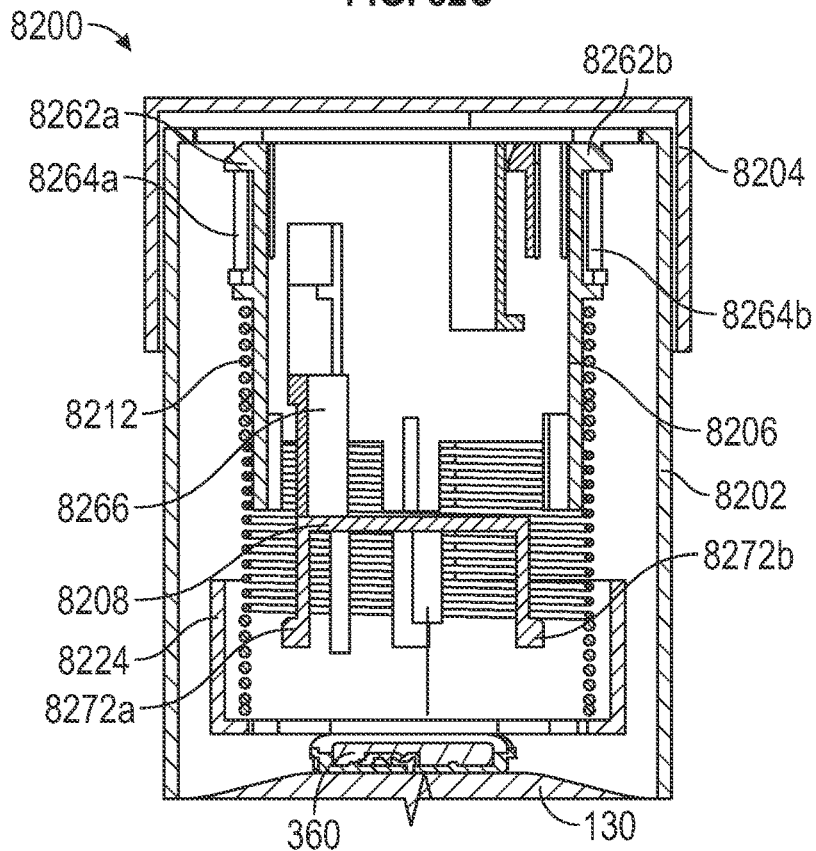

FIG. 82D illustrates a state of applicator 8200 after retraction, according to some embodiments. As illustrated, wearable retention elements 8272a, 8272b detach from on-skin sensor assembly 360 during retraction. First spring 8212 has translated deployment sleeve 8206 in the proximal direction. Because protrusion 8266 of needle carrier assembly 8208 is configured to contact deployment sleeve 8206 during retraction, as deployment sleeve 8206 is driven in the proximal direction, so is needle carrier assembly 8208 and insertion element 8274. In some embodiments, it is this proximal translation that causes wearable retention elements 8272a, 8272b to detach from on-skin sensor assembly 360. Since spring 8212 pushes holder 8224 in the distal direction and deployment sleeve 8206, needle carrier assembly 8208 and insertion element 8274 in the proximal direction, insertion element 8274 is locked, safely, in the second proximal retracted position.

Although not shown in FIGS. 82A-82D, applicator 8200 may further comprise a displacement-based lockout feature that prevents deployment sleeve 8206 from translating in the proximal direction, thereby preventing retraction, until holder 8224 has translated at least a predetermined distance in the distal direction. Such a displacement-based lockout feature may operate substantially as protrusions 7546, 8146 previously described in connection with FIGS. 75A and 81A-81D. For example, such a protrusion may extend in the proximal direction from one or more of holder 8224 or needle carrier assembly 8208 and may be configured to be in physical contact with deployment sleeve retention elements 8262a, 8262b at least until holder 8224 or needle carrier assembly 8208 has translated at least the predetermined distance in the distal direction, thereby preventing inertial (i.e., reaction force generated by the acceleration of mass) or accidental activation of applicator 8200, for example, due to concussive shock from dropping applicator 8200.

During manufacture, applicator 8200 may be assembled in stages. For example, and not limitation, if present, first barrier layer 7192 or similar may be affixed to housing 8202. Insertion element 8274 may be coupled to needle hub 7150, if present, which may then be coupled to on-skin sensor assembly 360. If needle hub 7150 is not present, insertion element 8274 may be coupled directly to on-skin sensor assembly 360. Needle carrier assembly 8208 may be at least partly disposed within deployment sleeve 8206 and spring 8212 may be placed into holder 7124. Deployment sleeve 8206 and needle carrier assembly 7108 may be disposed into holder 7124 and attached to needle hub 7150, if present, or directly to insertion element 8274 if needle hub 7150 is not present, and to on-skin sensor assembly 360 via wearable retention elements 8272a, 8272b. The assembly including holder 8224, deployment sleeve 8206 and needle carrier assembly 8208 may then be installed into housing 8202. If present, second barrier layer 7194 or similar may be affixed to housing 8202. If a separate element, activation element 8204 may then be disposed into housing 8202. Any labeling, sterilizing and/or packaging may then be applied to applicator 8200.

FIGS. 83-85 illustrate several alternatives for activation elements in an applicator. Such alternatives may be directly applied to any applicator described in this disclosure, especially, though not in any way limited to, applicators 7100, 8100 and 8200 described above.

FIG. 83 illustrates a cross-sectional view of an applicator 8300 comprising a deformable layer 8305 disposed over an activation element 8304, according to some embodiments. Although activation element 8304 is shown on a side of an outer housing 8301, any other suitable location for deformable layer 8305 and activation element 8304 is contemplated, e.g., a top, a high side, a low side of outer housing 8301. In some embodiments, deformable layer 8305 may be molded over activation element 8304. In some other embodiments, deformable layer 8305 may be glued or welded over activation element 8304, for example, utilizing ultrasonic, laser, radio frequency, heat stake welding processes, or any other suitable process. In some embodiments, deformable layer 8305 may comprise a film, an elastomer, a plastic or any other material with sufficient deformability to allow activation of activation element 8304 as well as to provide an air and/or fluid-tight sealed surface over activation element 8304.

FIG. 84 illustrates a perspective view of an applicator 8400 utilizing a twist-to-activate activation mechanism, according to some embodiments. Applicator 8400 comprises an outer housing 8401 and an inner housing 8402. In some embodiments, outer housing 8401 and inner housing 8402 may, together, comprise an activation element in that applicator 8400 is activated by pushing down on applicator 8400 with sufficient force to immobilize inner housing 8402 against the skin of the host as outer housing 8401 is twisted with respect to inner housing 8402. Such a design ensures applicator 8400 is pressed against the skin of the host with at least a minimum force, which can be designed to a particular desired threshold based on, for example, a predetermined amount of force that ensures proper seating and orientation of applicator 8400 for use, the friction coefficient between inner housing 8402 and the skin of the host, as well as based on the twisting force to trigger applicator 8400.

FIG. 85 illustrates a cross-sectional view of an applicator 8500 comprising a top-mounted activation element 8504, according to some embodiments. In some embodiments, activation element 8504 may comprise any type of activation element described in this disclosure, including, but not limited to, a dome-shaped button. In some embodiments, such a dome-shaped button may comprise a deformable material, as previously described in connection with FIG. 83 or, alternatively, may be sufficiently rigid to hold its form when pressed or otherwise utilized by the host.

Insertion Element Embodiments

Several embodiments of an insertion element, as previously described herein, will now be described in connection with at least FIGS. 47-50, in which the insertion element is illustrated as being a needle.

Figure 47:
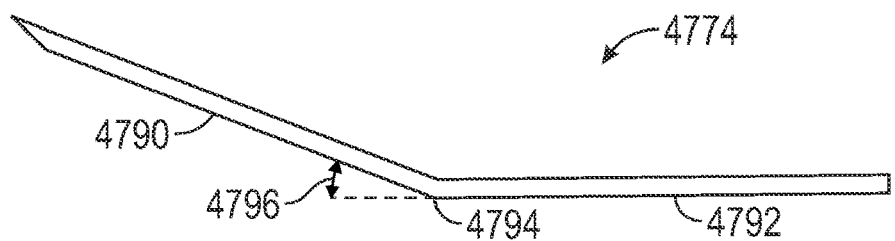
FIG. 47 illustrates a cross-section of a kinked needle for use in an applicator for an analyte sensor system, according to some embodiments.

FIG. 47 illustrates a cross-sectional view of a kinked needle 4774 for use in an applicator for an analyte sensor system, according to some embodiments. Kinked needle 4774 may have at least two substantially straight portions 4790, 4792 with a bend 4796 between each substantially straight portion such that an angle 4796 between the substantially straight portions is substantially optimized to reduce lateral motion of a tip of needle 4774 through the skin of the host as needle 4774 traces an arc during activation.

Figures 48A, 48B:
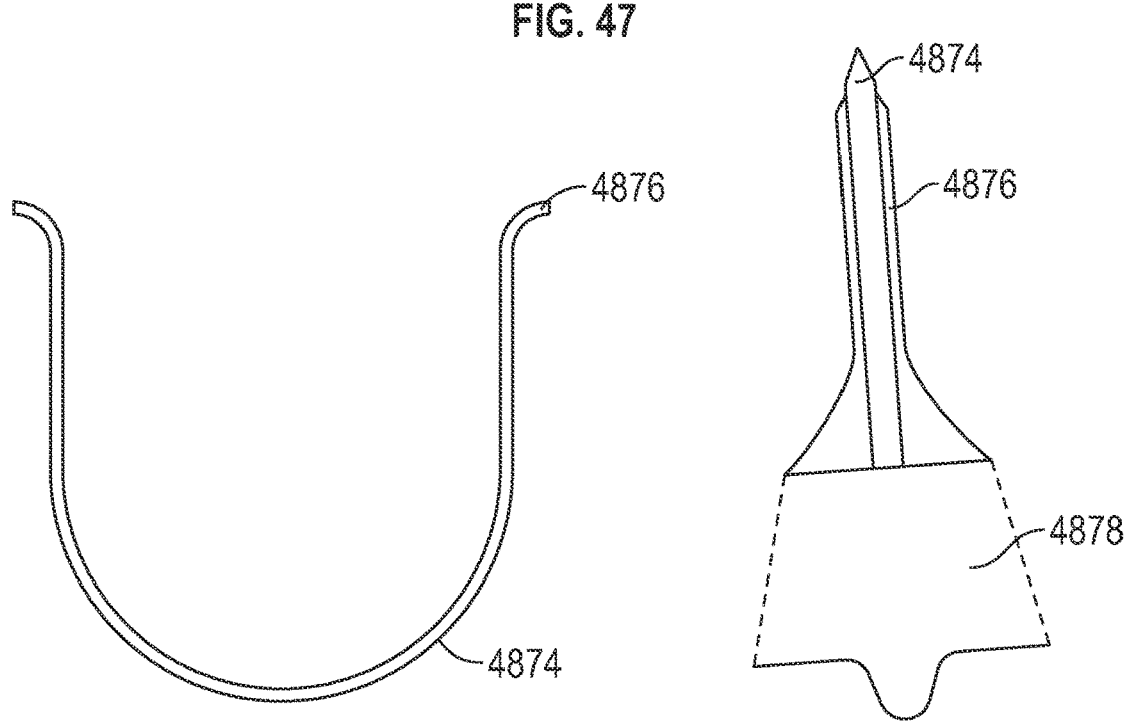
FIGS. 48A-48B illustrate a cross-section and a plan view, respectively, of a flared C-needle for use in an applicator for an analyte sensor system, according to some embodiments.

FIGS. 48A-48B illustrate a cross-section and a plan view, respectively, of a flared open-sided needle 4874 for use in an applicator for an analyte sensor system, according to some embodiments. Although FIGS. 48A-48B illustrate open-sided needle 4874 having a C-shaped cross-section, the open-sided needle 4874 may have any shaped cross-section, e.g., a C-shape, a U-shape, a V-shape. FIG. 48A illustrates a cross-section of an open-sided needle 4874 having at least one flared edge 4876. For example, flared edge 4876 may be flared in a lateral direction from a longitudinal centerline of open-sided needle 4874. Such a flared edge 4876 may prevent or substantially reduce the incidence of damage to sensor 138 (e.g., FIG. 1) caused by sharp edges of the open-sided needle coming in contact with sensor 138 before or during insertion into the skin of a host.

FIG. 48B illustrates a plan view of open-sided needle 4874. Open-sided needle 4874 is illustrated as formed with an end opposite its tip having a needle skirt 4878. Needle skirt 4878 may aid directing sensor 138 into the needle lumen to assist with loading of sensor 138 and/or reduce the opportunity for damage of sensor 138 during use and/or loading.

Figure 49:
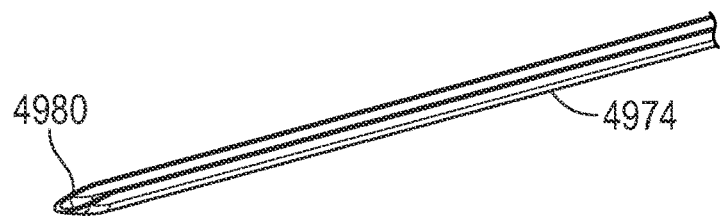
FIG. 49 illustrates a perspective view of a deflected-tip needle for use in an applicator for an analyte sensor system, according to some embodiments.

FIG. 49 illustrates a perspective view of a deflected-tip needle 4974 for use in an applicator for an analyte sensor system, according to some embodiments. Deflected-tip needle 4974 may comprise a substantially straight shaft having a substantially curved tip 4980, such that an angle of entry of deflected-tip needle 4974 is offset from the substantially straight shaft. Such angle offset of the substantially curved tip 4980 may be particularly useful for reducing tissue damage and insertion resistance for applicators such as applicator 2500, as previously described in connection with FIGS. 25-28H, that have an insertion path for the insertion element that is a substantially curved path. The substantially curved tip 4980 may steer deflected-tip needle 4974 in the direction of the substantially curved insertion path, thereby reducing tissue damage caused by lateral movement of the needle with respect to its direction of extension. FIG. 49 illustrates a magnified view 4950 of the curved tip 4980.

Figure 50:
FIG. 50 illustrates a perspective view of a curved needle for use in an applicator for an analyte sensor system, according to some embodiments.

FIG. 50 illustrates a curved needle 5074 for use in an applicator for an analyte sensor system, according to some embodiments. As shown, curved needle 5074 has a profile that is substantially curvilinear. Such a curvilinear profile may be particularly useful for reducing tissue damage and insertion resistance for applicators such as applicator 2500, as previously described in connection with FIGS. 25-28H, that have an insertion path for the insertion element that is a substantially curved path. The substantially curvilinear profile of needle 5074 may reduce tissue damage caused by lateral movement of the needle with respect to its direction of extension. In some embodiments, the curvilinear profile of needle 5074 may substantially track or trace the insertion path for the applicator, thereby substantially eliminating, or at least greatly reducing, lateral movement of the needle with respect to the skin of the host. In some embodiments, sensor 138 of on-skin sensor assembly 160 may have a curvilinear profile also, thereby allowing sensor 138 to rest within a portion of curved needle 5074. In yet other embodiments, the insertion element, for example a C-needle may have at least a portion coated with a polymer that prevents damage to the tissue of the host and/or to the sensor wire. Such a polymer may include, but is not limited to, cyanoacrylate, epoxy, elastomeric polymers, urethanes or any other suitable polymer.

In some embodiments, at least a sensing portion of sensor 138 may be coated with AgCl to improve the reference capacity of sensor 138. However, AgCl is a catalyst for corroding the metal in the insertion element (e.g., open-sided needle). Accordingly, an AgCl coating on sensor 138 that comes into contact with the insertion element may be undesirable. One method of decreasing corrosion of sensor 138 and/or the insertion element is to selectively remove or substantially decrease the content of AgCl on at least a proximal end of sensor 138 without substantially affecting the region of sensor 138 that is inserted into the skin of the host. This may be accomplished by exposing the desired portion of sensor 138 to a single frequency or multiple frequencies of ultraviolet radiation for a predetermined length of time and at a predetermined intensity. Such a process may be performed at any time, for example, during the skiving or singulation process. Another method of removing AgCl is to expose the desired portion of sensor 138 to an ammonia ($NH_3$) rinse at a desired concentration and for a desired length of time.

Sharp Protection

Figure 51A:
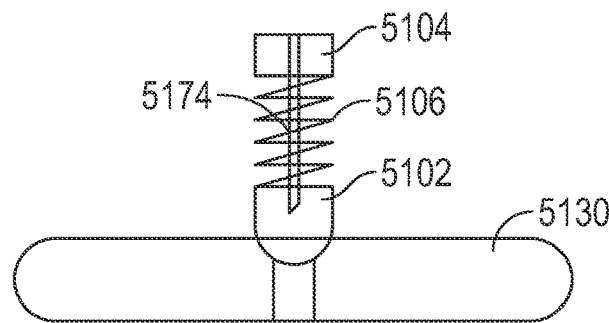
FIGS. 51A-51B illustrate cutaway views of a needle hub of an applicator for an analyte sensor system, according to some embodiments.
Figure 51B:
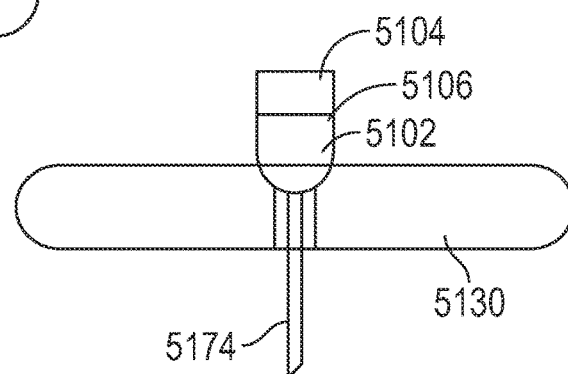

FIGS. 51A-51B illustrate cutaway views of a needle hub of an applicator for an analyte sensor system, according to some embodiments. FIG. 51A illustrates a needle hub 5104, an insertion element 5174, a needle guard 5102, a spring 5174, and a base 5130 of the applicator. First needle hub 5104 may be fixed to a portion other than a tip of insertion element 5174. Second needle hub 5102 may be configured to encapsulate the tip of insertion element 5174 and may comprise a material that insertion element 5174 may pierce during deployment and/or may include an aperture or hole through which insertion element 5174 may pass. Spring 5106 is configured to keep a predetermined spacing between needle hub 5104 and needle guard 5102 such that the tip of insertion element 5174 is encapsulated by needle guard 5102 when the predetermined spacing is maintained. FIG. 51A illustrates a pre-activation position that may be returned to after activation, under a returning force provided by spring 5106, compressed during deployment of insertion element 5174. In some embodiments, the spring can be integrated into needle hub 5104 or needle guard 5102.

FIG. 51B illustrates needle hub 5104, insertion element 5174, needle guard 5102, spring 5174, and base 5130 of the applicator in the distal, deployed position. As shown, insertion element 5174 has been driven through needle guard 5102 and through an opening in base 5130. Since needle hub 5104 is fixed to insertion element 5174, deployment of insertion element 5174 to the distal, deployed position closes the distance between needle hub 5104 and needle guard 5102, thereby compressing spring 5106 (not shown in FIG. 51B). The energy stored in compressing spring 5106 is then utilized to force needle guard 5102 substantially to its pre-activation position, thereby encapsulating the tip of insertion element 5174. It is contemplated that the features described in FIGS. 51A-51B provide protection from needle stick hazards.

Figure 52A:
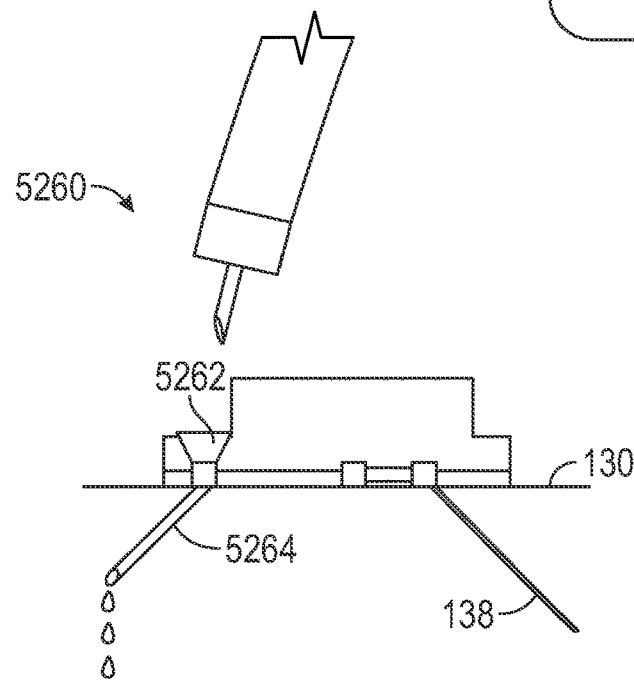
FIGS. 52A-52B illustrate a cross-sectional view and a plan view, respectively, of an infusion cannula integrated into an on-skin sensor assembly of an analyte sensor system, according to some embodiments.
Figure 52B:
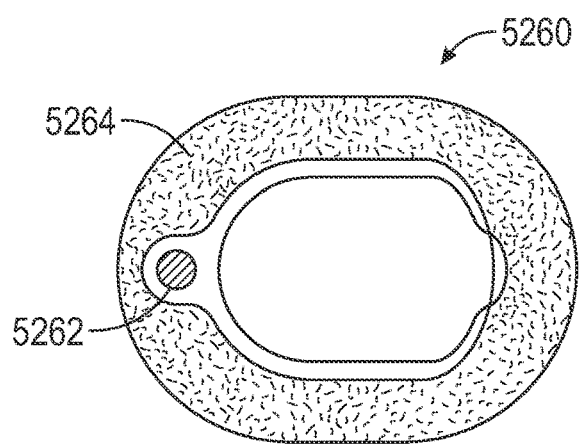

FIGS. 52A-52B illustrate a cross-sectional view and a top plan view, respectively, of an infusion cannula 5264 integrated into on-skin sensor assembly 160 of an analyte sensor system, according to some embodiments. In FIG. 52A, on-skin sensor assembly 160 is illustrated as including sensor 138 and a fill port 5262 configured to receive a fluid, gel, or medication (e.g., insulin) and cannula 5264 configured to deliver the fluid or gel through skin 130 of the host. In some embodiments, fill port 5262 comprises a septum material that maintains a seal for the transcutaneous cannula and is capable of being pierced (e.g. by a hypodermic needle attached to a syringe) and allow for dosing the medication. This septum may be configured to self-seal after removal of the needle from the skin of the host. The infusion cannula and analyte sensor may be inserted transcutaneously by the same applicator device. It is envisioned that a sharp (e.g. needle) placed within the lumen of an infusion cannula and placed in parallel with the insertion element (e.g. attached to needle carrier assembly such as 508) for analyte sensors may be added to the analyte applicators (e.g. applicator 500, 800, 900, 1000, etc.). In FIG. 52B, on-skin sensor assembly 160 is illustrated as including an adhesive patch 5264 configured to adhere on-skin sensor assembly 160 to skin 130 of the host.

Sensor Retention Embodiments

In some embodiments, an insertion element, such as an open-sided needle may be utilized to insert at least a portion of a sensor wire into the skin of a host. However, such embodiments generally operate best when the sensor wire remains seated in a channel of the open-sided needle before and during insertion. In addition, if the open-sided needle does not retain the sensor in the channel of the needle, the sensor may fail to deploy into the tissue. Accordingly, FIGS. 53-59 illustrate several embodiments of applicators that include sensor retention features configured to retain the sensor wire within a channel of the insertion element at least before activation of the applicator. Although particular applicators are shown, these retention features may be incorporated into any applicator described by this disclosure.

Figure 53:
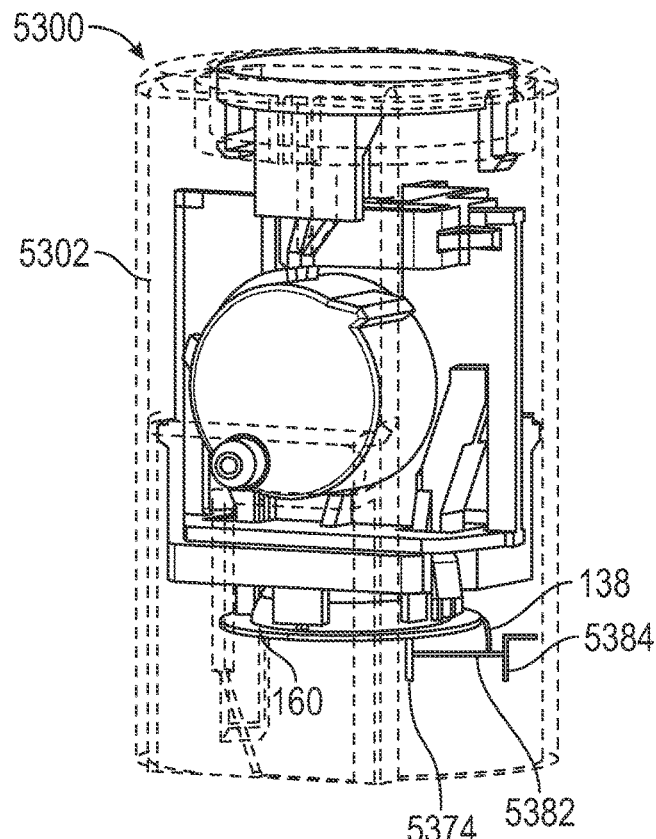
FIG. 53 illustrates a cross-sectional view of a sensor retention mechanism for an applicator for an analyte sensor system, according to some embodiments.

FIG. 53 illustrates a cross-sectional view of a sensor retention mechanism for an applicator 5300 for an analyte sensor system, according to some embodiments. Applicator 5300 includes an applicator housing 5302 having a retention feature 5384, for example a hook or protrusion. Applicator 5300 further includes on-skin sensor assembly 160 having sensor 138, and an insertion element 5374 configured to guide sensor 138. Applicator 5300 further comprises a retention element 5382, which may comprise an elastomeric band (e.g., a rubber band), a flexible plastic, or metallic wire configured to press against an open side of insertion element 5374 thereby retention sensor 138 in insertion element 5374. Upon activation of applicator 5300, an orientation or position of one or more of retention feature 5384, retention element 5382 or insertion element 5374 may be altered such that sensor 138 is no longer actively retained within insertion element 5374. For example, insertion element 5374 may be configured to progress in the proximal direction at the beginning of activation. The insertion element 5374 is withdrawn from the retention element allowing the retention element to recoil and clear the pathway of insertion for the on-skin sensor assembly.

Figure 54:
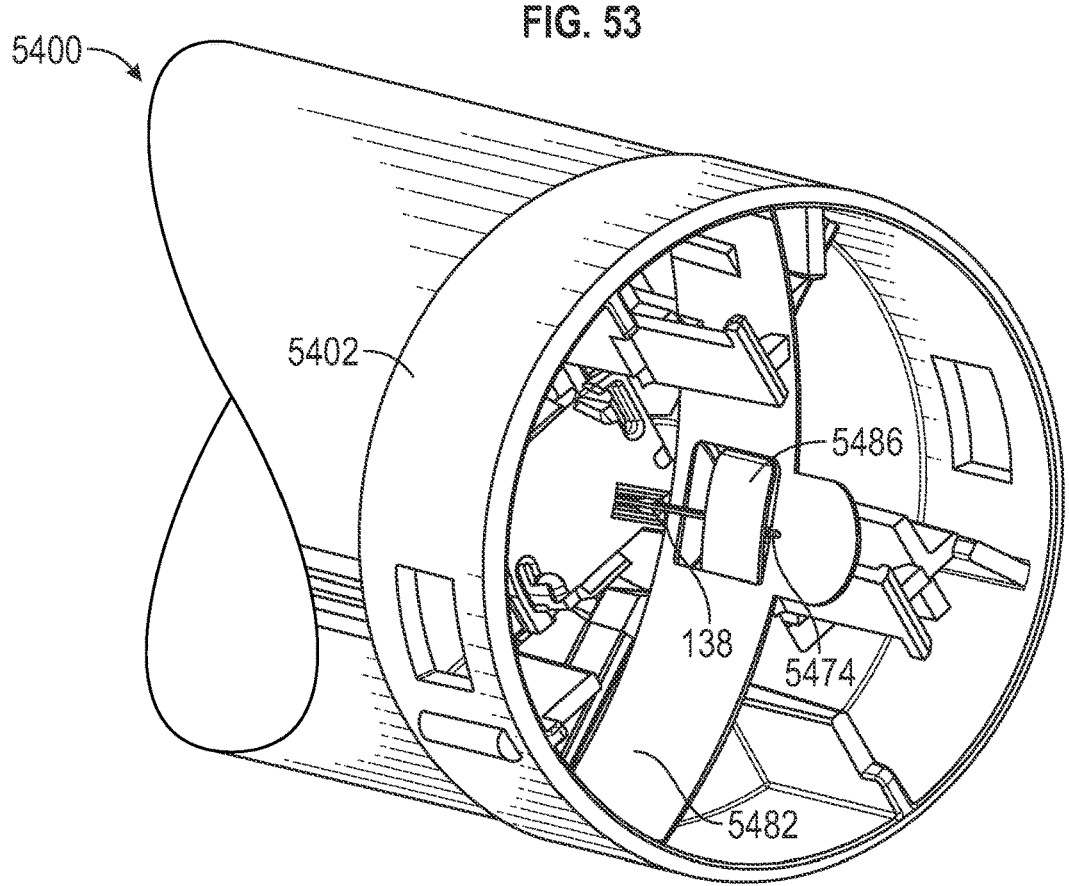
FIG. 54 illustrates a perspective view of another sensor retention mechanism for an applicator for an analyte sensor system, according to some embodiments.

FIG. 54 illustrates a perspective view of another sensor retention mechanism 5482 for an applicator 5400 for an analyte sensor system, according to some embodiments. In FIG. 54, sensor retention mechanism 5482 comprises a flexible or substantially rigid insert configured to rest against applicator housing 5402 and against insertion element 5474, thereby retention sensor 138 in insertion element 5474. For example, retention mechanism 5482 may comprise a paper, plastic, elastomeric, metallic or polymeric sheet configured for removal before activation of applicator 5400. In some embodiments, retention mechanism 5482 may be manufactured or cut to include a tab 5486 configured to press against insertion element 5474, thereby retention sensor 138 in insertion element 5474.

In some embodiments, retention mechanism 5482 may be coupled to a liner of an adhesive patch of on-skin sensor assembly 160 such that when the liner is removed, in preparation for application of on-skin sensor assembly 160, retention mechanism 5482 may be simultaneously removed.

In some other embodiments, tab 5486 may be disposed at such an angle that, rather than holding insertion element 5474 and sensor 138 between tab 5486 and another portion of retention mechanism 5482, insertion element 5474 and sensor 138 are configured to pierce and pass at least partially through tab 5486 such that sensor 138 is retained within a channel of insertion element 5474.

Figure 55:
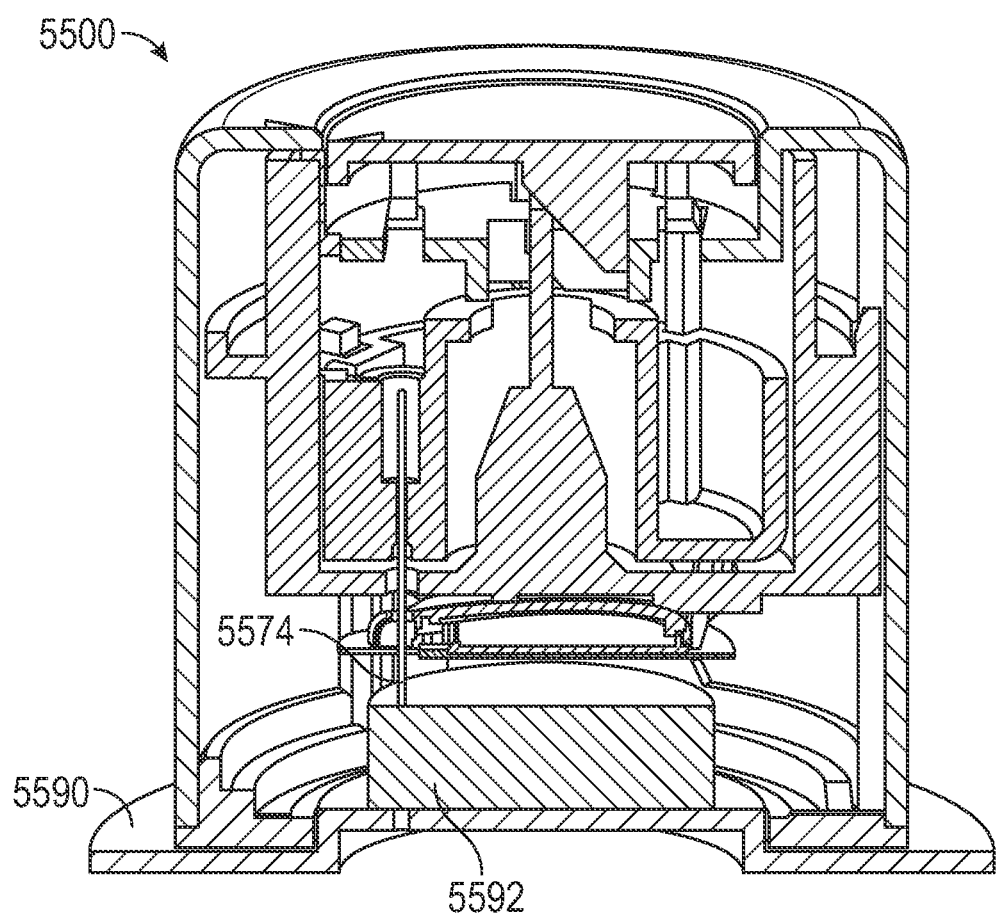
FIG. 55 illustrates a cutaway view of another sensor retention mechanism for an applicator for an analyte sensor system, according to some embodiments.

FIG. 55 illustrates a cutaway view of another sensor retention element 5592 for an applicator 5500 for an analyte sensor system, according to some embodiments. As shown, retention element 5592 may comprise a pad comprising foam, an elastomer, or any other suitable material, and insertion element 5574 may be inserted at least partially into retention element 5592 such that sensor 138 (not shown in FIG. 55) is retained within insertion element 5574. Retention element 5592 may be coupled to a bottom cap 5590 which is removable prior to activation of applicator 5500.

Figure 56A:
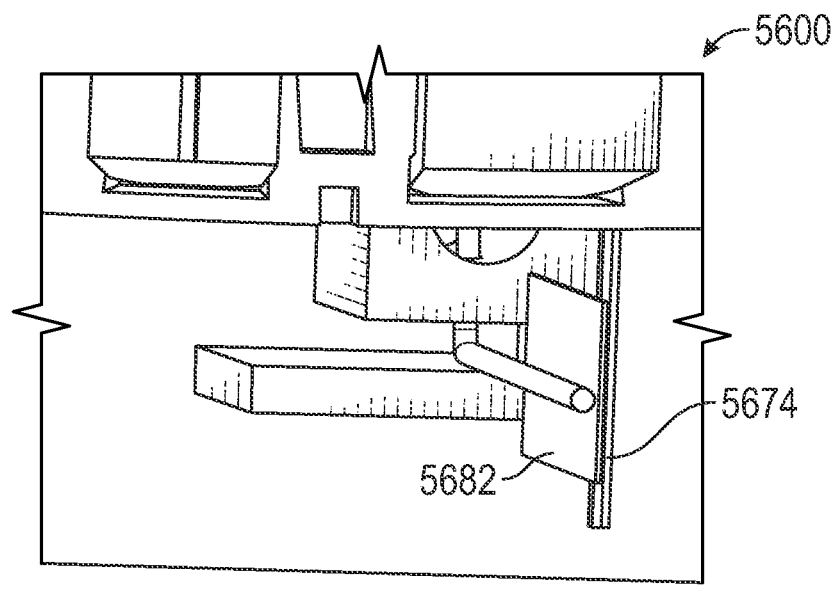
FIGS. 56A-56B illustrate perspective views of another sensor retention element for an applicator for an analyte sensor system, according to some embodiments.
Figure 56B:
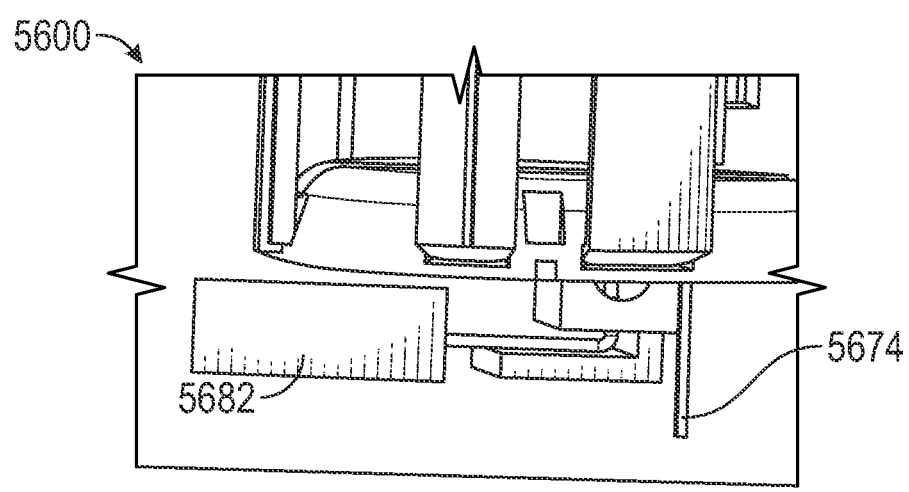

FIGS. 56A-56B illustrate perspective views of another sensor retention element 5682 for an applicator 5600 for an analyte sensor system, according to some embodiments. Sensor retention element 5682 may comprise a paddle or other surface configured to rest against insertion element 5674 in a retention position, thereby retention sensor 138 in the insertion element 5674. FIG. 56A illustrates sensor retention element 5682 in the retention position. Sensor retention element 5682 is configured to rotate, slide, or move away from insertion element 5674 into a non-retaining position, thereby putting applicator 5600 in a state for activation. In some embodiments the arm of sensor retention element 5682 is configured to automatically move during or after activation into a non-retaining position via a linkage attached to an element of the applicator. FIG. 56B illustrates sensor retention element 5682 in the non-retaining position.

In some embodiments, sensor 138 may be retained in a channel of an insertion element by an elastomeric band disposed around at least a portion of insertion element (e.g., an O-ring or any other flexible band material). The elastomeric band may be removed manually before deployment, or alternatively, may be removed from insertion element automatically by some operation of the applicator upon activation. In some embodiments (e.g. applicator 500) the insertion element is configured to move in the proximal direction during the first portion (e.g. by changing the starting position of the scotch-yoke mechanism) of the insertion cycle. In this embodiment the elastomeric element is able to clear the distal tip of the insertion element and recoil to clear the pathway of insertion of the on skin assembly.

In some other embodiments, sensor 138 may be retained in a channel of an insertion element by a foam, paper, cardboard, plastic, polymeric tab configured to be pierced by insertion element such that the tab is disposed substantially around a tip of insertion element, thereby retaining sensor 138 in the channel of the insertion element. The tab may be removed manually before deployment, or alternatively, may be removed from insertion element automatically by some operation of the applicator upon activation.

Figure 57:
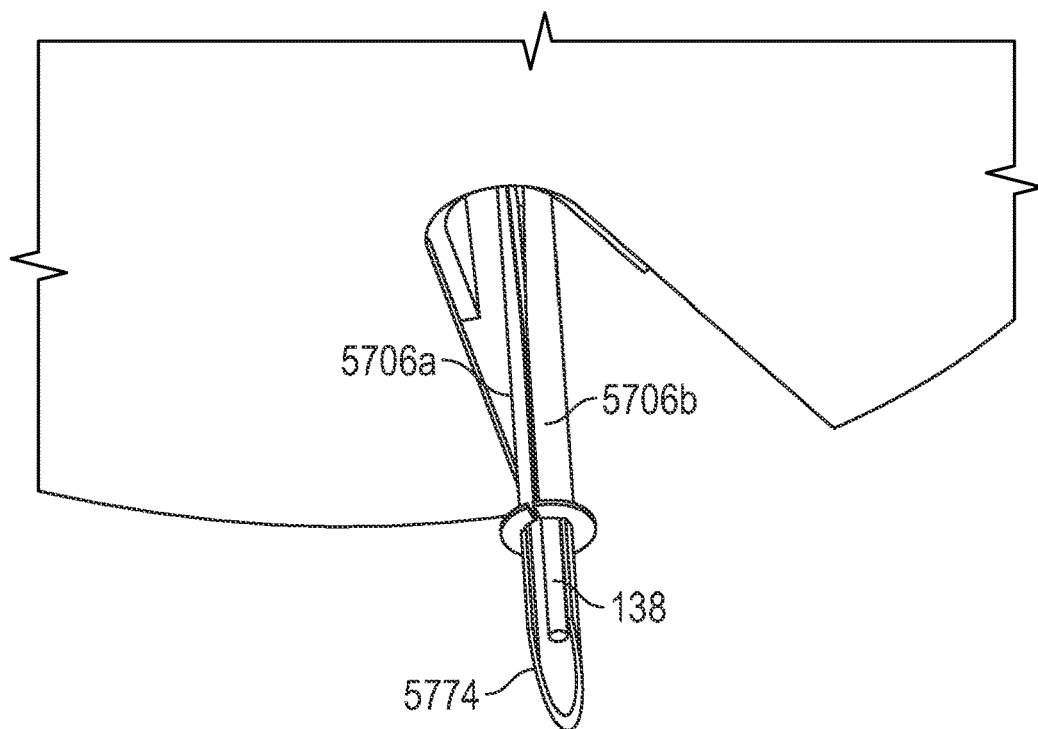
FIG. 57 illustrates a cross-sectional view of yet another sensor retention element for an applicator for an analyte sensor system, according to some embodiments.

FIG. 57 illustrates a perspective view of yet another sensor retention element 5782 for an applicator for an analyte sensor system, according to some embodiments. Sensor retention element 5782 includes a needle hub (not shown in FIG. 57) configured to guide insertion element 5774 (e.g., a C-needle), which is it turn configured to guide sensor 138. A flexible sleeve comprising a first portion 5706a and a second portion 5706b is disposed over sensor 138 and insertion element 5774, thereby retaining sensor 138 in insertion element 5774. Upon activation, the needle hub is configured to drive insertion element 5774 in the distal direction, thereby splitting the flexible sleeve and separating first portion 5706a and second portion 5706b. Once split, the flexible sleeve may no longer retain sensor 138 in insertion element 5774.

Figure 58:
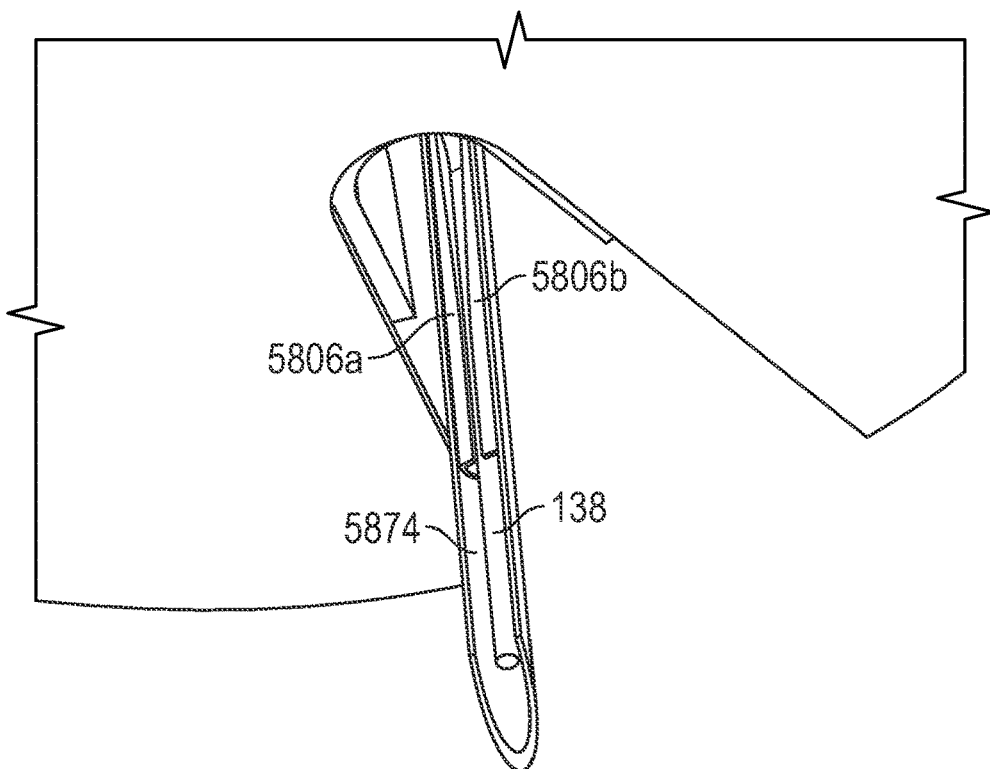
FIG. 58 illustrates a cross-sectional view of yet another sensor retention element for an applicator for an analyte sensor system, according to some embodiments.

FIG. 58 illustrates a perspective view of yet another sensor retention element 5882 for an applicator for an analyte sensor system, according to some embodiments. Sensor retention element 5882 includes a needle hub (not shown in FIG. 58) configured to guide insertion element 5874 (e.g., a C-needle), which is it turn configured to guide sensor 138. A flexible sleeve comprising a first portion 5806a and a second portion 5806b is disposed over sensor 138 within a channel of insertion element 5874, thereby retaining sensor 138 in insertion element 5874. Upon activation, the needle hub is configured to drive insertion element 5874 in the distal direction, thereby splitting the flexible sleeve and separating first portion 5806a and second portion 5806b. Once split, the flexible sleeve may no longer retain sensor 138 in insertion element 5874.

Figure 59A:
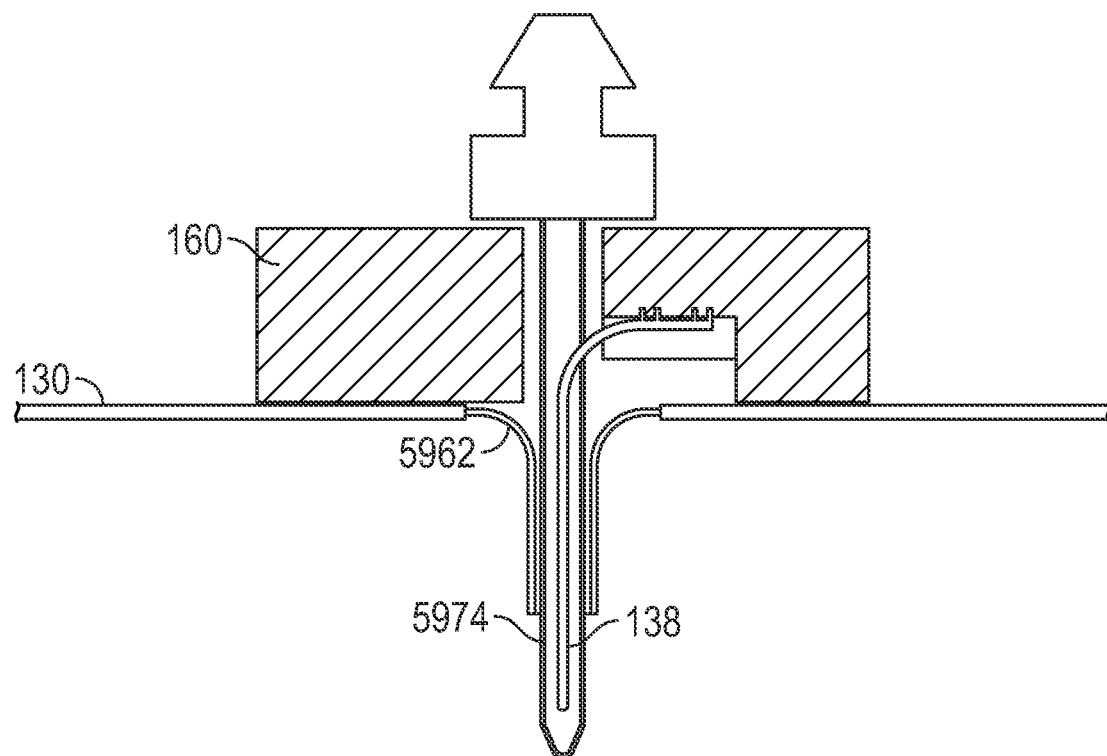
FIGS. 59A-59B illustrate cross-sectional views of yet another sensor retention element for an applicator for an analyte sensor system, according to some embodiments.
Figure 59B:
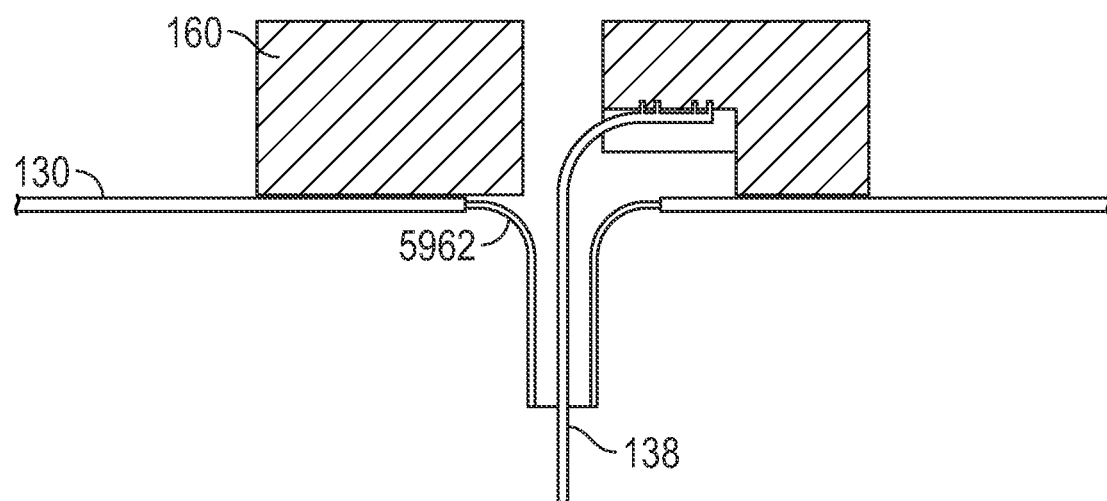

FIGS. 59A-59B illustrate cutaway views of yet another sensor retention element for an applicator for an analyte sensor system, according to some embodiments. FIG. 59A illustrates a position of on-skin sensor assembly 160, an insertion element 5974 guiding sensor 138, and a cannula (e.g. a tube such as PTFE, PE, polymer, metallic, etc.) 5962, configured to retain sensor 138 in an open sided insertion element 5974, during and before applicator activation. In FIG. 59A, cannula 5962 may be coupled to on-skin sensor assembly 160 or at least configured to be driven to the distal inserted position along with on-skin sensor assembly 160.

FIG. 59B illustrates on-skin sensor assembly 160, sensor assembly 138, and cannula 5962 in the inserted distal position with respect to skin 130 of the host, insertion element 5974 having been retracted to the proximal retracted position (not shown in FIG. 59B). As shown, sensor 138 may be inserted and disposed through cannula 5962, into skin 130 of the host. Cannula 5962 may provide strain relief and a minimum bend radius for sensor 138, thereby reducing the probability of damage to sensor 138 during deployment and operation. A significant portion of the elongated body of the analyte sensor may extend subcutaneously beyond the cannula so as not to interfere with sensor function.

On-Skin Sensor Assembly Features

Figure 68:
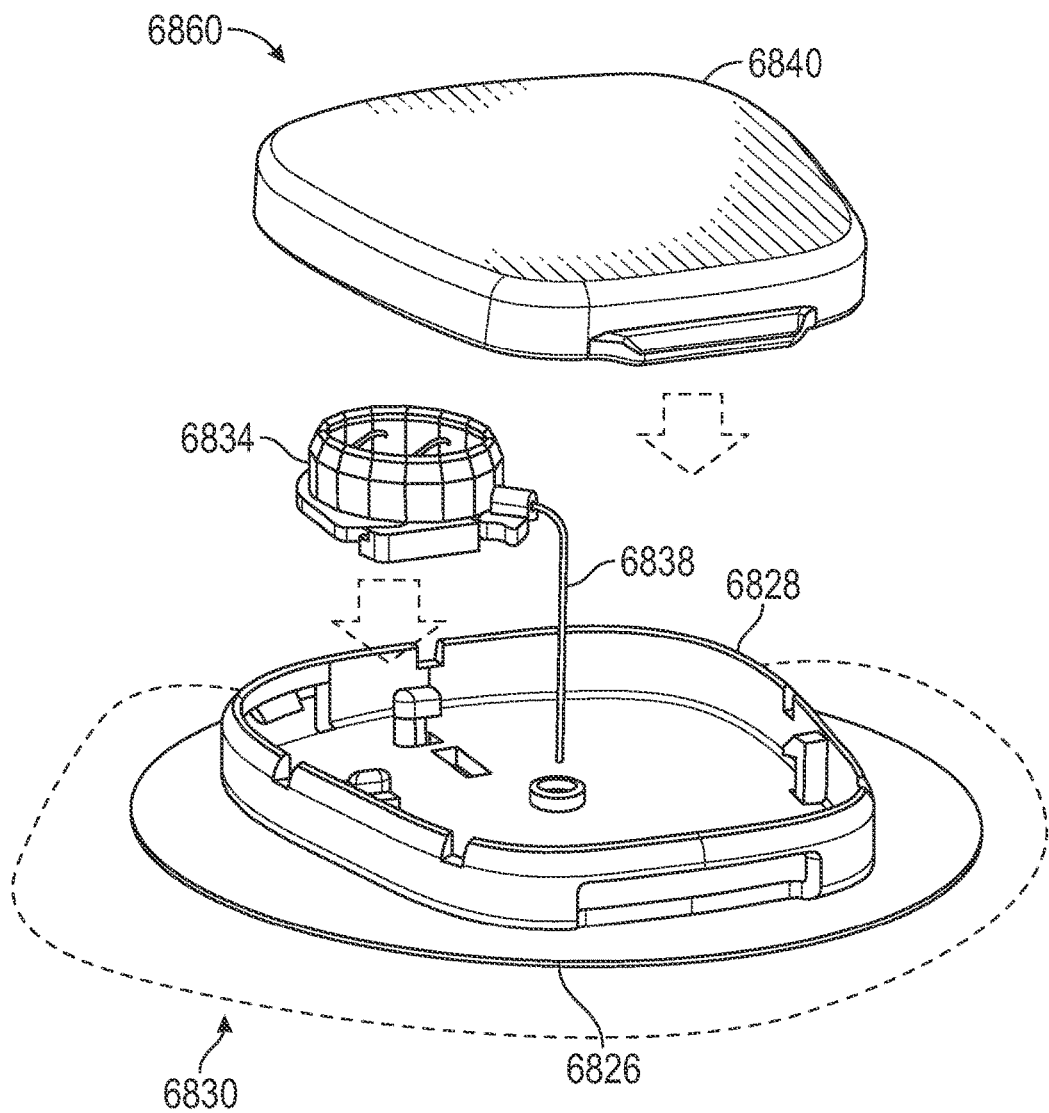
FIG. 68 illustrates a top perspective view of an on-skin sensor assembly, according to some embodiments.

FIG. 68 illustrates a perspective view of an on-skin sensor assembly 6860, which may include a base 6828. An adhesive patch 6826 can couple the base 6828 to the skin 6830 of the host. In some embodiments, the adhesive patch 6826 may comprise an adhesive suitable for skin adhesion, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated. An on-skin sensor assembly 6860 may comprise an electronics unit 6840 (e.g., a transmitter) which may further comprise a glucose sensor module 6834 coupled to a glucose sensor 6838 and to base 6828.

The applicator system can couple adhesive patch 6826 to skin 6830. The glucose sensor module 6834 may be secured to base 6828 (e.g., via retention elements such as snap fits and/or interference features, adhesive, welding, etc.) to ensure glucose sensor 6838 is coupled to base 6828. In alternative embodiments, the sensor module 6834 and base 6828 are preassembled or manufactured as a single component.

After on-skin sensor assembly 6860 is applied to a user's skin, a user (or an applicator) can couple electronics unit 6840 (e.g., a transmitter) to on-skin sensor assembly 6860 via retention elements such as snap fits and/or interference features. Electronics unit 6840 can measure and/or analyze glucose indicators sensed by glucose sensor 6838. Electronics unit 6840 can transmit information (e.g., measurements, analyte data, glucose data) to a remotely located device (e.g., 110-114 shown in FIG. 1).

On-skin sensor assembly 6860 may be attached to the host with use of an applicator adapted to provide convenient and secure application. Such an applicator may also be used for attaching electronics unit 6840 to base 6840, inserting sensor 6838 through the host's skin, and/or connecting sensor 6838 to electronics unit 6840. Once electronics unit 6840 is engaged with the base and sensor 6838 has been inserted into the skin (and is connected to the electronics unit 6840), the sensor assembly can detach from the applicator.

Figure 69:
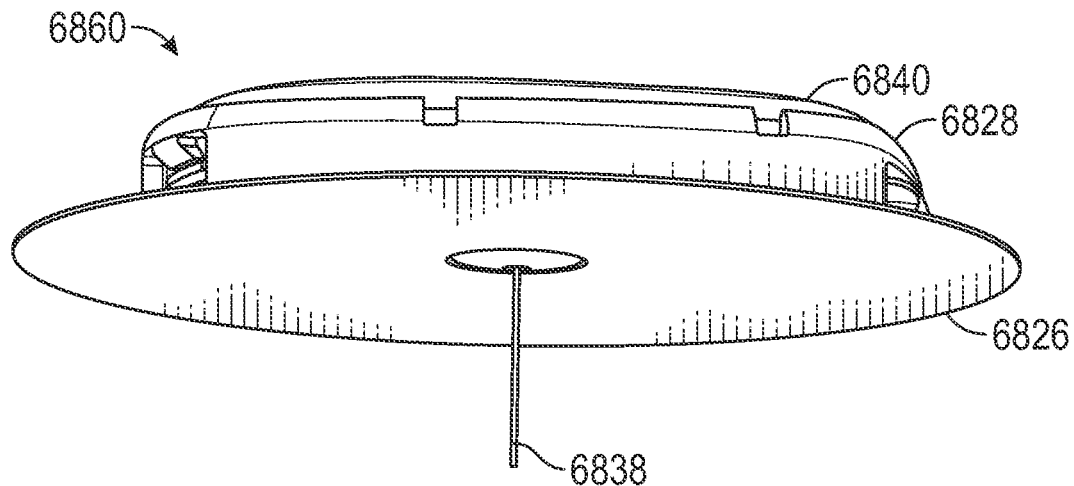
FIG. 69 illustrates a bottom perspective view of the on-skin sensor assembly of FIG. 68, according to some embodiments.

FIG. 69 illustrates a perspective view of electronics unit 6840 coupled to base 6828 via retention elements such as snap fits and/or interference features. In some embodiments, electronics unit 6840 and base 6828 are coupled by adhesive, welding, or other bonding techniques. Adhesive patch 6826, on a distal face of base 6828, is configured to couple sensor assembly 6860 to the skin.

Figure 70:
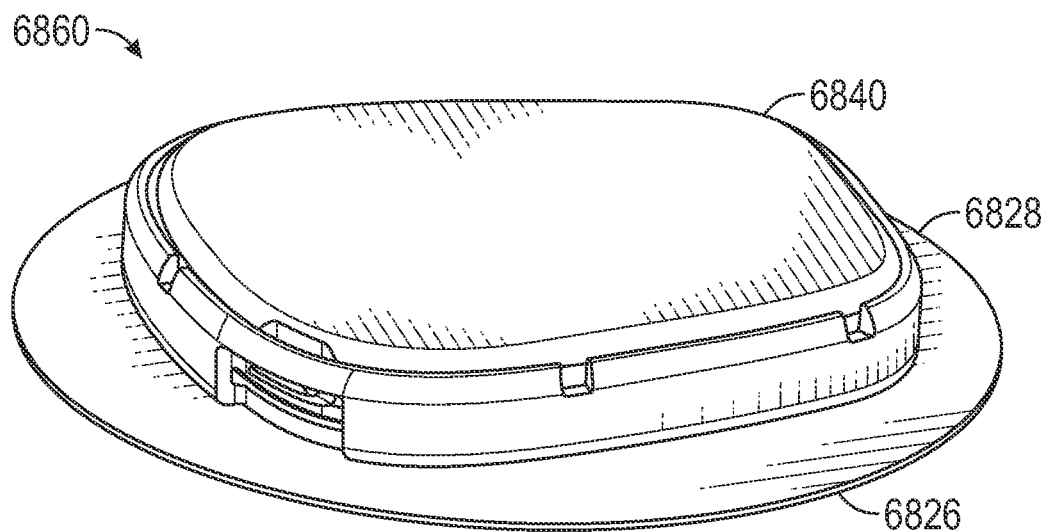
FIG. 70 illustrates a cross-sectional view of the on-skin sensor assembly of FIG. 68, according to some embodiments.

Reverting to on-skin sensor assembly 160 as previously described in connection with FIG. 1, FIG. 70 illustrates a perspective view of on-skin sensor assembly 6860. On-skin sensor assembly 6860 may be disposable or reusable. FIG. 70 further illustrates electronics unit 6840 coupled to a base 6828, and adhesive patch 6826 configured to be attached to on-skin sensor assembly 6860, which, when combined, may be held within the applicator. Adhesive patch 6826 may or may not have a non-adhesive liner when held in the applicator.

Further, with respect to any of on-skin sensor assembly 160, 260, 360 of FIGS. 1 and 2A-4, or on-skin sensor assembly 6860 of FIGS. 68-70, on-skin sensor assembly 160, 260, 360, 6860 is subjected to stress on portions of sensor 138, 238, 338, 6838 that are bent as the direction of extension of sensor 138, 238, 338, 6838 transitions from substantially horizontal, within on-skin sensor assembly 160, 260, 360, 6860 to substantially vertical, at the interface between on-skin sensor assembly 160, 260, 360, 6860 and skin 130. FIGS. 58-63 describe several embodiments that minimize the incidence of sensor damage as well as host discomfort at this interface. While the following description may identify portions of on-skin sensor assembly 160 of FIG. 1, such description may be equally applicable to on-skin sensor assembly 260, 360, 6860 of FIGS. 2A-4, and 68-70.

Figure 60:
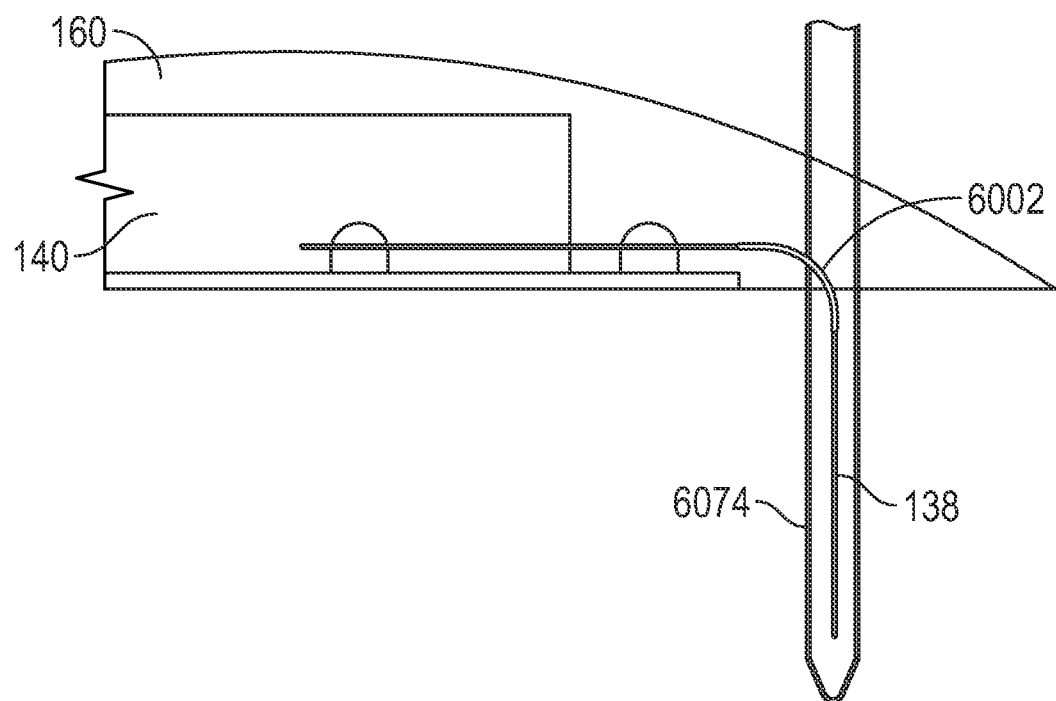
FIG. 60 illustrates a cutaway view of an on-skin sensor assembly having at least a portion of a sensor potted in a flexible material, according to some embodiments.

FIG. 60 illustrates a cutaway view of on-skin sensor assembly 160 having at least a portion of sensor 138 potted in a flexible material, according to some embodiments. On-skin sensor assembly 160 is shown as including at least sensor electronics 140, an insertion element 6074, such as a C-needle for example, passing through an opening in on-skin sensor assembly 160, and sensor 138 coupled or couplable to sensor electronics 140 at a first end, and having a portion that is bent along a bend radius such that a portion of sensor 138 beyond the bend is nested within or against insertion element 6074. Sensor 138 is further illustrated as having a flexible material 6002, e.g., an elastomeric material such as silicone, disposed around at least a portion of the bend in sensor 138. Flexible material 6002 may operate as a strain-relief element by limiting the bend radius of the bend to some predetermined minimum radius that substantially reduces or eliminates damage to sensor 138. In some embodiments, flexible material 6002 may extend to the hole through which sensor 138 passes at the on-skin sensor assembly-to-skin interface, which further provides a seal from moisture ingress to on-skin sensor assembly 160. In some embodiments, a dedicated seal comprising a flexible material may be provided at the hole through which sensor 128 passes in addition to or as an alternative to flexible material 6002.

Figure 61:
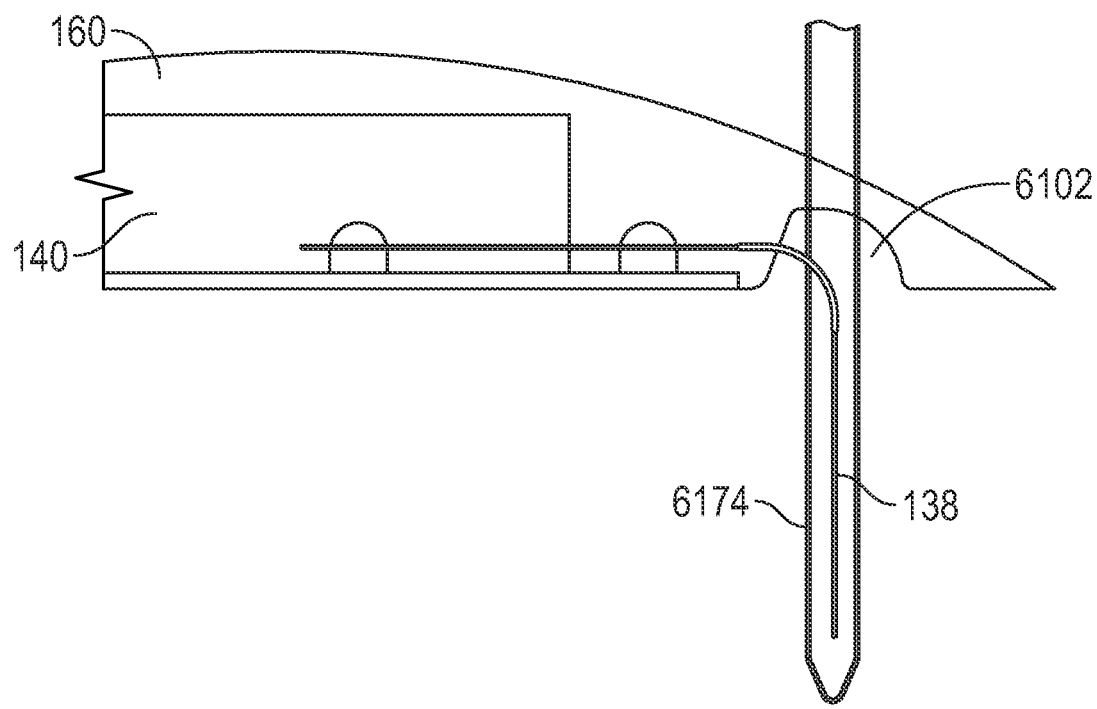
FIG. 61 illustrates a cutaway view of an on-skin sensor assembly comprising an open cavity configured to allow a larger bend radius in a sensor, according to some embodiments.

FIG. 61 illustrates a cutaway view of on-skin sensor assembly 160 comprising an open cavity configured to allow a larger bend radius in sensor 138, compared to that shown in FIG. 60, according to some embodiments. On-skin sensor assembly 160 is shown as including at least sensor electronics 140, an insertion element 6174, such as a C-needle for example, passing through an opening in on-skin sensor assembly 160, and sensor 138 coupled or couplable to sensor electronics 140 at a first end, and having a portion that is bent along a bend radius such that a portion of sensor 138 beyond the bend is nested within or against insertion element 6174. A bottom of on-skin sensor assembly 160 further includes an open cavity 6102. Open cavity 6102 allows sensor 138 to bend along a larger minimum bending radius than would be possible for an on-skin sensor assembly that does not include open cavity 6102. Sensor 138 is shown in FIG. 61 as initiating this bend in advance of reaching open cavity 6102 and arcing in an upward direction at the beginning of the bend, further increasing the potential minimum bend radius of sensor 138. Such a larger bend radius reduces stress and strain on sensor 138, thereby reducing the probability of damage to sensor 138.

Open cavity 6102 may further promote healing of the open wound caused by insertion of sensor 138 by insertion element 6174 by providing access air access that improves drying of the wound site. Although not shown in FIG. 61, on-skin sensor assembly 160 may further include a porous, woven, or spun lace material configured to wick away moisture from sweating or any other source, such as blood from the wound. Open cavity 6102 would further provide a location for small amounts of this liquid, e.g., blood, to collect, thereby preventing it from seeping out and being visible to the host. Although not shown in FIG. 61, sensor 138 may further include flexible material 6002, e.g., silicone, disposed around at least a portion of the bend in sensor 138 and/or a seal at the hole through which sensor 138 passes, as previously described in connection with FIG. 60.

Figure 62:
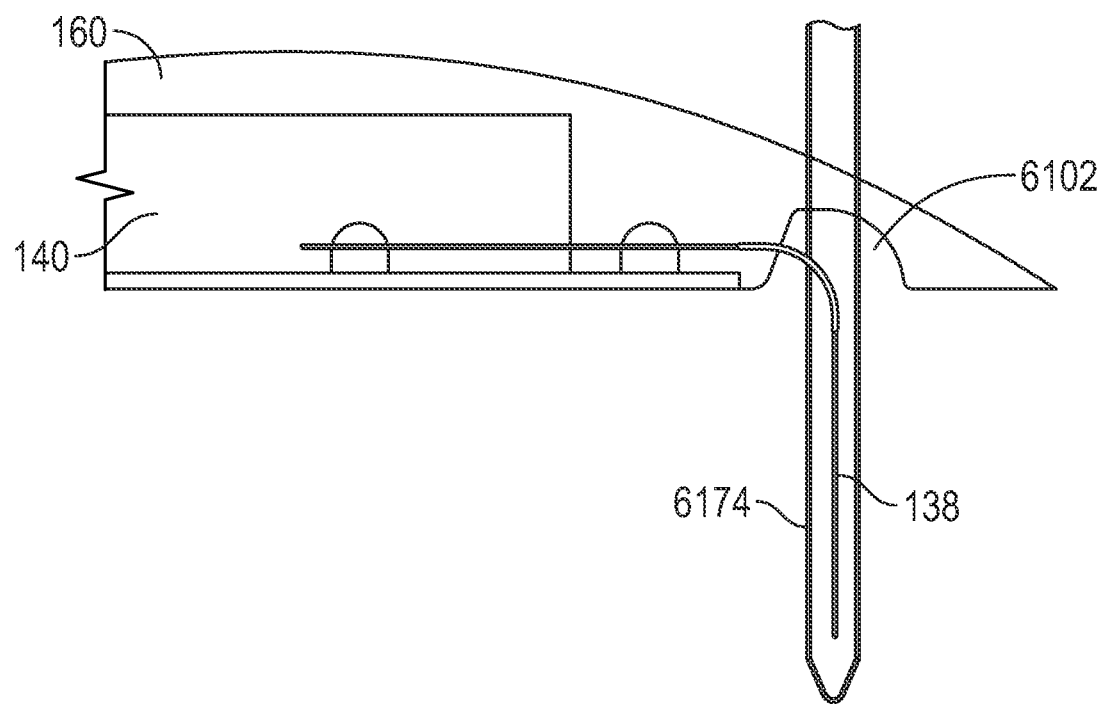
FIG. 62 illustrates a cutaway view of an on-skin sensor assembly comprising an open cavity configured to allow a larger bend radius in a sensor, according to some embodiments.

FIG. 62 illustrates a cutaway view of on-skin sensor assembly 160 comprising an open cavity configured to allow a larger bend radius in sensor 138, compared to that shown in FIG. 60, according to some embodiments. On-skin sensor assembly 160 is shown substantially as previously described in connection with FIG. 61, however, sensor 138 is shown as initiating the upward bend upon reaching, rather than in advance of reaching, open cavity 6102. Although not shown in FIG. 62, sensor 138 may further include flexible material 6002, e.g., silicone, disposed around at least a portion of the bend in sensor 138 and/or a seal at the hole through which sensor 138 passes, as previously described in connection with FIG. 60. Such a larger bend radius reduces stress and strain on sensor 138, thereby reducing the probability of damage to sensor 138.

Figure 63:
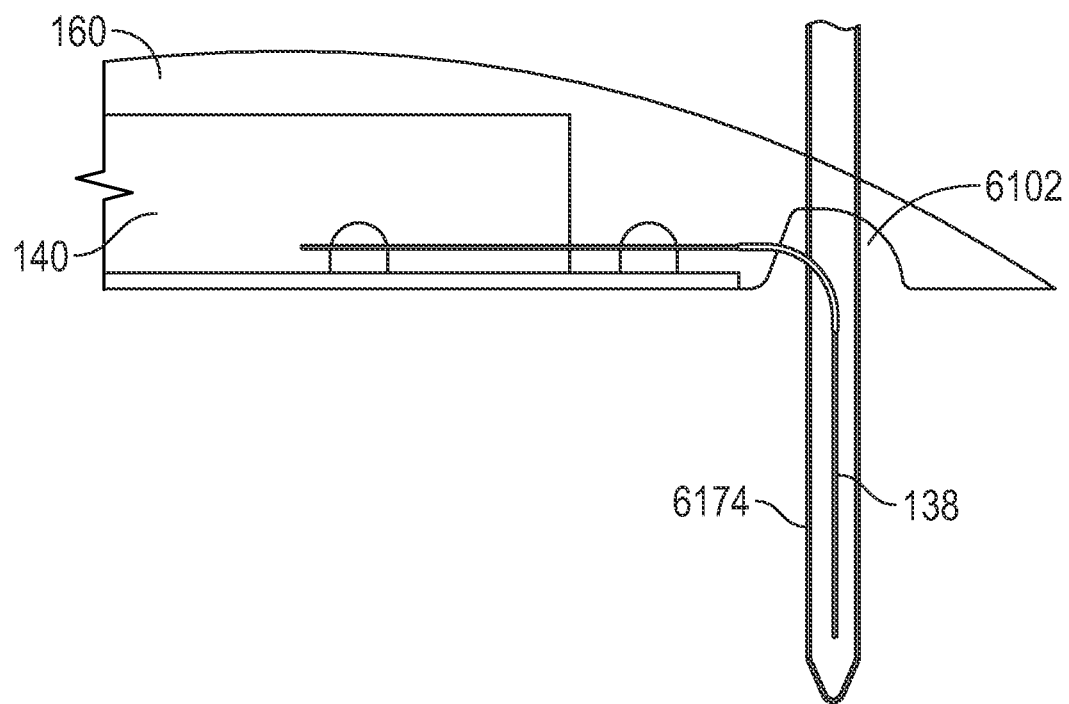
FIG. 63 illustrates a cutaway view of an on-skin sensor assembly comprising an open cavity configured to allow a larger bend radius in a sensor, according to some embodiments.

FIG. 63 illustrates a cutaway view of on-skin sensor assembly 160 comprising an open cavity configured to allow a larger bend radius in sensor 138, compared to that shown in FIG. 60, according to some embodiments. Such a larger bend radius reduces stress and strain on sensor 138, thereby reducing the probability of damage to sensor 138. On-skin sensor assembly 160 is shown substantially as previously described in connection with FIG. 61, however, sensor 138 is shown as initiating a bend upon reaching, rather than in advance of reaching, open cavity 6102 and this bend is substantially in the downward direction, rather than first in an upward direction. Although not shown in FIG. 63, sensor 138 may further include flexible material 6002, e.g., silicone, disposed around at least a portion of the bend in sensor 138 and/or a seal at the hole through which sensor 138 passes, as previously described in connection with FIG. 60.

In yet other embodiments, at least a portion of sensor 138 may have a braided polyurethane material disposed thereon to provide further strain relief. In addition, or in the alternative, additional materials such as an elastomer, flexible adhesive, or other braided or molded polymer material may be disposed thereon, in some embodiments, at least on the bend in sensor 138 and/or at a transition into on-skin sensor assembly 160, to provide further strain relief. It is contemplated that the components and features described above and/or with respect to FIGS. 60-63 can be implemented in other on-skin sensor assemblies described herein, such as on-skin sensor assembly 260 and 360.

In addition, during pressure fluctuations, such as at high altitude or vacuum during sterilization processes for example, air present within the applicator may exert a deforming force on on-skin sensor assembly 160. Although not shown in any of FIGS. 60-63, in some embodiments, on-skin sensor assembly 160 may have at least a portion formed with a reduced thickness and, therefore, reduced strength and rigidity, such that when applicator 460 is exposed to such pressure fluctuations, the portions having the reduced thickness expand in a controlled manner, thereby reducing or eliminating damage that would otherwise occur to on-skin sensor assembly 160 due to undesirable uncontrolled expansion of on-skin sensor assembly 160. Such a feature may be present in the applicator housing of any applicator described herein.

Figure 64A:
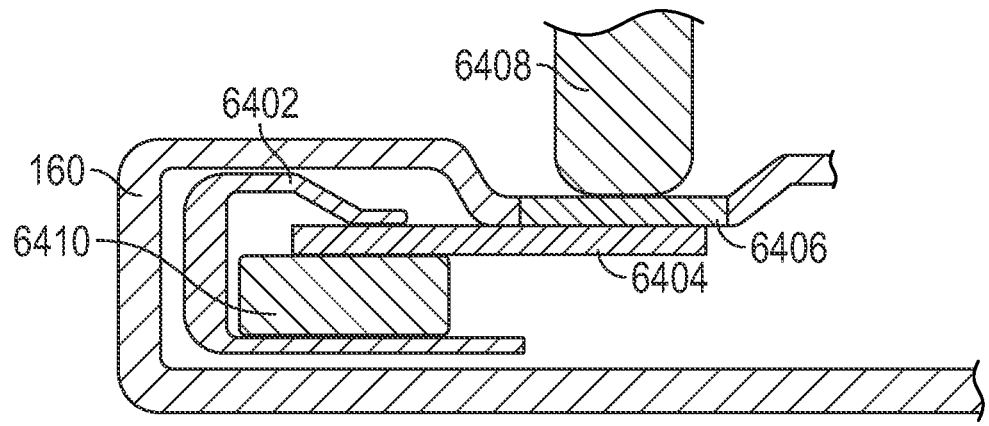
FIGS. 64A-64B illustrate a battery engagement feature for an on-skin sensor assembly, according to some embodiments.
Figure 64B:
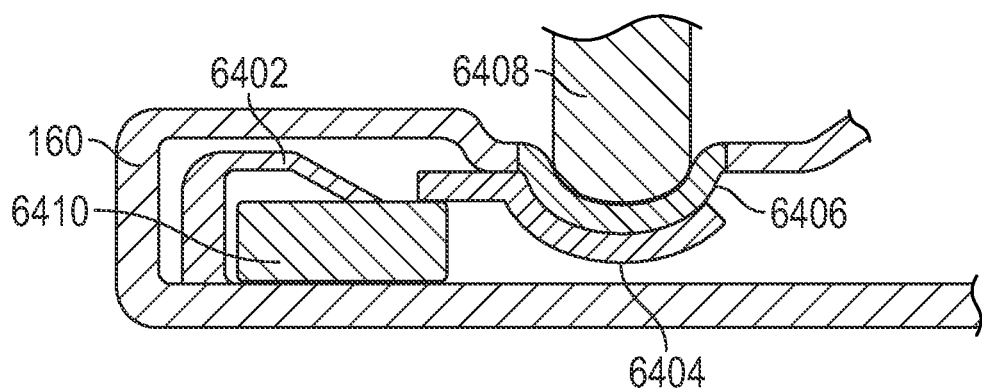

FIGS. 64A-64B illustrate an optional battery connection feature for on-skin sensor assembly 160, 260, 360 in accordance with some embodiments. FIG. 64A illustrates a storage mode, pre-activation. On-skin sensor assembly 160 is illustrated as including a battery 6410 configured to power at least sensor electronics (e.g., transmitter/sensor electronics 140, see FIG. 1). On-skin sensor assembly 160 further includes an electrical contact 6402, configured to physically and electrically contact battery 6410, an electrically insulating material 6404 (e.g., polyethylene terephthalate (PET), or any other electrically insulative material) disposed between electrical contact 6402, and a flexible material 6406 (e.g., ductile PET, TPSiV® or any other suitable material) coupled to on-skin sensor assembly 160 and to electrically insulating material 6404. In operation, pre-activation, electrically insulating material 6404 prevents electrical contact between electrical contact 6402 and battery 6410, maintaining on-skin sensor assembly 160 in an unpowered storage mode that prevents battery drain before deployment. During activation, some portion 6408 of applicator may be configured to push down on flexible material 6406, which is physically coupled to electrically insulating material 6404, thereby shifting electrically insulating material 6404 such that electrical contact 6402 comes into electrical contact with battery 6410 and shifting on-skin sensor assembly 160 into a battery connected operational mode, as will be shown in more detail in connection with FIG. 64B.

FIG. 64B illustrates the battery connected, operational mode of on-skin sensor assembly 160, 260, 360 discussed in FIG. 64A. Portion 6408 of applicator is illustrated as having pushed down or deformed flexible material 6406 and moved electrically insulating material 6404 laterally such that electrical contact 6402 is in electrical contact with battery 6410.

Figure 88A:
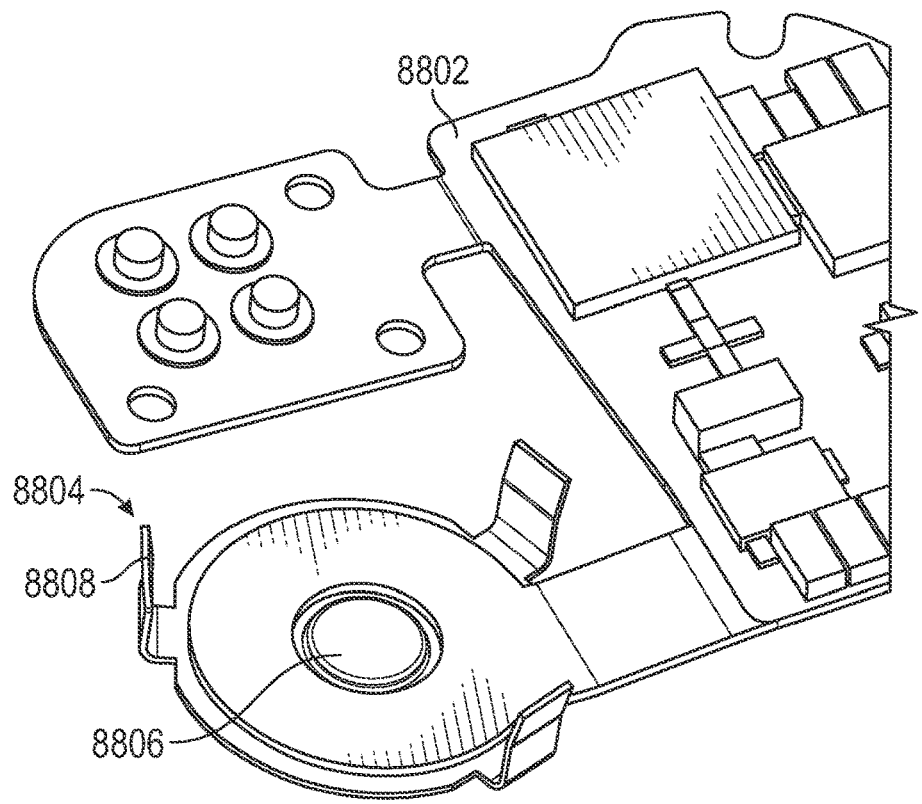
FIGS. 88A-88B illustrate perspective views of another optional battery connection feature for an on-skin sensor assembly, in accordance with some embodiments.
Figure 88B:
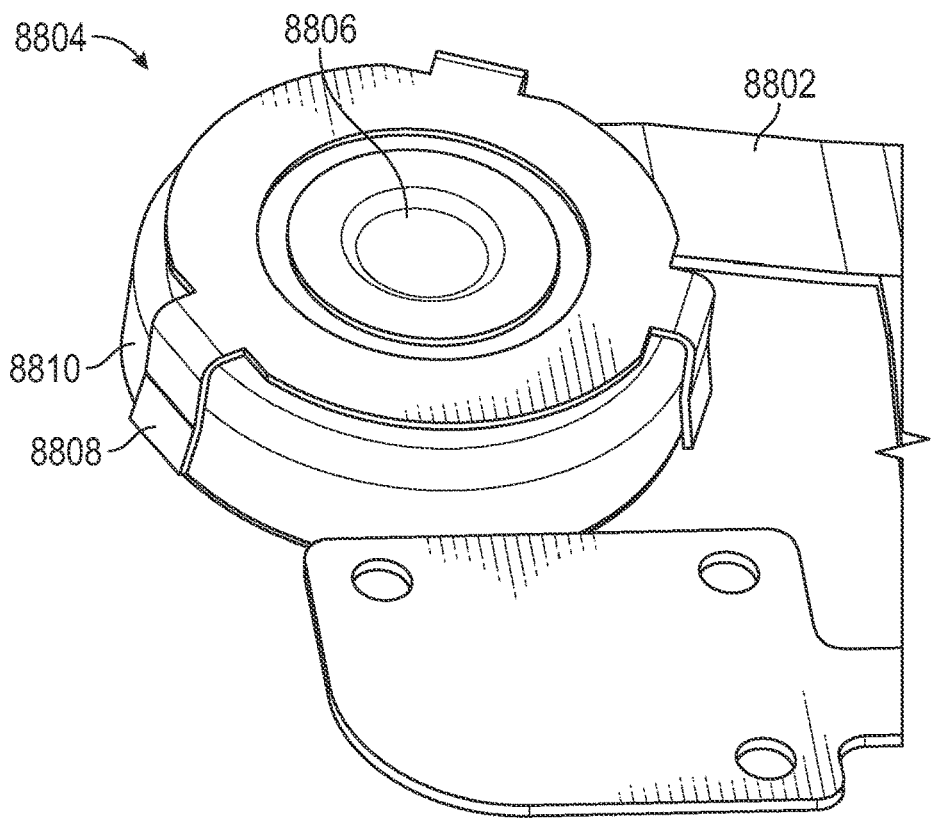

FIGS. 88A-88B illustrate another optional battery connection feature for on-skin sensor assembly 160, 260, 360 in accordance with some embodiments. FIG. 88A illustrates a first perspective view of a battery socket 8804 configured to hold a coin battery 8810 (see FIG. 88B), according to some embodiments. FIG. 88B illustrates a second perspective view of the battery socket 8804, according to some embodiments. Battery socket 8804 comprises a first terminal comprising a tab 8806, configured to make physical and electrical contact with one of a positive terminal or a negative terminal of battery 8810. Battery socket 8804 further comprises a second terminal comprising one or more clips 8808 configured to make physical and electrical contact with the other of the positive terminal or the negative terminal of battery 8810. In some embodiments, a portion of a PCB 8802 may insulate tab 8806 from the one or more clips 8808. In some embodiments, battery socket 8804 may be soldered to PCB 8802 to provide electrical and/or structural connections between battery socket 8804 and one or more electrical components on PCB 8802. In some embodiments, PCB 8802 may comprise a single unitary piece. In some embodiments, battery 8810 may be secured to battery socket 8804 during assembly of on-skin sensor assembly 160, 260, 360. In some embodiments, battery 8810 may be secured to tab 8806 via one or more tack welds. In some embodiments, battery 8810 may be additionally or alternatively secured to tab 8806 utilizing a spring, a piece of foam, or any other element disposed between battery 8810 and a housing or other portion of on-skin sensor assembly 160, 260, 360 and configured to push or retain battery 8810 against tab 8806. In some embodiments, battery 8810 may additionally or alternatively be secured to the one or more clips 8808 via one or more respective tack welds.

Sterilization, Packaging, and Sealing Embodiments

For any of the embodiments of applicators expressly described herein, sterilization, packaging, and/or sealing features may also be included. In some embodiments, a user removing the applicator from its packaging and/or its sterilization features may partially or fully energize the applicator (e.g., load unloaded springs). For example, motions such as pulling, twisting, pushing, or tilting required to remove an applicator from its packaging or to remove one or more sterilization and/or sealing features from the applicator may be harnessed to load partially unloaded or fully unloaded springs within the applicator. Such features would provide a benefit in that less energy would have to be stored in the springs of the applicator during its shelf life, prior to its use. Examples of sterilizing, sealing and packaging features contemplated for inclusion with any applicator described herein are described more fully in U.S. patent application Ser. No. 16/011,527, which is incorporated herein by reference it its entirety.

Figure 67:
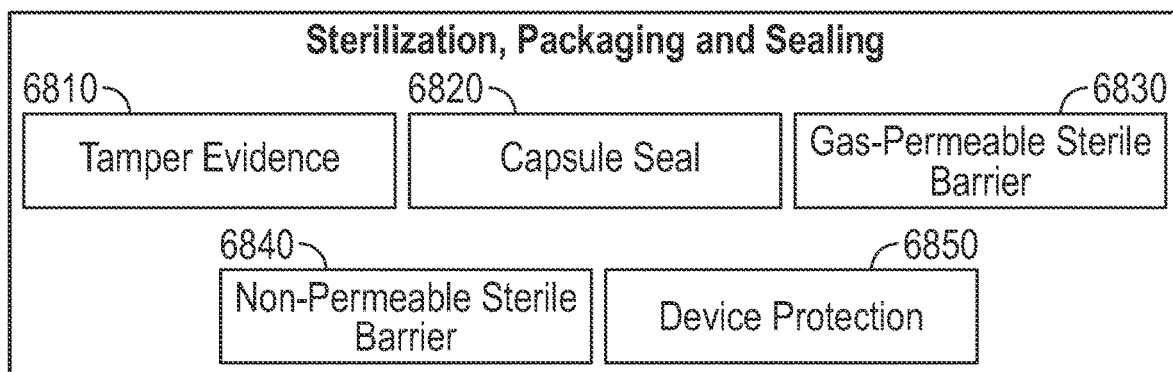
FIG. 67 illustrates exemplary sterilization, packaging and sealing features of an applicator configured to apply an on-skin sensor assembly to skin of a host, according to some embodiments.

FIG. 67 illustrates exemplary sterilization, packaging and sealing features of an applicator configured to apply an on-skin sensor assembly to skin of a host, according to some embodiments. In some embodiments, the applicator (e.g. applicator 500, 800, 900, 1000, etc.). may incorporate features such as sterile barrier, tamper evidence, device sealing and/or device protection. Methods of sterile barrier, tamper evidence, device sealing, and/or device protection are also described in U.S. patent application Ser. No. 16/011,527. Non-limiting examples may include a tamper evident feature 6810 (e.g. FIGS. 1A-5B), a capsule sealing feature 6820 (e.g. FIGS. 1A-3C), a gas permeable 6830 and/or non-gas permeable sterile barrier 6840 (e.g. FIGS. 1A, 2B, 4B, 5B, 7B, 8B, 9, 11A, 13A, 15A-27B, 29-30B), or device protection feature 6850 (e.g. FIG. 1A-24B).

Tamper evident sealing or other tamper evidence features 6810 allow a consumer to identify when an applicator has been previously used or containment has been breached and, thus, avoid using an applicator that may be faulty or pose an increased health risk if used. Non-limiting examples of tamper evident features 6810 also described in U.S. patent application Ser. No. 16/011,527, include ring, peelable layer, perforated tab, adhesive mounted tab, and/or twist-off collar. These features may be incorporated in current embodiments within an applicator housing (e.g. 502) or additional bodies added to the applicator assembly (e.g. cap, shell, lid, tab, peelable layer, frangible, ring, etc.).

Capsule sealing features 6820 create an enclosed volume from multiple components. Non limiting examples of capsule sealing features also described in U.S. patent application Ser. No. 16/011,527, include one or more removable caps on the top (e.g., proximal) or bottom (e.g., distal) ends of the applicator, through one or more trigger mechanisms comprising integrated caps, through one or more sealing layers that cover one or more orifices, apertures or vents of the applicator, through sterilizable gas-permeable polymers, through sterilizable gas-permeable trigger mechanisms, through protective cups, or any combinations of the same, described in more detail with at least some of FIGS. 1A-33. These features may be incorporated in current embodiments within an applicator housing (e.g. 502) or additional bodies added to the applicator assembly (e.g. cap, shell, lid, tab, peelable layer, elastomer, O-ring, adhesive, button, etc.).

Gas permeable sterile barriers 6830 allow a device to create an enclosed volume that is permeable to a gas (e.g. a sterilization gas) and maintain a microbial barrier to an exterior volume. A non-gas permeable sterile barrier 6840 performs the same functions of a gas permeable sterile barrier with the additional function of blocking gasses than may have deleterious effects (e.g. water vapor). Gas permeable 6830 and/or non-gas permeable sterile barrier 6840 may be used in conjunction or independently as also described in U.S. patent application Ser. No. 16/011,527. These features may be incorporated in current embodiments within an applicator housing (e.g. 502) or additional bodies added to the applicator assembly (e.g. cap, shell, lid, tab, peelable layer, packaging, seal, button, etc.).

Device protection features 6850 may be adapted to protect functional components of applicators (e.g. applicator 500, 800, 900, 1000, etc.). Functions may include inadvertent activation prevention, drop protection, needle damage protection, or other functions also disclosed in U.S. patent application Ser. No. 16/011,527. These features may be incorporated in current embodiments within an applicator housing (e.g. 502) or additional bodies added to the applicator assembly (e.g. cap, shell, lid, tab, peelable layer, frangible, packaging, seal, button, etc.).

Methods of Applying an On-Skin Sensor Assembly to Skin of a Host

FIG. 65 illustrates a flowchart 6500 of a method for applying an on-skin sensor assembly to skin of a host, according to some embodiments. Steps in flowchart 6500 may be performed utilizing any applicator as previously described in connection with any of the previous FIGS. Although certain steps are set forth below, a method of using such an applicator may comprise more, fewer, or different steps, in the same or different order from that set forth below.

Flowchart 6500 illustrates block 6502, including providing an applicator comprising an applicator housing, a needle carrier assembly comprising an insertion element configured to insert a sensor of the on-skin sensor assembly into the skin of the host, a holder releasably coupled to the needle carrier assembly and configured to guide the on-skin sensor assembly while coupled to the needle carrier assembly, a drive assembly, and an activation element. In some embodiments, the distal direction and the proximal direction extend along an insertion axis of the insertion element.

Flowchart 6500 further illustrates block 6504, including activating an activation element, wherein activating the activation element causes the drive assembly to drive the insertion element in a distal direction to a distal insertion position and in a proximal direction from the distal insertion position to a proximal retraction position, thereby inserting the sensor of the on-skin sensor assembly at least partially into the skin of the host.

FIG. 89 illustrates a flowchart 8900 of another method for applying an on-skin sensor assembly to skin of a host, according to some embodiments. Steps in flowchart 8900 may be performed utilizing any applicator as described in connection with any FIGS., for example but not limitation, FIGS. 71-88. Although certain steps are set forth below, a method of using such an applicator may comprise more, fewer, or different steps, in the same or different order from that set forth below.

Flowchart 8900 illustrates block 8902, including providing an applicator comprising a housing having an activation element, an insertion assembly, and a retraction assembly.

Flowchart 8900 further illustrates block 8904, including activating the activation element, wherein activating the activation element causes the insertion assembly to translate a needle carrier assembly and the on-skin sensor assembly in a distal direction from a proximal position to a distal insertion position, thereby inserting a sensor of the on-skin sensor assembly at least partially into the skin of the host, and the retraction assembly to translate the needle carrier assembly in a proximal direction from the distal inserted position to a proximal retracted position, the retraction assembly configured to activate in response to on-skin sensor assembly contacting the skin of the host. In some embodiments, the distal direction and the proximal direction extend along an insertion axis of an insertion element of the applicator.

Exemplary Mechanisms for Applicator Features

FIG. 66 illustrates exemplary mechanisms for several features of an applicator configured to apply an on-skin sensor assembly to skin of a host, according to some embodiments. The mechanisms described in connection with FIG. 66 are exemplary and not limiting.

For example, the feature activation element 6610 as used herein may be considered to include any type of mechanism that, when operated as intended, serves to activate a drive mechanism of an applicator and, thereby, apply an on-skin sensor assembly to skin of a host. For example, an activation element may include an element configured to trigger when pushed, pulled, switched, toggled, slid, triggered, deflected, rotated, deformed or flexed from a first position or state to at least a second position or state. General examples include but are not limited to buttons, slides, hooks, switches, a flexible portion of the applicator housing itself, tabs, or strings. Moreover, although certain embodiments of applicators are described herein as having an activation element in a particular location, any applicator described herein is also contemplated having one or more activation members in any other position, e.g., a top, upper side, medial side, lower side, or bottom of the applicator. Moreover, in some embodiments, two or more activation elements may be operated in tandem in order to activate the applicator. The above-described activation elements may be applied or utilized in connection with any applicator described herein.

The feature insertion element 6620 as used herein may be considered to include any type of mechanism that, when operated as intended, serves to insert a sensor or sensor wire at least partially into a skin of a host. For example, an insertion element may include, but is not limited to, a regular, circumferential needle, an open sided-needle (e.g., FIGS. 48A-48B), a needle with a deflected tip (e.g., FIG. 49), a curved, bent or kinked needle (e.g., FIGS. 47 and 50), a polymer-coated needle, a hypodermic needle, or the sensor or sensor wire tip itself.

The feature retention element or on-skin sensor assembly retention element 6630 as used herein may be considered to include any type of mechanism that, when operated as intended, serves to retain an on-skin sensor assembly in a particular position, orientation or constrain the feature to a particular path of motion. For example, a retention element may include, but is not limited to, a hook, a claw, a tab, an arm, an undercut and snap feature, a press fit feature, a deformable and/or elastomeric element (as described in connection with any of FIGS. 5-7D, 12-14E, 25-27E, 32A-37C and 41A-46), or any on-skin sensor assembly retention element illustrated in U.S. patent application Ser. No. 15/387,088 as described above.

The feature spring and/or energy source 6650 as used herein may be considered to include any suitable type of spring configured to store potential energy when loaded and configured to release at least a portion of that stored potential energy to drive one or more portions of an applicator as required or desired. For example, a spring may include, but is not limited to, a compression spring, which is configured to store energy when compressed to less than its resting length (e.g., FIG. 32), an extension spring, which is configured to store energy when stretched to greater than its resting length (e.g., FIG. 21), a single or double torsion spring (e.g., FIG. 12), clock spring or power spring, which are configured to store energy in torsional deformation of a portion of the spring from its resting profile, or a leaf spring (e.g., FIGS. 22 and 25), which is configured to store energy in the physical deformation of the spring from its resting profile.

Insertion and/or retraction mechanisms 6660 may be considered to include any suitable mechanism for causing a movement of an insertion element in a distal direction to a distal inserted position, and/or in a proximal direction to a proximal retracted position. For example, such mechanisms may include, but are not limited to, a scotch yoke mechanism (e.g., FIG. 5) a barrel cam (e.g., FIG. 29), opposing springs mechanism, a reverse toggling mechanism comprising a lever having a first end, a second end, and a fulcrum at a point between the first and second ends (e.g., FIG. 31), a flexible linkage (e.g., FIGS. 18-23), a spring linkage (e.g. FIG. 12-14E), or any hinging or pivoting (e.g. FIG. 25-28H) apparatus that operates as described in this disclosure.

Energy storage 6640, for example, as potential energy stored in a spring, for any applicator described in this disclosure may be pre-loaded (e.g., in the factory or before provision to a user), mechanism loaded (e.g., some operation of the applicator loads the spring), or user loaded (e.g., the user provides energy in some form of motion that is utilized to store potential energy in a spring).

Sensor retention 6670 for any applicator described in this disclosure may be user-removable (e.g., FIGS. 54, 57, 58), mechanism-removable (e.g., FIGS. 53, 56A-56B, 57 and 58), ex-vivo support feature (e.g., FIGS. 55-58), or in-vivo support feature (e.g., FIGS. 59A-59B). For example, an elastomeric element such as a rubber band (see FIG. 53), a foam, rubber or other pad (see FIG. 55), a frangible element (see FIGS. 57-58), an adhesive layer, or a wire.

Elements within each feature category (e.g., 6610, 6620, 6630, 6640, 6650, 6660, 6670) are interchangeable for any applicator described herein. For instance, applicator 500 shown in FIGS. 5-611 includes a push button and deflecting arm activation element 504, an open-sided needle insertion element 674, an undercut/snap feature 678a, 678b for on-skin sensor assembly 160 retention, a pre-loaded energy storage in which the energy source is a single torsion spring 512, and a scotch yoke insertion/retraction mechanism 510. However, in an alternative embodiment, applicator 500 may instead include a switch/toggle activation element, a curved/bent needle insertion element (e.g., 5074), a press fit on-skin sensor assembly retention, and an ex-vivo support feature sensor retention (e.g., FIGS. 55-58).

In another example, applicator 2500 shown in FIGS. 25-28H includes a push button and deflecting arm activation element 2504, an open-sided needle insertion element 2674, an undercut/snap feature (e.g., similar to 678a, 678b) on needle carrier assembly 2508 for on-skin sensor assembly 160 retention, a pre-loaded energy storage in which the energy source is a compression spring 2512 and leaf springs 2528, and a hinging or pivoting apparatus 2508, 2524. However, in an alternative embodiment, applicator 2500 may instead include a switch/toggle activation element, a curved/bent needle insertion element (e.g., 5074), a press fit on-skin sensor assembly retention, and an ex-vivo support feature sensor retention (e.g., FIGS. 55-58).

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

Methods and devices that are suitable for use in conjunction with aspects of the preferred embodiments are disclosed in U.S. Pat. Nos. 4,757,022; 4,994,167; 6,001,067; 6,558, 321; 6,702,857; 6,741,877; 6,862,465; 6,931,327; 7,074, 307; 7,081,195; 7,108,778; 7,110,803; 7,134,999; 7,136, 689; 7,192,450; 7,226,978; 7,276,029; 7,310,544; 7,364, 592; 7,366,556; 7,379,765; 7,424,318; 7,460,898; 7,467, 003; 7,471,972; 7,494,465; 7,497,827; 7,519,408; 7,583, 990; 7,591,801; 7,599,726; 7,613,491; 7,615,007; 7,632, 228; 7,637,868; 7,640,048; 7,651,596; 7,654,956; 7,657, 297; 7,711,402; 7,713,574; 7,715,893; 7,761,130; 7,771, 352; 7,774,145; 7,775,975; 7,778,680; 7,783,333; 7,792, 562; 7,797,028; 7,826,981; 7,828,728; 7,831,287; 7,835, 777; 7,857,760; 7,860,545; 7,875,293; 7,881,763; 7,885, 697; 7,896,809; 7,899,511; 7,901,354; 7,905,833; 7,914, 450; 7,917,186; 7,920,906; 7,925,321; 7,927,274; 7,933, 639; 7,935,057; 7,946,984; 7,949,381; 7,955,261; 7,959, 569; 7,970,448; 7,974,672; 7,976,492; 7,979,104; 7,986, 986; 7,998,071; 8,000,901; 8,005,524; 8,005,525; 8,010, 174; 8,027,708; 8,050,731; 8,052,601; 8,053,018; 8,060, 173; 8,060,174; 8,064,977; 8,073,519; 8,073,520; 8,118, 877; 8,128,562; 8,133,178; 8,150,488; 8,155,723; 8,160, 669; 8,160,671; 8,167,801; 8,170,803; 8,195,265; 8,206, 297; 8,216,139; 8,229,534; 8,229,535; 8,229,536; 8,231, 531; 8,233,958; 8,233,959; 8,249,684; 8,251,906; 8,255, 030; 8,255,032; 8,255,033; 8,257,259; 8,260,393; 8,265, 725; 8,275,437; 8,275,438; 8,277,713; 8,280,475; 8,282, 549; 8,282,550; 8,285,354; 8,287,453; 8,290,559; 8,290, 560; 8,290,561; 8,290,562; 8,292,810; 8,298,142; 8,311, 749; 8,313,434; 8,321,149; 8,332,008; 8,346,338; 8,364, 229; 8,369,919; 8,374,667; 8,386,004; 8,394,021; 8,527, 025; 7,896,809; 9,119,528; and 9,119,529.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-

A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196 Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-

A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013-0536650-A1; U.S. Patent Publication No. 2013-0053666-A1; U.S. Patent Publication No. 2010-0331644-A1; U.S. Patent Publication No. 2013-0053665-A1; U.S. Patent Publication No. 2013-0053666-A1; U.S. Patent Publication No. 2013-0060112-A1; U.S. Patent Publication No. 2013-0078912-A1; U.S. Patent Publication No. 2013-0076531-A1; U.S. Patent Publication No. 2013-0076532-A1; U.S. Patent Publication No. 2013-0131478-A1; U.S. Patent Publication No. 2014-0182350-A1; U.S. Patent Publication No. 2014-0188402-A1; U.S. Patent Publication No. 2013-0150692-A1; U.S. Patent Publication No. 2014-0005508-A1; U.S. Patent Publication No. 2014-0094671-A1; U.S. Patent Publication No. 2014-0107450-A1; U.S. Patent Publication No. 2013-0245412-A1; U.S. Patent Publication No. 2014-0088389-A1; U.S. Patent Publication No. 2014-0005505-A1; U.S. Patent Publication No. 2013-0325504-A1; U.S. Patent Publication No. 2013-0321425-A1; and U.S. Patent Publication No. 2014-0129151-A1.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An applicator for applying an on-skin sensor assembly to a skin of a host, the applicator comprising:
   an applicator housing;
   a needle hub coupled to an insertion element, the needle hub comprising:
      a base, and
      an anti-rotation feature extending from the base, the anti-rotation feature comprising a key, the key having a first shape; and
   an on-skin sensor assembly comprising:
      a sensor, the sensor configured to measure an analyte concentration of a host, and
      an aperture extending from a top surface of the on-skin sensor assembly, the aperture having a second shape, the second shape complementary to the first shape of the key; and
   wherein the key of the anti-rotation feature is configured to be at least partially disposed in the aperture of the on-skin sensor assembly; and
   wherein the anti-rotation feature is configured to prevent rotation of the base within the aperture.

2. The applicator of claim 1, wherein the insertion element comprises a needle.

3. The applicator of claim 2, wherein the needle comprises an open side configured to receive the sensor.

4. The applicator of claim 3, wherein the needle has a C-shaped, U-shaped, or V-shaped cross section.

5. The applicator of claim 1, wherein the needle hub is coupled to the insertion element by heat staking, snap-fit, friction-fit, clamshell, or insert molding.

6. The applicator of claim 1, wherein the on-skin sensor assembly comprises an electronics unit.

7. The applicator of claim 6, wherein the electronics unit is configured to communicate analyte data to a receiver after the on-skin sensor assembly is applied to a skin of the host.

8. The applicator of claim 7, wherein the electronics unit includes a power source, signal processing components, data storage components, and a communication module.

9. The applicator of claim 7, wherein the sensor is connected to the electronics unit in the applicator housing.

10. The applicator of claim 1, wherein the on-skin sensor assembly includes an adhesive patch configured to secure the on-skin sensor assembly to a skin of a host.

11. The applicator of claim 1, wherein the insertion element is configured to be inserted into the skin a predetermined depth.

12. The applicator of claim 1, wherein the analyte concentration comprises glucose.

13. The applicator of claim 1, further comprising an inner applicator housing.

14. The applicator of claim 1, further comprising a retraction spring configured to drive the insertion element from distal insertion position to a proximal retracted position.

15. An applicator for applying an on-skin sensor assembly to a skin of a host, the applicator comprising:
- an applicator housing;
- a needle hub coupled to a needle, wherein the needle comprises a portion configured to extend through the skin of the host, wherein the needle hub comprises a base, wherein the base comprises an anti-rotation key, wherein the anti-rotation key has a first shape; and
- an on-skin sensor assembly comprising:
  - a sensor configured to measure an analyte concentration of a host; and
  - an aperture extending from a top surface of the on-skin sensor assembly, wherein the aperture has a second shape, wherein the second shape is complementary to the first shape of the anti-rotation key; and
- wherein the anti-rotation key is configured to be at least partially disposed in the aperture of the on-skin sensor assembly; and
- wherein the anti-rotation key is configured to prevent rotation of the needle hub with respect to the on-skin sensor assembly.

16. The applicator of claim 15, wherein the needle comprises an open side configured to receive the sensor.

17. The applicator of claim 15, wherein the needle hub is coupled to the insertion element by heat staking, snap-fit, friction-fit, clamshell, or insert molding.

18. The applicator of claim 15, wherein the on-skin sensor assembly comprises an electronics unit.

19. The applicator of claim 18, wherein the electronics unit is configured to communicate analyte data to a receiver after the on-skin sensor assembly is applied to a skin of the host.

20. The applicator of claim 19, wherein the electronics unit includes a power source, signal processing components, data storage components, and a communication module.

21. The applicator of claim 18, wherein the sensor is connected to the electronics unit in the applicator housing.

22. The applicator of claim 18, wherein the needle is configured to be inserted through the electronics unit.

23. An applicator for applying an on-skin sensor assembly to a skin of a host, the applicator comprising:
- an applicator housing;
- a needle hub coupled to a needle, wherein the needle comprises a portion configured to extend through the skin of the host, wherein the needle hub comprises a base, wherein the base comprises an anti-rotation key, wherein the anti-rotation key has a first shape; and
- an on-skin sensor assembly comprising:
  - a sensor configured to measure an analyte concentration of a host; and
  - an aperture extending from a top surface of the on-skin sensor assembly, wherein the aperture has a second shape, wherein the second shape is complementary to the first shape of the anti-rotation key; and
- wherein the anti-rotation key is configured to be at least partially disposed in the aperture of the on-skin sensor assembly; and
- wherein the anti-rotation key is configured to prevent rotation of the base within the aperture.

24. The applicator of claim 23, wherein the needle comprises an open side configured to receive the sensor.

25. The applicator of claim 23, wherein the needle hub is coupled to the insertion element by heat staking, snap-fit, friction-fit, clamshell, or insert molding.

26. The applicator of claim 23, wherein the on-skin sensor assembly comprises an electronics unit.

27. The applicator of claim 26, wherein the electronics unit is configured to communicate analyte data to a receiver after the on-skin sensor assembly is applied to a skin of the host.

28. The applicator of claim 27, wherein the electronics unit includes a power source, signal processing components, data storage components, and a communication module.

29. The applicator of claim 26, wherein the sensor is connected to the electronics unit in the applicator housing.

30. The applicator of claim 26, wherein the needle is configured to be inserted through the electronics unit.

* * * * *